US012378557B2

(12) United States Patent
Horowitz et al.

(10) Patent No.: US 12,378,557 B2
(45) Date of Patent: Aug. 5, 2025

(54) TREATMENT OF SEPSIS WITH PCSK9 AND LDLR MODULATORS

(71) Applicant: Regeneron Pharmaceuticals, Inc., Tarrytown, NY (US)

(72) Inventors: Julie Horowitz, Tarrytown, NY (US); Luca Andrea Lotta, Tarrytown, NY (US); Manuel Allen Revez Ferreira, Tarrytown, NY (US); Amy Damask, Tarrytown, NY (US); Charles Paulding, Tarrytown, NY (US); Garen Manvelian, Tarrytown, NY (US); Michael Cantor, Tarrytown, NY (US); Aris Baras, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 887 days.

(21) Appl. No.: 17/411,460

(22) Filed: Aug. 25, 2021

(65) Prior Publication Data

US 2022/0064652 A1 Mar. 3, 2022

Related U.S. Application Data

(60) Provisional application No. 63/036,789, filed on Aug. 25, 2020.

(51) Int. Cl.

| | |
|---|---|
| ***C07H 21/04*** | (2006.01) |
| ***A61P 31/00*** | (2006.01) |
| ***C12N 9/22*** | (2006.01) |
| ***C12N 15/11*** | (2006.01) |
| ***C12N 15/113*** | (2010.01) |
| ***C12Q 1/6883*** | (2018.01) |

(52) U.S. Cl.

CPC .......... *C12N 15/1137* (2013.01); *A61P 31/00* (2018.01); *C12N 9/22* (2013.01); *C12N 15/11* (2013.01); *C12Q 1/6883* (2013.01); *C12N 2310/20* (2017.05); *C12Q 2600/156* (2013.01)

(58) Field of Classification Search

CPC ...... C12N 15/1137; C12N 9/22; C12N 15/11; A61P 31/00; C12Q 1/6883; C12Q 2600/156

See application file for complete search history.

(56) References Cited

U.S. PATENT DOCUMENTS

| | | | |
|---|---|---|---|
| 7,300,754 | B2 | 11/2007 | Fadel et al. |
| 8,080,377 | B2 | 12/2011 | Ryu et al. |
| 8,742,082 | B2 | 6/2014 | Tissot-Favre et al. |
| 8,883,157 | B1 | 11/2014 | Clube |
| 8,945,560 | B1 | 2/2015 | Clube |
| 8,951,523 | B1 | 2/2015 | Clube |
| 8,980,273 | B1 | 3/2015 | Clube |
| 8,986,691 | B1 | 3/2015 | Clube |
| 8,986,694 | B1 | 3/2015 | Clube |
| 8,992,927 | B1 | 3/2015 | Clube |
| 8,999,341 | B1 | 4/2015 | Clube |
| 9,017,678 | B1 | 4/2015 | Clube |
| 9,023,359 | B1 | 5/2015 | Clube |
| 9,034,331 | B1 | 5/2015 | Clube |
| 9,034,332 | B1 | 5/2015 | Clube |
| 9,040,052 | B1 | 5/2015 | Clube |
| 9,045,545 | B1 | 6/2015 | Clube |
| 9,045,548 | B1 | 6/2015 | Clube |
| 9,051,378 | B1 | 6/2015 | Clube |
| 9,062,105 | B1 | 6/2015 | Clube |
| 9,067,998 | B1 | 6/2015 | Clube |
| 9,068,012 | B1 | 6/2015 | Clube |
| 9,109,034 | B1 | 8/2015 | Clube |
| 9,139,648 | B1 | 9/2015 | Clube |
| 9,150,660 | B1 | 10/2015 | Clube |
| 9,187,562 | B1 | 11/2015 | Clube |
| 9,303,089 | B2 | 4/2016 | Clube |
| 9,394,568 | B2 | 7/2016 | Clube |
| 9,416,180 | B1 | 8/2016 | Clube |
| 9,428,578 | B2 | 8/2016 | Clube |
| 9,439,963 | B2 | 9/2016 | Clube |
| 9,526,720 | B2 | 12/2016 | Nagiec et al. |
| 9,914,769 | B2 | 3/2018 | Clube |
| 10,265,379 | B2 | 4/2019 | Oquendo |
| 10,329,620 | B2 | 6/2019 | Komman et al. |
| 10,337,070 | B2 | 7/2019 | Komman et al. |
| 10,611,849 | B2 | 4/2020 | Clube |

(Continued)

FOREIGN PATENT DOCUMENTS

| | | |
|---|---|---|
| WO | 2013043041 | 8/2013 |
| WO | 2013170367 | 11/2013 |

(Continued)

OTHER PUBLICATIONS

Dwivedi, Dhruva J., et al. ("Differential expression of PCSK9 modulates infection, inflammation, and coagulation in a murine model of sepsis." Shock 46.6 (2016): 672-680).*

Griffiths ("Sepsis, SIRS and MODS." Surgery (Oxford) 27.10 (2009): 446-449).*

Wu, Na-Qiong, and Jian-Jun Li. ("PCSK9 gene mutations and low-density lipoprotein cholesterol." Clinica Chimica Acta 431 (2014): 148-153).*

Meng et al., Meng, Fan-Hua, et al. ("New loss-of-function mutations in PCSK9 reduce plasma LDL cholesterol." Arteriosclerosis, Thrombosis, and Vascular Biology 43.7 (2023): 1219-1233).*

(Continued)

*Primary Examiner* — Kimberly Chong

(74) *Attorney, Agent, or Firm* — Armstrong Teasdale LLP

(57) ABSTRACT

The present disclosure provides methods of treating subjects having sepsis, SIRS, septic shock, and/or MODS, methods of identifying subjects having an increased risk of developing sepsis, SIRS, septic shock, and/or MODS, and methods of detecting Proprotein Convertase Subtilisin/Kexin Type 9 (PCSK9) and/or Low Density Lipoprotein Receptor (LDLR) variant nucleic acid molecules and variant polypeptides.

6 Claims, 5 Drawing Sheets

Specification includes a Sequence Listing.

(56) References Cited

U.S. PATENT DOCUMENTS

| | | | |
|---|---|---|---|
| 10,618,955 | B2 | 4/2020 | Clube |
| 10,618,971 | B2 | 4/2020 | Clube |
| 10,711,059 | B2 | 7/2020 | Clube |
| 10,751,388 | B2 | 8/2020 | Oquendo |
| 2012/0258183 | A1 | 10/2012 | Smith et al. |
| 2013/0252987 | A1 | 9/2013 | Rashid |
| 2014/0228253 | A1 | 8/2014 | Tissot-Favre et al. |
| 2014/0356370 | A1 | 12/2014 | Swergold et al. |
| 2015/0316566 | A1 | 11/2015 | Dasseux et al. |
| 2016/0017056 | A1 | 1/2016 | Clube |
| 2016/0305959 | A1 | 10/2016 | Levy et al. |
| 2016/0319017 | A1 | 11/2016 | Clube |
| 2018/0162935 | A1 | 6/2018 | Clube |
| 2018/0203025 | A1 | 7/2018 | Dasseux et al. |
| 2019/0017119 | A1 | 1/2019 | Khera et al. |
| 2019/0330371 | A1 | 10/2019 | Swergold et al. |
| 2019/0330698 | A1 | 10/2019 | Khera et al. |
| 2019/0341125 | A1 | 11/2019 | Khera et al. |
| 2019/0345557 | A1 | 11/2019 | Khera et al. |
| 2019/0345566 | A1 | 11/2019 | Khera et al. |
| 2019/0360048 | A1 | 11/2019 | Komman et al. |
| 2019/0365855 | A1 | 12/2019 | Oquendo |
| 2020/0010880 | A1 | 1/2020 | Ku et al. |
| 2020/0109216 | A1 | 4/2020 | Clube |
| 2020/0368239 | A1 | 11/2020 | Han et al. |
| 2021/0063391 | A1 | 3/2021 | Gooneswardena et al. |
| 2021/0113536 | A1 | 4/2021 | Natarajan et al. |
| 2021/0139990 | A1 | 5/2021 | Shalek et al. |
| 2021/0002724 | A1 | 7/2021 | Damask et al. |

FOREIGN PATENT DOCUMENTS

| | | |
|---|---|---|
| WO | 2015051214 | 4/2015 |
| WO | 2015073709 | 5/2015 |
| WO | 2015092393 | 6/2015 |
| WO | 2015092394 | 6/2015 |
| WO | 2016008899 | 1/2016 |
| WO | 2016023916 | 2/2016 |
| WO | 2016071701 | 5/2016 |
| WO | 2016114662 | 9/2016 |
| WO | 2017218798 | 12/2017 |
| WO | 2018054959 | 3/2018 |
| WO | 2020010181 | 1/2020 |
| WO | 2020010186 | 1/2020 |
| WO | 2020110008 | 6/2020 |
| WO | 2020235954 | 11/2020 |
| WO | 2021058597 | 4/2021 |

OTHER PUBLICATIONS

Lu et al. ("Coding-sequence variants are associated with blood lipid levels in 14,473 Chinese." 25.18 (2016): 4107-4116).*

Shukla et al., "Therapeutic interventions in sepsis: current and anticipated pharmacological agents", Br J Pharmacol, 2014, 171(22), pp. 5011-5031.

Leung et al., "Reduced Proprotein convertase subtilisin/kexin 9 (PCSK9) function increases lipoteichoic acid clearance and improves outcomes in Gram positive septic shock patients", Scientific Reports, 2019, 9(1), pp. 10588.

Momtazi et al., "PCSK9 inhibitors in sepsis: a new potential indication?", Expert Opinion on Investigational Drugs, 2016, 26(2), pp. 137-139.

Dwivedi et al., "Differential Expression of PCSK9 Modulates Infection, Inflammation, and Coagulation in a Murine Model of Sepsis", Shock, 2016, 46(6), pp. 672-680.

Walley et al., "PCSK9 is a critical regulator of the innate immune response and septic shock outcome", Science Translational Medicine, 2014, 6(258), pp. 1-10.

Feng et al., "A Genetic Approach to the Association Between PCSK9 and Sepsis", JAMA Network Open, 2019, 2(9), pp. e1911130.

Genga et al., "Impact of PCSK9 loss-of-function genotype on 1-year mortality and recurrent infection in sepsis survivors", EBiomedicine, 2018, 38, pp. 257-264.

Boyd et al., "Increased Plasma PCSK9 Levels Are Associated with Reduced Endotoxin Clearance and the Development of Acute Organ Failures during Sepsis", Journal of Innate Immunity, 2016, 8(2), pp. 211-220.

Walley et al., "The Central Role of Proprotein Convertase Subtilisin/Kexin Type 9 in Septic Pathogen Lipid Transport and Clearance", American Journal of Respiratory and Critical Care Medicine, 2015, 192(11), pp. 1275-1286.

* cited by examiner

Meta-Analysis of PCSK9 p.R46L and 28-day Mortality due to Severe Sepsis

| STUDY | N CASES RR\|RA\|AA | N CONTROLS RR\|RA\|AA | OR [95% CI] | PVALUE | AAF |
|---|---|---|---|---|---|
| GHS145K | 626\|13\|0 | 2023\|71\|1 | 0.637 [0.378,1.073] | 0.09 | 0.015 |
| UKB500K | 435\|22\|0 | 1094\|41\|0 | 1.315 [0.751,2.303] | 0.338 | 0.02 |
| Vanderbilt | 354\|11\|0 | 2929\|95\|1 | 0.734 [0.357,1.508] | 0.4 | 0.016 |
| HUNT | 754\|14\|0 | 2332\|67\|0 | 0.624 [0.366,1.063] | 0.083 | 0.013 |
| Copenhagen | 183\|7\|0 | 206\|10\|0 | 0.734 [0.273,1.98] | 0.542 | 0.02 |
| Estonia | 296\|11\|0 | 974\|36\|0 | 0.934 [0.447,1.954] | 0.857 | 0.018 |
| GEN-SEP | 147\|7\|0 | 268\|8\|0 | 2.092 [0.791,5.529] | 0.137 | 0.015 |
| SPH | 165\|4\|0 | 217\|8\|0 | 0.642 [0.183,2.255] | 0.489 | 0.015 |
| VASST | 177\|2\|0 | 344\|7\|0 | 0.568 [0.115,2.815] | 0.488 | 0.008 |
| **META** | **3137\|91\|0** | **10387\|343\|2** | **0.83 [0.653,1.057]** | **0.131** | |

TREATMENT OF SEPSIS WITH PCSK9 AND LDLR MODULATORS

REFERENCE TO SEQUENCE LISTING

This application includes a Sequence Listing submitted electronically as a text file named 18923805301SEQ, created on Aug. 24, 2021, with a size of 340 kilobytes. The Sequence Listing is incorporated herein by reference.

FIELD

The present disclosure relates generally to the treatment of subjects having sepsis, systemic inflammatory response syndrome (SIRS), septic shock, and/or multiple organ dysfunction syndrome (MODS) with a Proprotein Convertase Subtilisin/Kexin Type 9 (PCSK9) inhibitor and/or a Low Density Lipoprotein Receptor (LDLR) agonist, methods of identifying subjects having an increased risk of developing sepsis, SIRS, septic shock, and/or MODS, and methods of detecting PCSK9 and/or LDLR variant nucleic acid molecules and variant polypeptides.

BACKGROUND

Sepsis is a systemic inflammatory response to infection that can lead to organ failure and death. The annual incidence of sepsis is greater than 48 million cases responsible for about 20% of deaths worldwide (Rudd et al., Lancet, 2020, 395, 200-2011). Bacterial cell wall components, including lipopolysaccharide (LPS) and lipoteichoic acid (LTA) for gram-negative bacteria and gram-positive bacteria, respectively, are key mediators of sepsis and septic shock. In healthy individuals, LPS/LTA are incorporated into lipoprotein particles, including LDL and HDL, and are cleared from the plasma via the LDL receptor (LDLR) in hepatocytes as a primary step in sequestering pathogen toxins from circulation. In general, sepsis is two or more systemic inflammatory response criteria plus a known or suspected infection. Severe sepsis is sepsis with acute organ dysfunction. Sepsis can progress to severe sepsis when, in addition to signs of sepsis, there are signs of organ dysfunction, such as difficulty breathing (problems with the lungs), low or no urine output (kidneys), abnormal liver tests (liver), and changes in mental status (brain). Nearly all patients with severe sepsis require treatment in an intensive care unit (ICU). Septic shock is the most severe level and is diagnosed when a subject's blood pressure drops to dangerous levels.

Systemic inflammatory response syndrome (SIRS) is an exaggerated defense response of the body to a noxious stressor (infection, trauma, surgery, acute inflammation, ischemia or reperfusion, or malignancy to name a few) to localize and then eliminate the endogenous or exogenous source of the insult. It involves the release of acute-phase reactants which are direct mediators of widespread autonomic, endocrine, hematological and immunological alteration in a subject. The dysregulated cytokine storm has the potential to cause massive inflammatory cascade leading to reversible or irreversible end-organ dysfunction and death.

During sepsis, systemic hypotension, disturbed perfusion of the microcirculation, and direct tissue-toxicity caused by inflammatory immune reaction can occur and contribute to organ failure. The failure of two or more vital organ systems is termed multi-organ dysfunction syndrome (MODS) and resembles a very critical condition associated with high morbidity and mortality. Importantly, no specific treatment strategy exists to efficiently prevent the development of MODS during sepsis.

Proprotein convertase subtilisin/kexin type 9 is an enzyme (encoded by PCSK9) that binds LDLR and prevents recycling of LDLR to the cell surface. It has been observed that the addition of exogenous PCSK9 protein reduced LPS/LTA uptake into cells in vitro (Boyd, Inn.

Immunol., 2016; Grin, Sci. Rep., 2018; and Leung, Sci. Rep., 2019)

SUMMARY

The present disclosure provides methods of treating a subject having sepsis or severe sepsis, the method comprising administering a PCSK9 inhibitor and/or an LDLR agonist to the subject in need thereof.

The present disclosure also provides methods of treating a subject having SIRS, the method comprising administering aPCSK9 inhibitor and/or an LDLR agonist to the subject in need thereof.

The present disclosure also provides methods of treating a subject having septic shock, the method comprising administering a PCSK9 inhibitor and/or an LDLR agonist to the subject in need thereof.

The present disclosure also provides methods of treating a subject having MODS, the method comprising administering a PCSK9 inhibitor and/or an LDLR agonist to the subject in need thereof.

The present disclosure also provides methods of treating a subject with a therapeutic agent that treats or inhibits sepsis, SIRS, septic shock, and/or MODS, wherein the subject is suffering from sepsis, SIRS, septic shock, and/or MODS, the method comprising the steps of: determining whether the subject has: i) a PCSK9 variant nucleic acid molecule encoding a PCSL9 predicted loss-of-function polypeptide; and/or ii) an LDLR variant nucleic acid molecule encoding an LDLR predicted loss-of-function polypeptide; by: obtaining or having obtained a biological sample from the subject; and performing or having performed a sequence analysis on the biological sample to determine if the subject has a genotype comprising: i) the PCSK9 variant nucleic acid molecule; and/or ii) the LDLR variant nucleic acid molecule; and when the subject is PCSK9 reference and LDLR reference, then also administering or continuing to administer to the subject the therapeutic agent that treats or inhibits sepsis, SIRS, septic shock, and/or MODS in a standard dosage amount, and administering to the subject a PCSK9 inhibitor and/or an LDLR agonist; when the subject is LDLR reference and heterozygous for the PCSK9 variant nucleic acid molecule, then also administering or continuing to administer to the subject the therapeutic agent that treats or inhibits sepsis, SIRS, septic shock, and/or MODS in an amount that is the same as or less than a standard dosage amount, and administering to the subject a PCSK9 inhibitor and/or an LDLR agonist; when the subject is PCSK9 reference and heterozygous for the LDLR variant nucleic acid molecule, then also administering or continuing to administer to the subject the therapeutic agent that treats or inhibits sepsis, SIRS, septic shock, and/or MODS in an amount that is the same as or less than a standard dosage amount, and administering to the subject a PCSK9 inhibitor and/or an LDLR agonist; when the subject is LDLR reference and homozygous for the PCSK9 variant nucleic acid molecule, then also administering or continuing to administer to the subject the therapeutic agent that treats or inhibits sepsis, SIRS, septic shock, and/or MODS in an amount that is the same as or less than a standard dosage amount, and administering to the subject an LDLR agonist; when the subject is PCSK9 reference and homozygous for the LDLR variant nucleic acid molecule, then also administering or continuing to administer to the subject the therapeutic agent that treats or inhibits sepsis, SIRS, septic shock, and/or MODS in an amount that is the same as or less than a standard dosage amount, and administering to the subject a PCSK9 inhibitor; when the subject is heterozygous for both the PCSK9 variant nucleic acid molecule and the LDLR variant nucleic acid molecule, then also administering or continuing to administer to the subject the therapeutic agent that treats or inhibits sepsis, SIRS, septic shock, and/or MODS in an amount that is the same as or less than a standard dosage amount, and administering to the subject a PCSK9 inhibitor and/or an LDLR agonist; and when the subject is homozygous for both the PCSK9 variant nucleic acid molecule and the LDLR variant nucleic acid molecule, the subject is also administered the therapeutic agent that treats or inhibits sepsis, SIRS, septic shock, and/or MODS in a dosage amount that is the same as or less than a standard dosage amount; wherein the presence of a genotype having both the PCSK9 variant nucleic acid molecule encoding a PCSL9 predicted loss-of-function polypeptide, and the LDLR variant nucleic acid molecule encoding an LDLR predicted loss-of-function polypeptide indicates the subject has a decreased risk of developing sepsis, SIRS, septic shock, and/or MODS.

The present disclosure also provides methods of identifying a subject having a risk of developing sepsis, SIRS, septic shock, and/or MODS, the method comprising: determining or having determined the presence or absence of a PCSK9 variant nucleic acid molecule encoding a PCSL9 predicted loss-of-function polypeptide, and/or an LDLR variant nucleic acid molecule encoding an LDLR predicted loss-of-function polypeptide in a biological sample obtained from the subject; wherein when the subject is PCSK9 reference and LDLR reference, the subject has an increased risk of developing sepsis, SIRS, septic shock, and/or MODS; and when the subject is heterozygous or homozygous for an LDLR variant nucleic acid molecule, and/or heterozygous or homozygous for a PCSK9 variant nucleic acid molecule, the subject has a decreased risk of developing sepsis, SIRS, septic shock, and/or MODS.

The present disclosure also provides methods of detecting a PCSK9 variant nucleic acid molecule in a subject comprising assaying a sample obtained from the subject to determine whether a nucleic acid molecule in the sample is: a genomic nucleic acid molecule comprising a nucleotide sequence comprising a thymine at a position corresponding to position 427 according to SEQ ID NO:2, or the complement thereof; an mRNA molecule having a nucleotide sequence comprising a uracil at a position corresponding to: position 428 according to SEQ ID NO:17, or the complement thereof; position 217 according to SEQ ID NO:18, or the complement thereof; or position 137 according to SEQ ID NO:19, or the complement thereof; or a cDNA molecule produced from an mRNA molecule, wherein the cDNA molecule has a nucleotide sequence comprising a thymine at a position corresponding to: position 428 according to SEQ ID NO:32, or the complement thereof; position 217 according to SEQ ID NO:33, or the complement thereof; or position 137 according to SEQ ID NO:34, or the complement thereof.

The present disclosure also provides methods of detecting an LDLR variant nucleic acid molecule in a subject comprising assaying a sample obtained from the subject to determine whether a nucleic acid molecule in the sample is a genomic nucleic acid molecule comprising a nucleotide sequence comprising a thymine at a position corresponding to position 2,269 according to SEQ ID NO:4, or the complement thereof.

The present disclosure also provides methods of detecting the presence of a PCSK9 Arg46Leu polypeptide, comprising performing an assay on a sample obtained from a subject to determine whether a PCSK9 protein in the sample comprises a leucine at a position corresponding to position 46 according to SEQ ID NO:42.

The present disclosure also provides therapeutic agents that treat or inhibit sepsis, systemic inflammatory response syndrome (SIRS), septic shock, and/or multiple organ dysfunction syndrome (MODS), for use in the treatment of sepsis, SIRS, septic shock, and/or MODS in a subject having: a genomic nucleic acid molecule having a nucleotide sequence encoding a Proprotein Convertase Subtilisin/Kexin Type 9 (PCSK9) polypeptide, wherein the nucleotide sequence comprises a thymine at a position corresponding to position 427 according to SEQ ID NO:2, or the complement thereof; and/or a genomic nucleic acid molecule having a nucleotide sequence encoding a Low Density Lipoprotein Receptor (LDLR) polypeptide, wherein the nucleotide sequence comprises a thymine at a position corresponding to position 2,269 according to SEQ ID NO:4, or the complement thereof; an mRNA molecule having a nucleotide sequence encoding a PCSK9 polypeptide, wherein the nucleotide sequence comprises a uracil at a position corresponding to: position 428 according to SEQ ID NO:17, or the complement thereof; position 217 according to SEQ ID NO:18, or the complement thereof; or position 137 according to SEQ ID NO:19, or the complement thereof; or a cDNA molecule having a nucleotide sequence encoding a PCSK9 polypeptide, wherein the nucleotide sequence comprises a thymine at a position corresponding to: position 428 according to SEQ ID NO:32, or the complement thereof; position 217 according to SEQ ID NO:33, or the complement thereof; or position 137 according to SEQ ID NO:34, or the complement thereof.

The present disclosure also provides Proprotein Convertase Subtilisin/Kexin Type 9 (PCSK9) inhibitors and/or Low Density Lipoprotein Receptor (LDLR) agonists for use in the treatment of sepsis, systemic inflammatory response syndrome (SIRS), septic shock, and/or multiple organ dysfunction syndrome (MODS), in a subject that: a) is reference for a PCSK9 and/or an LDLR genomic nucleic acid molecule, a PCSK9 and/or an LDLR mRNA molecule, or a PCSK9 and/or an LDLR cDNA molecule; or b) is heterozygous for: i) a genomic nucleic acid molecule having a nucleotide sequence encoding a PCSK9 polypeptide, wherein the nucleotide sequence comprises a thymine at a position corresponding to position 427 according to SEQ ID NO:2; and/or ii) a genomic nucleic acid molecule having a nucleotide sequence encoding an LDLR polypeptide, wherein the nucleotide sequence comprises a thymine at a position corresponding to position 2,269 according to SEQ ID NO:4; an mRNA molecule having a nucleotide sequence encoding a PCSK9 polypeptide, wherein the nucleotide sequence comprises a uracil at a position corresponding to: position 428 according to SEQ ID NO:17, or the complement thereof; position 217 according to SEQ ID NO:18, or the complement thereof; or position 137 according to SEQ ID NO:19, or the complement thereof; or a cDNA molecule having a nucleotide sequence encoding a PCSK9 polypeptide, wherein the nucleotide sequence comprises a thymine at a position corresponding to: position 428 according to SEQ ID NO:32, or the complement thereof; position 217 according to SEQ ID NO:33, or the complement thereof; or position 137 according to SEQ ID NO:34, or the complement thereof.

BRIEF DESCRIPTION OF THE DRAWINGS

The accompanying figures, which are incorporated in and constitute a part of this specification, illustrate several features of the present disclosure.

DESCRIPTION

Figure 1:
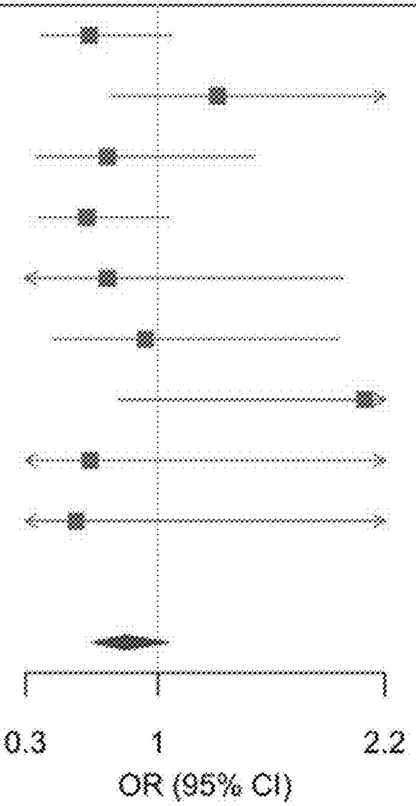
FIG. 1 shows summary data of a meta-analysis of PCSK9 p.R46L and 28-day mortality across all tested cohorts with severe sepsis.

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by +10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or alternatively phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician.

Rare variants in the PCSK9 and LDLR genes associated with a decreased risk of developing sepsis, SIRS, septic shock, and/or MODS in subjects has been identified in accordance with the present disclosure. For example, a genetic alteration that changes the guanine nucleotide of position 427 in the human PCSK9 reference (see, SEQ ID NO:1) to a thymine and/or a genetic alteration that changes the guanine nucleotide of position 2,269 in the human LDLR reference (see, SEQ ID NO:3) to a thymine has been observed to indicate that the human having such alterations may have a decreased risk of developing sepsis, severe sepsis, SIRS, septic shock, and/or MODS. It is believed that no such variants of the PCSK9 and LDLR genes have any known association with sepsis, severe sepsis, SIRS, septic shock, and/or MODS. Altogether, the genetic analyses described herein surprisingly indicate that the PCSK9 gene and LDLR gene and, in particular, a variant in the PCSK9 gene and LDLR gene, associates with a decreased risk of developing sepsis, severe sepsis, SIRS, septic shock, and/or MODS. Therefore, subjects that are PCSK9 and/or LDLR reference that have an increased risk of developing sepsis, SIRS, septic shock, and/or MODS, may be treated such that sepsis, severe sepsis, SIRS, septic shock, and/or MODS is prevented, the symptoms thereof are reduced, and/or development of symptoms is repressed. Accordingly, the present disclosure provides methods of leveraging the identification of such variants in subjects to identify or stratify risk in such subjects of developing sepsis, severe sepsis, SIRS, septic shock, and/or MODS, or to diagnose subjects as having an increased risk of developing sepsis, severe sepsis, SIRS, septic shock, and/or MODS, such that subjects at risk or subjects with active disease may be treated accordingly.

For purposes of the present disclosure, any particular subject can be categorized as having any one of the following PCSK9 and LDLR genotypes: i) PCSK9 reference and LDLR reference; ii) heterozygous or homozygous for a PCSK9 variant nucleic acid molecule encoding a PCSK9 predicted loss-of-function polypeptide and LDLR reference; iii) heterozygous or homozygous for an LDLR variant nucleic acid molecule encoding an LDLR predicted loss-of-function polypeptide and a PCSK9 reference; or iii) heterozygous or homozygous for both a PCSK9 variant nucleic acid molecule encoding a PCSK9 predicted loss-of-function polypeptide and an LDLR variant nucleic acid molecule encoding an LDLR predicted loss-of-function polypeptide. A subject is a PCSK9 and/or an LDLR reference when the subject does not have a copy of a PCSK9 and/or an LDLR variant nucleic acid molecule. A subject is heterozygous for a PCSK9 and/or an LDLR variant nucleic acid molecule when the subject has a single copy of a PCSK9 and/or an LDLR variant nucleic acid molecule. As used herein, a PCSK9 and/or an LDLR variant nucleic acid molecule is any PCSK9 and/or any LDLR nucleic acid molecule (such as, a genomic nucleic acid molecule, an mRNA molecule, or a cDNA molecule) having a genetic variation described herein, encoding a polypeptide having a partial loss-of-function, a complete loss-of-function, a predicted partial loss-of-function, or a predicted complete loss-of-function. A subject who has a PCSK9 polypeptide having a partial loss-of-function (or predicted partial loss-of-function) is hypomorphic for a PCSK9. The PCSK9 variant nucleic acid molecule can be any nucleic acid molecule encoding a PCSK9 Arg46Leu polypeptide. A subject is homozygous for a PCSK9 and/or an LDLR variant nucleic acid molecule when the subject has two copies of a PCSK9 and/or an LDLR variant nucleic acid molecule.

For subjects that are genotyped or determined to be PCSK9 reference and LDLR reference, such subjects have an increased risk of developing sepsis, severe sepsis, SIRS, septic shock, and/or MODS. For subjects that are genotyped or determined to be heterozygous for a PCSK9 variant nucleic acid molecule and/or heterozygous for an LDLR variant nucleic acid molecule, such subjects can be treated with a PCSK9 inhibitor and/or an agent that reduces LDL, such as an LDLR agonist.

In any of the embodiments described herein, the PCSK9 variant nucleic acid molecule and/or the LDLR variant nucleic acid molecule can be any PCSK9 nucleic acid molecule and/or any LDLR nucleic acid molecule (such as, for example, genomic nucleic acid molecule, mRNA molecule, or cDNA molecule) encoding a polypeptide having a partial loss-of-function, a complete loss-of-function, a predicted partial loss-of-function, or a predicted complete loss-of-function. For example, the PCSK9 variant nucleic acid molecule can be any nucleic acid molecule encoding a PCSK9 Arg46Leu polypeptide.

In any of the embodiments described herein, the PCSK9 predicted loss-of-function polypeptide can be any PCSK9 polypeptide having a partial loss-of-function, a complete loss-of-function, a predicted partial loss-of-function, or a predicted complete loss-of-function. In any of the embodiments described herein, the PCSK9 predicted loss-of-function polypeptide can be any of the PCSK9 polypeptides described herein including, for example, a PCSK9 Arg46Leu polypeptide.

In any of the embodiments described herein, the subject can have sepsis, severe sepsis, SIRS, septic shock, and/or MODS. In any of the embodiments described herein, the subject can have sepsis. In any of the embodiments described herein, the subject can have severe sepsis. In any of the embodiments described herein, the subject can have SIRS. In any of the embodiments described herein, the subject can have septic shock. In any of the embodiments described herein, the subject can have MODS.

Symptoms of sepsis include, but are not limited to, fever, diarrhea, a decrease in blood pressure, leaky blood vessels, and/or disseminated blood clotting in a variety of organs. The underlying dysfunctions include, but are not limited to, arterial hypotension, metabolic acidosis, decreased systemic vascular resistance, tachypnea, organ dysfunction, and septicemia.

Symptoms of SIRS include, but are not limited to, any two or more of the following conditions: 1) body temperature >38° C. or <36° C.; 2) heart rate >90 beats/minute; 3) frequency of respiration >20 breaths/minute or $PaCO_2$<32 mmHg; and 4) number of leukocytes >12,000/μl or <4000/μl, or ratio of stab neutrophil >10%.

Symptoms of septic shock include, but are not limited to, a decrease in blood pressure to dangerous levels in a subject having sepsis.

Symptoms of MODS include, but are not limited to, failure of two or more vital organ systems.

The present disclosure provides methods of treating a subject having sepsis, SIRS, septic shock, and/or MODS, the methods comprising administering a PCSK9 inhibitor and/or an LDLR agonist to the subject.

The present disclosure also provides methods of treating a subject having sepsis, the methods comprising administering a PCSK9 inhibitor and/or an LDLR agonist to the subject.

The present disclosure also provides methods of treating a subject having SIRS, the methods comprising administering a PCSK9 inhibitor and/or an LDLR agonist to the subject. The present disclosure also provides methods of treating a subject having septic shock, the methods comprising administering a PCSK9 inhibitor and/or an LDLR agonist to the subject.

The present disclosure also provides methods of treating a subject having MODS, the methods comprising administering a PCSK9 inhibitor and/or an LDLR agonist to the subject.

In some embodiments, the PCSK9 inhibitor and/or LDLR agonist comprise an inhibitory nucleic acid molecule. Examples of inhibitory nucleic acid molecules include, but are not limited to, antisense nucleic acid molecules, small interfering RNAs (siRNAs), and short hairpin RNAs (shRNAs). Such antisense molecules can be designed to target any region of a PCSK9 and/or an LDLR nucleic acid molecule, such as an mRNA molecule. In some embodiments, the antisense molecule, siRNA, or shRNA hybridizes to a sequence within a PCSK9 and/or an LDLR genomic nucleic acid molecule or mRNA molecule and decreases expression of the PCSK9 and/or LDLR polypeptide in a cell in the subject. In some embodiments, the PCSK9 inhibitor and/or LDLR agonist comprise an antisense molecule that hybridizes to a PCSK9 and/or an LDLR genomic nucleic acid molecule or mRNA molecule and decreases expression of the PCSK9 and/or LDLR polypeptide in a cell in the subject. In some embodiments, the PCSK9 inhibitor and/or LDLR agonist comprise an siRNA that hybridizes to a PCSK9 and/or an LDLR genomic nucleic acid molecule or mRNA molecule and decreases expression of the PCSK9 and/or LDLR polypeptide in a cell in the subject. In some embodiments, the PCSK9 inhibitor and/or LDLR agonist comprise an shRNA that hybridizes to a PCSK9 and/or an LDLR genomic nucleic acid molecule or mRNA molecule and decreases expression of the PCSK9 and/or LDLR polypeptide in a cell in the subject.

In some embodiments, the PCSK9 inhibitor and/or LDLR agonist comprise a nuclease agent that induces one or more nicks or double-strand breaks at a recognition sequence(s) or a DNA-binding protein that binds to a recognition sequence within a PCSK9 genomic nucleic acid molecule and/or an LDLR genomic nucleic acid molecule. The recognition sequence can be located within a coding region of the PCSK9 gene and/or LDLR gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the PCSK9 gene and/or LDLR gene. For example, the recognition sequence can be located about 10, about 20, about 30, about 40, about 50, about 100, about 200, about 300, about 400, about 500, or about 1,000 nucleotides from the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair, about 15-18 bp for each ZFN, about 36 bp for a TALE protein or TALEN, and about 20 bp for a CRISPR/Cas guide RNA.

In some embodiments, CRISPR/Cas systems can be used to modify a PCSK9 genomic nucleic acid molecule and/or an LDLR genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of PCSK9 nucleic acid molecules and/or LDLR nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in a PCSK9 genomic nucleic acid molecule and/or an LDLR genomic nucleic acid molecule or it can be a nickase that creates a single-strand break in a PCSK9 genomic nucleic acid molecule and/or an LDLR genomic nucleic acid molecule. Additional examples of Cas proteins include, but are not limited to, Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of the PCSK9 genomic nucleic acid molecule and/or the LDLR genomic nucleic acid molecule can be generated by contacting a cell with a Cas protein and one or more gRNAs that hybridize to one or more gRNA recognition sequences within a target genomic locus in the PCSK9 genomic nucleic acid molecule and/or the LDLR genomic nucleic acid molecule. For example, a gRNA recognition sequence can be located within a region of SEQ ID NO:1 and/or SEQ ID NO:3. The gRNA recognition sequence can also include or be proximate to a position corresponding to: position 427 according to SEQ ID NO:1, or position 2,269 according to SEQ ID NO:3. For example, the gRNA recognition sequence can be located from about 1000, from about 500, from about 400, from about 300, from about 200, from about 100, from about 50, from about 45, from about 40, from about 35, from about 30, from about 25, from about 20, from about 15, from about 10, or from about 5 nucleotides of a position corresponding to: position 427 according to SEQ ID NO:1, or position 2,269 according to SEQ ID NO:3. The gRNA recognition sequence can include or be proximate to the start codon of the PCSK9 genomic nucleic acid molecule and/or the LDLR genomic nucleic acid molecule or the stop codon of the PCSK9 genomic nucleic acid molecule and/or the LDLR genomic nucleic acid molecule. For example, the gRNA recognition sequence can be located from about 10, from about 20, from about 30, from about 40, from about 50, from about 100, from about 200, from about 300, from about 400, from about 500, or from about 1,000 nucleotides of the start codon or the stop codon.

The gRNA recognition sequences within a target genomic locus in the PCSK9 genomic nucleic acid molecule and/or the LDLR genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within the PCSK9 genomic nucleic acid molecule and/or the LDLR genomic nucleic acid molecule. An exemplary gRNA is a gRNA effective to direct a Cas enzyme to bind to or cleave the PCSK9 genomic nucleic acid molecule and/or the LDLR genomic nucleic acid molecule, wherein the gRNA comprises a DNA-targeting segment that hybridizes to a gRNA recognition sequence within the PCSK9 genomic nucleic acid molecule and/or the LDLR genomic nucleic acid molecule that includes or is proximate to a position corresponding to: position 427 according to SEQ ID NO:1, or position 2,269 according to SEQ ID NO:3. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of a position corresponding to: position 427 according to SEQ ID NO:1, or position 2,269 according to SEQ ID NO:3. Other exemplary gRNAs comprise a DNA-targeting segment that hybridizes to a gRNA recognition sequence present within the PCSK9 genomic nucleic acid molecule and/or the LDLR genomic nucleic acid molecule that includes or is proximate to the start codon or the stop codon. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the start codon or located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the PCSK9 reference gene are set forth in Table 1 as SEQ ID NOS: 43-68. Examples of suitable gRNA recognition sequences located within the LDLR reference gene are set forth in Table 1 as SEQ ID NOS: 69-89.

TABLE 1

Guide RNA Recognition Sequences Near the PCSK9 and/or LDLR Variation(s)

| Strand | PCSK9 gRNA Recognition Sequence | SEQ ID NO: |
|---|---|---|
| − | CCCGGTCCTTGGCGCGCGGT | 43 |
| + | AGGACGAGGACGGCGACACG | 44 |
| − | CCGTGCTCGGGTGCTTCGGC | 45 |
| − | CCGGTCCTTGGCGCGCGGTG | 46 |
| − | CTTCGGCCGGCCGTCCTCCT | 47 |
| + | AGCCACCCCACCGCGCGCCA | 48 |
| − | GGTTCCGTGCTCGGGTGCTT | 49 |
| − | TCCCGGTCCTTGGCGCGCGG | 50 |
| + | GAGGACGGCGACACGAGGAG | 51 |
| + | ACCGCGCGCCAAGGACCGGG | 52 |
| + | CCGCGCGCCAAGGACCGGGA | 53 |
| + | CCCACCGCGCGCCAAGGACC | 54 |
| − | GCCGGCCGTCCTCCTCGGCG | 55 |
| − | GGTGGCTGTGGTTCCGTGCT | 56 |
| − | CCCTCCCGGTCCTTGGCGCG | 57 |
| + | AGGACGGCGACACGAGGAGC | 58 |
| + | ACCGGGAGGGCCGGCACCAC | 59 |
| − | GTGGCTGTGGTTCCGTGCTC | 60 |
| + | CCCCACCGCGCGCCAAGGAC | 61 |
| − | GTGCCGGCCCTCCCGGTCCT | 62 |
| + | AGGAGCGGGCAGCCGCGCCG | 63 |
| + | CGGGAGGGCCGGCACCACGG | 64 |
| + | AGCGGGCAGCCGCGCCGAGG | 65 |
| + | CCGGGAGGGCCGGCACCACG | 66 |
| + | GACCGGGAGGGCCGGCACCA | 67 |
| − | GTCCTTGGCGCGCGGTGGGG | 68 |
| Strand | LDLR gRNA Recognition Sequence | SEQ ID NO: |
| − | GTCATAGGAAGAGACGCCGT | 69 |
| + | CGGATACCAAGGGCGTGAAG | 70 |
| − | TGTCATAGGAAGAGACGCCG | 71 |
| + | CGTGGTCGCTCTGGACACGG | 72 |
| + | TGTCTCTGTTGCGGATACCA | 73 |
| − | GTCCACAGCCAGCCCGTCGG | 74 |
| − | AGACCAGTAGATTCTATTGC | 75 |
| − | CGGTCCAGTAGATGTTGCTG | 76 |
| − | CGCCGTGGGCTCTGTCAAGC | 77 |
| + | GAACGTGGTCGCTCTGGACA | 78 |
| + | CTACTGGACCGACTCTGTCC | 79 |
| + | AGAGACATCCAGGCCCCCGA | 80 |
| − | TCTGCTGATGACGGTGTCAT | 81 |
| + | GAGACATCCAGGCCCCCGAC | 82 |
| − | GCCGTGGGCTCTGTCAAGCT | 83 |
| + | GTCTCTGTTGCGGATACCAA | 84 |
| + | GGTCGCTCTGGACACGGAGG | 85 |
| + | TGGCCAGCAATAGAATCTAC | 86 |

TABLE 1-continued

| Guide RNA Recognition Sequences Near the PCSK9 and/or LDLR Variation(s) | | |
|---|---|---|
| + | CATCCAGGCCCCCGACGGGC | 87 |
| - | GGGTGCTGCAGATCATTCTC | 88 |
| + | TACTGGACCGACTCTGTCCT | 89 |

The Cas protein and the gRNA form a complex, and the Cas protein cleaves the target PCSK9 genomic nucleic acid molecule and/or target LDLR genomic nucleic acid molecule. The Cas protein can cleave the nucleic acid molecule at a site within or outside of the nucleic acid sequence present in the target PCSK9 genomic nucleic acid molecule and/or LDLR genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the PCSK9 genomic nucleic acid molecule and/or LDLR genomic nucleic acid molecule to which a DNA-targeting segment of a gRNA will bind.

Such methods can result, for example, in a PCSK9 genomic nucleic acid molecule and/or an LDLR genomic nucleic acid molecule in which a region of SEQ ID NO:1 or SEQ ID NO:3, respectively, is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the PCSK9 genomic nucleic acid molecule and/or the LDLR genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the PCSK9 inhibitor comprises a small molecule or an antibody. In some embodiments, the PCSK9 inhibitor is alirocumab or evolocumab, or a combination thereof. In some embodiments, the PCSK9 inhibitor is the monoclonal antibody SAR236553/REGN727 or AMG145, or a combination thereof. In some embodiments, the PCSK9 inhibitor is lupin peptide, resveratrol, lycopene, or eugenol, or any combination thereof.

In some embodiments, the LDLR agonist comprises a small molecule or an antibody. In some embodiments, the LDLR agonist is one of the PCSK9 inhibitors described herein. In some embodiments, the LDLR agonist is lupin peptide, resveratrol, lycopene, suramin, or puromycin, or any combination thereof.

In some embodiments, the methods of treatment further comprise detecting the presence or absence of a PCSK9 variant nucleic acid molecule and/or an LDLR variant nucleic acid molecule in a biological sample from the subject. As used throughout the present disclosure, a "PCSK9 variant nucleic acid molecule" is any PCSK9 nucleic acid molecule (such as, for example, genomic nucleic acid molecule, mRNA molecule, or cDNA molecule) encoding a PCSK9 polypeptide having a partial loss-of-function, a complete loss-of-function, a predicted partial loss-of-function, or a predicted complete loss-of-function.

The present disclosure also provides methods of treating a subject with a therapeutic agent that treats or inhibits sepsis, SIRS, septic shock, and/or MODS. In some embodiments, the subject is suffering from sepsis, SIRS, septic shock, and/or MODS. In some embodiments, the subject is suffering from sepsis. In some embodiments, the subject is suffering from SIRS. In some embodiments, the subject is suffering from septic shock. In some embodiments, the subject is suffering from MODS. In some embodiments, the methods comprise determining whether the subject has a PCSK9 variant nucleic acid molecule and/or an LDLR variant nucleic acid molecule by obtaining or having obtained a biological sample from the subject, and performing or having performed a sequence analysis on the biological sample to determine if the subject has a genotype comprising the PCSK9 variant nucleic acid molecule and/or the LDLR variant nucleic acid molecule.

In some embodiments, when the subject is PCSK9 reference and LDLR reference, the therapeutic agent that treats or inhibits sepsis, SIRS, septic shock, and/or MODS is administered or continued to be administered to the subject in a standard dosage amount, and a PCSK9 inhibitor and/or the LDLR agonist is administered to the subject.

In some embodiments, when the subject is LDLR reference and heterozygous for a PCSK9 variant nucleic acid molecule, the therapeutic agent that treats or inhibits sepsis, SIRS, septic shock, and/or MODS is administered or continued to be administered in an amount that is the same as or less than a standard dosage amount, and the PCSK9 inhibitor and/or the LDLR agonist is administered to the subject.

In some embodiments, when the subject is PCSK9 reference and heterozygous for an LDLR variant nucleic acid molecule, the therapeutic agent that treats or inhibits sepsis, SIRS, septic shock, and/or MODS is administered or continued to be administered in an amount that is the same as or less than a standard dosage amount, and the PCSK9 inhibitor and/or the LDLR agonist is administered to the subject.

In some embodiments, when the subject is LDLR reference and homozygous for a PCSK9 variant nucleic acid molecule, the therapeutic agent that treats or inhibits sepsis, SIRS, septic shock, and/or MODS is administered or continued to be administered in an amount that is the same as or less than a standard dosage amount, and an LDLR agonist is administered to the subject.

In some embodiments, when the subject is PCSK9 reference and homozygous for an LDLR variant nucleic acid molecule, the therapeutic agent that treats or inhibits sepsis, SIRS, septic shock, and/or MODS is administered or continued to be administered in an amount that is the same as or less than a standard dosage amount, and a PCSK9 inhibitor is administered to the subject.

In some embodiments, when the subject is heterozygous for both a PCSK9 variant nucleic acid molecule and an LDLR variant nucleic acid molecule, the therapeutic agent that treats or inhibits sepsis, SIRS, septic shock, and/or MODS is administered or continued to be administered in an amount that is the same as or less than a standard dosage amount, and the PCSK9 inhibitor and/or the LDLR agonist is administered to the subject.

In some embodiments, when the subject is homozygous for both a PCSK9 variant nucleic acid molecule and an LDLR variant nucleic acid molecule, the therapeutic agent that treats or inhibits sepsis, SIRS, septic shock, and/or MODS is administered or continued to be administered in a dosage amount that is the same as or less than a standard dosage amount.

The presence of a genotype having the PCSK9 variant nucleic acid molecule and/or the LDLR variant nucleic acid molecule indicates the subject has a decreased risk of developing sepsis, SIRS, septic shock, and/or MODS. In some embodiments, the subject is PCSK9 reference and LDLR reference. In some embodiments, the subject is heterozygous or homozygous for a PCSK9 variant nucleic acid molecule and LDLR reference. In some embodiments, the subject is heterozygous or homozygous for an LDLR variant nucleic acid molecule and PCSK9 reference. In some embodiments, the subject is heterozygous or homozygous for an LDLR variant nucleic acid molecule and PCSK9 heterozygous or homozygous for a PCSK9 variant nucleic acid molecule.

Detecting the presence or absence of a PCSK9 variant nucleic acid molecule and/or an LDLR variant nucleic acid molecule in a biological sample from a subject and/or determining whether a subject has a PCSK9 variant nucleic acid molecule and/or an LDLR variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when the subject is PCSK9 reference and/or LDLR reference, the subject is also administered a therapeutic agent that treats or inhibits sepsis, SIRS, septic shock, and/or MODS in a standard dosage amount. In some embodiments, when the subject is heterozygous or homozygous for a PCSK9 variant nucleic acid molecule and/or an LDLR variant nucleic acid molecule, the subject is also administered a therapeutic agent that treats or inhibits sepsis, SIRS, septic shock, and/or MODS in a dosage amount that is the same as or less than a standard dosage amount.

In some embodiments, the treatment methods further comprise detecting the presence or absence of a PCSK9 predicted loss-of-function polypeptide in a biological sample from the subject. In some embodiments, when the subject does not have a PCSK9 predicted loss-of-function polypeptide, the subject is also administered a therapeutic agent that treats or inhibits sepsis, SIRS, septic shock, and/or MODS in a standard dosage amount. In some embodiments, when the subject has a PCSK9 predicted loss-of-function polypeptide, the subject is also administered a therapeutic agent that treats or inhibits sepsis, SIRS, septic shock, and/or MODS in a dosage amount that is the same as or less than a standard dosage amount.

The present disclosure also provides methods of treating a subject with a therapeutic agent that treats or inhibits sepsis, SIRS, septic shock, and/or MODS. In some embodiments, the subject is suffering from sepsis, SIRS, septic shock, and/or MODS. In some embodiments, the subject is suffering from sepsis. In some embodiments, the subject is suffering from SIRS. In some embodiments, the subject is suffering from septic shock. In some embodiments, the subject is suffering from MODS. In some embodiments, the method comprises determining whether the subject has a PCSK9 predicted loss-of-function polypeptide by obtaining or having obtained a biological sample from the subject, and performing or having performed an assay on the biological sample to determine if the subject has a PCSK9 predicted loss-of-function polypeptide. When the subject does not have a PCSK9 predicted loss-of-function polypeptide, the therapeutic agent that treats or inhibits sepsis, SIRS, septic shock, and/or MODS is administered or continued to be administered to the subject in a standard dosage amount, and a PCSK9 inhibitor and/or an LDLR agonist is administered to the subject. When the subject has a PCSK9 predicted loss-of-function polypeptide, the therapeutic agent that treats or inhibits sepsis, SIRS, septic shock, and/or MODS is administered or continued to be administered to the subject in an amount that is the same as or less than a standard dosage amount, and a PCSK9 inhibitor and/or an LDLR agonist is administered to the subject. The presence of a PCSK9 predicted loss-of-function polypeptide indicates the subject has a decreased risk of developing sepsis, SIRS, septic shock, and/or MODS. In some embodiments, the subject has a PCSK9 predicted loss-of-function polypeptide. In some embodiments, the subject does not have a PCSK9 predicted loss-of-function polypeptide.

Detecting the presence or absence of a PCSK9 predicted loss-of-function polypeptide in a biological sample from a subject and/or determining whether a subject has a PCSK9 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

Examples of therapeutic agents and therapies that treat or inhibit sepsis, severe sepsis, SIRS, septic shock, and/or MODS can depend on the affected organ(s), the severity of the condition, the time of diagnosis, and underlying cause(s) (e.g. infection, trauma, etc.). Early treatment includes antibiotics and intravenous fluids, as well as high-flow oxygen. Treatment can also include administering red blood cells, vasopressors (e.g., norepinephrine in case of hypotensive septic shock), and, in some cases, steroids. Surgical interventions may be used to control the infection source (e.g., drainage of pus from an abscess). Further sepsis management includes monitoring organ function to identify the organs and systems affected. Additional therapies may then be implemented to specifically target the affected organs. In the case of particularly severe sepsis that results in MODS, therapy is usually mostly limited to supportive care (i.e., safeguarding hemodynamics), and respiration. In addition, several classes of therapeutics are used in sepsis management in the clinic, including recombinant activated protein C, TLR4 antagonists, C5a antagonists, C1 inhibitors, endotoxin removal devices, caspase inhibitors, Oestrogen receptor-β, and statins, among others (reviewed in Shukla et al., Br. J. Pharmacol., 2014, 171, 5011-5031).

In some embodiments, the dose of the therapeutic agents that treat or inhibit sepsis, SIRS, septic shock, and/or MODS can be reduced by about 10%, by about 20%, by about 30%, by about 40%, by about 50%, by about 60%, by about 70%, by about 80%, or by about 90% for subjects that are heterozygous for a PCSK9 variant nucleic acid molecule and/or an LDLR variant nucleic acid molecule (i.e., less than the standard dosage amount) compared to subjects that are PCSK9 reference and/or LDLR reference (who may receive a standard dosage amount). In some embodiments, the dose of the therapeutic agents that treat or inhibit sepsis, SIRS, septic shock, and/or MODS can be reduced by about 10%, by about 20%, by about 30%, by about 40%, or by about 50%. In addition, the dose of therapeutic agents that treat or inhibit sepsis, SIRS, septic shock, and/or MODS in subjects that are heterozygous for a PCSK9 variant nucleic acid molecule and/or an LDLR variant nucleic acid molecule can be administered less frequently compared to subjects that are PCSK9 reference and/or LDLR reference.

Administration of the therapeutic agents that treat or inhibit sepsis, SIRS, septic shock, and/or MODS and/or a PCSK9 inhibitor and/or an LDLR agonist can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit sepsis, SIRS, septic shock, and/or MODS and/or a PCSK9 inhibitor and/or an LDLR agonist can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in sepsis, SIRS, septic shock, and/or MODS (i.e., condition), a decrease/reduction in the severity of sepsis, SIRS, septic shock, and/or MODS (such as, for example, a reduction or inhibition of development or sepsis, SIRS, septic shock, and/or MODS), a decrease/reduction in symptoms and condition-related effects, delaying the onset of symptoms and condition-related effects, reducing the severity of symptoms of condition-related effects, reducing the severity of an acute episode, reducing the number of symptoms and condition-related effects, reducing the latency of symptoms and condition-related effects, an amelioration of symptoms and condition-related effects, reducing secondary symptoms, reducing secondary infections, preventing relapse to sepsis, SIRS, septic shock, and/or MODS, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of sepsis, SIRS, septic shock, and/or MODS development/progression (such as, for example, a complete or partial avoidance/inhibition or a delay), and an increased survival time of the affected host animal, following administration of a therapeutic protocol. Treatment of sepsis, SIRS, septic shock, and/or MODS encompasses the treatment of subjects already diagnosed as having any form of sepsis, SIRS, septic shock, and/or MODS at any clinical stage or manifestation, the delay of the onset or evolution or aggravation or deterioration of the symptoms or signs of sepsis, SIRS, septic shock, and/or MODS, and/or preventing and/or reducing the severity of sepsis, SIRS, septic shock, and/or MODS.

As used herein, the phrase "in need thereof" means that the "individual," "subject," or "patient" has been identified as having a need for the particular method, prevention, or treatment. In some embodiments, the identification can be by any means of diagnosis. In any of the methods, preventions, and treatments described herein, the "individual," "subject," or "patient" can be in need thereof.

The present disclosure also provides methods of identifying a subject having an increased risk of developing sepsis, SIRS, septic shock, and/or MODS. In some embodiments, the methods identify a subject having an increased risk of developing sepsis. In some embodiments, the methods identify a subject having an increased risk of developing SIRS. In some embodiments, the methods identify a subject having an increased risk of developing septic shock. In some embodiments, the methods identify a subject having an increased risk of developing MODS. In some embodiments, the methods comprise determining or having determined in a biological sample obtained from the subject the presence or absence of a PCSK9 variant nucleic acid molecule and/or an LDLR variant nucleic acid molecule (such as a genomic nucleic acid molecule, mRNA molecule, and/or cDNA molecule). When the subject lacks a PCSK9 variant nucleic acid molecule and an LDLR variant nucleic acid molecule (i.e., the subject is genotypically categorized as PCSK9 reference and LDLR reference), then the subject has an increased risk of developing sepsis, SIRS, septic shock, and/or MODS. When the subject has a PCSK9 variant nucleic acid molecule and/or an LDLR variant nucleic acid molecule (i.e., the subject is heterozygous or homozygous for a PCSK9 variant nucleic acid molecule and/or an LDLR variant nucleic acid molecule), then the subject has a decreased risk of developing sepsis, SIRS, septic shock, and/or MODS.

Having a single copy of a PCSK9 variant nucleic acid molecule and/or an LDLR variant nucleic acid molecule is more protective of a subject from developing sepsis, SIRS, septic shock, and/or MODS than having no copies of a PCSK9 variant nucleic acid molecule and/or an LDLR variant nucleic acid molecule. Without intending to be limited to any particular theory or mechanism of action, it is believed that a single copy of a PCSK9 variant nucleic acid molecule and/or an LDLR variant nucleic acid molecule (i.e., heterozygous for a PCSK9 variant nucleic acid molecule and/or an LDLR variant nucleic acid molecule) is protective of a subject from developing sepsis, SIRS, septic shock, and/or MODS, and it is also believed that having two copies of a PCSK9 variant nucleic acid molecule and/or an LDLR variant nucleic acid molecule (i.e., homozygous for a PCSK9 variant predicted loss-of-function and/or an LDLR variant predicted loss-of-function) may be more protective of a subject from developing sepsis, SIRS, septic shock, and/or MODS, relative to a subject with a single copy. Thus, in some embodiments, a single copy of a PCSK9 variant nucleic acid molecule and/or an LDLR variant nucleic acid molecule may not be completely protective, but instead, may be partially or incompletely protective of a subject from developing sepsis, SIRS, septic shock, and/or MODS. While not desiring to be bound by any particular theory, there may be additional factors or molecules involved in the development of sepsis, SIRS, septic shock, and/or MODS that are still present in a subject having a single copy of a PCSK9 variant nucleic acid molecule and/or an LDLR variant nucleic acid molecule, thus resulting in less than complete protection from the development of sepsis, SIRS, septic shock, and/or MODS.

Determining whether a subject has a PCSK9 variant nucleic acid molecule and/or an LDLR variant nucleic acid molecule in a biological sample from a subject and/or determining whether a subject has a PCSK9 variant nucleic acid molecule and/or an LDLR variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when a subject is identified as having an increased risk of developing sepsis, SIRS, septic shock, and/or MODS, the subject is further treated with a therapeutic agent that treats or inhibits sepsis, SIRS, septic shock, and/or MODS and/or a PCSK9 inhibitor and/or an LDLR agonist, as described herein. For example, when the subject is PCSK9 reference and/or LDLR reference, and therefore has an increased risk of developing sepsis, SIRS, septic shock, and/or MODS, the subject is administered a PCSK9 inhibitor and/or an LDLR agonist. In some embodiments, such a subject is also administered a therapeutic agent that treats or inhibits sepsis, SIRS, septic shock, and/or MODS. In some embodiments, when the subject is heterozygous for a PCSK9 variant nucleic acid molecule and/or an LDLR variant nucleic acid molecule, the subject is administered the therapeutic agent that treats or inhibits sepsis, SIRS, septic shock, and/or MODS in a dosage amount that is the same as or less than a standard dosage amount, and is also administered a PCSK9 inhibitor and/or an LDLR agonist.

In some embodiments, the subject is PCSK9 reference and LDLR reference. In some embodiments, the subject is heterozygous or homozygous for a PCSK9 variant nucleic acid molecule and LDLR reference. In some embodiments, the subject is heterozygous or homozygous for an LDLR variant nucleic acid molecule and PCSK9 reference. In some embodiments, the subject is heterozygous or homozygous for an LDLR variant nucleic acid molecule and PCSK9 heterozygous or homozygous for a PCSK9 variant nucleic acid molecule.

The present disclosure also provides methods of detecting the presence or absence of a PCSK9 variant genomic nucleic acid molecule and/or an LDLR variant genomic nucleic acid molecule in a biological sample from a subject, and/or a PCSK9 variant mRNA molecule in a biological sample from a subject, and/or a PCSK9 variant cDNA molecule produced from an mRNA molecule in a biological sample from a subject. It is understood that gene sequences within a population and mRNA molecules encoded by such genes can vary due to polymorphisms such as single-nucleotide polymorphisms. The sequences provided herein for the PCSK9 and/or LDLR variant genomic nucleic acid molecule, the PCSK9 variant mRNA molecules, and the PCSK9 variant cDNA molecules are only exemplary sequences. Other sequences for the PCSK9 and/or LDLR variant genomic nucleic acid molecule, variant mRNA molecules, and variant cDNA molecules are also possible.

The biological sample can be derived from any cell, tissue, or biological fluid from the subject. The biological sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any PCSK9 and/or any LDLR variant nucleic acid molecule, preliminary processing designed to isolate or enrich the biological sample for the genomic DNA can be employed. A variety of techniques may be used for this purpose. When detecting the level of any PCSK9 and/or any LDLR variant mRNA molecule, different techniques can be used enrich the biological sample with mRNA molecules. Various methods to detect the presence or level of an mRNA molecule or the presence of a particular variant genomic DNA locus can be used.

In some embodiments, detecting a PCSK9 variant nucleic acid molecule and/or LDLR variant nucleic acid molecule in a subject comprises assaying or genotyping a biological sample obtained from the subject to determine whether a PCSK9 genomic nucleic acid molecule and/or an LDLR genomic nucleic acid molecule in the biological sample, and/or a PCSK9 mRNA molecule in the biological sample, and/or a PCSK9 cDNA molecule produced from an mRNA molecule in the biological sample, comprises one or more variations that cause a loss-of-function (partial or complete) or are predicted to cause a loss-of-function (partial or complete).

In some embodiments, the methods of detecting the presence or absence of a PCSK9 variant nucleic acid molecule and/or an LDLR variant nucleic acid molecule (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence.

In some embodiments, the PCSK9 nucleotide sequence comprises: a thymine at a position corresponding to position 427 according to SEQ ID NO:2 (for genomic nucleic acid molecules); a uracil at a position corresponding to position 428 according to SEQ ID NO:17, a uracil at a position corresponding to position 217 according to SEQ ID NO:18, or a uracil at a position corresponding to position 137 according to SEQ ID NO:19 (for mRNA molecules); or a thymine at a position corresponding to position 428 according to SEQ ID NO:32, a thymine at a position corresponding to position 217 according to SEQ ID NO:33, or a thymine at a position corresponding to position 137 according to SEQ ID NO:34 (for cDNA molecules obtained from mRNA molecules).

In some embodiments, the PCSK9 genomic nucleotide sequence comprises a thymine at a position corresponding to position 427 according to SEQ ID NO:2, or the complement thereof.

In some embodiments, the PCSK9 mRNA nucleotide sequence comprises a uracil at a position corresponding to: position 428 according to SEQ ID NO:17, or the complement thereof; position 217 according to SEQ ID NO:18, or the complement thereof; or position 137 according to SEQ ID NO:19, or the complement thereof.

In some embodiments, the PCSK9 cDNA nucleotide sequence comprises a thymine at a position corresponding to: position 428 according to SEQ ID NO:32, or the complement thereof; position 217 according to SEQ ID NO:33, or the complement thereof; or position 137 according to SEQ ID NO:34, or the complement thereof.

In some embodiments, the LDLR nucleotide sequence comprises a thymine at a position corresponding to position 2,269 according to SEQ ID NO:4 (for genomic nucleic acid molecules). In some embodiments, the LDLR genomic nucleotide sequence comprises a thymine at a position corresponding to position 2,269 according to SEQ ID NO:4, or the complement thereof.

In some embodiments, the biological sample comprises a cell or cell lysate. Such methods can further comprise, for example, obtaining a biological sample from the subject comprising a PCSK9 genomic nucleic acid molecule or mRNA molecule and/or an LDLR genomic nucleic acid molecule, and if mRNA, optionally reverse transcribing the mRNA into cDNA. Such assays can comprise, for example determining the identity of these positions of the particular a PCSK9 nucleic acid molecule and/or an LDLR nucleic acid molecule. In some embodiments, the method is an in vitro method.

In some embodiments, the determining step, detecting step, or sequence analysis comprises sequencing at least a portion of the nucleotide sequence of a PCSK9 genomic nucleic acid molecule and/or an LDLR genomic nucleic acid molecule, a PCSK9 mRNA molecule, or a PCSK9 cDNA molecule produced from an mRNA molecule in the biological sample, wherein the sequenced portion comprises one or more variations described herein.

In some embodiments, the determining step, detecting step, or sequence analysis comprises sequencing at least a portion of: i) the nucleotide sequence of the PCSK9 and/or the LDLR genomic nucleic acid molecule in the biological sample, wherein the sequenced portion comprises: a position corresponding to position 427 according to SEQ ID NO:2, or the complement thereof; or a position corresponding to position 2,269 according to SEQ ID NO:4, or the complement thereof; ii) the nucleotide sequence of the PCSK9 mRNA molecule in the biological sample, wherein the sequenced portion comprises a position corresponding to: position 428 according to SEQ ID NO:17, or the complement thereof; position 217 according to SEQ ID NO:18, or the complement thereof; or position 137 according to SEQ ID NO:19, or the complement thereof; and/or iii) the nucleotide sequence of the PCSK9 cDNA molecule produced from the mRNA in the biological sample, wherein the sequenced portion comprises a position corresponding to: position 428 according to SEQ ID NO:32, or the complement thereof; position 217 according to SEQ ID NO:33, or the complement thereof; or position 137 according to SEQ ID NO:34, or the complement thereof. When the sequenced portion of the PCSK9 genomic nucleic acid molecule and/or the LDLR genomic nucleic acid molecule in the biological sample comprise: a thymine at a position corresponding to position 427 according to SEQ ID NO:2, or a thymine at a position corresponding to position 2,269 according to SEQ ID NO:4, respectively; or when the sequenced portion of the PCSK9 mRNA molecule in the biological sample comprises a uracil at a position corresponding to: position 428 according to SEQ ID NO:17, position 217 according to SEQ ID NO:18, or position 137 according to SEQ ID NO:19; or when the sequenced portion of the PCSK9 cDNA molecule in the biological sample comprises a thymine at a position corresponding to: position 428 according to SEQ ID NO:32, position 217 according to SEQ ID NO:33, or position 137 according to SEQ ID NO:34; then the PCSK9 nucleic acid molecule and/or the LDLR nucleic acid molecule in the biological sample is a PCSK9 variant nucleic acid molecule and/or an LDLR variant nucleic acid molecule.

In some embodiments, the determining step, detecting step, or sequence analysis comprises sequencing at least a portion of the nucleotide sequence of the PCSK9 genomic nucleic acid molecule and/or the LDLR genomic nucleic acid molecule in the biological sample, wherein the sequenced portion comprises: a position corresponding to position 427 according to SEQ ID NO:2, or the complement thereof; or a position corresponding to position 2,269 according to SEQ ID NO:4, or the complement thereof. When the sequenced portion of the PCSK9 nucleic acid molecule and/or the LDLR nucleic acid molecule in the biological sample comprises: a thymine at a position corresponding to position 427 according to SEQ ID NO:2, or a thymine at a position corresponding to position 2,269 according to SEQ ID NO:4, respectively, then the PCSK9 nucleic acid molecule and/or the LDLR nucleic acid molecule in the biological sample is a PCSK9 variant nucleic acid molecule and/or an LDLR variant nucleic acid molecule.

In some embodiments, the determining step, detecting step, or sequence analysis comprises sequencing at least a portion of the nucleotide sequence of the PCSK9 mRNA molecule in the biological sample, wherein the sequenced portion comprises a position corresponding to: position 428 according to SEQ ID NO:17, or the complement thereof; position 217 according to SEQ ID NO:18, or the complement thereof; or position 137 according to SEQ ID NO:19, or the complement thereof. When the sequenced portion of the PCSK9 nucleic acid molecule in the biological sample comprises a uracil at a position corresponding to: position 428 according to SEQ ID NO:17, position 217 according to SEQ ID NO:18, or position 137 according to SEQ ID NO:19, then the PCSK9 nucleic acid molecule in the biological sample is a PCSK9 variant nucleic acid molecule.

In some embodiments, the determining step, detecting step, or sequence analysis comprises sequencing at least a portion of the nucleotide sequence of the PCSK9 cDNA molecule produced from the mRNA molecule in the biological sample, wherein the sequenced portion comprises a position corresponding to: position 428 according to SEQ ID NO:32, or the complement thereof; position 217 according to SEQ ID NO:33, or the complement thereof; or position 137 according to SEQ ID NO:34, or the complement thereof. When the sequenced portion of the PCSK9 nucleic acid molecule in the biological sample comprises a thymine at a position corresponding to: position 428 according to SEQ ID NO:32, position 217 according to SEQ ID NO:33, or position 137 according to SEQ ID NO:34, then the PCSK9 nucleic acid molecule in the biological sample is a PCSK9 variant nucleic acid molecule.

In some embodiments, the determining step, detecting step, or sequence analysis comprises: a) contacting the biological sample with a primer hybridizing to a portion of the nucleotide sequence of: a PCSK9 genomic nucleic acid molecule that is proximate to a position corresponding to position 427 according to SEQ ID NO:2, or an LDLR genomic nucleic acid molecule that is proximate to a position corresponding to position 2,269 according to SEQ ID NO:4; a PCSK9 mRNA molecule that is proximate to a position corresponding to: position 428 according to SEQ ID NO:17, position 217 according to SEQ ID NO:18, or position 137 according to SEQ ID NO:19; and/or a PCSK9 cDNA molecule that is proximate to a position corresponding to: position 428 according to SEQ ID NO:32, position 217 according to SEQ ID NO:33, or position 137 according to SEQ ID NO:34; b) extending the primer at least through the position of the nucleotide sequence of: the PCSK9 genomic nucleic acid molecule corresponding to position 427 according to SEQ ID NO:2, or the LDLR genomic nucleic acid molecule corresponding to position 2,269 according to SEQ ID NO:4; the PCSK9 mRNA molecule corresponding to: position 428 according to SEQ ID NO:17, position 217 according to SEQ ID NO:18, or position 137 according to SEQ ID NO:19; and/or the PCSK9 cDNA molecule corresponding to: position 428 according to SEQ ID NO:32, position 217 according to SEQ ID NO:33, or position 137 according to SEQ ID NO:34; and c) determining whether the extension product of the primer comprises: i) a thymine at a position corresponding to position 427 according to SEQ ID NO:2, or a thymine at a position corresponding to position 2,269 according to SEQ ID NO:4; ii) a uracil at a position corresponding to: position 428 according to SEQ ID NO:17, position 217 according to SEQ ID NO:18, or position 137 according to SEQ ID NO:19; and/or iii) a thymine at a position corresponding to: position 428 according to SEQ ID NO:32, position 217 according to SEQ ID NO:33, or position 137 according to SEQ ID NO:34.

In some embodiments, the determining step, detecting step, or sequence analysis comprises: a) contacting the biological sample with a primer hybridizing to a portion of the nucleotide sequence of the PCSK9 genomic nucleic acid molecule and/or the LDLR genomic nucleic acid molecule that is proximate to a position corresponding to: position 427 according to SEQ ID NO:2, or position 2,269 according to SEQ ID NO:4, respectively; b) extending the primer at least through the position of the nucleotide sequence of the PCSK9 genomic nucleic acid molecule and/or the LDLR genomic nucleic acid molecule corresponding to: position 427 according to SEQ ID NO:2, or position 2,269 according to SEQ ID NO:4, respectively; and c) determining whether the extension product of the primer comprises: a thymine at a position corresponding to position 427 according to SEQ ID NO:2, or a thymine at a position corresponding to position 2,269 according to SEQ ID NO:4.

In some embodiments, the determining step, detecting step, or sequence analysis comprises: a) contacting the biological sample with a primer hybridizing to a portion of the nucleotide sequence of the PCSK9 mRNA molecule that is proximate to a position corresponding to: position 428 according to SEQ ID NO:17, position 217 according to SEQ ID NO:18, or position 137 according to SEQ ID NO:19; b) extending the primer at least through the position of the nucleotide sequence of the PCSK9 mRNA molecule corresponding to: position 428 according to SEQ ID NO:17, position 217 according to SEQ ID NO:18, or position 137 according to SEQ ID NO:19; and c) determining whether the extension product of the primer comprises a uracil at a position corresponding to: position 428 according to SEQ ID NO:17, position 217 according to SEQ ID NO:18, or position 137 according to SEQ ID NO:19. In some embodiments, the determining step, detecting step, or sequence analysis comprises: a) contacting the biological sample with a primer hybridizing to a portion of the nucleotide sequence of the PCSK9 cDNA molecule that is proximate to a position corresponding to: position 428 according to SEQ ID NO:32, position 217 according to SEQ ID NO:33, or position 137 according to SEQ ID NO:34; b) extending the primer at least through the position of the nucleotide sequence of the PCSK9 cDNA molecule corresponding to: position 428 according to SEQ ID NO:32, position 217 according to SEQ ID NO:33, or position 137 according to SEQ ID NO:34; and c) determining whether the extension product of the primer comprises a thymine at a position corresponding to: position 428 according to SEQ ID NO:32, position 217 according to SEQ ID NO:33, or position 137 according to SEQ ID NO:34.

In some embodiments, the determining step, detecting step, or sequence analysis comprises: a) contacting the biological sample with: i) a first primer hybridizing to a portion of the nucleotide sequence of the PCSK9 genomic nucleic acid molecule that is proximate to a position corresponding to position 427 according to SEQ ID NO:2, and ii) a second primer hybridizing to a portion of the nucleotide sequence of the LDLR genomic nucleic acid molecule that is proximate to position 2,269 according to SEQ ID NO:4; b) extending the first primer at least through the position of the nucleotide sequence of the PCSK9 genomic nucleic acid molecule corresponding to position 427 according to SEQ ID NO:2; and extending the second primer at least through the position of the nucleotide sequence of the LDLR genomic nucleic acid molecule corresponding to position 2,269 according to SEQ ID NO:4; and c) determining whether the extension product of the first primer comprises a thymine at the position corresponding to position 427 according to SEQ ID NO:2; and determining whether the extension product of the second primer comprises a thymine at the position corresponding to position 2,269 according to SEQ ID NO:4.

In some embodiments, the assay comprises sequencing the entire nucleic acid molecule. In some embodiments, only a PCSK9 genomic nucleic acid and/or an LDLR genomic nucleic acid molecule is analyzed. In some embodiments, only a PCSK9 mRNA molecule is analyzed. In some embodiments, only a PCSK9 cDNA molecule obtained from a mRNA molecule is analyzed.

In some embodiments, the determining step, detecting step, or sequence analysis comprises: a) amplifying at least a portion of: i) the genomic nucleic acid molecule that encodes the PCSK9 polypeptide and/or the LDLR polypeptide, wherein the amplified portion comprises: a thymine at a position corresponding to position 427 according to SEQ ID NO:2, or the complement thereof; or a thymine at a position corresponding to position 2,269 according to SEQ ID NO:4, or the complement thereof; ii) the PCSK9 mRNA molecule that encodes the PCSK9 polypeptide, wherein the amplified portion comprises a uracil at a position corresponding to: position 428 according to SEQ ID NO:17, or the complement thereof; position 217 according to SEQ ID NO:18, or the complement thereof; or position 137 according to SEQ ID NO:19, or the complement thereof; or iii) the PCSK9 cDNA molecule that encodes the PCSK9 polypeptide, wherein the amplified portion comprises a thymine at a position corresponding to: position 428 according to SEQ ID NO:32, or the complement thereof; position 217 according to SEQ ID NO:33, or the complement thereof; or position 137 according to SEQ ID NO:34, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a thymine at a position corresponding to position 427 according to SEQ ID NO:2, or the complement thereof; a thymine at a position corresponding to position 2,269 according to SEQ ID NO:4, or the complement thereof; ii) a uracil at a position corresponding to: position 428 according to SEQ ID NO:17, or the complement thereof; position 217 according to SEQ ID NO:18, or the complement thereof; or position 137 according to SEQ ID NO:19, or the complement thereof; and/or iii) a thymine at a position corresponding to: position 428 according to SEQ ID NO:32, or the complement thereof; position 217 according to SEQ ID NO:33, or the complement thereof; or position 137 according to SEQ ID NO:34, or the complement thereof; and d) detecting the detectable label.

In some embodiments, the determining step, detecting step, or sequence analysis comprises: a) amplifying at least a portion of the nucleic acid molecule that encodes the PCSK9 and/or the LDLR polypeptide, wherein the amplified portion comprises: a thymine at a position corresponding to position 427 according to SEQ ID NO:2, or the complement thereof; or a thymine at a position corresponding to position 2,269 according to SEQ ID NO:4, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a thymine at a position corresponding to position 427 according to SEQ ID NO:2, or the complement thereof; or a thymine at a position corresponding to position 2,269 according to SEQ ID NO:4, or the complement thereof; and d) detecting the detectable label.

In some embodiments, the determining step, detecting step, or sequence analysis comprises: a) amplifying at least a portion of the nucleic acid molecule that encodes the PCSK9 polypeptide, wherein the amplified portion comprises a uracil at a position corresponding to: position 428 according to SEQ ID NO:17, or the complement thereof; position 217 according to SEQ ID NO:18, or the complement thereof; or position 137 according to SEQ ID NO:19, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a uracil at a position corresponding to: position 428 according to SEQ ID NO:17, or the complement thereof; position 217 according to SEQ ID NO:18, or the complement thereof; or position 137 according to SEQ ID NO:19, or the complement thereof; and d) detecting the detectable label.

In some embodiments, the determining step, detecting step, or sequence analysis comprises: a) amplifying at least a portion of the nucleic acid molecule that encodes the PCSK9 polypeptide, wherein the amplified portion comprises a thymine at a position corresponding to: position 428 according to SEQ ID NO:32, or the complement thereof; position 217 according to SEQ ID NO:33, or the complement thereof; or position 137 according to SEQ ID NO:34, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a thymine at a position corresponding to: position 428 according to SEQ ID NO:32, or the complement thereof; position 217 according to SEQ ID NO:33, or the complement thereof; or position 137 according to SEQ ID NO:34, or the complement thereof; and d) detecting the detectable label.

In some embodiments, the nucleic acid molecule is mRNA and the determining step further comprises reverse-transcribing the mRNA into a cDNA prior to the amplifying step.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of: i) the amplified genomic nucleic acid molecule comprising: a thymine at a position corresponding to position 427 according to SEQ ID NO:2, or the complement thereof; a thymine at a position corresponding to position 2,269 according to SEQ ID NO:4, or the complement thereof; ii) the amplified mRNA molecule comprising a uracil at a position corresponding to: position 428 according to SEQ ID NO:17, or the complement thereof; position 217 according to SEQ ID NO:18, or the complement thereof; or position 137 according to SEQ ID NO:19, or the complement thereof; and/or iii) the amplified cDNA molecule comprising a thymine at a position corresponding to: position 428 according to SEQ ID NO:32, or the complement thereof; position 217 according to SEQ ID NO:33, or the complement thereof; or position 137 according to SEQ ID NO:34, or the complement thereof; and detecting the detectable label.

In some embodiments, the determining step, detecting step, or sequence analysis comprises: contacting the genomic nucleic acid molecule in the biological sample with an alteration-specific probe comprising a detectable label, wherein the alteration-specific probe comprises a nucleotide sequence which hybridizes under stringent conditions to the nucleotide sequence of the amplified PCSK9 nucleic acid molecule and/or LDLR nucleic acid molecule comprising: a thymine at a position corresponding to position 427 according to SEQ ID NO:2, or the complement thereof, or a thymine at a position corresponding to position 2,269 according to SEQ ID NO:4, or the complement thereof, respectively; and detecting the detectable label.

In some embodiments, the determining step, detecting step, or sequence analysis comprises: contacting the mRNA molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a uracil at a position corresponding to: position 428 according to SEQ ID NO:17, or the complement thereof; position 217 according to SEQ ID NO:18, or the complement thereof; or position 137 according to SEQ ID NO:19, or the complement thereof; and detecting the detectable label.

In some embodiments, the determining step, detecting step, or sequence analysis comprises: contacting the cDNA molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a thymine at a position corresponding to: position 428 according to SEQ ID NO:32, or the complement thereof; position 217 according to SEQ ID NO:33, or the complement thereof; or position 137 according to SEQ ID NO:34, or the complement thereof; and detecting the detectable label.

In some embodiments, the determining step, detecting step, or sequence analysis comprises: contacting the genomic nucleic acid molecule in the biological sample with a first alteration-specific probe comprising a first detectable label, wherein the first alteration-specific probe comprises a nucleotide sequence which hybridizes under stringent conditions to the nucleotide sequence of the amplified nucleic acid molecule comprising a thymine at a position corresponding to position 427 according to SEQ ID NO:2, or the complement thereof; and contacting the nucleic acid molecule in the biological sample with a second alteration-specific probe comprising a second detectable label, wherein the second alteration-specific probe comprises a nucleotide sequence which hybridizes under stringent conditions to the nucleotide sequence of the amplified nucleic acid molecule comprising a thymine at a position corresponding to position 2,269 according to SEQ ID NO:4, or the complement thereof; and detecting the first and the second detectable labels.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject. In some embodiments, the assay comprises contacting the biological sample with a primer or probe, such as an alteration-specific primer or alteration-specific probe, that specifically hybridizes to a PCSK9 variant genomic sequence, variant mRNA sequence, or variant cDNA sequence, and/or an LDLR variant genomic sequence, and not the corresponding PCSK9 reference and/or LDLR reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a PCSK9 variant genomic nucleic acid molecule, variant mRNA molecule, or variant cDNA molecule, and/or an LDLR variant genomic nucleic acid molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

In some embodiments, to determine whether a PCSK9 nucleic acid molecule (genomic nucleic acid molecule, mRNA molecule, or cDNA molecule), or complement thereof, and/or an LDLR nucleic acid molecule (genomic nucleic acid molecule), or complement thereof, within a biological sample comprises a nucleotide sequence comprising: i) a thymine at a position corresponding to position 427 according to SEQ ID NO:2, or a thymine at a position corresponding to position 2,269 according to SEQ ID NO:4 (genomic nucleic acid molecules), ii) a uracil at a position corresponding to: position 428 according to SEQ ID NO:17, position 217 according to SEQ ID NO:18, or position 137 according to SEQ ID NO:19 (mRNA molecules), or iii) a thymine at a position corresponding to: position 428 according to SEQ ID NO:32, position 217 according to SEQ ID NO:33, or position 137 according to SEQ ID NO:34 (cDNA molecules), the biological sample can be subjected to an amplification method using a primer pair that includes a first primer derived from the 5' flanking sequence adjacent to: i) a thymine at a position corresponding to position 427 according to SEQ ID NO:2, or a thymine at a position corresponding to position 2,269 according to SEQ ID NO:4; ii) a uracil at a position corresponding to: position 428 according to SEQ ID NO:17, position 217 according to SEQ ID NO:18, or position 137 according to SEQ ID NO:19; or iii) a thymine at a position corresponding to: position 428 according to SEQ ID NO:32, position 217 according to SEQ ID NO:33, or position 137 according to SEQ ID NO:34; and a second primer derived from the 3' flanking sequence adjacent to: i) a thymine at a position corresponding to position 427 according to SEQ ID NO:2, or a thymine at a position corresponding to position 2,269 according to SEQ ID NO:4; ii) a uracil at a position corresponding to: position 428 according to SEQ ID NO:17, position 217 according to SEQ ID NO:18, or position 137 according to SEQ ID NO:19; or iii) a thymine at a position corresponding to: position 428 according to SEQ ID NO:32, position 217 according to SEQ ID NO:33, or position 137 according to SEQ ID NO:34; to produce an amplicon that is indicative of the presence of the SNP at positions encoding: i) a thymine at a position corresponding to position 427 according to SEQ ID NO:2, or a thymine at a position corresponding to position 2,269 according to SEQ ID NO:4; ii) a uracil at a position corresponding to: position 428 according to SEQ ID NO:17, position 217 according to SEQ ID NO:18, or position 137 according to SEQ ID NO:19; or iii) a thymine at a position corresponding to: position 428 according to SEQ ID NO:32, position 217 according to SEQ ID NO:33, or position 137 according to SEQ ID NO:34. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising: i) a thymine at a position corresponding to position 427 according to SEQ ID NO:2, or a thymine at a position corresponding to position 2,269 according to SEQ ID NO:4; ii) a uracil at a position corresponding to: position 428 according to SEQ ID NO:17, position 217 according to SEQ ID NO:18, or position 137 according to SEQ ID NO:19; or iii) a thymine at a position corresponding to: position 428 according to SEQ ID NO:32, position 217 according to SEQ ID NO:33, or position 137 according to SEQ ID NO:34; and at least 1, 2, 3, 4, 5, 6, 7, 8, 9, 10, or more nucleotides on each side of positions comprising: i) a thymine at a position corresponding to position 427 according to SEQ ID NO:2, or a thymine at a position corresponding to position 2,269 according to SEQ ID NO:4; ii) a uracil at a position corresponding to: position 428 according to SEQ ID NO:17, position 217 according to SEQ ID NO:18, or position 137 according to SEQ ID NO:19; or iii) a thymine at a position corresponding to: position 428 according to SEQ ID NO:32, position 217 according to SEQ ID NO:33, or position 137 according to SEQ ID NO:34.

Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6X sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium. The present disclosure also provides methods of detecting the presence of a PCSK9 predicted loss-of-function polypeptide comprising performing an assay on a biological sample obtained from a subject to determine whether a PCSK9 polypeptide in the subject contains one or more variations that causes the polypeptide to have a loss-of-function (partial or complete) or predicted loss-of-function (partial or complete). The PCSK9 predicted loss-of-function polypeptide can be any of the PCSK9 variant polypeptides described herein. In some embodiments, the methods detect the presence of the PCSK9Arg46Leu variant polypeptide.

In some embodiments, the methods comprise performing an assay on a sample obtained from a subject to determine whether a PCSK9 polypeptide in the sample comprises a leucine at a position corresponding to position 46 according to SEQ ID NO:42. In some embodiments, the detecting step comprises sequencing at least a portion of the polypeptide that comprises a position corresponding to position 46 according to SEQ ID NO:42 or SEQ ID NO:35.

In some embodiments, the detecting step comprises an immunoassay for detecting the presence of a polypeptide that comprises a position corresponding to position 46 according to SEQ ID NO:42 or SEQ ID NO:35.

In some embodiments, when the subject does not have a PCSK9 predicted loss-of-function polypeptide, the subject has an increased risk of developing sepsis, SIRS, septic shock, and/or MODS. In some embodiments, when the subject has a PCSK9 predicted loss-of-function polypeptide, the subject has a decreased risk of developing sepsis, SIRS, septic shock, and/or MODS.

The present disclosure also provides isolated nucleic acid molecules that hybridize to a PCSK9 variant genomic nucleic acid molecule, and/or an LDLR variant genomic nucleic acid molecule, PCSK9 variant mRNA molecules, and/or PCSK9 variant cDNA molecules (such as any of the genomic variant nucleic acid molecules, mRNA variant molecules, and cDNA variant molecules disclosed herein). In some embodiments, the isolated nucleic acid molecules hybridize to a portion of the PCSK9 nucleic acid molecule and/or an LDLR nucleic acid molecule that includes a position corresponding to: i) position 427 according to SEQ ID NO:2, or position 2,269 according to SEQ ID NO:4; ii) position 428 according to SEQ ID NO:17, position 217 according to SEQ ID NO:18, or position 137 according to SEQ ID NO:19, or iii) position 428 according to SEQ ID NO:32, position 217 according to SEQ ID NO:33, or position 137 according to SEQ ID NO:34.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to PCSK9 variant nucleic acid molecules (such as genomic nucleic acid molecules, mRNA molecules, and/or cDNA molecules) and/or an LDLR variant nucleic acid molecule (such as a genomic nucleic acid molecule) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to a PCSK9 variant genomic nucleic acid molecule and/or an LDLR variant genomic nucleic acid molecule, PCSK9 variant mRNA molecules, and/or PCSK9 variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a PCSK9 polypeptide and/or an LDLR polypeptide, wherein the portion comprises a position corresponding to: i) position 247 according to SEQ ID NO:17, or the complement thereof; or position 2,269 according to SEQ ID NO:4, or the complement thereof; ii) position 428 according to SEQ ID NO:17, or the complement thereof; position 217 according to SEQ ID NO:18, or the complement thereof; or position 137 according to SEQ ID NO:19, or the complement thereof; or iii) position 428 according to SEQ ID NO:32, or the complement thereof; position 217 according to SEQ ID NO:33, or the complement thereof; or position 137 according to SEQ ID NO:34, or the complement thereof. In some embodiments, the alteration-specific probe or alteration-specific primer comprises a nucleotide sequence which is complementary to a portion of a nucleotide sequence comprising positions corresponding to: i) positions 426 to 428 according to SEQ ID NO:2, or the complement thereof; ii) positions 427 to 429 according to SEQ ID NO:17, or the complement thereof; positions 216 to 218 according to SEQ ID NO:18, or the complement thereof; or positions 136 to 138 according to SEQ ID NO:19, or the complement thereof; and/or iii) positions 427 to 429 according to SEQ ID NO:32, or the complement thereof; positions 216 to 218 according to SEQ ID NO:33, or the complement thereof; or positions 136 to 138 according to SEQ ID NO:34, or the complement thereof. In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within the PCSK9 variant genomic nucleic acid molecule and/or the LDLR variant genomic nucleic acid molecule, any of the PCSK9 variant mRNA molecules, and/or any of the PCSK9 variant cDNA molecules disclosed herein. The primers described herein can be used to amplify a PCSK9 variant genomic nucleic acid molecule and/or an LDLR variant genomic nucleic acid molecule, any of the PCSK9 variant mRNA molecules, or any of the PCSK9 variant cDNA molecules described herein, or any fragment thereof.

The present disclosure also provides pairs of primers comprising any of the primers described above. For example, if one of the primers' 3'-ends hybridizes to a guanine at a position corresponding to position 427 according to SEQ ID NO:1 (rather than a thymine) in a particular a PCSK9 genomic nucleic acid molecule, then the presence of the amplified fragment would indicate the presence of the PCSK9 reference genomic nucleic acid molecule. Conversely, if one of the primers' 3'-ends hybridizes to a thymine at a position corresponding to position 427 according to SEQ ID NO:2 (rather than a guanine) in a particular PCSK9 genomic nucleic acid molecule, then the presence of the amplified fragment would indicate the presence of the PCSK9 variant genomic nucleic acid molecule. In some embodiments, the nucleotide of the primer complementary to the thymine at a position corresponding to position 427 according to SEQ ID NO:2 can be at the 3' end of the primer. In addition, if one of the primers' 3'-ends hybridizes to a guanine at a position corresponding to: position 428 according to SEQ ID NO:17, position 217 according to SEQ ID NO:18, or position 137 according to SEQ ID NO:19 (rather than a uracil) in a particular PCSK9 mRNA molecule, then the presence of the amplified fragment would indicate the presence of a PCSK9 reference mRNA molecule. Conversely, if one of the primers' 3'-ends hybridizes to a uracil at a position corresponding to: position 428 according to SEQ ID NO:17, position 217 according to SEQ ID NO:18, or position 137 according to SEQ ID NO:19 (rather than a guanine) in a particular PCSK9 mRNA molecule, then the presence of the amplified fragment would indicate the presence of a PCSK9 variant mRNA molecule. In some embodiments, the nucleotide of the primer complementary to the uracil at a position corresponding to: position 428 according to SEQ ID NO:17, position 217 according to SEQ ID NO:18, or position 137 according to SEQ ID NO:19, can be at the 3' end of the primer. In addition, if one of the primers' 3'-ends hybridizes to a guanine at a position corresponding to: position 428 according to SEQ ID NO:32, position 217 according to SEQ ID NO:33, or position 137 according to SEQ ID NO:34 (rather than a thymine) in a particular PCSK9 cDNA molecule, then the presence of the amplified fragment would indicate the presence of a PCSK9 reference cDNA molecule. Conversely, if one of the primers' 3'-ends hybridizes to a thymine at a position corresponding to: position 428 according to SEQ ID NO:32, position 217 according to SEQ ID NO:33, or position 137 according to SEQ ID NO:34 (rather than a guanine) in a particular PCSK9 cDNA molecule, then the presence of the amplified fragment would indicate the presence of a PCSK9 variant cDNA molecule. In some embodiments, the nucleotide of the primer complementary to: the thymine at a position corresponding to position 428 according to SEQ ID NO:32, the thymine at a position corresponding to position 217 according to SEQ ID NO:33, or the thymine at a position corresponding to position 137 according to SEQ ID NO:34, can be at the 3' end of the primer.

In the context of the disclosure "specifically hybridizes" means that the probe or primer (such as, for example, the alteration-specific probe or alteration-specific primer) does not hybridize to a nucleic acid sequence encoding a PCSK9 reference genomic nucleic acid molecule and/or an LDLR reference genomic nucleic acid molecule, a PCSK9 reference mRNA molecule, and/or a PCSK9 reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The present disclosure also provides molecular complexes comprising or consisting of any of the PCSK9 nucleic acid molecules (genomic nucleic acid molecules, mRNA molecules, or cDNA molecules), or complement thereof, described herein and any of the alteration-specific primers or alteration-specific probes described herein. The present disclosure also provides molecular complexes comprising or consisting of any of the LDLR nucleic acid molecules (genomic nucleic acid molecules), or complement thereof, described herein and any of the alteration-specific primers or alteration-specific probes described herein. In some embodiments, the PCSK9 nucleic acid molecules (genomic nucleic acid molecule, mRNA molecules, or cDNA molecules), or complement thereof, and/or the LDLR nucleic acid molecule (genomic nucleic acid molecule), or complement thereof, in the molecular complexes are single-stranded. In some embodiments, the PCSK9 nucleic acid molecule and/or the LDLR nucleic acid molecule is any of the genomic nucleic acid molecules described herein. In some embodiments, the PCSK9 nucleic acid molecule is any of the mRNA molecules described herein. In some embodiments, the PCSK9 nucleic acid molecule is any of the cDNA molecules described herein. In some embodiments, the molecular complex comprises or consists of any of the PCSK9 nucleic acid molecules (genomic nucleic acid molecules, mRNA molecules, or cDNA molecules), or complement thereof, described herein and any of the alteration-specific primers described herein. In some embodiments, the molecular complex comprises or consists of any of the LDLR nucleic acid molecules (genomic nucleic acid molecules), or complement thereof, described herein and any of the alteration-specific primers described herein. In some embodiments, the molecular complex comprises or consists of any of the PCSK9 nucleic acid molecules (genomic nucleic acid molecule, mRNA molecules, or cDNA molecules), or complement thereof, described herein and any of the alteration-specific probes described herein. In some embodiments, the molecular complex comprises or consists of any of the LDLR nucleic acid molecules (genomic nucleic acid molecule), or complement thereof, described herein and any of the alteration-specific probes described herein.

In some embodiments, the molecular complex comprises or consists of an alteration-specific primer or an alteration-specific probe hybridized to a genomic nucleic acid molecule comprising a nucleotide sequence encoding a PCSK9 polypeptide, wherein the alteration-specific primer or the alteration-specific probe is hybridized to a thymine at a position corresponding to position 427 according to SEQ ID NO:2, or the complement thereof. In some embodiments, the molecular complex comprises or consists of an alteration-specific primer or an alteration-specific probe hybridized to a genomic nucleic acid molecule comprising a nucleotide sequence encoding an LDLR polypeptide, wherein the alteration-specific primer or the alteration-specific probe is hybridized to a thymine at a position corresponding to position 2,269 according to SEQ ID NO:4, or the complement thereof.

In some embodiments, the molecular complex comprises or consists of an alteration-specific primer or an alteration-specific probe that is hybridized to a CTT codon at positions corresponding to positions 426 to 428 according to SEQ ID NO:2.

In some embodiments, the molecular complex comprises or consists of a genomic nucleic acid molecule that comprises SEQ ID NO:2. In some embodiments, the molecular complex comprises or consists of a genomic nucleic acid molecule that comprises SEQ ID NO:4.

In some embodiments, the molecular complex comprises or consists of an alteration-specific primer or an alteration-specific probe hybridized to a PCSK9 mRNA molecule comprising a nucleotide sequence encoding a PCSK9 polypeptide, wherein the alteration-specific primer or the alteration-specific probe is hybridized to: a uracil at a position corresponding to position 428 according to SEQ ID NO:17, or the complement thereof; a uracil at a position corresponding to position 217 according to SEQ ID NO:18, or the complement thereof; or a uracil at a position corresponding to position 137 according to SEQ ID NO:19, or the complement thereof.

In some embodiments, the molecular complex comprises or consists of an alteration-specific primer or an alteration-specific probe that is hybridized to a CUU codon at positions corresponding to: positions 427 to 429 according to SEQ ID NO:17, positions 216 to 218 according to SEQ ID NO:18, or positions 136 to 138 according to SEQ ID NO:19. In some embodiments, the molecular complex comprises or consists of a PCSK9 mRNA molecule that comprises SEQ ID NO:17. In some embodiments, the molecular complex comprises or consists of an mRNA molecule that comprises SEQ ID NO:18. In some embodiments, the molecular complex comprises or consists of an mRNA molecule that comprises SEQ ID NO:19.

In some embodiments, the molecular complex comprises or consists of an alteration-specific primer or an alteration-specific probe hybridized to a PCSK9 cDNA molecule comprising a nucleotide sequence encoding a PCSK9 polypeptide, wherein the alteration-specific primer or the alteration-specific probe is hybridized to a thymine at a position corresponding to: position 428 according to SEQ ID NO:32, or the complement thereof; position 217 according to SEQ ID NO:33, or the complement thereof; or position 137 according to SEQ ID NO:34, or the complement thereof.

In some embodiments, the molecular complex comprises or consists of an alteration-specific primer or an alteration-specific probe that is hybridized to a CTT codon at positions corresponding to: positions 427 to 429 according to SEQ ID NO:32, positions 216 to 218 according to SEQ ID NO:33, or positions 136 to 138 according to SEQ ID NO:34.

In some embodiments, the molecular complex comprises or consists of a PCSK9 cDNA molecule that comprises SEQ ID NO:32. In some embodiments, the molecular complex comprises or consists of a cDNA molecule that comprises SEQ ID NO:33. In some embodiments, the molecular complex comprises or consists of an DNA molecule that comprises SEQ ID NO:34.

In some embodiments, the molecular complex comprises an alteration-specific probe or an alteration-specific primer comprising a label. In some embodiments, the label is a fluorescent label, a radiolabel, or biotin. In some embodiments, the molecular complex further comprises a non-human polymerase.

The nucleotide sequence of a PCSK9 reference genomic nucleic acid molecule is set forth in SEQ ID NO:1. Referring to SEQ ID NO:1, position 427 is a guanine.

A variant genomic nucleic acid molecule of PCSK9 exists, wherein the guanine at position 427 is replaced with a thymine. The nucleotide sequence of this PCSK9 variant genomic nucleic acid molecule is set forth in SEQ ID NO:2.

The nucleotide sequence of an LDLR reference genomic nucleic acid molecule is set forth in SEQ ID NO:3. Referring to SEQ ID NO:3, position 2,269 is a guanine.

A variant genomic nucleic acid molecule of LDLR exists, wherein the guanine at position 2,269 is replaced with a thymine. The nucleotide sequence of this LDLR variant genomic nucleic acid molecule is set forth in SEQ ID NO:4.

The nucleotide sequence of a first PCSK9 reference mRNA molecule is set forth in SEQ ID NO:5. Referring to SEQ ID NO:5, position 428 is a guanine. The nucleotide sequence of a second PCSK9 reference mRNA molecule is set forth in SEQ ID NO:6. Referring to SEQ ID NO:6, position 217 is a guanine. The nucleotide sequence of a third PCSK9 reference mRNA molecule is set forth in SEQ ID NO:7. Referring to SEQ ID NO:7, position 137 is a guanine.

A first PCSK9 variant mRNA molecule exists, wherein the guanine at position 428 (referring to SEQ ID NO:5) is replaced with a uracil. The nucleotide sequence of this PCSK9 variant mRNA molecule is set forth in SEQ ID NO:17. The first PCSK9 variant mRNA molecule comprises a CUU codon at positions 427 to 429 according to SEQ ID NO:17.

A second PCSK9 variant mRNA molecule exists, wherein the guanine at position 217 (referring to SEQ ID NO:6) is replaced with a uracil. The nucleotide sequence of this PCSK9 variant mRNA molecule is set forth in SEQ ID NO:18. The second PCSK9 variant mRNA molecule comprises a CUU codon at positions 216 to 218 according to SEQ ID NO:18.

A third PCSK9 variant mRNA molecule exists, wherein the guanine at position 137 (referring to SEQ ID NO:7) is replaced with a uracil. The nucleotide sequence of this PCSK9 variant mRNA molecule is set forth in SEQ ID NO:19. The third PCSK9 variant mRNA molecule comprises a CUU codon at positions 136 to 138 according to SEQ ID NO:19.

The nucleotide sequence of a first PCSK9 reference cDNA molecule is set forth in SEQ ID NO:20. Referring to SEQ ID NO:20, position 428 is a guanine. The nucleotide sequence of a second PCSK9 reference cDNA molecule is set forth in SEQ ID NO:21. Referring to SEQ ID NO:21, position 217 is a guanine. The nucleotide sequence of a third PCSK9 reference cDNA molecule is set forth in SEQ ID NO:22. Referring to SEQ ID NO:22, position 137 is a guanine.

A first PCSK9 variant cDNA molecule exists, wherein the guanine at position 428 (referring to SEQ ID NO:20) is replaced with a thymine. The nucleotide sequence of this PCSK9 variant cDNA molecule is set forth in SEQ ID NO:32. The first PCSK9 variant cDNA molecule comprises a CTT codon at positions 427 to 429 according to SEQ ID NO:32.

A second PCSK9 variant cDNA molecule exists, wherein the guanine at position 217 (referring to SEQ ID NO:21) is replaced with a thymine. The nucleotide sequence of this PCSK9 variant cDNA molecule is set forth in SEQ ID NO:33. The second PCSK9 variant cDNA molecule comprises a CTT codon at positions 216 to 218 according to SEQ ID NO:33.

A third PCSK9 variant cDNA molecule exists, wherein the guanine at position 137 (referring to SEQ ID NO:22) is replaced with a thymine. The nucleotide sequence of this PCSK9 variant cDNA molecule is set forth in SEQ ID NO:34. The third PCSK9 variant cDNA molecule comprises a CTT codon at positions 136 to 138 according to SEQ ID NO:34.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3XFLAG, 6XHis or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O—, S—, or N-alkyl; O—, S—, or N-alkenyl; O—, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $—O[(CH_2)_nO]_mCH_3$, $—O(CH_2)_nOCH_3$, $—O(CH_2)_nNH_2$, $—O(CH_2)_nCH_3$, $—O(CH_2)_n—ONH_2$, and $—O(CH_2)_nON[(CH_2)_nCH_3)]_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

Desired regulatory sequences for mammalian host cell expression can include, for example, viral elements that direct high levels of polypeptide expression in mammalian cells, such as promoters and/or enhancers derived from retroviral LTRs, cytomegalovirus (CMV) (such as, for example, CMV promoter/enhancer), Simian Virus 40 (SV40) (such as, for example, SV40 promoter/enhancer), adenovirus, (such as, for example, the adenovirus major late promoter (AdMLP)), polyoma and strong mammalian promoters such as native immunoglobulin and actin promoters. Methods of expressing polypeptides in bacterial cells or fungal cells (such as, for example, yeast cells) are also well known. A promoter can be, for example, a constitutively active promoter, a conditional promoter, an inducible promoter, a temporally restricted promoter (such as, for example, a developmentally regulated promoter), or a spatially restricted promoter (such as, for example, a cell-specific or tissue-specific promoter).

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions comprising any one or more of the isolated nucleic acid molecules, genomic nucleic acid molecules, mRNA molecules, and/or cDNA molecules disclosed herein. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1 (PCSK9 genomic), SEQ ID NO:5, SEQ ID NO:6, or SEQ ID NO:7 (PCSK9 mRNA), or SEQ ID NO:20, SEQ ID NO:21, or SEQ ID NO:22 (PCSK9 cDNA)). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a nucleic acid molecule comprising a nucleotide sequence encoding a PCSK9 polypeptide, wherein the nucleotide sequence comprises a thymine at a position corresponding to position 427 according to SEQ ID NO:2 means that if the nucleotide sequence of the PCSK9 genomic nucleic acid molecule is aligned to the sequence of SEQ ID NO:2, the PCSK9 sequence has a thymine residue at the position that corresponds to position 427 of SEQ ID NO:2. The same applies for mRNA molecules comprising a nucleotide sequence encoding a PCSK9 polypeptide, wherein the nucleotide sequence comprises a uracil at a position corresponding to position 428 according to SEQ ID NO:17, and cDNA molecules comprising a nucleotide sequence encoding a PCSK9 polypeptide, wherein the nucleotide sequence comprises a thymine at a position corresponding to position 428 according to SEQ ID NO:32. In other words, these phrases refer to a nucleic acid molecule encoding a PCSK9 polypeptide, wherein the genomic nucleic acid molecule has a nucleotide sequence that comprises a thymine residue that is homologous to the thymine residue at position 427 of SEQ ID NO:2 (or wherein the mRNA molecule has a nucleotide sequence that comprises a uracil residue that is homologous to the uracil residue at position 428 of SEQ ID NO:17, or wherein the cDNA molecule has a nucleotide sequence that comprises a thymine residue that is homologous to the thymine residue at position 428 of SEQ ID NO:32).

As described herein, a position within a PCSK9 genomic nucleic acid molecule and/or an LDLR genomic nucleic acid molecule that corresponds to position 427 according to SEQ ID NO:2 or position 2,269 according to SEQ ID NO:4, respectively, for example, can be identified by performing a sequence alignment between the nucleotide sequence of a particular a PCSK9 nucleic acid molecule and/or an LDLR nucleic acid molecule and the nucleotide sequence of SEQ ID NO:2 or SEQ ID NO:4, respectively. A variety of computational algorithms exist that can be used for performing a sequence alignment to identify a nucleotide position that corresponds to, for example, position 427 in SEQ ID NO:2, or position 2,269 in SEQ ID NO:4. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

The amino acid sequence of a PCSK9 reference polypeptide is set forth in SEQ ID NO:35. Referring to SEQ ID NO:35, the PCSK9 reference polypeptide is 692 amino acids in length. Referring to SEQ ID NO:35, position 46 is an arginine.

A PCSK9 variant polypeptide exists (Arg46Leu or R46L), the amino acid sequence of which is set forth in SEQ ID NO:42. Referring to SEQ ID NO:42, the PCSK9 variant polypeptide is also 692 amino acids in length. Referring to SEQ ID NO:42, position 46 is a leucine.

The amino acid sequence of a first LDLR reference polypeptide is set forth in SEQ ID NO:36. Referring to SEQ ID NO:36, the LDLR reference polypeptide is 860 amino acids in length. The amino acid sequence of a second LDLR reference polypeptide is set forth in SEQ ID NO:37. Referring to SEQ ID NO:37, the LDLR reference polypeptide is 682 amino acids in length. The amino acid sequence of a third LDLR reference polypeptide is set forth in SEQ ID NO:38. Referring to SEQ ID NO:38, the LDLR reference polypeptide is 692 amino acids in length. The amino acid sequence of a fourth LDLR reference polypeptide is set forth in SEQ ID NO:39. Referring to SEQ ID NO:39, the LDLR reference polypeptide is 819 amino acids in length. The amino acid sequence of a fifth LDLR reference polypeptide is set forth in SEQ ID NO:40. Referring to SEQ ID NO:40, the LDLR reference polypeptide is 858 amino acids in length. The amino acid sequence of a sixth LDLR reference polypeptide is set forth in SEQ ID NO:41. Referring to SEQ ID NO:41, the LDLR reference polypeptide is 739 amino acids in length.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat or inhibit sepsis, SIRS, septic shock, and/or MODS for use in the treatment of sepsis, SIRS, septic shock, and/or MODS (or for use in the preparation of a medicament for treating sepsis, SIRS, septic shock, and/or MODS) in a subject, wherein the subject has any of the PCSK9 genomic nucleic acid molecules, mRNA molecules, and/or cDNA molecules described herein and/or has any of the LDLR genomic nucleic acid molecules, mRNA molecules, and/or cDNA molecules described herein. The therapeutic agents that treat or inhibit sepsis, SIRS, septic shock, and/or MODS can be any of the therapeutic agents that treat or inhibit sepsis, SIRS, septic shock, and/or MODS described herein. In some embodiments, the subject comprises: i) a genomic nucleic acid molecule having a nucleotide sequence encoding a PCSK9 polypeptide, wherein the nucleotide sequence comprises a thymine at a position corresponding to position 427 according to SEQ ID NO:2, or the complement thereof; and/or a genomic nucleic acid molecule having a nucleotide sequence encoding an LDLR polypeptide, wherein the nucleotide sequence comprises a thymine at a position corresponding to position 2,269 according to SEQ ID NO:4, or the complement thereof; ii) an mRNA molecule having a nucleotide sequence encoding a PCSK9 polypeptide, wherein the nucleotide sequence comprises a uracil at a position corresponding to: position 428 according to SEQ ID NO:17, or the complement thereof; position 217 according to SEQ ID NO:18, or the complement thereof; or position 137 according to SEQ ID NO:19, or the complement thereof; or iii) a cDNA molecule having a nucleotide sequence encoding a PCSK9 polypeptide, wherein the nucleotide sequence comprises a thymine at a position corresponding to: position 428 according to SEQ ID NO:32, or the complement thereof; position 217 according to SEQ ID NO:33, or the complement thereof; or position 137 according to SEQ ID NO:34, or the complement thereof.

The present disclosure also provides a PCSK9 inhibitor and/or an LDLR agonist for use in the treatment of sepsis, systemic inflammatory response syndrome (SIRS), septic shock, and/or multiple organ dysfunction syndrome (MODS), in a subject. In some embodiments, the subject is reference for a PCSK9 and/or an LDLR genomic nucleic acid molecule, a PCSK9 and/or an LDLR mRNA molecule, or a PCSK9 and/or an LDLR cDNA molecule. In some embodiments, the subject is heterozygous for: i) a genomic nucleic acid molecule having a nucleotide sequence encoding a PCSK9 polypeptide, wherein the nucleotide sequence comprises a thymine at a position corresponding to position 427 according to SEQ ID NO:2; and/or ii) a genomic nucleic acid molecule having a nucleotide sequence encoding an LDLR polypeptide, wherein the nucleotide sequence comprises a thymine at a position corresponding to position 2,269 according to SEQ ID NO:4; an mRNA molecule having a nucleotide sequence encoding a PCSK9 polypeptide, wherein the nucleotide sequence comprises a uracil at a position corresponding to: position 428 according to SEQ ID NO:17, or the complement thereof; position 217 according to SEQ ID NO:18, or the complement thereof; or position 137 according to SEQ ID NO:19, or the complement thereof; or a cDNA molecule having a nucleotide sequence encoding a PCSK9 polypeptide, wherein the nucleotide sequence comprises a thymine at a position corresponding to: position 428 according to SEQ ID NO:32, or the complement thereof; position 217 according to SEQ ID NO:33, or the complement thereof; or position 137 according to SEQ ID NO:34, or the complement thereof.

In some embodiments, the PCSK9 inhibitor is an antisense nucleic acid molecule, an siRNA, or an shRNA that hybridizes to a PCSK9 mRNA. In some embodiments, the PCSK9 inhibitor comprises a Cas protein and gRNA that hybridizes to a gRNA recognition sequence within a PCSK9 genomic nucleic acid molecule. In some embodiments, the Cas protein is Cas9 or Cpf1. In some embodiments, the gRNA recognition sequence includes or is proximate to position 427 according to SEQ ID NO:1. In some embodiments, the gRNA recognition sequence is located from about 1000, from about 500, from about 400, from about 300, from about 200, from about 100, from about 50, from about 45, from about 40, from about 35, from about 30, from about 25, from about 20, from about 15, from about 10, or from about 5 nucleotides of a position corresponding to position 427 according to SEQ ID NO:1. In some embodiments, a PAM sequence is about 2 to about 6 nucleotides downstream of the gRNA recognition sequence. In some embodiments, the gRNA comprises from about 17 to about 23 nucleotides. In some embodiments, the gRNA recognition sequence comprises a nucleotide sequence according to any one of SEQ ID NOS: 43-68.

In some embodiments, the LDLR agonist is an antisense nucleic acid molecule, an siRNA, or an shRNA that hybridizes to an LDLR mRNA molecule. In some embodiments, the LDLR agonist comprises a Cas protein and gRNA that hybridizes to a gRNA recognition sequence within an LDLR genomic nucleic acid molecule. In some embodiments, the Cas protein is Cas9 or Cpf1. In some embodiments, the gRNA recognition sequence includes or is proximate to position 2,269 according to SEQ ID NO:3. In some embodiments, the gRNA recognition sequence is located from about 1000, from about 500, from about 400, from about 300, from about 200, from about 100, from about 50, from about 45, from about 40, from about 35, from about 30, from about 25, from about 20, from about 15, from about 10, or from about 5 nucleotides of a position corresponding to position 2,269 according to SEQ ID NO:3. In some embodiments, a PAM sequence is about 2 to about 6 nucleotides downstream of the gRNA recognition sequence. In some embodiments, the gRNA comprises from about 17 to about 23 nucleotides. In some embodiments, the gRNA recognition sequence comprises a nucleotide sequence according to any one of SEQ ID NOS: 69-89.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: Human Genetics for PCSK9 and Sepsis Mortality

To assess whether loss of function in PCSK9 and/or LDLR associates with improved sepsis survival, the association between loss-of-function in PCSK9 and 28-day mortality due to severe sepsis (as defined by ICD10 codes) was examined using particular genetic data from GHS and UKB cohorts. In addition, summary data was collected and a meta-analysis of the 28-day mortality due to severe sepsis (that was either clinically defined or defined by ICD10 codes for suspected/confirmed infection and acute organ failure) was performed across 9 cohorts, including a total of 3,228 severe sepsis cases who died and 10,732 sepsis cases who survived. The cohorts with summary data that were included in the meta-analysis included GHS, Gen-Sep, Vanderbilt, SPH, VASST, UKB, NTNU, Estonia, and Copenhagen (see, FIG. 1).

The meta-analysis focused on PCSK9 p.Arg46Leu (rs11591147, AAF 0.012), a well-characterized missense variant that acts as a loss-of-function in terms of having a large effect on LDL lowering (in UKB: ref carriers: 138.23 mg/dl, het carriers: 126.8 mg/dl, hom carriers: 103.8 mg/dl (Cohen, N. Eng. J. Med., 2005; p-value=4.9E-324 in UKB), and significantly reduced odds of coronary artery disease (UKB: OR=0.79, p=6.4E-14). Further, in GHS, the LDLR intronic variant (rs6511720, AAF 0.12) with significant effects on LDL lowering (−5.9 mg/dl per allele, p=3.9E-324) and significantly reduced odds of CAD (OR=0.90, p=6.2E-13) was also tested. The results of the meta-analysis for association between PCSK9 p.Arg46Leu and 28-day mortality due to severe sepsis showed an OR=0.83 (0.65, 1.06) and p=0.13, consistent with PCSK9 p.Arg46Leu associating with reduced odds of death due to severe sepsis.

Figure 2:
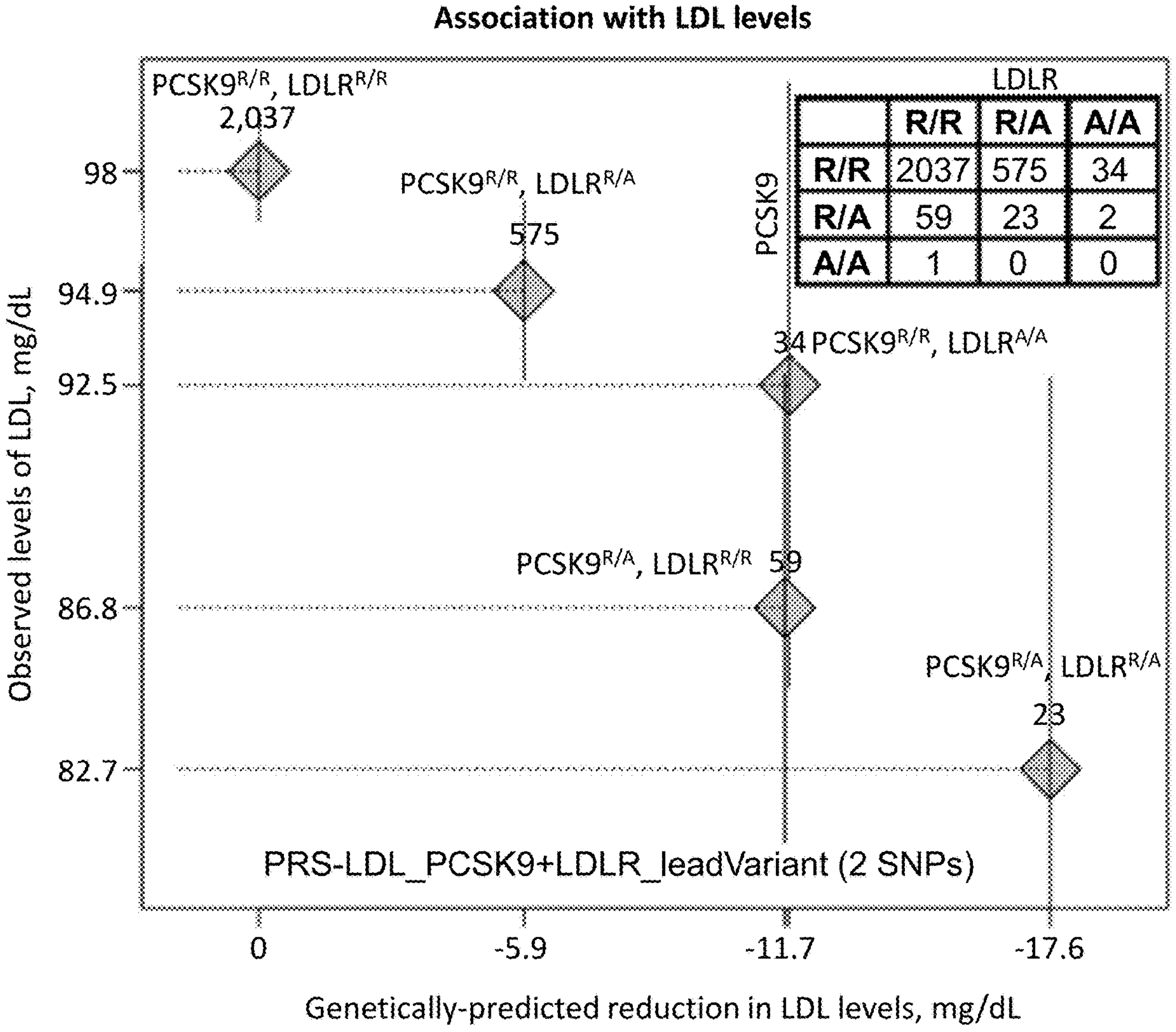
FIG. 2 shows genetically-predicted reduction in LDL levels and sepsis mortality rate based on genotype groups (calculated as: N_Alt_alleles_rs11591147×LDL_weight_rs11591147+N_Alt_alleles_rs6511720×LDL_weight_rs6511720; SNP weights were jointly estimated using linear regression (covariates: age and sex) in the UKB500K, with LDL levels measured on the raw scale (mg/dL); weights were −11.7 for the PCSK9 variant, and −5.9 for the LDLR variant).
Figure 2:
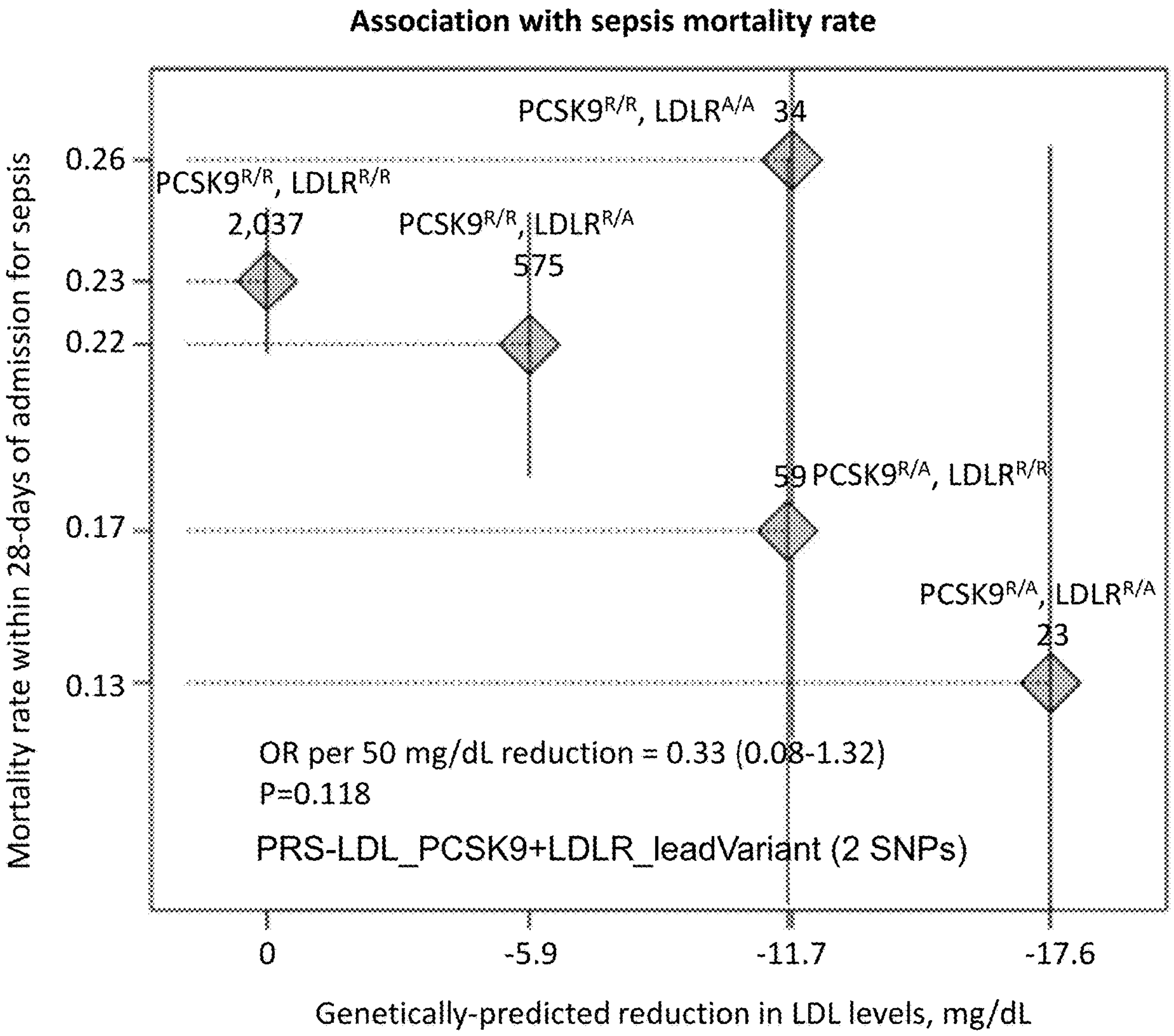
Figure 3:
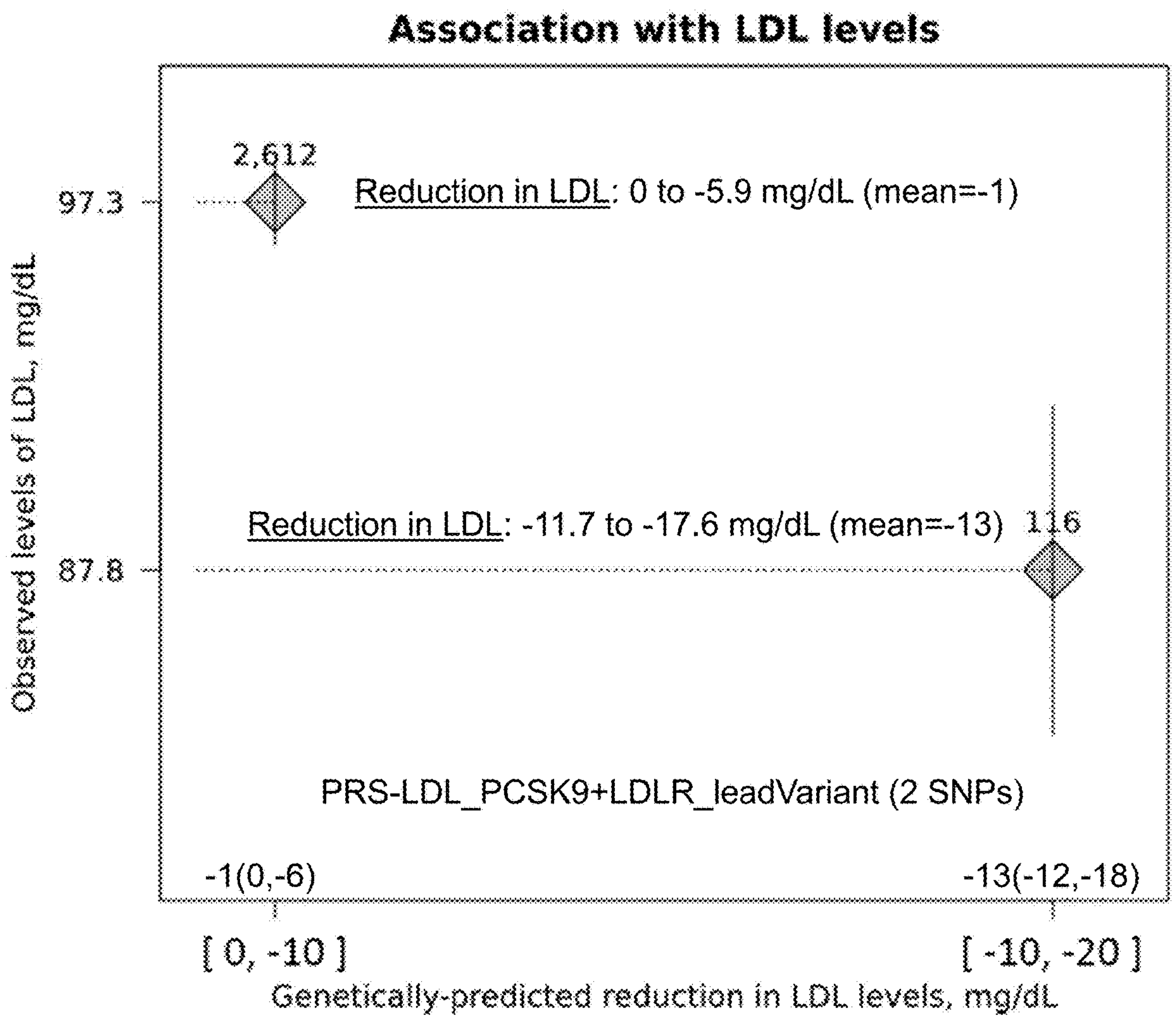
FIG. 3 shows genetically-predicted reduction in LDL levels and sepsis mortality rate based on 10 mg/dl groups.
Figure 3:
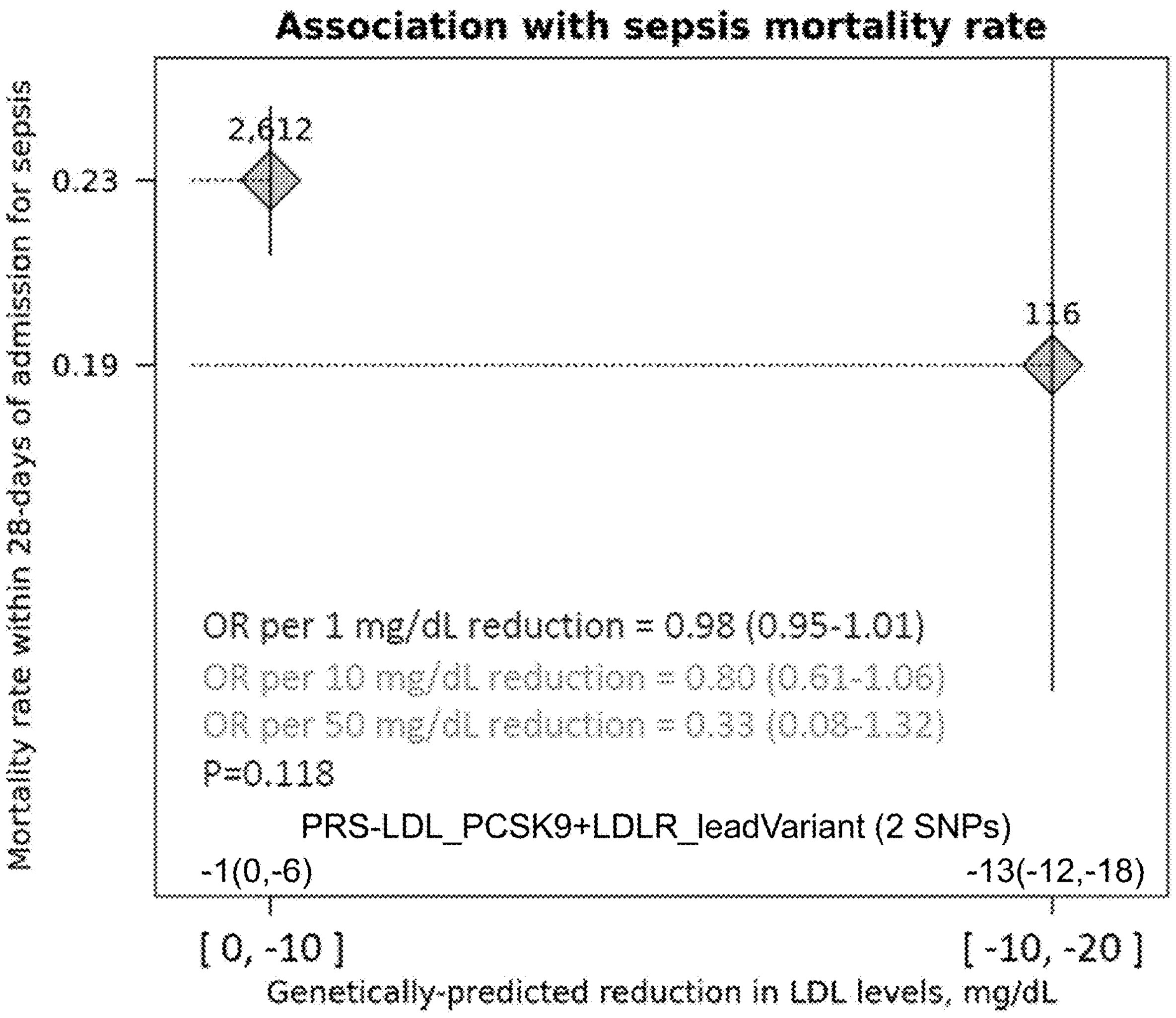

Further, the combined effects of the loss of PCSK9 and LDLR on 28-day sepsis mortality was analyzed. From this analysis, it was found that the combined effects of sepsis mortality on carriers of both PCSK9 p.Arg46Leu and LDLR rs6511720 were OR=0.33 (0.08, 1.32) and p=0.12 (see, FIG. 2 and FIG. 3), consistent with reduced odds of death due to sepsis. Similar combined effects in replication analysis was observed with Estonia and HUNT. In sum, an association between PCSK9 p.R46L and reduced mortality due to severe sepsis was observed.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of identifying a subject having a risk of developing sepsis, systemic inflammatory response syndrome (SIRS), septic shock, and/or multiple organ dysfunction syndrome (MODS), the method comprising:

determining or having determined in a biological sample obtained from the subject the presence or absence of: i) a Proprotein Convertase Subtilisin/Kexin Type 9 (PCSK9) variant nucleic acid molecule encoding PCSK9 Arg46Leu; and ii) a Low Density Lipoprotein Receptor (LDLR) variant nucleic acid molecule comprising the single nucleotide polymorphism rs6511720;

wherein when the subject does not have a PCSK9 variant nucleic acid molecule encoding PCSK9 Arg46Leu, the subject has an increased risk of developing sepsis, SIRS, septic shock, and/or MODS;

wherein when the subject has a PCSK9 variant nucleic acid molecule encoding PCSK9 Arg46Leu and is heterozygous for an LDLR variant nucleic acid molecule comprising rs6511720 , the subject has a decreased risk of developing sepsis, SIRS, septic shock, and/or MODS; and wherein when the subject does not have a PCSK9 variant nucleic acid molecule encoding PCSK9 Arg46Leu and is not heterozygous for an LDLR variant nucleic acid molecule comprising rs6511720, administering a PCSK9 inhibitor.

2. The method according to claim 1, wherein the PCSK9 inhibitor comprises an antisense nucleic acid molecule, a small interfering RNA (siRNA), or a short hairpin RNA (shRNA), that hybridizes to PCSK9 mRNA.

3. The method according to claim 1, wherein the PCSK9 inhibitor comprises alirocumab or evolocumab, or a combination thereof.

4. The method according to claim 1, wherein the PCSK9 inhibitor comprises alirocumab.

5. The method according to claim 1, wherein the PCSK9 inhibitor comprises the monoclonal antibody SAR236553/REGN727 or AMG145, or a combination thereof.

6. The method according to claim 1, wherein the PCSK9 inhibitor comprises lupin peptide, resveratrol, lycopene, or eugenol, or any combination thereof.

* * * * *

SEQUENCE LISTING

```
<160> NUMBER OF SEQ ID NOS: 89

<210> SEQ ID NO 1
<211> LENGTH: 25305
<212> TYPE: DNA
```

-continued

<213> ORGANISM: homo sapien

<400> SEQUENCE: 1
agcgacgtcg aggcgctcat ggttgcaggc gggcgccgcc gttcagttca gggtctgagc 60
ctggaggagt gagccaggca gtgagactgg ctcgggcggg ccgggacgcg tcgttgcagc 120
agcggctccc agctcccagc caggattccg cgcgcccctt cacgcgccct gctcctgaac 180
ttcagctcct gcacagtcct ccccaccgca aggctcaagg cgccgccggc gtggaccgcg 240
cacggcctct aggtctcctc gccaggacag caacctctcc cctggccctc atgggcaccg 300
tcagctccag gcggtcctgg tggccgctgc cactgctgct gctgctgctg ctgctcctgg 360
gtcccgcggg cgcccgtgcg caggaggacg aggacggcga ctacgaggag ctggtgctag 420
ccttgcgttc cgaggaggac ggcctggccg aagcacccga gcacggaacc acagccacct 480
tccaccgctg cgccaaggtg cgggtgtagg gatgggaggc cggggcgaac ccgcagccgg 540
gacggtgcgg tgctgtttcc tctcgggcct cagtttcccc ccatgtaaga gaggaagtgg 600
agtgcaggtc gccgagggct cttcgcttgg cacgatcttg gggactgcag gcaaggcggc 660
gggggaggac gggtagtggg gagcacggtg gagagcgggg acggccggct ctttggggac 720
ttgctggggc gtgcggctgc gctattcagt gggaaggttc gcggggttgg gagacccgga 780
ggccgaggaa gggcgagcag agcactgcca ggatatcctg cccagatttc ccagtttctg 840
cctcgccgcg gcacaggtgg gtgaaggagt gaatgcctgg aacgtactgg gaactgcacc 900
aggcacagag aaagcgggct tgccattata gtgggttccg atttggtttg gaaaacatgg 960
gcagcggagg gtggagggcc tggagagaag gccctacccg agacaggggc ggggtgggaa 1020
ggacggcaga tgctgggagc acgaggcaat ttctttatga cacagaactc atgctctagt 1080
attccatctg tttcagccga agaaaagaac cagctgaagg ggcaggggag aaggggcgga 1140
ggtattctcg aggcccattg gcgtccttta ggactcaggc agggaagggc ccttggtgct 1200
ctggagccgg aggtggtgcg cctggtactg ggaccccgga gctgagcccg gcgcctcagc 1260
ccacctggct gtctgccgac cgtgtgcggg gcgagtttgc tcaacaactc tgccagcttc 1320
tggccctcag gctgtgggaa gcttcttccc ggggcgagac cactagcttt ttctaagtat 1380
taccagccca ggacttggct gaggttctgt gtcccccagc ttggagtcag atgtggggtt 1440
gaatcttggc ttcctctcac tagctgtggt gcttgacaag tcacttatcc ttgagcctcc 1500
attgcctaat ctttaaaagg gaggtgacaa tcgtccctac ggctcagtgg cagcagatgg 1560
ggagatgaag ggaaagttct gttgaccatg agtgaactta caatgcaagc cccgggggga 1620
tcacttgcag ttttgtccct gtctgcagtg tgacctgttg gtgacattgt ctttgctcca 1680
aaccacagct cctggggcag aggggaaaat tctgccactc acagctgcct gcccacgctt 1740
ctgtctgagt gtgctgggtg gcaggatggc aagtccttac tcagctcagt atagccctct 1800
tccttgttcc ctgagccttt gactttctcg agggatgttg tggggttgtg gccaggataa 1860
gaaagggcat ttcaagttac cactgctcca aaacaactgt tctggaaata gtgagtaccc 1920
catcctgaga ggtgagtaag cagaggctgt atgaccacct gaaccaagcc cttgaggatg 1980
tttcttctct ggtggaagtt tggaacagga gcctcctcaa gttcatttat tcattcattc 2040
aatggttatt ttgtgggaat cgaatttaga atgaaaatat tttttggcaa gcagaaaata 2100
atttttagac caatcctttt cttttagtca tgagaaactg aggcccagag agaggaggtc 2160
accccaggtg cattagaact gggtttccag aactgacact ccactgcaca gagtactctc 2220
ccaattcatt caatttttat ttagcggaag gcattttcag atgggtcttt gaagcattag 2280

-continued

```
taggagttca gcgatgatgg tgtcatgaga attttattct aggattagga ggtaccatga   2340
acaaagatac agagctggga aaaccagagg tggaagataa ggagcacatg tccacagttc   2400
tttttctttt ttttttgaga tggagtttcg ctcttgttgc ccaggctgga gtgcaatggt   2460
gcagtctcag ctcactgcaa catctgtctc ccgggttcaa gtggttctcc tgcctcagcc   2520
tcccaagaag ctgggattac aggtacctgc caccacgccc ggctaatttt tgtattttta   2580
gtagagaagg ggtttcacca cgttggccag gctagtcgca aactcctgac ctcctcagtg   2640
gatccgagga ggtgatcctc ccgcctcagc ctcccaaagt gctcgaatta caggtgtgag   2700
ccaccacgcc tggcctccac agttctttat ccaccgtctg aaatgtaaaa tgttacgaaa   2760
accaaaagtt ttttttgtga tttatttgat ggtagcacct gacgtgaact gacatgagat   2820
tatttttaat ttagttgtgt gaatatgcat attcatatat tttgctgcat agattacagt   2880
atgcagctcc agattcttcc aagcagactc tgattgccca ttactgcctt tctaaaatcc   2940
aaacaagttc tgaggttcaa aaccgttttg gccctaaggc tttgggtaaa gggggtggac   3000
tctgttctac tctgactgga gtccaagatg catatataca gagatatggg tgatggggct   3060
gcaaggtagg ttgaggtagg ggccaaggag gagcatggag tttggacttg attcatgagg   3120
ctgtggggag ccagtgaagg ttcttaagca ggtatgtctg cctgagagca gttggagcag   3180
acaagagcta aaaaccaaac aaatcaccat agatagtggc tgctataatt tgtttgtccc   3240
ctccaaatct catgtggaaa tttggtcctc agtgttggaa gtggggccta atgggaggtg   3300
tttgggtcat gggggaggaa cccctgtgaa aggcttggtg ccgtccttgt gataatgagt   3360
aagttctccc gctatgattt cccttgaagg ctgattatta aaaagagctt ggcacctccc   3420
tctcttctct cttgcttctt ctcttgccat gtgattgatc tctgcacatg taggctcccc   3480
ttcaccttct gccatcagtg aaagcagctt aaggccctca ccagaagcag atgctggtgc   3540
catgcttcct ggagagcttg cagaatcatg agctgaataa atccctttttc cttgtaaatt   3600
actcaccttc aggtattcct ttatatagca acacaaaagg actaagacag tggccttgac   3660
ttttctctct ctttaagaag tgttgccttt gctcacttag tcatcccttc tgcctgcatt   3720
tgtagagcat ctggatggga gatttatata accgtcactc ttgactttcc cagcaggcct   3780
atgtcatagg tactgtggtc tctacaatac agcagaggta tctgaggctc cgagaggttg   3840
agtgacttgc tcatggctgc acaaccagta aatattggag ctggaattca ggtccacggt   3900
ttcctggctc caaagcccat gattttttcc ctcaatttat tctgactggg gcatggggga   3960
gggggtggcc tttgggcagg gccaccagga gcgaccaggc ccgtagagag ctgggtgcag   4020
gtacagagga aaacctgttg tcgagtgtgg cccgtagttc ccatttttgc ctgaatggca   4080
catttgaaag tgttatataa ccatgtgaat aataatagtt ggcctatatg agttctttaa   4140
tttgcttttt ggtccgcatt tggtaacttc tttatcatct actatactct gttgtgtctc   4200
ttttgttgta atttgtaagt aggggtgaga taaagtacac ctagggtttg ctgggtttct   4260
tccatgtcat catgttcctc cttgcatggg gccaggatcc gtggaggttg cctggcacct   4320
acgtggtggt gctgaaggag gagacccacc tctcgcagtc agagcgcact gcccgccgcc   4380
tgcaggccca ggctgcccgc cggggatacc tcaccaagat cctgcatgtc ttccatggcc   4440
ttcttcctgg cttcctggtg aagatgagtg gcgacctgct ggagctggtg agccaccctt   4500
tttgggaatg gcacttcctg atagggctgg gccactgcat atacactggg gactgtgctt   4560
agtaggccca ttgctgaaaa tcagaagggg acagcaagta tgtattgagc acttatcggg   4620
```

-continued

```
taccaagcac agtaactact ggctttctgt atagaattcc ctttaagcct ggccatgccc   4680
cagtggtacg tctatcttca tttgaaagac gaggagactg aagttcagag gggaccacac   4740
agacagctag ggtagagcc tggatcaaac ccattggtct gcctgccagc cattcttgtg   4800
ccaatgcatc tgctgcctac ggaaacctgt agggacaagg ccctgggatg ttcagtggag   4860
cctgagtcat tttataaaaa agcatgactc tagggtccaa aattcctttg aagctgttgc   4920
tatccagagt gaagtccctt ctttaggaca gggtggccct cctccctcct ggatgtcaca   4980
tcttcggtgg aggggcagaa aggggactgg gtattctcct caccctggcc ctagtgcttc   5040
aaatcttaaa aaaacgtttt tatttgtgct tctgcaccac cttctagccc acctcgtttc   5100
ctggcctcta acttgatgag agcgtgtgtc attttcacac tgattctcca catggcaggc   5160
ggtgcttctt agcctcctgc agacagtgag gccccacggt cttgtccaag gtcacacagc   5220
gtgtaatggg cagggtcaga gtctggagtc tggacctggg tctcctagct gcactgcact   5280
gctgccccat gggttaatca gctcagcata ccgtggctga acagctacct cataccaagg   5340
cctgtggcgc catgacaggg attgacaggg tccctgcctt ggaaacccgt agtctaagta   5400
gaggagactg acaagtcaat gccttccatc agtctgctca acacacgttt accaagtgcc   5460
tactgtgtgc tgcagaggcg aagatgacac agctcaggcc tttcccttga gcttacagtt   5520
caggaggaga gactgaccag tgactgccag tacagttgac tatgggacaa tgtgctcagc   5580
cttggggaga gacgaagaag gtacccgtat agcaccagat gacaggcacg agccccacag   5640
gccagggcag ctgctcagag gagagtaggc caagcagaag gcaaacagaa ggctgcaggc   5700
atttgccatc gagagctgga cttcaaactg ggcatcatac cagcctgggt tcgagtcctg   5760
cccagcccct tattggctgt ctaaccctga gcaaatccct tcacctctct gagcctcatt   5820
cctctatctg taaaccagtt ataataattg gaacattcat ttaaggacta aatgaggtcg   5880
tgaagcattc agcagatgct aggtacggaa actcgctgaa gtgggggcag gttaagaagc   5940
ctctggggat acgaaggcat ccagggacta gttgtggcag gaggctgtta ccacttaggt   6000
ctgaagggta aggagaggga atagctttcc ctctgcccag ttggagccgg tggcatggag   6060
gagaggctgc ctgtggggaa tcacccgagg gttcaccgct gccatgcgca gggagtcagg   6120
aggtagggag ggagtggggc agatgcacac catttttttt tttttttgag actctgttgc   6180
ccagactgga gtgcagtggt gccatatctg cacctctgcc tcccgggttc aagctcactg   6240
caacctctgc ctcccgggtt caagcgattc tcctgcctca gcctcccgag tagctgggac   6300
tacaggtgtg tgccaccatg cctggctaat ttttgtattt ttaatagaga tggggtttca   6360
ccatgttggc caggctggtc tcgaactctc gacctcaggt gatcccccac ctcggcctcc   6420
caaagtgctg ggattacagg cgtgagtcac cgctcccagc tgctgatgca ctcttgtcct   6480
tctaactcct gctagtgcct cccattggct gagcccaact ggaagctttg caagggagct   6540
ggtgctgcag tttgcactga gcaggctgga gaaggctgga gaatagacta ggggacaaac   6600
cgaattgcca gtgctgttat gtcatgattt aggcatggag tccagggcct gagcttcact   6660
ccatgtccat cctgcccaga gccttggcac agcctggctc ccagacaaga tgtcaagttc   6720
agaatccttc ctaaaaggaa tcctctatgc cagaccgtgt tgcagggata tgggagtgct   6780
gggctcccag cctgatcaag gagcgagaaa actcaggctc ctagtctgtc ctccggggca   6840
ctagcaggga caaggtggga ggctgctggg ctgggatgtg gggacaggtt tgatcaggta   6900
aggccaggct gtggctgtgt ttgctgctgt ccaaatggct taagcagagt cccccggcct   6960
ctctggcttc tgcaggcctt gaagttgccc catgtcgact acatcgagga ggactcctct   7020
```

```
gtctttgccc agagcatccc gtggaacctg gagcggatta cccctccacg gtaccgggcg   7080
gatgaatacc agccccccgg taagaccccc atctgtgccc tgccccaccc catctgagct   7140
gaatccattt gctctgccct ggcctggcct ccctgctggt ggtttccact tctcgggggg   7200
ctttgggact cagcacctcc actgacccct ttttttctgt cccatcccca tcccctgcag   7260
cccccactgc ctgccttcct gttgccccac aaatgcaaaa gtcttgcctt aaatgatcct   7320
cttttccttc ttttctcttg ttttcctttt ctcaccattt ggaatggccc agcaggctgc   7380
acttaccttg gaaggagggt tcatctgatg gtgactctac ctagggcccc caggcctcta   7440
taactcccag tgccctgcag actggaccag atcctttaat gggatagaca caaccctgtc   7500
tgggatgcct ctgcctacct tcctgttttg ctgctccacc tgcctccagc tccgtttggc   7560
ttcctggggc tccctgcctg ggccactttg tgtcttccct ctaggccttt ctttccactg   7620
ttccctctgc ctggtgtggc ctggctatgg aagggaggga ggaggagcgg ccatggaaaa   7680
cggtctgcat tctagcaggg acttgcaggt ggcaattcag tcggggaaga ctctagatgc   7740
acctggcctg aggagagaat gaagggttct agttggactg tgttaagttt gaggtgccca   7800
tggtgtgagg tctggagctc agcgcagaga tgatgcaatg tggtgggtcc atgcaacatg   7860
gtgccaggac gcagagcttg gggtgaactc agctttcacc ccttaccggt tctcgtggga   7920
tcttgggaag ccactttctt ctatgagctt tgtcgttctt gtctgtaaaa tgggcacata   7980
accctgtccc tgtccttctc acaggttgct gtgagactcc aatgagttga aggatgtgca   8040
gatgcttttg gaagtgaaaa gttggggggc tactgtgtga ctttgcatac acccaaactg   8100
tgtgaccttg catatgtctg agttgctgcc attgcaacag atcagagctg gtgggctggg   8160
tgtggagaaa gggtttgtgt gggggacatc ctctggcaag ggtggcagca gcagaagtga   8220
ggggcctggt cggtcatgtg tgctgacccg gcctgggcag cctgtggcca gggagaggac   8280
agctcctctg taggaagagc ctgttccttt ccaaccaggt gagacctctt cagtggagcc   8340
ctggagcccc ctgtactcca catcagtgcc tcagggacct cccggagcag gctaatatca   8400
gagaccaaga gggacactgg cagaggatca cagagacccc agtccaggca gggactgaga   8460
agatcttgcc ccctaagtta gtttcctagc actgctgtga caaattacca ccccctcggt   8520
tggaacaagt tgattctctg cagtcctgga ggccagaagc ctgaatcagt gtcggcagga   8580
ccactttctc ccggggggct ccagggagaa gcttctcttg cctcttccgt gtcccaacag   8640
cggcagcaca ccaatcccag cctctgtctt cacacagcct tctctgtgtc tctctcctct   8700
tcattgtctc ataaggacac ttgtcattgg atttagggcc cactggatcc tccaggatga   8760
tctcatgtgg ggaaccttaa ccacatctgc aaggaccctt tttccaaata aggtcacagc   8820
cacaggttgt gggggttagg atgtgagtgt atctctttgg cagccactgt tccctcctct   8880
cccttgggcc agaagcagac gtggggccct ttcttcccca taggatgccc atggattgcc   8940
ccccttcccg cttcccccga gtgtctgtgg gaggtggcag gaatggcagg caggggtgtg   9000
gaacccctte tggagtcata tcaagggctt ggctggagga agtcctcctg gagctgttgg   9060
gctggcatgg ggcaggctgg ctgggcccag cagcagcttc ttcattcatg gggaggccac   9120
aagcatgggc cctagagctg gctgccgccc tcaaacccag accctgcact cttaactgtg   9180
tgaccttgca tacgtcactc accctctctg atcttcaggt tcctctgcaa aagggaggta   9240
atgataaccc tcactctggg gggctgtttg gagggttaaa tcagttattg ctgtagcatg   9300
catttctctg tcaggtattg agtgaggtgc tgtgatttta gccctgcatt tttcttttct   9360
```

-continued

```
taccattcaa taataacgtt ttgagcaccc actgtgcgcc aggcaccata ttaggtgctg   9420
gggatacaaa tgtgaatgaa atgaatgtgg tctcttcccc caacagtgta tccagaagat   9480
taatccattc cttaaacaaa tgctacttga cacagattag ttctggatag gctgagagct   9540
ctgaaggagt gcaggcagct gcgagcctgt gtatccagca gaaggatcag gaaaggattc   9600
ctggaggaag cgctgttcta gccaagacct acgggggcat tattaaccag gcaaagggga   9660
cggtgtccaa gcagtggaat gaacgtggat tgaagctgtg aggcaggagg gagtgtggcc   9720
tgtgcagaag ggaccgaggc tggtgagacc aggagggcct gggtggcctc caggtcagat   9780
gtgaaaggaa gaacttggcc acagtctgag cttctcaggc gtatggcagg gctgcctggt   9840
gagagggaat gagctccctg ctctggaggt atgcaagcag gactgggctc tcacctgcca   9900
gaggccacag agctttccag aggctggaag aggccactcc aaggcctctt tgcccctgag   9960
agtggtggct cttcttgagg ccaccttgcc acgctgtcac agggaactag cagcccctgc  10020
ctcacccggg ggtttggaag atagagggag gcctaggaag ggccctgtgt ctcatccgag  10080
ctgggcccct ttccagcctc tcactggaag gaagcccaag gatgttcctg tgggggcttt  10140
taccaggccc acctgccctc tgctggccat gcttgcagcc tcctgaccct gtcccagcag  10200
gacagtgggc tggtgtgagc gggcaggaac cgcctgcact tagaaggtgt ggggctgcct  10260
ccccgagctt ccatctgccg ctggggccac accccaggcc cagggatggg accccacagt  10320
ggtcacatca tcttgcagca gaacccaggt acagctcctg gagcagatgg tggtcccaag  10380
cacgggtggg accagaaagg actctcacct gggctaactc agctgcagcc tcagttccct  10440
cctcacacac gacgaggaac atggactgga agcctgccca gcaggccttc tgctcgatgt  10500
gcgttgtgtg gcttacgtcc agggagggaa gcagcctctg tgctgtcttc tagataagcc  10560
tgtattcccc gggctgtctg ccaatgtatc cagttgtccc gtcagcctgg aagctctgag  10620
ggaaaacctt gggctgcttc ctgagcacct gtatcccctg cagccagccc ggggcctctg  10680
ctaggagcag actgagcatg gcttatgggc ctggcaccat ctggcctctg cccaccttgc  10740
tggccttgtc ttgtgtctgc cccttcgaca ttccatagcc cagctcaata tctagtggtt  10800
cctctagggt ggcgagcact gtttggtctc cagatgtctt caggtcggag ctcacagcgc  10860
tctcagccac cccttcccag tgtagcaccg ggcacatggt agatgcctat tgatgagtga  10920
aagctcctaa cacactcaga gagcaaggac tccgcctcat cccacagcct gggaggagag  10980
gcagactgcc aaggacctgc tcagcatgct acagaagaaa ccaaagtgcc cacgggactg  11040
atcagtggag cttcctgccg agactggagg ccttagggca gggtagacag tgtgtgtgca  11100
ggctggggac tcacagttcg gactgtgccc agacctacta gcatagtggg tgggtgggag  11160
gatgcgggac tgggggccga ccttgcctga aattcatgtg ggatctcaga gcagccactg  11220
aattgctctg tagggggcta aatagtggcc cccacagata cacacaccca gacagagcct  11280
gtgagccaga ccttatttgg agaaaaggtc tttgtagatg taattaagca tctcaagatg  11340
gcatcatctg gattatgcgg tgggctgtaa gtcctgtgat gtgtctttat gagagaaagg  11400
cagagggaga tttgacacac acaggagggg ccacgtggag acagaggtgg agattggaga  11460
aatgtggcca caagccaggg aacaccagca gccaccagaa gccggaagac gtgaggcagg  11520
gttcttccca gagccttcgc tgctgagtct gggaatttgt gaccgaagcc ataagaagtg  11580
ggtacacgcc ctgagcctcc cacacttgct cacctgtcct gagatgagaa tctctactct  11640
gcagcatatt tggaggatca ctgcgggggc cacagaggtg ctgttcagat ggcacttcag  11700
aagactcagg agaccctggg gcaggagcag tttgactgac agcccagagg gctgccctct  11760
```

-continued

```
gattccacct gaggccctgc ttttcctggc tgcaggggtt ccagggccag gccatttccg  11820
ctggcgcagg actctgctag cagcaacctg cctgaagtct tcctttggcc tggctgagag  11880
tttctgagac ctgcgctgga gcggaggtgc ttccttcctt gcttcctttc ttcctctctc  11940
ccttctccat ccagcaggct ggacctgcct ggcatctgtg agctctccct actttctcct  12000
ataccctaac ctttgtcctg catgggcgac tcccccagtg agtctcttgc agcttttacc  12060
ccagtgcctg cttcttggag aatccaaact gatccagtta gggatgataa agtgtagggt  12120
aggcgctcgg tgactgtttt ctctgaggtt gtgactcgtg tgaggcagaa gcagtccccg  12180
tgagccctcc tggtatcttg tggagtggag aacgcttgga cctggagcca ggaggcccag  12240
acatacatcc tgtccgagct gcagcttcct gtctctaaaa tgagccggcc agcgcaggtg  12300
gccagacatc actgttattc tcctttgagt ctttaaatct tgttgtcttt cttgcagact  12360
cggtgagctg tgaaaggcta taataggggc tttattttac actttgatac tatttttga  12420
acattcatat tattgttaga tattgatatt catatgaagg agcaggatga cttgggtcct  12480
tcttggcagt agcattgcca gctgatggcc ttggacagtt acctgccctc tctaggcctc  12540
cctttccttg tctatgaaat acattataga ataggatgta gtgtgtgagg attttttgga  12600
ggttaaacga gtgaatatat ttaaggcgct ttcaccagtg cctgggatgt gctctgtagt  12660
ttctgtgtgt taactataag gttgacttta tgctcattcc ctcctctccc acaaatgtcg  12720
ccttggaaag acggaggcag cctggtggag gtgtatctcc tagacaccag catacagagt  12780
gaccaccggg aaatcgaggg cagggtcatg gtcaccgact tcgagaatgt gcccgaggag  12840
gacgggaccc gcttccacag acaggtaagc acggccgtct gatgggaggg ctgcctctgc  12900
ccatatcccc atcctggagg tgggtgggga ctgccacccc agagcgttgc agctgtactc  12960
ctgggttgca cccccccag ctgtcactgt cccctccctg ccatcagttg tgggaagggc  13020
gttcatccat ccagccacct gctgatttgt tatagggtgg aggggggtc tttctcatgt  13080
ggtccttgtg ttcgtcgagc aggccagcaa gtgtgacagt catggcaccc acctggcagg  13140
ggtggtcagc ggccgggatg ccggcgtggc caagggtgcc agcatgcgca gcctgcgcgt  13200
gctcaactgc caagggaagg gcacggttag cggcaccctc ataggtaagt gatggcccca  13260
gacgctggtc tctctccatc tggacctggc ctgggaggtg gcttgggctg ggcccaggga  13320
gagctaatgt ctcctaacca agaatgctgt ggcagcctct gccgcagagc cagagaacca  13380
gagtgccaag gctggcaggg ttcccagtgg ccacgagtgc agatgaagaa acccaggccc  13440
caagagggtc atgcaggtag cccagggagt tcagccttga ccctgggtca atgacctttc  13500
cacagttcca cactgctccc cttttaaaat ccggtgatgt ctttatgtct tttgttatgt  13560
tatcttcaat gtggagggac tcgaggtgat ctaagcaaac tttttctatc ttctgcttgc  13620
atacctctga gaccagggga ctcactcact tgcatgactg ggccctgcag gtcacactgg  13680
ccaggcagat gtggtggagg aactggcaga ggactttttc tagactgtga ctacatttag  13740
tccacccagc ggcccccta tgaagtccag ttgagaacta ggactctggg ggccggtgga  13800
cagagaagag ggagggttct ctcccttact gacttccttc tgtggccaga cattgagcaa  13860
ggcctctgta cagcatgtcc tggggctggc cttgccgtag ctgctaaata gttgacgaaa  13920
ccagtccaga gaggggaggt gactgccagg gtcgcacagc tcaagctggg gaactcgctg  13980
ggaaaactgt cagctctggg cagcagcttg acttccactg taagccccag cccccagggt  14040
caaacactgg ctctggtgct ggcagaggca gcccactagc ctgtttcaaa ggctgagaag  14100
```

-continued

```
gcccaggagt ctgccctgtg ctccaccagt tctgccctga gactttccta cagagtacag  14160
gttttgatgt tcagttttaa aggcaagaat caataacctt ctgccccatc aggtgacccc  14220
ttgtgcctgt cccacccctt tattgactga cctcggctca gtcaggtcag ttcctgaagg  14280
tcagtgtgtg gaggggaggc tgttctttcc cagaaaggcc ttccccaggc ctggtgctct  14340
ggcctctgga ggacttcctg gagaagtccc ttctttgggg tcccagtcag tgtatgggaa  14400
gcccttattg catgacctgg cacggggcag gggctcaaca gtcactattg ccttccttgc  14460
cactgccatt tcctcctctg taagcaggtg attgtgtgtc cagtctgagc acagagataa  14520
gcacacagca ggtgcttaat aactagcagc tgtaggctgg gcgcggtggc tcatgcctgt  14580
aatcccagca ctttgggagg ccgaggtggg cagatcacct gaggtcagga gttcgagacc  14640
agcctgttca acatggtgaa accccgtctc tactaaaaat acaaaaatta gccaggcatg  14700
gtggtgggtg tctgtatccc agctacttgg gaggctaagg caggagaatc gcttgaaccc  14760
aggaggtgga ggttgcagtg agctgagatc gtgccactgc aatccagcct gagtgataga  14820
gcgagattcc atctcaaaaa taaataagta aataactagc agctgtaaat gtggctgttg  14880
ttcttcacct ccacactcag tgccactcca ctccctccct ccgtggtgtg aggggcctca  14940
ctagctgtct cctaggagga gcatggctgt gagattccag ctccatcctt ggccacggct  15000
cctggagaca tcttagaggc caggatccag aaggctccca cacctcattt gacaggggag  15060
aagctgtcag ttccaggtcc ccttgcacat cagggccaga gctgcgttag gcctccagtc  15120
tccaggccac tgggccagag ctcacaggct ggcagagggt tagaactgtt actggtggct  15180
gggtgcagtg gctcacgcct gtaatcttag cactttggga gggcaaggcg ggaggatcat  15240
gaggtcagga catcgagacc atccttgcta acacggtgaa gccccgtctc tactaaaact  15300
acaaaaaatt agccgggcgt ggtggcaggc gcctgtagtc ccagctactc aggaggctga  15360
ggcaggagaa tggcgtgaac ccgggaggcg gagcttgcag tgagccgaga ttgcgccact  15420
gcactccagc ctgggcaata gagcgagact ccgtctggaa agaaaaaaaa aaaaaagagc  15480
tgttactgtt gacagtagca tgaggtagac catggcctgc accaaaatgg gggagtggag  15540
tgccactgag gccagaagga accacaccct caagggtggg gagttatggt atggggggtc  15600
ctaggcatgg agtcttttaa ttctttagac aatcctggga gcaactgtcc ctgtttcaca  15660
gagggcgggg ccacacagct ggtgagtggg cagccaagac tctgttcaag tttgtgtggg  15720
tccaacactt gcggccacgg tggaggggca tctgagccag gcctcagaga gtggcggggg  15780
aagttgggtg gggaagtgtg cccttctcat tcctctgagg ctcatcctct tggtgcctct  15840
ctttcatgga aagggataat aaggttattg tgaggatccc ctgagttcgt atattcagac  15900
gcttagacag agccaggcac agagaagggc ccggggttgg ctagtttgat tgctggtgta  15960
attgctaata tcttccagtt tgtattggtc aaggttctgc agagaagcag aaccagtagg  16020
atgtatatat taagagtttc aagctcatgt gaccgtgcgg gctggcaagt ctgaaatccg  16080
cagggcaggc caggcaggct ggcaattcct gcagaatttg atgttgcaat actgagtcct  16140
aaggcagtcc tggggcagaa ttccttcttc cctgggaggc ctcagtctgt tctcttaagg  16200
ccttcaactg attaaatgag gcctgcccaa gttatagaga gtaacctgcc ttactccgtc  16260
ttctgattta aatgttagtc acatctaaaa aatattttcg cagcagcatt tccactggct  16320
tttgaccaaa catcaggcca caaagttgat ccccaaaatt aaccatcact ctgtgcctgt  16380
aagggagggg ctgggaaagg ggagcaggtc tccccaaggg gtgaccttgg ctttgttcct  16440
cccaggcctg gagtttattc ggaaaagcca gctggtccag cctgtggggc cactggtggt  16500
```

gctgctgccc ctggcgggtg ggtacagccg cgtcctcaac gccgcctgcc agcgcctggc 16560
gagggctggg gtcgtgctgg tcaccgctgc cggcaacttc cgggacgatg cctgcctcta 16620
ctccccagcc tcagctcccg aggtaggtgc tggggctgct gccccaaggc gcgggtaggg 16680
ggcggagggc ggagggcgga gggagggcgg gcgggcaggc gggcttcttg tggcacgtgg 16740
gcttcttgtg gcacgttcct ggaggccgaa cccttctggc tttggaagga gtcgtcagag 16800
acccccgcca tgcgggaggc tggggaggaa ggggctcgaa acctccatca tcgcagagtc 16860
tgaatagcag tggccccgcc atgcgcccac gtagcggcgc ctacgtagcc acgcccccac 16920
accccgtcct ggccactctc cctcctgaag gtcttctggt acccgccccc tccccatctc 16980
catccccagg ccctgcgtcc tctgcccaat actctttggg cctccctgtt gtccagctct 17040
ctccgcggct ccatgactga caacttgagc aaggctaatg tgaatgggag cggttgaggg 17100
ctcagacctc tcacccgagg aacatccaca gagtgtgccg catgcccggt gcagtgtggc 17160
tgcggggaca cagacacgga gcctcggccc tgaggagctg gggggcagtg accgtccctc 17220
ctctgaccca ccactcctcc agtgtcagga cactgcgggt atctagggga aggaatcttg 17280
ttccacttca agtctggaac ttcaagtctg tgtgtgtgcg tgcgcgcgcg cgcgttgggg 17340
gtgggggttg cagagcagat gcgtacctga cagcggtaac ctaggtcccc cctggcctat 17400
caaggcttcc ctggcggccg aatttaaagg catcaagcaa acaaagccca acacatctct 17460
gccttgtcct ctcagtttcc ccccgtggca cttagaacca cttgatacac cgaatagttt 17520
cctatctccc ccactaggat gtaaactcca caggggcatt gggaatgctg cctggctatg 17580
gtagggacag aggggagcac cagggcgggg caggggtgcc agagttctgc ctgggcagtc 17640
agattttcct taggagggga catttgagtg ggacccaaac aggtgtatag cagttgtcca 17700
gcccagctgg caaggcctga gtctgcctct gcaacccctc tcttgggctc ctttctctgc 17760
cacccacctc ctcacctttc caggtcatca cagttggggc caccaatgcc caagaccagc 17820
cggtgaccct ggggactttg gggaccaact ttggccgctg tgtggacctc tttgccccag 17880
gggaggacat cattggtgcc tccagcgact gcagcacctg ctttgtgtca cagagtggga 17940
catcacaggc tgctgcccac gtggctggta agtcaccacc ccactgcctc ggccaccgtg 18000
atgctaacag ccccttggc agtcagggtc tgtgccggga cctccagtgc caggctctgt 18060
gcagggggac cagagatgaa gtaggcctga tggtgccttc aaggacactc agtctgatga 18120
gggaggcgag tgcacagagg aaacacgagg tcagggctgt attagaggga gcccagagga 18180
ggcacctgcc cagcccgagg gtcagagaag gcatcttgga ggagggacat ttgatcggga 18240
gcttgatgga tgaataggag ttcacctggc cgataagaca gcaactacca aggcttagag 18300
gtgtgagagg aggctgtctt acctcactga gtaaggactg caggcggctt accttcgaga 18360
agagagctta gtgtctgtgt gcacgtgtgt ttgtgtgtat gtgtgtgcgt gtgtgcactg 18420
gcaggagtcc cctgctgggg caggagggcc gggccatcac catctttcac cattcacccc 18480
tgcaccaggc attgcagcca tgatgctgtc tgccgagccg gagctcaccc tggccgagtt 18540
gaggcagaga ctgatccact tctctgccaa agatgtcatc aatgaggcct ggttccctga 18600
ggaccagcgg gtactgaccc ccaacctggt ggccgccctg ccccccagca cccatggggc 18660
aggtaagcag gatggcaggg tgggcaagtc caggctgggg cttgggaggt ctgtgtgacc 18720
ttgacagtct ctcccttctc ccttgtctgt gtaaggagga tgacgccacc ttaaatagga 18780
ttaaatgaga atggggctct gaaagggctg tgcaatattt tcataacgtg tttttataga 18840

-continued

```
gacagttgag tatgttcttt aagccctcct ctctcctacc atgaactaaa gatttctgtg  18900
gaggtcccct cactcccagc accccctcct catcccaggc ccttttttgca ggttggcagc  18960
tgttttgcag gactgtatgg tcagcacact cggggcctac acggatggcc acagccgtcg  19020
cccgctgcgc cccagatgag gagctgctga gctgctccag tttctccagg agtgggaagc  19080
ggcggggcga gcgcatggag gtgactgtac ccctccttcg tgtgtgtgtg tgtgtgtgtg  19140
tgtgtgtgtg tgtgtgtgtg tgtgtgtgtg tcagtgctgg gccctcaggg acccccagca  19200
agcccctcca tcctccagac tccagctctt ctgtaagctt acagggctgg ccagaccagg  19260
agtggggcac tcctcacttc acgcggctgg gggctgctgg agagagccac agcgggaagg  19320
gtttcctaga ggctgcagga cagtgctgga tggattttca atgctcacct gggtgtgagc  19380
gtgcggcagg gccgcgtgag ggtcagcgat ctgctactct ggactcagcc atctctaggc  19440
ccctctcact caggtgctcc atggttctgg gagctgagaa atctcaaacc agcaaaaaag  19500
tggaattgat gttgatgcta caggatagtg cacagatgcc atctggttgc agcattttgg  19560
tggaagggca gtgcccagct aggagagtga ggaggggcag gcatttctgg cttgaggaga  19620
tggggtctta atgctcgtgt gagaggcaga gtgggtggag tggagctggc tggatccttg  19680
ctttggcctc ctggatttct ctctatctcc attttgaaac cactctgtgt ttggaagaac  19740
ttttgagtat tcagagctgc ccactggcag aacagtcttc cttgggcagg agtgagctcc  19800
ttgtccccag aaggctgggt ctggctggcc cctggcaggg acactgatga gggtgcttga  19860
gttgatcctg tctagtccct ttctgtgttt tcaaagccca ttctaaagca gattcccatt  19920
tccgtctttg actctaaggc ccaagggggc aagctggtct gccgggccca caacgctttt  19980
gggggtgagg gtgtctacgc cattgccagg tgctgcctgc taccccaggc caactgcagc  20040
gtccacacag ctccaccagc tgaggccagc atggggaccc gtgtccactg ccaccaacag  20100
ggccacgtcc tcacaggtag gaggctgggc ttgccctggg gtgaggaggg gtctctttct  20160
ccttatgcac ccactgcccg cgaggcttgg tcctcacaag tgtgatccat gagactcaag  20220
cctgacttgc agttccatac tctggttctg ccacttccat gccctttgag cctgggcagg  20280
tgaccttact tctcctcatc tcagcttcct cctccataag agggaaaaag gtattacctg  20340
cctcattgtg ttgcaaggag atgggcagca tctagggcac tggcctggag tatcgcaggt  20400
gctttgccta aggtggtgca gtccaggaga ggcagctcca gagagaggcc cccggctggg  20460
gctgaaagga gggcagacct cggtttgaat ttcaccctgc cgctctatag ctgtgtgact  20520
tgggcaaatt acttaacatc tctgtatgag gaaatgatga gtgctaagca cttagcttag  20580
tgccgggaca atataaattc tagctatcgt tactattgtt ttcatcaccc gttgctttaa  20640
aatccagcct ctggtatagg caactattga cgggctaccc tgtgtcgaaa acatgcccag  20700
gcaggtagca ggaagtcaca gatggggacc tcttggggca tcaagggatg gtgccctgag  20760
gctgagctgt tctggttggg tggagcatga gaggtctggg aagacagtgg gactccagcc  20820
tggaataaga ggctcagagt tgattctcgt ctgagcacgt ccaggggaac cactgagggt  20880
ttgggaacag gagagtgagg gtgagaacct ggttctgggc acagcaggct ggcatgtagg  20940
atggatgttc aggaaagatg agcatagtca ggtggctggt gcccttgtcc aggggagagg  21000
ctccgtcagg ttcaggggtc ctggcttgga gggaagtccg ccatgctcta atcacgctcc  21060
cctttggaag tgctcagccg atgagctcac aggcacatgt cagtttgaag tcatggaatc  21120
tgactccatg aagcgcacct caaagagcac cattttgcag ctaagggaac tgcaggctgg  21180
acatgctgag tggctgcccc gagcccttgc agctaggaca tagagaatgc tagtaaccac  21240
```

aaccctacca tgttcagagc acatgccagg ctccatgctg gggcttcgca cgtgtcatct 21300
tcacagtgtc cctgtgagta ggtgtggttt ctctttccat cttacaaatg agtaaacaga 21360
gcctcagtgt agctaagtaa ccactatttt aggtttctta gccaatgggt gtgtctgact 21420
cctaagccca tggagggcat tctgaggtgg ttcagacaga ccccggctta cccttgaact 21480
tctgcctgct ggctgcatag ggaggggctg gggggagttt gagcatctca ggccatagag 21540
cccctgcctc actgtctcca tctctgggtg gaaagatggt gttttccctg agaaactaag 21600
gctcagagag gttgaatggc tctcccaagg tcacacagct ggtcagctgc agagttgaga 21660
acacaggagt cctggtgctc aggccagcat ctcttttttt ctttgagttg tttctaggtt 21720
tcctagctct tgcctcagac cttaaagaga gagggtctga tggggatggg cactggagac 21780
ggagcatccc agcatttcac atctgagctg gctttcctct gccccaggct gcagctccca 21840
ctgggaggtg gaggaccttg gcacccacaa gccgcctgtg ctgaggccac gaggtcagcc 21900
caaccagtgc gtgggccaca gggaggccag catccacgct tcctgctgcc atgccccagg 21960
tctggaatgc aaagtcaagg agcatggaat cccggcccct caggagcagg tgaagaggcc 22020
cgtgaggccg ggtgggtggg gtgctgcgtg tctctcctgc acagcttttc tgtgtcagtt 22080
tgtgccacca ccataccgcc atgcatcagg gtggcggttt gccaggtaga tgctgtgggc 22140
agcttccgcc attgtgtgga cagcatgtat atgtgtctct gtgtggctgg gtctgttttt 22200
gcttttgtcc agatcagtaa ggtttgctac ctgggtaccc cactccactt ggagtagaat 22260
gtgcataaat atggcataaa gaaatgcaat atgcatgcat ttattgattg atctattttt 22320
ttctgagatg gggtcttgct gtgttgccca ggctggtctc aaattcctgg gctcaagcaa 22380
tcctctggtc tcagcctccc caagtgttgg gattataggc atgagccgct gcacctggcc 22440
tctctgatct atttaacaaa cctgctggga gggtctcagg gtcaggagca gcactgggct 22500
ctgaggacac agagctcact cagccgtgac ccagaggggg tgcctgagct gcatgctgaa 22560
ggttgttagc atgaccagca aggcaagaaa aggccctgcc gagattagca aggcatgtgc 22620
caagccctgg aatgtgacag ccgggccttc tagaaacctg agtgtataac tctccttaaa 22680
agccagtagg agctcctcaa aaggcagccc taaggagtcc actcttaaat gaactcagag 22740
tcagttttaa aatgcaagtc tgtgttgatt ctggtctgga tggtgcattc ctcgagagca 22800
aaagacagtc ttggtcttgg atccacttgc cctgggtaca ctgagggctg ctaggttcca 22860
ggtgctcttc ctggcactgg ggagggatac aggcccaaga gacatgctgt tctccctcct 22920
ggagcatcta ttttagtgga ggaagacaga aaacaaacca ttaatataga gtactgaaaa 22980
gatgcgatgg agaaaactat agcaaggaag ggaatggggt gggagagagg tcaggagagg 23040
tctcgctgac aaggtggacg aaacaggcca tgaggcagag aacatgttcc aggcaaagca 23100
aaggccccca ggtggggatg tgcagggagt accaggaaac cagagaggtg ggaatagtta 23160
tgagatgggg ggtgcctcag aggggacagg gccaagtcag gtgagacctg agggtcacag 23220
tcagcagtga gctggggcca tgcaggggtc tggcctcaga ggagtgtggt ctggcctgga 23280
tctgaacctc tcactgtggc ctagctgctg agctgagaag agatgacaag gaccttgggc 23340
agaagcaggg agactggagg gaggcggtgg agggtccagg cgttggggcg gggctcaggc 23400
tggagtctga agggagcctg caggcctggt gggtggatgt gggtgggaga gggggaggat 23460
ggcaccaagg ctcgggcccc tggacagatg gagttgccat taagtgggat ggggcaggct 23520
atggggccat cagtttcaga gggatgagtt tggcactggc atggtaggca tctgtctatc 23580

-continued

```
tccacggccc tcaaaccagg catgaagcag gagctcacgt gtttggtcag ccatggtgca  23640

gaaccgcctg ggtgggaggt gcggggtggg agatacacgg ttgtgtccca aatgggctct  23700

gagccagcga gggccgtctg cactttggcc tcacagaagg atgtcggagg gagaaatgaa  23760

gtgtgggtgg gggtcccggg ccacgctaga catgtgcttt cttttcctcg ggctctggca  23820

ggtgaccgtg gcctgcgagg agggctggac cctgactggc tgcagtgccc tccctgggac  23880

ctcccacgtc ctgggggcct acgccgtaga caacacgtgt gtagtcagga gccgggacgt  23940

cagcactaca ggcagcacca gcgaaggggc cgtgacagcc gttgccatct gctgccggag  24000

ccggcacctg gcgcaggcct cccaggagct ccagtgacag ccccatccca ggatgggtgt  24060

ctggggaggg tcaagggctg gggctgagct ttaaaatggt tccgacttgt ccctctctca  24120

gccctccatg gcctggcacg aggggatggg gatgcttccg cctttccggg gctgctggcc  24180

tggcccttga gtggggcagc ctccttgcct ggaactcact cactctgggt gcctcctccc  24240

caggtggagg tgccaggaag ctccctccct cactgtgggg catttcacca ttcaaacagg  24300

tcgagctgtg ctcgggtgct gccagctgct cccaatgtgc cgatgtccgt gggcagaatg  24360

acttttattg agctcttgtt ccgtgccagg cattcaatcc tcaggtctcc accaaggagg  24420

caggattctt cccatggata ggggaggggg cggtaggggc tgcagggaca aacatcgttg  24480

gggggtgagt gtgaaaggtg ctgatggccc tcatctccag ctaactgtgg agaagcccct  24540

gggggctccc tgattaatgg aggcttagct ttctggatgg catctagcca gaggctggag  24600

acaggtgcgc ccctggtggt cacaggctgt gccttggttt cctgagccac ctttactctg  24660

ctctatgcca ggctgtgcta gcaacaccca aaggtggcct gcggggagcc atcacctagg  24720

actgactcgg cagtgtgcag tggtgcatgc actgtctcag ccaacccgct ccactacccg  24780

gcagggtaca cattcgcacc cctacttcac agaggaagaa acctggaacc agagggggcg  24840

tgcctgccaa gctcacacag caggaactga gccagaaacg cagattgggc tggctctgaa  24900

gccaagcctc ttcttacttc acccggctgg gctcctcatt tttacgggta acagtgaggc  24960

tgggaagggg aacacagacc aggaagctcg gtgagtgatg gcagaacgat gcctgcaggc  25020

atggaacttt ttccgttatc acccaggcct gattcactgg cctggcggag atgcttctaa  25080

ggcatggtcg ggggagaggg ccaacaactg tccctccttg agcaccagcc ccacccaagc  25140

aagcagacat ttatcttttg ggtctgtcct ctctgttgcc tttttacagc caacttttct  25200

agacctgttt tgcttttgta acttgaagat atttattctg ggttttgtag catttttatt  25260

aatatggtga ctttttaaaa taaaaacaaa caaacgttgt cctaa                  25305
```

```
<210> SEQ ID NO 2
<211> LENGTH: 25305
<212> TYPE: DNA
<213> ORGANISM: homo sapien

<400> SEQUENCE: 2

agcgacgtcg aggcgctcat ggttgcaggc gggcgccgcc gttcagttca gggtctgagc     60

ctggaggagt gagccaggca gtgagactgg ctcgggcggg ccgggacgcg tcgttgcagc    120

agcggctccc agctcccagc caggattccg cgcgcccctt cacgcgccct gctcctgaac    180

ttcagctcct gcacagtcct ccccaccgca aggctcaagg cgccgccggc gtggaccgcg    240

cacggcctct aggtctcctc gccaggacag caacctctcc cctggccctc atgggcaccg    300

tcagctccag gcggtcctgg tggccgctgc cactgctgct gctgctgctg ctgctcctgg    360

gtcccgcggg cgcccgtgcg caggaggacg aggacggcga ctacgaggag ctggtgctag    420
```

-continued

```
ccttgctttc cgaggaggac ggcctggccg aagcacccga gcacggaacc acagccacct    480
tccaccgctg cgccaaggtg cgggtgtagg gatgggaggc cggggcgaac ccgcagccgg    540
gacggtgcgg tgctgtttcc tctcgggcct cagtttcccc ccatgtaaga gaggaagtgg    600
agtgcaggtc gccgagggct cttcgcttgg cacgatcttg gggactgcag gcaaggcggc    660
gggggaggac gggtagtggg gagcacggtg gagagcgggg acggccggct ctttggggac    720
ttgctggggc gtgcggctgc gctattcagt gggaaggttc gcggggttgg gagacccgga    780
ggccgaggaa gggcgagcag agcactgcca ggatatcctg cccagatttc ccagtttctg    840
cctcgccgcg gcacaggtgg gtgaaggagt gaatgcctgg aacgtactgg gaactgcacc    900
aggcacagag aaagcgggct tgccattata gtgggttccg atttggtttg gaaaacatgg    960
gcagcggagg gtggagggcc tggagagaag gccctacccg agacaggggc ggggtgggaa   1020
ggacggcaga tgctgggagc acgaggcaat ttctttatga cacagaactc atgctctagt   1080
attccatctg tttcagccga agaaaagaac cagctgaagg ggcaggggag aaggggcgga   1140
ggtattctcg aggcccattg gcgtccttta ggactcaggc agggaagggc ccttggtgct   1200
ctggagccgg aggtggtgcg cctggtactg ggaccccgga gctgagcccg gcgcctcagc   1260
ccacctggct gtctgccgac cgtgtgcggg gcgagtttgc tcaacaactc tgccagcttc   1320
tggccctcag gctgtgggaa gcttcttccc ggggcgagac cactagcttt ttctaagtat   1380
taccagccca ggacttggct gaggttctgt gtccccccagc ttggagtcag atgtggggtt   1440
gaatcttggc ttcctctcac tagctgtggt gcttgacaag tcacttatcc ttgagcctcc   1500
attgcctaat ctttaaaagg gaggtgacaa tcgtccctac ggctcagtgg cagcagatgg   1560
ggagatgaag ggaaagttct gttgaccatg agtgaactta caatgcaagc cccgggggga   1620
tcacttgcag ttttgtccct gtctgcagtg tgacctgttg gtgacattgt ctttgctcca   1680
aaccacagct cctggggcag aggggaaaat tctgccactc acagctgcct gcccacgctt   1740
ctgtctgagt gtgctgggtg gcaggatggc aagtccttac tcagctcagt atagccctct   1800
tccttgttcc ctgagccttt gactttctcg agggatgttg tggggttgtg gccaggataa   1860
gaaagggcat ttcaagttac cactgctcca aaacaactgt tctggaaata gtgagtaccc   1920
catcctgaga ggtgagtaag cagaggctgt atgaccacct gaaccaagcc cttgaggatg   1980
tttcttctct ggtggaagtt tggaacagga gcctcctcaa gttcatttat tcattcattc   2040
aatggttatt ttgtgggaat cgaatttaga atgaaaatat tttttggcaa gcagaaaata   2100
atttttagac caatcctttt cttttagtca tgagaaactg aggcccagag agaggaggtc   2160
accccaggtg cattagaact gggtttccag aactgacact ccactgcaca gagtactctc   2220
ccaattcatt caatttttat ttagcggaag gcattttcag atgggtcttt gaagcattag   2280
taggagttca gcgatgatgg tgtcatgaga attttattct aggattagga ggtaccatga   2340
acaaagatac agagctggga aaaccagagg tggaagataa ggagcacatg tccacagttc   2400
tttttctttt ttttttgaga tggagtttcg ctcttgttgc ccaggctgga gtgcaatggt   2460
gcagtctcag ctcactgcaa catctgtctc ccgggttcaa gtggttctcc tgcctcagcc   2520
tcccaagaag ctgggattac aggtacctgc caccacgccc ggctaatttt tgtattttta   2580
gtagagaagg ggtttcacca cgttggccag gctagtcgca aactcctgac ctcctcagtg   2640
gatccgagga ggtgatcctc ccgcctcagc ctcccaaagt gctcgaatta caggtgtgag   2700
ccaccacgcc tggcctccac agttctttat ccaccgtctg aaatgtaaaa tgttacgaaa   2760
```

-continued

```
accaaaagtt ttttttgtga tttatttgat ggtagcacct gacgtgaact gacatgagat   2820
tatttttaat ttagttgtgt gaatatgcat attcatatat tttgctgcat agattacagt   2880
atgcagctcc agattcttcc aagcagactc tgattgccca ttactgcctt tctaaaatcc   2940
aaacaagttc tgaggttcaa aaccgttttg gccctaaggc tttgggtaaa gggggtggac   3000
tctgttctac tctgactgga gtccaagatg catatataca gagatatggg tgatggggct   3060
gcaaggtagg ttgaggtagg ggccaaggag gagcatggag tttggacttg attcatgagg   3120
ctgtggggag ccagtgaagg ttcttaagca ggtatgtctg cctgagagca gttggagcag   3180
acaagagcta aaaaccaaac aaatcaccat agatagtggc tgctataatt tgtttgtccc   3240
ctccaaatct catgtggaaa tttggtcctc agtgttggaa gtggggccta atgggaggtg   3300
tttgggtcat gggggaggaa cccctgtgaa aggcttggtg ccgtccttgt gataatgagt   3360
aagttctccc gctatgattt cccttgaagg ctgattatta aaaagagctt ggcacctccc   3420
tctcttctct cttgcttctt ctcttgccat gtgattgatc tctgcacatg taggctcccc   3480
ttcaccttct gccatcagtg aaagcagctt aaggccctca ccagaagcag atgctggtgc   3540
catgcttcct ggagagcttg cagaatcatg agctgaataa atccctttc cttgtaaatt    3600
actcaccttc aggtattcct ttatatagca acacaaaagg actaagacag tggccttgac   3660
ttttctctct ctttaagaag tgttgccttt gctcacttag tcatcccttc tgcctgcatt   3720
tgtagagcat ctggatggga gatttatata accgtcactc ttgactttcc cagcaggcct   3780
atgtcatagg tactgtggtc tctacaatac agcagaggta tctgaggctc cgagaggttg   3840
agtgacttgc tcatggctgc acaaccagta aatattggag ctggaattca ggtccacggt   3900
ttcctggctc caaagcccat gatttttcc ctcaatttat tctgactggg gcatggggga    3960
gggggtggcc tttgggcagg gccaccagga gcgaccaggc ccgtagagag ctgggtgcag   4020
gtacagagga aaacctgttg tcgagtgtgg cccgtagttc ccatttttgc ctgaatggca   4080
catttgaaag tgttatataa ccatgtgaat aataatagtt ggcctatatg agttctttaa   4140
tttgcttttt ggtccgcatt tggtaacttc tttatcatct actatactct gttgtgtctc   4200
ttttgttgta atttgtaagt aggggtgaga taaagtacac ctagggtttg ctgggtttct   4260
tccatgtcat catgttcctc cttgcatggg gccaggatcc gtggaggttg cctggcacct   4320
acgtggtggt gctgaaggag gagacccacc tctcgcagtc agagcgcact gcccgccgcc   4380
tgcaggccca ggctgcccgc cggggatacc tcaccaagat cctgcatgtc ttccatggcc   4440
ttcttcctgg cttcctggtg aagatgagtg gcgacctgct ggagctggtg agccacccctt  4500
tttgggaatg gcacttcctg atagggctgg gccactgcat atacactggg gactgtgctt   4560
agtaggccca ttgctgaaaa tcagaagggg acagcaagta tgtattgagc acttatcggg   4620
taccaagcac agtaactact ggctttctgt atagaattcc ctttaagcct ggccatgccc   4680
cagtggtacg tctatcttca tttgaaagac gaggagactg aagttcagag gggaccacac   4740
agacagctag gggtagagcc tggatcaaac ccattggtct gcctgccagc cattcttgtg   4800
ccaatgcatc tgctgcctac ggaaacctgt agggacaagg ccctgggatg ttcagtggag   4860
cctgagtcat tttataaaaa agcatgactc tagggtccaa aattcctttg aagctgttgc   4920
tatccagagt gaagtccctt ctttaggaca gggtggccct cctccctcct ggatgtcaca   4980
tcttcggtgg aggggcagaa aggggactgg gtattctcct caccctggcc ctagtgcttc   5040
aaatcttaaa aaaacgtttt tatttgtgct tctgcaccac cttctagccc acctcgtttc   5100
ctggcctcta acttgatgag agcgtgtgtc attttcacac tgattctcca catggcaggc   5160
```

-continued

```
ggtgcttctt agcctcctgc agacagtgag gccccacggt cttgtccaag gtcacacagc   5220
gtgtaatggg cagggtcaga gtctggagtc tggacctggg tctcctagct gcactgcact   5280
gctgccccat gggttaatca gctcagcata ccgtggctga acagctacct cataccaagg   5340
cctgtggcgc catgacaggg attgacaggg tccctgcctt ggaaacccgt agtctaagta   5400
gaggagactg acaagtcaat gccttccatc agtctgctca acacacgttt accaagtgcc   5460
tactgtgtgc tgcagaggcg aagatgacac agctcaggcc tttcccttga gcttacagtt   5520
caggaggaga gactgaccag tgactgccag tacagttgac tatgggacaa tgtgctcagc   5580
cttggggaga gacgaagaag gtacccgtat agcaccagat gacaggcacg agccccacag   5640
gccagggcag ctgctcagag gagagtaggc caagcagaag gcaaacagaa ggctgcaggc   5700
atttgccatc gagagctgga cttcaaactg ggcatcatac cagcctgggt tcgagtcctg   5760
cccagcccct tattggctgt ctaaccctga gcaaatccct tcacctctct gagcctcatt   5820
cctctatctg taaaccagtt ataataattg gaacattcat ttaaggacta aatgaggtcg   5880
tgaagcattc agcagatgct aggtacggaa actcgctgaa gtgggggcag gttaagaagc   5940
ctctggggat acgaaggcat ccagggacta gttgtggcag gaggctgtta ccacttaggt   6000
ctgaagggta aggagaggga atagctttcc ctctgcccag ttggagccgg tggcatggag   6060
gagaggctgc ctgtggggaa tcacccgagg gttcaccgct gccatgcgca gggagtcagg   6120
aggtagggag ggagtggggc agatgcacac catttttttt tttttttgag actctgttgc   6180
ccagactgga gtgcagtggt gccatatctg cacctctgcc tcccgggttc aagctcactg   6240
caacctctgc ctcccgggtt caagcgattc tcctgcctca gcctcccgag tagctgggac   6300
tacaggtgtg tgccaccatg cctggctaat tttgtatttt ttaatagaga tggggtttca   6360
ccatgttggc caggctggtc tcgaactctc gacctcaggt gatcccccac ctcggcctcc   6420
caaagtgctg ggattacagg cgtgagtcac cgctcccagc tgctgatgca ctcttgtcct   6480
tctaactcct gctagtgcct cccattggct gagcccaact ggaagctttg caagggagct   6540
ggtgctgcag tttgcactga gcaggctgga gaaggctgga gaatagacta ggggacaaac   6600
cgaattgcca gtgctgttat gtcatgattt aggcatggag tccagggcct gagcttcact   6660
ccatgtccat cctgcccaga gccttggcac agcctggctc ccagacaaga tgtcaagttc   6720
agaatccttc ctaaaaggaa tcctctatgc cagaccgtgt tgcagggata tgggagtgct   6780
gggctcccag cctgatcaag gagcgagaaa actcaggctc ctagtctgtc ctccggggca   6840
ctagcaggga caaggtggga ggctgctggg ctgggatgtg gggacaggtt tgatcaggta   6900
aggccaggct gtggctgtgt ttgctgctgt ccaaatggct taagcagagt cccccggcct   6960
ctctggcttc tgcaggcctt gaagttgccc catgtcgact acatcgagga ggactcctct   7020
gtctttgccc agagcatccc gtggaacctg gagcggatta cccctccacg gtaccgggcg   7080
gatgaatacc agcccccggg taagaccccc atctgtgccc tgccccaccc catctgagct   7140
gaatccattt gctctgccct ggcctggcct ccctgctggt ggtttccact tctcgggggg   7200
ctttgggact cagcacctcc actgacccct ttttttctgt cccatcccca tcccctgcag   7260
cccccactgc ctgccttcct gttgccccac aaatgcaaaa gtcttgcctt aaatgatcct   7320
cttttccttc ttttctcttg ttttcctttt ctcaccattt ggaatggccc agcaggctgc   7380
acttaccttg gaaggagggt tcatctgatg gtgactctac ctagggcccc caggcctcta   7440
taactcccag tgccctgcag actggaccag atcctttaat gggatagaca caaccctgtc   7500
```

-continued

```
tgggatgcct ctgcctacct tcctgttttg ctgctccacc tgcctccagc tccgtttggc   7560
ttcctggggc tccctgcctg ggccactttg tgtcttccct ctaggccttt ctttccactg   7620
ttccctctgc ctggtgtggc ctggctatgg aagggaggga ggaggagcgg ccatggaaaa   7680
cggtctgcat tctagcaggg acttgcaggt ggcaattcag tcggggaaga ctctagatgc   7740
acctggcctg aggagagaat gaagggttct agttggactg tgttaagttt gaggtgccca   7800
tggtgtgagg tctggagctc agcgcagaga tgatgcaatg tggtgggtcc atgcaacatg   7860
gtgccaggac gcagagcttg ggtgaactc agctttcacc ccttaccggt tctcgtggga    7920
tcttgggaag ccactttctt ctatgagctt tgtcgttctt gtctgtaaaa tgggcacata   7980
accctgtccc tgtccttctc acaggttgct gtgagactcc aatgagttga aggatgtgca   8040
gatgcttttg gaagtgaaaa gttggggggc tactgtgtga ctttgcatac acccaaactg   8100
tgtgaccttg catatgtctg agttgctgcc attgcaacag atcagagctg gtgggctggg   8160
tgtggagaaa gggtttgtgt gggggacatc ctctggcaag ggtggcagca gcagaagtga   8220
ggggcctggt cggtcatgtg tgctgacccg gcctgggcag cctgtggcca gggagaggac   8280
agctcctctg taggaagagc ctgttccttt ccaaccaggt gagacctctt cagtggagcc   8340
ctggagcccc ctgtactcca catcagtgcc tcagggacct cccggagcag gctaatatca   8400
gagaccaaga gggacactgg cagaggatca cagagacccc agtccaggca gggactgaga   8460
agatcttgcc ccctaagtta gtttcctagc actgctgtga caaattacca ccccctcggt   8520
tggaacaagt tgattctctg cagtcctgga ggccagaagc ctgaatcagt gtcggcagga   8580
ccactttctc ccggggggct ccagggagaa gcttctcttg cctcttccgt gtcccaacag   8640
cggcagcaca ccaatcccag cctctgtctt cacacagcct tctctgtgtc tctctcctct   8700
tcattgtctc ataaggacac ttgtcattgg atttagggcc cactggatcc tccaggatga   8760
tctcatgtgg ggaaccttaa ccacatctgc aaggaccctt tttccaaata aggtcacagc   8820
cacaggttgt gggggttagg atgtgagtgt atctctttgg cagccactgt tccctcctct   8880
cccttgggcc agaagcagac gtggggccct ttcttcccca taggatgccc atggattgcc   8940
ccccttcccg cttcccccga gtgtctgtgg gaggtggcag gaatggcagg cagggtgtg    9000
gaacccccttc tggagtcata tcaagggctt ggctggagga agtcctcctg gagctgttgg  9060
gctggcatgg ggcaggctgg ctgggcccag cagcagcttc ttcattcatg gggaggccac   9120
aagcatgggc cctagagctg gctgccgccc tcaaacccag accctgcact cttaactgtg   9180
tgaccttgca tacgtcactc accctctctg atcttcaggt tcctctgcaa aagggaggta   9240
atgataaccc tcactctggg gggctgtttg gagggttaaa tcagttattg ctgtagcatg   9300
catttctctg tcaggtattg agtgaggtgc tgtgatttta gccctgcatt tttcttttct   9360
taccattcaa taataacgtt ttgagcaccc actgtgcgcc aggcaccata ttaggtgctg   9420
gggatacaaa tgtgaatgaa atgaatgtgg tctcttcccc caacagtgta tccagaagat   9480
taatccattc cttaaacaaa tgctacttga cacagattag ttctggatag gctgagagct   9540
ctgaaggagt gcaggcagct gcgagcctgt gtatccagca gaaggatcag gaaaggattc   9600
ctggaggaag cgctgttcta gccaagacct acgggggcat tattaaccag gcaaagggga   9660
cggtgtccaa gcagtggaat gaacgtggat tgaagctgtg aggcaggagg gagtgtggcc   9720
tgtgcagaag ggaccgaggc tggtgagacc aggagggcct gggtggcctc caggtcagat   9780
gtgaaaggaa gaacttggcc acagtctgag cttctcaggc gtatggcagg gctgcctggt   9840
gagagggaat gagctccctg ctctggaggt atgcaagcag gactgggctc tcacctgcca   9900
```

-continued

```
gaggccacag agctttccag aggctggaag aggccactcc aaggcctctt tgcccctgag   9960
agtggtggct cttcttgagg ccaccttgcc acgctgtcac agggaactag cagcccctgc  10020
ctcacccggg ggtttggaag atagagggag gcctaggaag ggccctgtgt ctcatccgag  10080
ctgggcccct ttccagcctc tcactggaag gaagcccaag gatgttcctg tgggggcttt  10140
taccaggccc acctgccctc tgctggccat gcttgcagcc tcctgaccct gtcccagcag  10200
gacagtgggc tggtgtgagc gggcaggaac cgcctgcact tagaaggtgt ggggctgcct  10260
ccccgagctt ccatctgccg ctggggccac accccaggcc cagggatggg accccacagt  10320
ggtcacatca tcttgcagca gaacccaggt acagctcctg gagcagatgg tggtcccaag  10380
cacgggtggg accagaaagg actctcacct gggctaactc agctgcagcc tcagttccct  10440
cctcacacac gacgaggaac atggactgga agcctgccca gcaggccttc tgctcgatgt  10500
gcgttgtgtg gcttacgtcc agggagggaa gcagcctctg tgctgtcttc tagataagcc  10560
tgtattcccc gggctgtctg ccaatgtatc cagttgtccc gtcagcctgg aagctctgag  10620
ggaaaacctt gggctgcttc ctgagcacct gtatcccctg cagccagccc ggggcctctg  10680
ctaggagcag actgagcatg gcttatgggc ctggcaccat ctggcctctg cccaccttgc  10740
tggccttgtc ttgtgtctgc cccttcgaca ttccatagcc cagctcaata tctagtggtt  10800
cctctagggt ggcgagcact gtttggtctc cagatgtctt caggtcggag ctcacagcgc  10860
tctcagccac cccttcccag tgtagcaccg ggcacatggt agatgcctat tgatgagtga  10920
aagctcctaa cacactcaga gagcaaggac tccgcctcat cccacagcct gggaggagag  10980
gcagactgcc aaggacctgc tcagcatgct acagaagaaa ccaaagtgcc cacgggactg  11040
atcagtggag cttcctgccg agactggagg ccttagggca gggtagacag tgtgtgtgca  11100
ggctggggac tcacagttcg gactgtgccc agacctacta gcatagtggg tgggtgggag  11160
gatgcgggac tgggggccga ccttgcctga aattcatgtg ggatctcaga gcagccactg  11220
aattgctctg tagggggcta aatagtggcc cccacagata cacacaccca gacagagcct  11280
gtgagccaga ccttatttgg agaaaaggtc tttgtagatg taattaagca tctcaagatg  11340
gcatcatctg gattatgcgg tgggctgtaa gtcctgtgat gtgtctttat gagagaaagg  11400
cagagggaga tttgacacac acaggagggg ccacgtggag acagaggtgg agattggaga  11460
aatgtggcca caagccaggg aacaccagca gccaccagaa gccggaagac gtgaggcagg  11520
gttcttccca gagccttcgc tgctgagtct gggaatttgt gaccgaagcc ataagaagtg  11580
ggtacacgcc ctgagcctcc cacacttgct cacctgtcct gagatgagaa tctctactct  11640
gcagcatatt tggaggatca ctgcgggggc cacagaggtg ctgttcagat ggcacttcag  11700
aagactcagg agaccctggg gcaggagcag tttgactgac agcccagagg gctgccctct  11760
gattccacct gaggccctgc ttttcctggc tgcaggggtt ccagggccag gccatttccg  11820
ctggcgcagg actctgctag cagcaacctg cctgaagtct tcctttggcc tggctgagag  11880
tttctgagac ctgcgctgga gcggaggtgc ttccttcctt gcttcctttc ttcctctctc  11940
ccttctccat ccagcaggct ggacctgcct ggcatctgtg agctctccct actttctcct  12000
ataccctaac ctttgtcctg catgggcgac tcccccagtg agtctcttgc agcttttacc  12060
ccagtgcctg cttcttggag aatccaaact gatccagtta gggatgataa agtgtagggt  12120
aggcgctcgg tgactgtttt ctctgaggtt gtgactcgtg tgaggcagaa gcagtccccg  12180
tgagccctcc tggtatcttg tggagtggag aacgcttgga cctggagcca ggaggcccag  12240
```

-continued

```
acatacatcc tgtccgagct gcagcttcct gtctctaaaa tgagccggcc agcgcaggtg  12300
gccagacatc actgttattc tcctttgagt ctttaaatct tgttgtcttt cttgcagact  12360
cggtgagctg tgaaaggcta taataggggc tttattttac actttgatac tattttttga  12420
acattcatat tattgttaga tattgatatt catatgaagg agcaggatga cttgggtcct  12480
tcttggcagt agcattgcca gctgatggcc ttggacagtt acctgccctc tctaggcctc  12540
cctttccttg tctatgaaat acattataga ataggatgta gtgtgtgagg atttttttgga  12600
ggttaaacga gtgaatatat ttaaggcgct ttcaccagtg cctgggatgt gctctgtagt  12660
ttctgtgtgt taactataag gttgacttta tgctcattcc ctcctctccc acaaatgtcg  12720
ccttggaaag acggaggcag cctggtggag gtgtatctcc tagacaccag catacagagt  12780
gaccaccggg aaatcgaggg cagggtcatg gtcaccgact tcgagaatgt gcccgaggag  12840
gacgggaccc gcttccacag acaggtaagc acggccgtct gatgggaggg ctgcctctgc  12900
ccatatcccc atcctggagg tgggtgggga ctgccacccc agagcgttgc agctgtactc  12960
ctgggttgca cccccccag ctgtcactgt cccctccctg ccatcagttg tgggaagggc  13020
gttcatccat ccagccacct gctgatttgt tatagggtgg agggggggtc tttctcatgt  13080
ggtccttgtg ttcgtcgagc aggccagcaa gtgtgacagt catggcaccc acctggcagg  13140
ggtggtcagc ggccgggatg ccggcgtggc caagggtgcc agcatgcgca gcctgcgcgt  13200
gctcaactgc caagggaagg gcacggttag cggcaccctc ataggtaagt gatggcccca  13260
gacgctggtc tctctccatc tggacctggc ctgggaggtg gcttgggctg ggcccaggga  13320
gagctaatgt ctcctaacca agaatgctgt ggcagcctct gccgcagagc cagagaacca  13380
gagtgccaag gctggcaggg ttcccagtgg ccacgagtgc agatgaagaa acccaggccc  13440
caagagggtc atgcaggtag cccagggagt tcagccttga ccctgggtca atgacctttc  13500
cacagttcca cactgctccc cttttaaaat ccggtgatgt ctttatgtct tttgttatgt  13560
tatcttcaat gtggagggac tcgaggtgat ctaagcaaac tttttctatc ttctgcttgc  13620
atacctctga gaccagggga ctcactcact tgcatgactg ggccctgcag gtcacactgg  13680
ccaggcagat gtggtggagg aactggcaga ggactttttc tagactgtga ctacatttag  13740
tccacccagc ggcccccta tgaagtccag ttgagaacta ggactctggg ggccggtgga  13800
cagagaagag ggagggttct ctcccttact gacttccttc tgtggccaga cattgagcaa  13860
ggcctctgta cagcatgtcc tggggctggc cttgccgtag ctgctaaata gttgacgaaa  13920
ccagtccaga gaggggaggt gactgccagg gtcgcacagc tcaagctggg gaactcgctg  13980
ggaaaactgt cagctctggg cagcagcttg acttccactg taagccccag cccccagggt  14040
caaacactgg ctctggtgct ggcagaggca gcccactagc ctgtttcaaa ggctgagaag  14100
gcccaggagt ctgccctgtg ctccaccagt tctgccctga gactttccta cagagtacag  14160
gttttgatgt tcagttttaa aggcaagaat caataacctt ctgccccatc aggtgacccc  14220
ttgtgcctgt cccacccctt tattgactga cctcggctca gtcaggtcag ttcctgaagg  14280
tcagtgtgtg gaggggaggc tgttctttcc cagaaaggcc ttccccaggc ctggtgctct  14340
ggcctctgga ggacttcctg gagaagtccc ttctttgggg tcccagtcag tgtatgggaa  14400
gcccttattg catgacctgg cacggggcag ggctcaaca gtcactattg ccttccttgc  14460
cactgccatt tcctcctctg taagcaggtg attgtgtgtc cagtctgagc acagagataa  14520
gcacacagca ggtgcttaat aactagcagc tgtaggctgg gcgcggtggc tcatgcctgt  14580
aatcccagca ctttgggagg ccgaggtggg cagatcacct gaggtcagga gttcgagacc  14640
```

-continued agcctgttca acatggtgaa accccgtctc tactaaaaat acaaaaatta gccaggcatg 14700
gtggtgggtg tctgtatccc agctacttgg gaggctaagg caggagaatc gcttgaaccc 14760
aggaggtgga ggttgcagtg agctgagatc gtgccactgc aatccagcct gagtgataga 14820
gcgagattcc atctcaaaaa taaataagta aataactagc agctgtaaat gtggctgttg 14880
ttcttcacct ccacactcag tgccactcca ctccctccct ccgtggtgtg aggggcctca 14940
ctagctgtct cctaggagga gcatggctgt gagattccag ctccatcctt ggccacggct 15000
cctggagaca tcttagaggc caggatccag aaggctccca cacctcattt gacaggggag 15060
aagctgtcag ttccaggtcc ccttgcacat cagggccaga gctgcgttag gcctccagtc 15120
tccaggccac tgggccagag ctcacaggct ggcagagggt tagaactgtt actggtggct 15180
gggtgcagtg gctcacgcct gtaatcttag cactttggga gggcaaggcg ggaggatcat 15240
gaggtcagga catcgagacc atccttgcta acacggtgaa gccccgtctc tactaaaact 15300
acaaaaaatt agccgggcgt ggtggcaggc gcctgtagtc ccagctactc aggaggctga 15360
ggcaggagaa tggcgtgaac ccgggaggcg gagcttgcag tgagccgaga ttgcgccact 15420
gcactccagc ctgggcaata gagcgagact ccgtctggaa agaaaaaaaa aaaaaagagc 15480
tgttactgtt gacagtagca tgaggtagac catggcctgc accaaaatgg gggagtggag 15540
tgccactgag gccagaagga accacaccct caagggtggg gagttatggt atggggggtc 15600
ctaggcatgg agtcttttaa ttctttagac aatcctggga gcaactgtcc ctgtttcaca 15660
gagggcgggg ccacacagct ggtgagtggg cagccaagac tctgttcaag tttgtgtggg 15720
tccaacactt gcggccacgg tggaggggca tctgagccag gcctcagaga gtggcggggg 15780
aagttgggtg gggaagtgtg cccttctcat tcctctgagg ctcatcctct tggtgcctct 15840
ctttcatgga aagggataat aaggttattg tgaggatccc ctgagttcgt atattcagac 15900
gcttagacag agccaggcac agagaagggc ccggggttgg ctagtttgat tgctggtgta 15960
attgctaata tcttccagtt tgtattggtc aaggttctgc agagaagcag aaccagtagg 16020
atgtatatat taagagtttc aagctcatgt gaccgtgcgg gctggcaagt ctgaaatccg 16080
cagggcaggc caggcaggct ggcaattcct gcagaatttg atgttgcaat actgagtcct 16140
aaggcagtcc tggggcagaa ttccttcttc cctgggaggc ctcagtctgt tctcttaagg 16200
ccttcaactg attaaatgag gcctgcccaa gttatagaga gtaacctgcc ttactccgtc 16260
ttctgattta aatgttagtc acatctaaaa aatattttcg cagcagcatt tccactggct 16320
tttgaccaaa catcaggcca caaagttgat ccccaaaatt aaccatcact ctgtgcctgt 16380
aagggagggg ctgggaaagg ggagcaggtc tccccaaggg gtgaccttgg ctttgttcct 16440
cccaggcctg gagtttattc ggaaaagcca gctggtccag cctgtggggc cactggtggt 16500
gctgctgccc ctggcgggtg ggtacagccg cgtcctcaac gccgcctgcc agcgcctggc 16560
gagggctggg gtcgtgctgg tcaccgctgc cggcaacttc cgggacgatg cctgcctcta 16620
ctccccagcc tcagctcccg aggtaggtgc tggggctgct gccccaaggc gcgggtaggg 16680
ggcggagggc ggagggcgga gggagggcgg gcgggcaggc gggcttcttg tggcacgtgg 16740
gcttcttgtg gcacgttcct ggaggccgaa cccttctggc tttggaagga gtcgtcagag 16800
acccccgcca tgcgggaggc tggggaggaa ggggctcgaa acctccatca tcgcagagtc 16860
tgaatagcag tggccccgcc atgcgcccac gtagcggcgc ctacgtagcc acgcccccac 16920
accccgtcct ggccactctc cctcctgaag gtcttctggt acccgccccc tccccatctc 16980

-continued

```
catccccagg ccctgcgtcc tctgcccaat actctttggg cctccctgtt gtccagctct  17040
ctccgcggct ccatgactga caacttgagc aaggctaatg tgaatgggag cggttgaggg  17100
ctcagacctc tcacccgagg aacatccaca gagtgtgccg catgcccggt gcagtgtggc  17160
tgcggggaca cagacacgga gcctcggccc tgaggagctg gggggcagtg accgtccctc  17220
ctctgaccca ccactcctcc agtgtcagga cactgcgggt atctagggga aggaatcttg  17280
ttccacttca agtctggaac ttcaagtctg tgtgtgtgcg tgcgcgcgcg cgcgttgggg  17340
gtgggggttg cagagcagat gcgtacctga cagcggtaac ctaggtcccc cctggcctat  17400
caaggcttcc ctggcggccg aatttaaagg catcaagcaa acaaagccca acacatctct  17460
gccttgtcct ctcagtttcc ccccgtggca cttagaacca cttgatacac cgaatagttt  17520
cctatctccc ccactaggat gtaaactcca caggggcatt gggaatgctg cctggctatg  17580
gtagggacag aggggagcac cagggcgggg caggggtgcc agagttctgc ctgggcagtc  17640
agattttcct taggagggga catttgagtg ggacccaaac aggtgtatag cagttgtcca  17700
gcccagctgg caaggcctga gtctgcctct gcaacccctc tcttgggctc ctttctctgc  17760
cacccacctc ctcacctttc caggtcatca cagttggggc caccaatgcc caagaccagc  17820
cggtgaccct ggggactttg gggaccaact ttggccgctg tgtggacctc tttgccccag  17880
gggaggacat cattggtgcc tccagcgact gcagcacctg ctttgtgtca cagagtggga  17940
catcacaggc tgctgcccac gtggctggta agtcaccacc ccactgcctc ggccaccgtg  18000
atgctaacag cccctttggc agtcagggtc tgtgccggga cctccagtgc caggctctgt  18060
gcagggggac cagagatgaa gtaggcctga tggtgccttc aaggacactc agtctgatga  18120
gggaggcgag tgcacagagg aaacacgagg tcagggctgt attagaggga gcccagagga  18180
ggcacctgcc cagcccgagg gtcagagaag gcatcttgga ggagggacat ttgatcggga  18240
gcttgatgga tgaataggag ttcacctggc cgataagaca gcaactacca aggcttagag  18300
gtgtgagagg aggctgtctt acctcactga gtaaggactg caggcggctt accttcgaga  18360
agagagctta gtgtctgtgt gcacgtgtgt ttgtgtgtat gtgtgtgcgt gtgtgcactg  18420
gcaggagtcc cctgctgggg caggagggcc gggccatcac catctttcac cattcacccc  18480
tgcaccaggc attgcagcca tgatgctgtc tgccgagccg gagctcaccc tggccgagtt  18540
gaggcagaga ctgatccact tctctgccaa agatgtcatc aatgaggcct ggttccctga  18600
ggaccagcgg gtactgaccc ccaacctggt ggccgccctg ccccccagca cccatggggc  18660
aggtaagcag gatggcaggg tgggcaagtc caggctgggg cttgggaggt ctgtgtgacc  18720
ttgacagtct ctcccttctc ccttgtctgt gtaaggagga tgacgccacc ttaaatagga  18780
ttaaatgaga atggggctct gaaagggctg tgcaatattt tcataacgtg tttttataga  18840
gacagttgag tatgttcttt aagccctcct ctctcctacc atgaactaaa gatttctgtg  18900
gaggtcccct cactcccagc accccctcct catcccaggc cctttttgca ggttggcagc  18960
tgttttgcag gactgtatgg tcagcacact cggggcctac acggatggcc acagccgtcg  19020
cccgctgcgc cccagatgag gagctgctga gctgctccag tttctccagg agtgggaagc  19080
ggcggggcga gcgcatggag gtgactgtac ccctccttcg tgtgtgtgtg tgtgtgtgtg  19140
tgtgtgtgtg tgtgtgtgtg tgtgtgtgtg tcagtgctgg gccctcaggg acccccagca  19200
agcccctcca tcctccagac tccagctctt ctgtaagctt acagggctgg ccagaccagg  19260
agtggggcac tcctcacttc acgcggctgg gggctgctgg agagagccac agcgggaagg  19320
gtttcctaga ggctgcagga cagtgctgga tggattttca atgctcacct gggtgtgagc  19380
```

```
gtgcggcagg gccgcgtgag ggtcagcgat ctgctactct ggactcagcc atctctaggc  19440
ccctctcact caggtgctcc atggttctgg gagctgagaa atctcaaacc agcaaaaaag  19500
tggaattgat gttgatgcta caggatagtg cacagatgcc atctggttgc agcattttgg  19560
tggaagggca gtgcccagct aggagagtga ggaggggcag gcatttctgg cttgaggaga  19620
tggggtctta atgctcgtgt gagaggcaga gtgggtggag tggagctggc tggatccttg  19680
ctttggcctc ctggatttct ctctatctcc attttgaaac cactctgtgt ttggaagaac  19740
ttttgagtat tcagagctgc ccactggcag aacagtcttc cttgggcagg agtgagctcc  19800
ttgtccccag aaggctgggt ctggctggcc cctggcaggg acactgatga gggtgcttga  19860
gttgatcctg tctagtccct ttctgtgttt tcaaagccca ttctaaagca gattcccatt  19920
tccgtctttg actctaaggc ccaagggggc aagctggtct gccgggccca caacgctttt  19980
gggggtgagg gtgtctacgc cattgccagg tgctgcctgc taccccaggc caactgcagc  20040
gtccacacag ctccaccagc tgaggccagc atggggaccc gtgtccactg ccaccaacag  20100
ggccacgtcc tcacaggtag gaggctgggc ttgccctggg gtgaggaggg gtctctttct  20160
ccttatgcac ccactgcccg cgaggcttgg tcctcacaag tgtgatccat gagactcaag  20220
cctgacttgc agttccatac tctggttctg ccacttccat gccctttgag cctgggcagg  20280
tgaccttact tctcctcatc tcagcttcct cctccataag agggaaaaag gtattacctg  20340
cctcattgtg ttgcaaggag atgggcagca tctagggcac tggcctggag tatcgcaggt  20400
gctttgccta aggtggtgca gtccaggaga ggcagctcca gagagaggcc cccggctggg  20460
gctgaaagga gggcagacct cggtttgaat ttcaccctgc cgctctatag ctgtgtgact  20520
tgggcaaatt acttaacatc tctgtatgag gaaatgatga gtgctaagca cttagcttag  20580
tgccgggaca atataaattc tagctatcgt tactattgtt ttcatcaccc gttgctttaa  20640
aatccagcct ctggtatagg caactattga cgggctaccc tgtgtcgaaa acatgcccag  20700
gcaggtagca ggaagtcaca gatggggacc tcttggggca tcaagggatg gtgccctgag  20760
gctgagctgt tctggttggg tggagcatga gaggtctggg aagacagtgg gactccagcc  20820
tggaataaga ggctcagagt tgattctcgt ctgagcacgt ccaggggaac cactgagggt  20880
ttgggaacag gagagtgagg gtgagaacct ggttctgggc acagcaggct ggcatgtagg  20940
atggatgttc aggaaagatg agcatagtca ggtggctggt gcccttgtcc aggggagagg  21000
ctccgtcagg ttcaggggtc ctggcttgga gggaagtccg ccatgctcta atcacgctcc  21060
cctttggaag tgctcagccg atgagctcac aggcacatgt cagtttgaag tcatggaatc  21120
tgactccatg aagcgcacct caaagagcac cattttgcag ctaagggaac tgcaggctgg  21180
acatgctgag tggctgcccc gagcccttgc agctaggaca tagagaatgc tagtaaccac  21240
aaccctacca tgttcagagc acatgccagg ctccatgctg gggcttcgca cgtgtcatct  21300
tcacagtgtc cctgtgagta ggtgtggttt ctctttccat cttacaaatg agtaaacaga  21360
gcctcagtgt agctaagtaa ccactatttt aggtttctta gccaatgggt gtgtctgact  21420
cctaagccca tggagggcat tctgaggtgg ttcagacaga ccccggctta cccttgaact  21480
tctgcctgct ggctgcatag ggaggggctg gggggagttt gagcatctca ggccatagag  21540
cccctgcctc actgtctcca tctctgggtg gaaagatggt gttttccctg agaaactaag  21600
gctcagagag gttgaatggc tctcccaagg tcacacagct ggtcagctgc agagttgaga  21660
acacaggagt cctggtgctc aggccagcat ctcttttttt ctttgagttg tttctaggtt  21720
```

tcctagctct tgcctcagac cttaaagaga gagggtctga tggggatggg cactggagac 21780
ggagcatccc agcatttcac atctgagctg gctttcctct gccccaggct gcagctccca 21840
ctgggaggtg gaggaccttg gcacccacaa gccgcctgtg ctgaggccac gaggtcagcc 21900
caaccagtgc gtgggccaca gggaggccag catccacgct tcctgctgcc atgccccagg 21960
tctggaatgc aaagtcaagg agcatggaat cccggcccct caggagcagg tgaagaggcc 22020
cgtgaggccg ggtgggtggg gtgctgcgtg tctctcctgc acagcttttc tgtgtcagtt 22080
tgtgccacca ccataccgcc atgcatcagg gtggcggttt gccaggtaga tgctgtgggc 22140
agcttccgcc attgtgtgga cagcatgtat atgtgtctct gtgtggctgg gtctgttttt 22200
gcttttgtcc agatcagtaa ggtttgctac ctgggtaccc cactccactt ggagtagaat 22260
gtgcataaat atggcataaa gaaatgcaat atgcatgcat ttattgattg atctattttt 22320
ttctgagatg gggtcttgct gtgttgccca ggctggtctc aaattcctgg gctcaagcaa 22380
tcctctggtc tcagcctccc caagtgttgg gattataggc atgagccgct gcacctggcc 22440
tctctgatct atttaacaaa cctgctggga gggtctcagg gtcaggagca gcactgggct 22500
ctgaggacac agagctcact cagccgtgac ccagaggggg tgcctgagct gcatgctgaa 22560
ggttgttagc atgaccagca aggcaagaaa aggccctgcc gagattagca aggcatgtgc 22620
caagccctgg aatgtgacag ccgggccttc tagaaacctg agtgtataac tctccttaaa 22680
agccagtagg agctcctcaa aaggcagccc taaggagtcc actcttaaat gaactcagag 22740
tcagttttaa aatgcaagtc tgtgttgatt ctggtctgga tggtgcattc ctcgagagca 22800
aaagacagtc ttggtcttgg atccacttgc cctgggtaca ctgagggctg ctaggttcca 22860
ggtgctcttc ctggcactgg ggagggatac aggcccaaga gacatgctgt tctccctcct 22920
ggagcatcta ttttagtgga ggaagacaga aaacaaacca ttaatataga gtactgaaaa 22980
gatgcgatgg agaaaactat agcaaggaag ggaatggggt gggagagagg tcaggagagg 23040
tctcgctgac aaggtggacg aaacaggcca tgaggcagag aacatgttcc aggcaaagca 23100
aaggccccca ggtggggatg tgcagggagt accaggaaac cagagaggtg ggaatagtta 23160
tgagatgggg ggtgcctcag aggggacagg gccaagtcag gtgagacctg agggtcacag 23220
tcagcagtga gctggggcca tgcaggggtc tggcctcaga ggagtgtggt ctggcctgga 23280
tctgaacctc tcactgtggc ctagctgctg agctgagaag agatgacaag gaccttgggc 23340
agaagcaggg agactggagg gaggcggtgg agggtccagg cgttggggcg gggctcaggc 23400
tggagtctga agggagcctg caggcctggt gggtggatgt gggtgggaga gggggaggat 23460
ggcaccaagg ctcgggcccc tggacagatg gagttgccat taagtgggat ggggcaggct 23520
atggggccat cagtttcaga gggatgagtt tggcactggc atggtaggca tctgtctatc 23580
tccacggccc tcaaaccagg catgaagcag gagctcacgt gtttggtcag ccatggtgca 23640
gaaccgcctg ggtgggaggt gcggggtggg agatacacgg ttgtgtccca aatgggctct 23700
gagccagcga gggccgtctg cactttggcc tcacagaagg atgtcggagg gagaaatgaa 23760
gtgtgggtgg gggtcccggg ccacgctaga catgtgcttt cttttcctcg ggctctggca 23820
ggtgaccgtg gcctgcgagg agggctggac cctgactggc tgcagtgccc tccctgggac 23880
ctcccacgtc ctgggggcct acgccgtaga caacacgtgt gtagtcagga gccgggacgt 23940
cagcactaca ggcagcacca gcgaaggggc cgtgacagcc gttgccatct gctgccggag 24000
ccggcacctg gcgcaggcct cccaggagct ccagtgacag ccccatccca ggatgggtgt 24060
ctggggaggg tcaagggctg ggctgagct ttaaaatggt tccgacttgt ccctctctca 24120

```
gccctccatg gcctggcacg aggggatggg gatgcttccg cctttccggg gctgctggcc  24180
tggcccttga gtggggcagc ctccttgcct ggaactcact cactctgggt gcctcctccc  24240
caggtggagg tgccaggaag ctccctccct cactgtgggg catttcacca ttcaaacagg  24300
tcgagctgtg ctcgggtgct gccagctgct cccaatgtgc cgatgtccgt gggcagaatg  24360
acttttattg agctcttgtt ccgtgccagg cattcaatcc tcaggtctcc accaaggagg  24420
caggattctt cccatggata ggggaggggg cggtaggggc tgcagggaca aacatcgttg  24480
gggggtgagt gtgaaaggtg ctgatggccc tcatctccag ctaactgtgg agaagcccct  24540
gggggctccc tgattaatgg aggcttagct ttctggatgg catctagcca gaggctggag  24600
acaggtgcgc ccctggtggt cacaggctgt gccttggttt cctgagccac ctttactctg  24660
ctctatgcca ggctgtgcta gcaacaccca aaggtggcct gcggggagcc atcacctagg  24720
actgactcgg cagtgtgcag tggtgcatgc actgtctcag ccaacccgct ccactacccg  24780
gcagggtaca cattcgcacc cctacttcac agaggaagaa acctggaacc agagggggcg  24840
tgcctgccaa gctcacacag caggaactga gccagaaacg cagattgggc tggctctgaa  24900
gccaagcctc ttcttacttc acccggctgg gctcctcatt tttacgggta acagtgaggc  24960
tgggaagggg aacacagacc aggaagctcg gtgagtgatg gcagaacgat gcctgcaggc  25020
atggaacttt ttccgttatc acccaggcct gattcactgg cctggcggag atgcttctaa  25080
ggcatggtcg ggggagaggg ccaacaactg tccctccttg agcaccagcc ccacccaagc  25140
aagcagacat ttatcttttg ggtctgtcct ctctgttgcc tttttacagc caacttttct  25200
agacctgttt tgcttttgta acttgaagat atttattctg ggttttgtag catttttatt  25260
aatatggtga ctttttaaaa taaaaacaaa caaacgttgt cctaa                  25305
```

<210> SEQ ID NO 3
<211> LENGTH: 42802
<212> TYPE: DNA
<213> ORGANISM: homo sapien

<400> SEQUENCE: 3

```
ctcttgcagt gaggtgaaga catttgaaaa tcaccccact gcaaactcct ccccctgcta     60
gaaacctcac attgaaatgc tgtaaatgac gtgggccccg agtgcaatcg cgggaagcca    120
gggtttccag ctaggacaca gcaggtcgtg atccgggtcg ggacactgcc tggcagaggc    180
tgcgagcatg gggccctggg gctggaaatt gcgctggacc gtcgccttgc tcctcgccgc    240
ggcggggact gcaggtaagg cttgctccag gcgccagaat aggttgagag ggagcccccg    300
gggggccctt gggaatttat ttttttgggt acaaataatc actccatccc tgggagactt    360
gtggggtaat ggcacggggt ccttcccaaa cggctggagg gggcgctgga ggggggcgct    420
gaggggagcg cgagggtcgg gaggagtctg agggatttaa gggaaacggg gcaccgctgt    480
cccccaagtc tccacagggt gagggaccgc atcttctttg agacggagtc tagctctgtc    540
gcccaggatg gagtgcagtg gcacgatctc agctcactgc aacctccgcc tcccgggttt    600
aagcgagtct cctctctcag cctcccgaat agctgggatt acaggcgccc aaccaccacg    660
cccgcctaat ttttgtattt ttagtagaga cgggttttca ccattttggc caggctggtc    720
tcgaaccccg acctcaggtg atctgcccaa aagtgctggg attacaggcg tcagccaccg    780
cgcccggccg ggaccctctc ttctaactcg gagctgggtg tggggacctc cagtcctaaa    840
acaagggatc actcccaccc ccgccttaag tccttctggg ggcgagggcg actggagacc    900
```

-continued

```
cggatgtcca gcctggaggt caccgcgggc tcaggggtcc cgatccgctt tgcgcgaccc    960
cagggcgcca ctgccatcct gagttgggtg cagtcccggg attccgccgc gtgctccggg   1020
acgggggcca ccccctcccg cccctgcccc cgcccctttg gcccgccccc cgaattccat   1080
tgggtgtagt ccaacaggcc accctcgagc cactcccctt gtccaatgtg aggcggtgga   1140
ggcggaggcg ggcgtcggga ggacggggct tgtgtacgag cggggcgggg ctggcgcgga   1200
agtctgagcc tcaccttgtc cggggcgagg cggatgcagg ggaggcctgg cgttcctccg   1260
cggttcctgt cacaaaggcg acgacaagtc ccgggtcccc ggagccgcct ccgcgacata   1320
cacgagtcgc cctccgttat cctgggccct cctggcgaag tccccggttt ccgctgtgct   1380
ctgtggcgac acctccgtcc ccaccttgtc ctgggggcg ccctcgcccc accagccccg   1440
atcaagttca cagaggggcc cccggccacc ctcaaggcct cggttcctta cgaggttgaa   1500
acgttgcctc agaatctccc cgcccctcct tggtctgcag ccgagatctt cagccacggt   1560
ggggcagcta tcccccggga ccgacccccct ggggtggcct cgcttcttca gaggctgtga   1620
atggcttcgg ttcagctgtc caagcggcga tttttcctct gggtgaaatg gattagattt   1680
tagatttcca caagaggctg gttagtgcat gatcctgagt tagagctttt taggtggctt   1740
taaattagtt gcagagagac agcctcgccc tagacaacag ctacatggcc ctttccctcc   1800
tgagaaccag cctagcctag aaaaggattg ggattgcctg atgaacacaa ggattgcagg   1860
aaactttttt tttaattggc aagggggttg gctttgactg gatggagagc tttgaactgc   1920
cttgaaattc acgctgtaac taacacacca gtttcctctg ggaggccaga gagggaggga   1980
gggtgtaatg aaatacggat gattgttctt ttatttttat ttacttattt atttttttaac   2040
tttttgtaga gatgaggtct cgcttggttg ctcaggctgg tcttgaactc ctggcctcaa   2100
gcgatcctcc tacctcagcc tcccaaagtg ttgggattac aggagtgagc caccgcgccc   2160
caccggggat gatgatgatt gcaaacattc tgccactcag ttttacaaaa gaaagagagg   2220
cactggatta atgtgtatct cactcaccaa tcaacctctt ccttaagaga aaatgttaag   2280
gaagtcttag gcaaggcctt gtttgttcat cactttagtt tctctctccc gggatggctg   2340
agaatgtgat gtttcctctg ttgtcaagga gactacaccc ctgatgtttt cctccagact   2400
tctgagagct ggtgtgtgtt tctagcactt tctagctgca ccacctcacg ctgtagctgg   2460
cttcaaggca tatccagggg ggagtttctt gtccatttcc tttacaaagg gaagttgttg   2520
gaatctgaac cgcaagcctt cacttagacc aaaatcaggc aacagcggtg agcgcagctc   2580
caaacgtgtc aatgactcac ccaaatttga gtaagggagt tggctgcttt aacgagccgc   2640
agggtgattc ccttgtcatt tccggaaata cctatcttcc agggaacact gggaaaaaac   2700
agggagacct ttgttgagac agaaaacctg taggggaatt ctgttcctca ttcctgctct   2760
tatctgtaga cttcctccct gataagatcc aattctagat gggtcggttg ctccttgctt   2820
tgatgggtgc tttgatgggc tttattatta ttattattat tattattatt attttgatgg   2880
gctttttgat gtcccttttc cttccacact ctgtcccaac tgtcaagcaa atagcctttt   2940
gttgctaaga gactgcagat gtaaccgacc agcagcaaac agtgagtcag gctctctctt   3000
ccggaagcaa aatcaattgc tgagatcact ctggggaaaa tacccacctt atttggaaag   3060
aagcactgat caattgatgt ctattttttt ttttttgag ttggagtctc gccctgtcac   3120
ccaggctgga gtgcaatggc ataatctcgc ctcactgcaa tccccgcctc ccgggttcca   3180
gcaattctcc tgcctcagcc tcctgagtag ctggaattat aggcgcctgc cacaacaccc   3240
ggctaatttt tgtatttgta gtagagatgg ggtttcacca cgttggccag gctggtctcg   3300
```

-continued

```
aactcctgac ctcgtgatcc acccgcctca gcctcccaaa gtccaaggat tgcaggcgtg   3360
acccactgtg ccagccaatc aattgatttc tcattcattt tcagctggct ctgttccctt   3420
aagccagggg attttcgttt gtttgtttcc ccttcaagga aatgattcta gctacagttt   3480
tgatttcctt gtacaactgt tttcagtagc acagggaaag aaaacatcga aagcattcac   3540
cacctcattt gtgtgctggg ggaaaaagca gaaatgtgta ttctcttttt ttgtttcgat   3600
gaccttgttc ctgacttgtt actcgtgact tgagagatca gagggctaga ggactagaat   3660
ttatagaggt gttttttttg tttgtttatt tttgttcgag ttgcccaggc tggagtgcag   3720
tggcgcaatc tcggctcact gcaacctctg cctcccaggt tcaagcgatt cttcggcctc   3780
agcctcctga gtagctggaa ctacaggcgc ccgccaccac acccagctaa tttttgtatt   3840
tttcagtaga gatgggattt caccatattg gtcaagctgg cctcgaactc ctgacctcgt   3900
gatccacccg cctcagtttc ccaaagtgct gggagtacag gcgtgagccg ccgtgcccgg   3960
cctttttgtg tttttgtgtt tttgagagga gctcattgct ttttaggctt ccctagcgtg   4020
agaaaatctg ggatccatgg ctctagttta cttccttttt tttttttttt ttgagatgga   4080
gtctcgctta gattgcctaa tctcagctca ttgcaacttc tgcctccggg gttcaaggga   4140
ttctcgtgtc tcagcctcct gggtagctag gatacgggca cccgctacca tgcctggcta   4200
attttgtact tttagtagag acagggtttc gccacgttgg ccaggctggt ctcgaactcc   4260
tgacctcagg tgagccgcct gccttggcct cccaaagtgc tgagattaca ggcgtgagcc   4320
accgcgcttg gcctaatttg cttttcctga aattcaaatg gtctaatatg aaaaacgcca   4380
accttgcttg aaagaataag aaagaggtgc ggtttcgttg ggccgttgat gtttggaaca   4440
ggactggttt tgtccccttg ctcggaaagg gcagcaactg tgaggacagc tccctgacgt   4500
gctctcactc agcactgttc cgttcctgag cactgtcccc actagctagg ccaagggagc   4560
tcatttggca ggcaactgct gtctggctgc gcctgtggca gtaaaatctg cctttatttt   4620
ttggaggcag ggtcttgccc tgtcgctcag gctgaagtgt gcagttatag ctcactgcag   4680
cctccagctt ctgtactcaa ctgatcctcc tctctcagcc tcctgagtag ctgggactat   4740
acgcacgtgt taccactccc acctcagttt gtttgtttat ttatttattt atttatttat   4800
tgagatggag ttttgctctt gctgcccagg ctggagtgca atggcgcgat ctcggctcac   4860
cgcaacctcc acctcctggt tcaagcgatt ctcctgcctc agcctcctga gtagctggga   4920
ttacaggcat gcaccaccac gcccggctaa ttttgtattt ttcgtagaga tggggtttct   4980
ccacattggt tcaggctgtt ctcgaactcc caacctcagg tgatccaccc gcctcagcct   5040
cccaaagtgc tgggattata ggcgtgagcc cccgaacccg gccactccca gctaagttta   5100
aatttttgt ttgtttgttc gtttgttttt atttttgag acagagtctc ccgcccaggc   5160
tggagcgcag atcactgcat ccttgacctc ccaggcttaa gccatcctcc ccactcagcc   5220
tcccaagtag ctgggattac aggtgtgtgc cactatgctt ggctaagttg tgtatttttt   5280
gtagagatgg ggttcaaggg attctcgctt tgttgcctcg gttggtctca aactcctggg   5340
ctcaagcagt cctccctcct cagcctccca aggtgctggg gaaatccact tttgaaacat   5400
tgtctggaga gttgcccagg tggtagatca cagaaatagg tcatcgtggg gtccttccca   5460
tgggtgcagt cttgagccac ctgtggccag caaatatttg gagaataata gtcaggggag   5520
agcttgaggt ccagggaaag gttttgtttt tcttcaggga aaggttttta ttgttcttta   5580
tccctcctta aaggaccttc aggtgttact gacattcccg gtctacccag tggcacattt   5640
```

-continued

```
agtttgtaag ctgggccctc gtacagaggt agggaggtga gagcattgga ttagtggtca   5700
ccaaagctgc ggtcacctag tggggtgatc agaggctcct ccccttaagat cttgattgcc   5760
aacgcctctg gcccaacttt cctttttatt tatcgcaagc ctcctggaat ctcaattgct   5820
ttttgcccac ccggtgtgtc agcacaagaa atgagtcatt tcctccttta agcacagttg   5880
aaattgagct gtgagtcagt gaggtgtgta cgatattgtc aaagcggggt gtgtacagta   5940
ttgacagatc tgtagttggg caagagaatt atcagagttt gtgaccacag cagattccaa   6000
agctcgactc attttcttct ctcttccttc cctttttct tttctttttt tttttttttt   6060
tgacagagtc tcgctctgtt gcccaggctg gagtgcagtg gcacaatctg ggctcactgc   6120
agcccctgcc tcctgggttc aaatgattct catgtttcag cctcccgagt agctgcaatt   6180
acaggcattc gggttcaagt gattctcctg cctcagccac ctgagcagct gggattacag   6240
gcgcccgcca ccacgcccgg ctaatttttg tatttttagt agagacgggg tttcaccatg   6300
ttggccaggc tggtctcgaa ctcctgaact caggtgatcc gcccacttcg gcctcccaaa   6360
gtgctgagat tacagacgtg agtcaccgcg cccagcctgt tctgttcttt aattctcaaa   6420
acaccctcta ggaagtagag actgccattc tcccccattt tacagatcag gaaactgagt   6480
cccagaagga tttagtcagt tacccaagtt gttctagtta aatggcctgg aaagccagtg   6540
aagcccagga ttgtctatct aaccccctta ctactctaac tttcagggaa tccacatgaa   6600
tgtgctgggt caaccatcaa agttgaaatg gataaagggg gctggatgcg gtggctgatg   6660
cctgtaatcc tagcactttg ggaggccgag atgggtgggt ggattgcttg agcccaagag   6720
tttgagacca gcctgggcaa catagtgaga cacctgtctc tgcaaaaaat aaataaaaag   6780
ttagctgagt gtgatggtgc acccctctag tcacagctgt tgagttaggc ttaggcagga   6840
ggatcgcatg aacctgggag gtggaggcgg ccgtgagcct cagtcatgcc actgcactcc   6900
aacctgggca acagagtgaa agccggtgtc cgaaagagaa agaaaaaaag acatagatac   6960
atcttttaaa gttaggttgt atgttaatta cctacaactc agtttcaact gtgcttaaag   7020
gaggaaatga ctcatttctt gctacatatc aaattagccc aaaatgtagt ggcttaaaac   7080
aacacattta tgatttctca gtttttgcgt gtcaggaatt tggaagcagc acagctagac   7140
ggttccagct cagggtctct catgaagttg caatcaaaat attggcagga gagaaaaaca   7200
tattttcaga agctgcaggc ataggaagac ttggctgggg ttgaaggatc cacttccaag   7260
atggcgcact cagtggctct tggctggagg cctcagttcc ctgctgcgtg gagctctccc   7320
tccagctgct tgagtggact catgacatgc agctggcctc ccctggagca gtcgatccaa   7380
caatgagcat ggccatgaac taggctcaga agccactccc tgtcgtctct acattttcct   7440
atcagaagca agtcattaaa agtccagtgc cactccaggg gagacgaatt aggctctgcc   7500
ttctgaaagg attatcacag aagatgcggt cctatattct ttttttaaaa ttattctttt   7560
ttttattttg tagagatggg gtcttggtat gttgcctagg ccagtctgga attcctgggc   7620
tcaaacaatc ctgtctctgc ctcccaaagt gttgggatta caggcatgag ccactgcacc   7680
tggtcatgtg gtcatatttt ctttttcttt tttttttttt tttgagacag agtctctgtc   7740
gcccaggctg gagtatggtg gcgtgatctc agttcactgc agcctccgcc tcccgggttc   7800
aagcgattct cctgcctcag cctcctgagt agctgggatt acaggcgccc gccaacatgc   7860
ccagctaatt tttttagtag agatggggtt tcaccatgtt agccaggatg gtctcgatct   7920
cctgatttgg tgatccgccc accttggcct cccaaagttt caaccatcga tcagaactta   7980
ttgatgtact tatgtagcta ggcacggtgg cgcgtgcctg taatcccagc tacttggaag   8040
```

-continued

```
ggttaaggca ggagaatcgc ttgaacctgg gaggcagagg ttacagtgag tcaagatcat   8100
accattgcac tccagtctgg gcaacagaat gagactctgt ctcaaaaaca aaaaacaaac   8160
ccttgtatgt gattttcctg gatagcatct gttacatctt cacaaagata aaaagtcaga   8220
cttggctggg catggtggct cacacctgta atcccagcac tgagaggctg aggcaggcag   8280
atcacttgag gtcaggaatt tgagaccagg ctgggcagca tggtgaaacc ccgtctctac   8340
aaaaaataca aaaattagcc gggtgtggtg tcacgcacct gtattcccaa gctactcagg   8400
aagctaaggc aggagaatca cttgaaccca gaggtggagg tttgcagtga gttgagattg   8460
tgccattgca ctccagcctg ggcgacagag tgagactctg tgtcaaaaat aaaataaaat   8520
aaaatttaa aaaaggcaga ttttttttc ttcttggtat tgttacctta ttatagtaat   8580
aataagtgca tagtgcatgc tgagataagc aatcataatt tgttattgcg gccgggcatg   8640
gtggctccag cctataatcc cagcactttg gtcaggagtt caaggccagc ctggccaata   8700
tagtgaaact ccatctctac taaaatacaa gaaattacct gggcatggtg gcagttgctg   8760
gtgatcccca gctacttggg aggctgaggc aggagaatcg cttgaacctg ggaagcagag   8820
gttgcagtga gccaagattg caccactgca ctccagcctg ggtgacagag tgagactctg   8880
tctgaaaata ataataataa taatttgtta ttgcttttat tgccttagtt tacataggga   8940
atcaaagttt atactttgat ttataaaagt tgctttgatt ctagttcaca gaaccagaat   9000
ctttcatata aaggtattag agggcccagt gtggtggctc atgcctgtaa tcccagcata   9060
ttgggaggct gaggagggag gatcacttta ggagtttgag gccagcctag gcaacatagt   9120
gagaccttgt ctctacaaaa aattccaaca ttagctgggc atggtggcat gtgcctgtag   9180
tcccatttat ttggggggct gaggcaggag gatcacttga gcccacgagg ttcaatccag   9240
gttgcagtaa gccatgatcc tgccactgca ctccagtttg ggtaacagag cgaagctatg   9300
tctcaaaaaa agaaaaaaaa agtattctaa atccaaattt aatatataaa actaaatgca   9360
ggccaagtgt ggtggcatat acctataatc acaacacttt gggaggctga ggtgggagga   9420
ttgcttgagc ccaagagttc aagaccagcc taggtaacac agtaagaccc catctctaca   9480
aaaagtagaa aaattagcct ggcatggtgg tgagtgcttt taatcccaac tacttagggg   9540
gctgagatgg gaagattgct tgagcctcag agtttgaggc tgcagtgggc cgtgatcgct   9600
ccactgatcg ctctaaagtg agaccctgtc tcaaaaaaaa agaaaataga agaaaactaa   9660
atacattcaa taagactttg atctcttttc caaggtgtaa atatattttg ggaaattttc   9720
cagttacttt gttctcattt taatgtaata atctaagtct tggttttcta aggaaaagtt   9780
ttctcttatt atatcttttg ttaatgtttc tctcccattt cttttgatct gatcttcaga   9840
tacatgatta tcttcactgc taaatttgtg ttctctggcc tctacattta taatttctca   9900
taattcttta tctaagtatt tcttccctac ctactgaaga aaactcaagt tttcttccac   9960
cttaatgatt atgctgtgtc tgtgagtttt cttcatgact ctttacagta caagtttttt  10020
gtttttgttt ttttaatggt cagatggata gaacaacaca ggttttgttt gttttgtttt  10080
aacttttaaa aaaattataa tagataaagg gtctcactac gttgtccagg ctgatctcat  10140
actcctgggc tcaagcaatc cacccacctc tgcctcccaa agtgctggga ttacagtcat  10200
gagccaacat gcctgggcag tacaggtttt ttttgagacg gagttttgtt cttgttgccg  10260
aggctggagt gcaatggcac aatcttggct caccacaaag tctgcctccc aggttcaagt  10320
gattctcctg cctcagcctc ctgagtagct gggattacag gcatgtgcca ccacgcccag  10380
```

-continued

```
ctaattttgt atttttagta gagacggggt ttcaccatgt tggccaggct ggtttcgaac  10440
tgctgacctc aggtgatctg cccacctcgg cctcccaaag tgctgggatt acaggcatga  10500
gccaccatgc ccagctgtag tacaggtttt aatatgctaa atactcttcc tttctttatt  10560
aatgtgcatg gaagttctaa tatttttttc ccatacccca gagagtccat attttggaat  10620
caacaacact agcctttgtt gacaagtgtc tctcttgggt tccttctttg tgtcctccac  10680
tgaattttgg ggttcataaa atttcatttg ttgtgcttgc ttaattccct gggaatcaga  10740
ctgttcctga tcggatgaca tttctggtta attctttagt tggcaggaaa tagacacagg  10800
aaacgtggtc agtttctgat tctggcgttg agagaccctt tctccttttc ctctctctca  10860
gtgggcgaca gatgcgaaag aaacgagttc cagtgccaag acgggaaatg catctcctac  10920
aagtgggtct gcgatggcag cgctgagtgc caggatggct ctgatgagtc ccaggagacg  10980
tgctgtgagt cccctttggg catgatatgc atttattttt gtaatagaga cagggtctcg  11040
ccatgttggc caggctggtc ttgaatttct ggtctcaagt gatccgctgg cctcggcctc  11100
ccaaagtgct gggattacag gcaccacgcc tggcctgtga cacgattctt aacccctttt  11160
tgatgatggc ggctggaaaa gtggccagtg gattttgatg tattcaatca tgaattagga  11220
ggtggggaga gaatgaatta ttggagcttt ccttaaagcc attaaatggc tctattgttt  11280
tttcaattga tgtgaatttc acataacatg aaattaacca gctcagtggc attaatacat  11340
ctgcaatgct gtgtggccac cacctctatc ttgttccaaa actttgcata acctaatgtc  11400
tttttttttt tttttttttg agacggagtc tcgttccatc acccaggctg gagtgcagtg  11460
gtgtgatctc agctcactgc aacctccgcc tcccaggttc acgccatcct cctgcctcag  11520
cctcccgagt agctgggact acaggcaccc tccaccacat ccggctaatt ttttgtatct  11580
ttagtagaga tggggtttca ccatgttagc cgggatggtc tcgatctcct gacctcgtga  11640
tccacctgcc tccgcctccc aaagtgctgg cattacaggc gtgagccacc atgcccggcc  11700
tatttttttt tttaagagat ggagtctaat tctgttgccc aggctggagt ccagtggtac  11760
catcatactt cactgcagcc ttgacctctt gggctcaagt gattctcttg cctcgaactc  11820
ccaaagtatt gggattacag gtgtgagcca ccgcactcag cctaatgtcc agtttttaac  11880
aagctccatt taaatgccct ccgttttgac ccataaaggg gtaggcttgg ccgggcacaa  11940
tggcttgtgt ctgtagtccc agctacttgg gaggctgagg cagaaaggca gaaagattgc  12000
tttataaagc ccaggagttt gagggccacc tgggtggcat agctagacct catctctaaa  12060
aaataagtaa taaataaata tttgtttttg tttttttctt tttcttttct tttttttttt  12120
tttttgagac ggagtcttgc tctgttgccc aggctggagt gcagtggcgc gatctcagct  12180
cactgcaagc tgtgcctcct gggttcatgc cattctcctg cctcagcctc ccgagtagct  12240
gggactacag gcgcccacta ccacgcccag ctaatttttt gtatttttag tagagatggg  12300
gtttcaccac gttagccagg atggtctcaa tctcctgacc tcgtgatccg ccagctttgg  12360
cctcccaaag tgttgggatt acaggcgtga gccactgagc ccgcccccata tgtatgtata  12420
tatatatttt tttaaaatgg gagaccaggc atggtggctc atgcctagaa tcccagcact  12480
ttgggaagct gaggtaggcg gatcacttga ggccatgagt ttgagaccag cctgctcaac  12540
atgatgaaac ttctatctct actaaaaaaa aaagtgggat taggtcaggc acggtggctc  12600
acacctgtaa tcccagcact ttcagaggcc gaggcaggag gatcatgagg tcaggagatc  12660
gagaccatcc tggctaacac ggtgaaaccc cgtctctact aaaaaaatac aaaaaattag  12720
ccaggcgtgg tggcgggtgc ctgtagtccc agctactcag gaggctgagg caggagaatg  12780
```

```
gcgtgaaccc gggaggcgga gcttgcagtg agccaagatc gtgccactgt actccagcct  12840
gggcgacaga gcaagactct gtctcaaaaa aaaaaaaaaa agtgggattg acattctctt  12900
caaagttctg gggttttcct ttgcaaagac aggattggca aggccagtgg gtcttttttg  12960
tgtgtgtgtg tgtgacggag tctcactctg ccacccaggc tggagtgcaa tggcaggatc  13020
tcggctcacc gcaacctcct cctcccaggt taaagtgatt ctcctgcctc agcctcccga  13080
gtagctggga ctacaggtgc ccgccaccac acccaactaa tttttgtatt tttagtagag  13140
acagggtttc actatattgg ccaggctggt cttgaacccc tgacctcacg tgatccaccc  13200
gccttggcct cccaaagtgc tgggattaca ggcgtgagcc actgtgctcg gcctcagtgg  13260
gtctttcctt tgagtgacag ttcaatcctg tctcttctgt agtgtctgtc acctgcaaat  13320
ccggggactt cagctgtggg ggccgtgtca accgctgcat tcctcagttc tggaggtgcg  13380
atggccaagt ggactgcgac aacggctcag acgagcaagg ctgtcgtaag tgtggccctg  13440
cctttgctat tgagcctatc tgagtcctgg ggagtggtct gactttgtct ctacggggtc  13500
ctgctcgagc tgcaaggcag ctgccccgaa ctgggctcca tctcttgggg gctcatacca  13560
agcctcttcc gcccttcaaa tccccccttg accaggaggc attacaaagt ggggatggtg  13620
ctacctcttc gggtttgtca cgcacagtca gggaggctgt ccctgccgag ggctagccac  13680
ctggcacaca cactggcaag ccgctgtgat tcccgctggt cgtgatcccc gtgatcctgt  13740
gatccccgcc ccgtgaggct gaacacatag tgacgcttgc tagccaagcc tcaatgaccc  13800
acgtaacatg aagggggaaa agccagaaag ttctgccaag gagcaaggcc aagaatcccg  13860
aagggaaatg gactttgaag ctgggcgtct tcttggctgt cttaatacaa gtggcacatc  13920
caaatccaaa accccgaaat tcaaagtctt gagcacccga aattctgaaa cgtcttgagc  13980
actgaccttt agaaggaaat gcttattgga gcattttgga tttcggattt ttaccactga  14040
gtgtggagtc ctaattagga aaaaaaccag gctgaccgaa ccaaaggaaa gcaataaaag  14100
aaggcagata gggtcaggca cggtggctca cccctgtaat cccagccttt tgagaggctg  14160
aggcgggtgg atcacttgag gtcaggagtt cgagagcagc ctggccaaca cggtgaaacc  14220
ccatctctac tgaaaataca aaaactagcc aggtatggtg gcgtctgcct gtaatcccag  14280
ctactcggga ggctgagaca ggagaatcac ttgaacctgg gaggcagagg ttgcagtgag  14340
ccaatatcac gccattgcac tccagcctgg gggacaagag cgaaattctg tctcaaaaaa  14400
aaagaagaag aaggccgaca aactatgtaa ctctgccttt ctccatggtc cagaacacac  14460
agccctcctg cgtaaataac tccttatctt cctgctccca gctatcatca gacacctcgg  14520
ctgatagaaa attgcaagtt agctcactgc aacctcggca ttataagtac tgcacaaagc  14580
cctcttcagc gcacagcaca agcaccattc tataaaatct ccagcaagcg gccaggtgca  14640
gtggctcata cctgtaatcc cagcattttg ggagactgag gcgggcggat cacctgaggt  14700
caggagtttg agaccagcct ggccaacatg gtgaaacccc gtctctatta aaaatacaaa  14760
aaaattagcc aggcgtggtg gcaggtgcct gtaatcccag ctacttggaa ggctgaggca  14820
ggagaatcgc ttgaacccgg gaggtggaag ttgcagtgag ccgagatctt gccatcgcac  14880
tccagcctgg gggacaagag tgagacttcg tctcaaaaaa aaaaaaaaaa attcccagca  14940
agcctttgtc ttctggcagt cagctcctct cttgctgacc tgctcattgc tttcttgcaa  15000
ggtattttcc tacctacttt ctggaataaa tctgtctttc tgtacttaca actacctttt  15060
ttaaaatttc tttcttttt gagatggagt ctcactctgt ttgcccaggc tggagttcag  15120
```

-continued

```
tggtgcaatc tcagctcact gcaacctcta cctactgggt tcaagcgatt ctcctgcctc  15180
agcttcccga gtagctggga ttacaggcgt gcaccagcac gcaggctaat tttgtattt  15240
ttagtagaga cggggtttca ccatgttggc caaggtggtc ttgaactcct gacctcaagt  15300
gatcctccca cctcagcctc ccaaagcgct aggattacgg ccatgagcca ctgaggccgg  15360
ctgcacctac aactgtcttg ataaattctt acccccacac cactggtcca gatagtcagt  15420
gctcacccac aacattaagg atattccaaa tttgaaacat tccaaaatca gaaaaatatt  15480
ccaactctga aaatattcca aaatccaaaa aaattcaaaa tccaaaacac ttctggtccc  15540
aagcatttta gagaagggat actcaaccca aaataaggac agcaattcta taaattgtgc  15600
taccatcttg caggtctcag tttaacagct ttacacctat tagcgcacca gtgctcatag  15660
cagtgctggg aaatgtgtac agatgaggaa actgaggcac cgagagggca gtggttcaga  15720
gtccatggcc cctgactgct ccccagcccg cctttccagg ggcctggcct cactgcggca  15780
gcgtccccgg ctatagaatg ggctggtgtt gggagacttc acacggtgat ggtggtctcg  15840
gcccatccat ccctgcagcc cccaagacgt gctcccagga cgagtttcgc tgccacgatg  15900
ggaagtgcat ctctcggcag ttcgtctgtg actcagaccg ggactgcttg gacggctcag  15960
acgaggcctc ctgcccggtg ctcacctgtg gtcccgccag cttccagtgc aacagctcca  16020
cctgcatccc ccagctgtgg gcctgcgaca acgaccccga ctgcgaagat ggctcggatg  16080
agtggccgca gcgctgtagg ggtctttacg tgttccaagg ggacagtagc ccctgctcgg  16140
ccttcgagtt ccactgccta agtggcgagt gcatccactc cagctggcgc tgtgatggtg  16200
gccccgactg caaggacaaa tctgacgagg aaaactgcgg tatgggcggg gccagggtgg  16260
gggcggggcg tcctatcacc tgtccctggg ctcccccagg tgtgggacat gcagtgattt  16320
aggtgccgaa gtggatttcc aacaacatgc caagaaagta ttcccatttc atgtttgttt  16380
ctttttttc ttttctttct ttattttgtt tttgagatgg agtctcactc tgtgattttt  16440
ttcatctcta aatttcctac atccatatgg ccaccatgag gccccaggct ggccgatggt  16500
tgctgttagc ttattgggaa atcactgttt ggaaggtgct ggttgttttt tgttgtttgt  16560
tgtttttgtt tttgtttttg ttttgagacg gagtctcgct ctgtcgccag ggtggagtgc  16620
agtggcgcga tcagctcact gcaacctccg cttcctgggt tcaagccatt ctcctgcctc  16680
agcctcccaa gtagcgcgga ttacaggcat gtgccaccac ctccggctat ttttttttct  16740
atttagtaga gatggggttt caccatgtta gtcaggctgg tcatgaactc ttgacctcag  16800
gtgatccacc cgcctcggcc tcccaaagtg ctgggattac aggcgtgcac tgctgcaccc  16860
agccttttt tgttttttg agacagggtc ttgctgtcac ccaggttgaa gtaaggtggc  16920
acgattatgg ctcactgcgg ccttgatctc cttggctcaa gcgatcctct cacttcagcc  16980
tctcaagcag ttggaaccac aggctgtacc accaagcctg gccaattttt ttgtacagac  17040
acaggctggt cttgaactcc tgggctcaag caatcctcct gccttggcct cccaaagtgc  17100
tgggattcca ggcatgagcc gctgcacccg gcaaaaggcc ctgcttcttt ttctctggtt  17160
gtctcttctt gagaaaatca acacactctg tcctgttttc cagctgtggc cacctgtcgc  17220
cctgacgaat tccagtgctc tgatggaaac tgcatccatg gcagccggca gtgtgaccgg  17280
gaatatgact gcaaggacat gagcgatgaa gttggctgcg ttaatggtga gcgctggcca  17340
tctggttttc catcccccat tctctgtgcc ttgctgcttg caaatgattt gtgaagccag  17400
agggcgcttc cctggtcagc tctgcaccag ctgtgcgtct gtgggcaagt gacttgactt  17460
ctcagagcct cacttccttt tgttttgaga cggagtctcg ctctgacacc caggctggag  17520
```

-continued

```
tgctgtggca caatcacagc tcacggcagc ctctgcctct gatgtccagt gattctcctg  17580
cctcagcctc ccgagtagct gagattaaag gcgtatacca ccacgcccgg ctaatttttt  17640
gtatttttat tagagacagg gtttctccat gttggccagg ctggtcttga actcctggtc  17700
tcaggtgatc cacccgcctc ggcctcccaa agtgctagga ttacaggtgt gagccactgc  17760
gccaggccta attttttgt atttttagta gagatgcggt tttgccatat tgcccaggct  17820
ggtctcgaac tcctgggctc aagcgatctg cctgccttgg cctcccaaag tgctgggatt  17880
acaggcacaa accaccgtgc ccgacgcgtt ttcttaatga atccatttgc atgcgttctt  17940
atgtgaataa actattatat gaatgagtgc caagcaaact gaggctcaga cacacctgac  18000
cttcctcctt cctctctctg gctctcacag tgacactctg cgagggaccc aacaagttca  18060
agtgtcacag cggcgaatgc atcaccctgg acaaagtctg caacatggct agagactgcc  18120
gggactggtc agatgaaccc atcaaagagt gcggtgagtc tcggtgcagg cggcttgcag  18180
agtttgtggg gagccaggaa agggactgag acatgagtgc tgtagggttt tgggaactcc  18240
actctgccca ccctgtgcaa agggctcctt ttttcatttt gagacagtct cgcacggtcg  18300
cccaggctgg agcgcaatgg cgcgatctcg gctcactgca acctctgcct cccaggttca  18360
agtgattctc ctgcctcagc ctcctgagta gctgggatta caggcgccca ccaccaagcc  18420
cgggtaattt tttgtatgtt tagtagagat ggggtttcac tatgttggcc aggctggtgt  18480
tgaactcctg acctcatgat ccgcccacct cggcctccca aagtgctggg attacaggcg  18540
tgacccaccc catgaaaaaa aattaaaaaa tgaagcgatg ctgggcgcgg tggatcacgc  18600
ctgtaatccc agcactttgg gaagctgagg caggcagatc acgagggcag gagattgaga  18660
ccatcctggc taatacggtg aaaccccatc tctactaaaa ctacaaaaaa ttagccgggt  18720
gtggtggcag gcacctgtga tcccagctac tcaggaggct gaggcaggag aatcgcttga  18780
acccaggagg tggaggttgc agtgagccgg gatcacacca ttgcactcca gcctgggtga  18840
cagagtgaga ctctgtctca aaaaaaaaaa aaaaaaaaaa agcgaattct gaaatacatg  18900
aattcttttc cttagatgcc tgcttctgtc ttgaggtttg ttgttgttat ttcgaaacag  18960
agtcttgctc tgtcgctcag gctggagtgc agtggcatga tcttggctca ccacaacctc  19020
cggctcccag gttcaagcga ttcttctgcc tcagcctcct gagtagctgg gattacagct  19080
gaatgccacc ttgctgggct aatttttgta tttttagtag agatggggtt tcaccatgtt  19140
ggccaggctg gcctcgaact cctgacctcg agtgatctgc ccgcctcctg aagtgctggg  19200
attacaggcg tgagccacct cgtcctggtg agggtttttt tttttcccca accctctgtg  19260
gtggatactg aaagaccata ttaggataac tgtacagtat agagaaggca gtggcaagtt  19320
ttctctgtca tataccagag tgggcttggg catggtggca tactcctgta gtctcagcta  19380
atcaggaggc tgaggaagga ggatcgcttg ggcccaggag ttggagactg tagtgagctg  19440
tgatcacacc accacacttc aatctgggca acagagcaag agaccctatc tctaaaaaaa  19500
agtaagtatt tcggacactg tgggccatac ggtctctggt gcagtttctc aacatggctg  19560
ttgggtgaac acaaccacgc acagaacgca aaccaataca cgtggctgtg ggcccagaaa  19620
atgttattta tggacacaaa aattggaatt tcatataact gttttgtgtc atgaaaatga  19680
tttcccttt tatttttatt tttcttctca agtatttaaa tatgtaaaag ccatttttag  19740
gcctggcagg atggttcaca gctgtaatcc cagcactttg ggaggtcgag gcgggaggat  19800
cacgaggtca ggagatcgag accatcctgg ccaacacagt gaaaccccgt ctctactaaa  19860
```

-continued

```
aatacaaaaa attaaccagg cttggtggcg cgcgtctgta gtcccagctg ctcaggaggc  19920
tgaggcagga gaatcgcttg aatgcaggag gcggaggttg tagtgagccg aggttgcacc  19980
actgcactcc agcctgagcg acagagtgag agtccgcctc aaacaaaaaa atgtttgccc  20040
atgctggtct tgaactcctg ggctcaagct atctgcctgc cttggtctcc caaagttctg  20100
ggattacagg catgagctac agcgcccgga cttttgttgt tttatatcta tatatctata  20160
tataacttgt tttatgtata tatataactt gttttatata tatacataaa ctgcagtaaa  20220
aaacatgtaa cataaaattt accttctcaa accttattaa gtgcacagtt ctgtgccatt  20280
agcaaattca cactgttgta caacatcaca accaccatct ccagaacttt tttttttttt  20340
tttattcttt ttgagacaga gtctcactcg tcgcacgggc tggagtgcag tggtgcgatc  20400
tcggttcact gcaacctcca cctaccaggt tcaagcaatt ctcctgcctc agccccctca  20460
gtagctggga ttacaggtgc ccgtcctacc acgcccagct aatttttgta ttttcagtag  20520
agactgactg ggtttcacca tgttggccag gctggtctcg aactcctgac ctcaagtgat  20580
cctcccacct cagcctccca aagtgctggg aatacaggca tgagccactg cgcccggccc  20640
cagaactctt ttatcttccc aaactgaagc tctgtcccca tgaaacactc actctccatc  20700
ccctccccaa ctcctggcac ccaccattct actttctgtc cctatgaatg tgatggctct  20760
agggacctcc tctgagtgga atcagacagc attttccttt tttgactggc ttatttcact  20820
gagccaagtg cggtggcaca cgcctgtaat cccaaaactt tgggagaccg aggcgggcgc  20880
atcacctgag gtcaggagtt cgagaccagc ccggccaaca tggtgaaacc ccatctctag  20940
taaaaataca aaaaattagc ctgtcatggt cgtgggtgcc tgtaatccca gctaagtggg  21000
aggctgaggc aggagaatcg cttgtaccca ggaggcggag gtcgcagtga gccgagatcg  21060
tgccattaca ctccagcctg ggcaacaaga gtgaaactcc gtctctccta aaaatacaaa  21120
aaaattagct gggcatggtg gcacatgcct gtagtcccag ctacttggga ggctgaggca  21180
ggagaatcac ttgaacccgg gaggtggagg ttgtaatgag ccaaggttgg cggcgaaggg  21240
atgggtaggg gcccgagagt gaccagtctg catcccctgg ccctgcgcag ggaccaacga  21300
atgcttggac aacaacggcg gctgttccca cgtctgcaat gaccttaaga tcggctacga  21360
gtgcctgtgc cccgacggct tccagctggt ggcccagcga agatgcgaag gtgattcccg  21420
ggtgggactg agccctgggc cccctctgcg cttcctgaca tggcaaccaa acccctcatg  21480
cctcagtttc cccatctgtt aagtgtgctt gaaagcagtt aggagggttt catgagattc  21540
cacctgcatg gaaaactatc attggctggc cagagtttct tgcctctggg gattagtaat  21600
taagaaattt caggccgggt gcgtaatccc tgtaatccca acaccttggg acgccgaggc  21660
gggcagatca cctgaggtcg ggagttccag accagcctga ccaacatgga gaaaccccgt  21720
ctctactaaa aatacaaaat tagccgggct tggtggtgca tgcctataat cccagctact  21780
caggaggctg aggcaggaga atcacttgaa cctgggaggt ggaggttgtg gtgagccaag  21840
atcgtgccat tgcactccag cctgggcaac aagagtgaaa ctccatccaa aaaaaaaaga  21900
aaagaaaaga aaaaaaagaa aagaaatttc agctgacaca gcttcacact cttggttggg  21960
ttcccgtggt gaatgatgag gtcaggtgat gactggggat gacacctggc tgtttccttg  22020
attacatctc ccgagaggct gggctgtctc ctggctgcct tcgaaggtgt gggttttggc  22080
ctgggcccca tcgctccgtc tctagccatt ggggaagagc ctccccacca agcctctttc  22140
tctctcttcc agatatcgat gagtgtcagg atcccgacac ctgcagccag ctctgcgtga  22200
acctggaggg tggctacaag tgccagtgtg aggaaggctt ccagctggac ccccacacga  22260
```

```
aggcctgcaa ggctgtgggt gagcacggga aggcggcggg tgggggcggc ctcacccctt  22320
gcaggcagca gtggtggggg agtttcatcc tctgaacttt gcacagactc atatcccctg  22380
accgggaggc tgtttgctcc tgagggctct ggcaggggag tctgccgccc tgttaggact  22440
tgggcttgcc agggggatgc ctgcatatgt cctagttttt gggaatatcc agttaacgga  22500
accctcagcc ctactggtgg aacaggaacc ggctttcctt tcagggacaa cctggggagt  22560
gacttcaagg ggttaaagaa aaaaaattag ctgggcatgg tgccacacac ctgtggtccc  22620
agctactcag aaggctgagg cgggaggatt gcttgagggc aggaggattg gttgatcctc  22680
ccacctcagc ctccggagta gctgggacct caggtgcatg ccactatgcc tggctaattt  22740
tctttttct ttttttttt ttttcgagac ggagtctcgc tctgttgccc aggctggagt  22800
gcagtggcag gatctcggct cactgcaagc tccgcctccc gggttcacgc cattctcctg  22860
cctcagcctc cccagtagct gggactacag gagcccgcca ctgcaccagg ccaatttttt  22920
tgtattttta gtagagacgg ggtttcactg tgttagccag gatggtctcg atctcctgac  22980
ttcgtgatcc gcccacctcg gccttccaaa gtgctcggat tacaggcgtg agccactgcg  23040
cccagccgct aattttcata tttttagtaa aaacagggtt tcaccatgtt ggccaggcta  23100
gtcttgaact cctgaaccca agtgatcctc ctgccttggc ctcccaaagt gctgggatta  23160
cagacaccac acctggctat tattattttt tagagacagg gtgctgctct atcttccagc  23220
ctgtagtgca gtgcagcctc catcatagct cgctgcagcc ttgacctcct gggttcacgt  23280
gatcgtcccg cctaagcctc tggaggagct gggagtactg gcatgtgcca ccatgcctgg  23340
ttaatttttt ttttttttt tttgagacag agtctcattc tgtcacccag gctggagtgc  23400
ggtggtgcga tcttggctta ctgaaacctc cacctcccag gttccagcaa ttctcctgcc  23460
tcacccttct gagtagctgg gattacaggt tccggctacc aaacctggct agtttttgta  23520
tgtttagtag agacagggtt tcaccatgtt ggtgaggctg gtctcgattc tcccgcctca  23580
gcctcccaaa gtgctgggat tacaggcttg agccaccgtg cctggctttt tttttttttt  23640
tttttttgt ggcaataagg tctcattgtc ttgcccaggc tagccttatg ctcctagcct  23700
caagtgatcc tcctccctca gcctcccaaa gtgctgggat tacaggtggg cgccactgtg  23760
cctgttcccg ttgggaggtc ttttccaccc tctttttctg ggtgcctcct ctggctcagc  23820
cgcaccctgc aggatgacac aaggggatgg ggaggcactc ttggttccat cgacgggtcc  23880
cctctgaccc cctgacctcg ctccccggac ccccaggctc catcgcctac ctcttcttca  23940
ccaaccggca cgaggtcagg aagatgacgc tggaccggag cgagtacacc agcctcatcc  24000
ccaacctgag gaacgtggtc gctctggaca cggaggtggc cagcaataga atctactggt  24060
ctgacctgtc ccagagaatg atctgcaggt gagcgtcgcc cctgcctgca gccttggccc  24120
gcaggtgaga tgagggctcc tggcgctgat gcccttctct cctcctgcct cagcacccag  24180
cttgacagag cccacggcgt ctcttcctat gacaccgtca tcagcagaga catccaggcc  24240
cccgacgggc tggctgtgga ctggatccac agcaacatct actggaccga ctctgtcctg  24300
ggcactgtct ctgttgcgga taccaagggc gtgaagagga aaacgttatt cagggagaac  24360
ggctccaagc caagggccat cgtggtggat cctgttcatg ggtgcgtatc cacgacgctg  24420
agggctgcag agggaatgga gggagcagga aggagcttca ggaactggtt agtgggctgg  24480
gcatggtggc tcaaagcacc tgtaatccca gcactttggg aggccaaggt gggtggatca  24540
tcaagaccag cctgaccaac atggtgaaac ctcgtctcta ctaaaaatac aaaaattagc  24600
```

```
cgggtgtggt ggtgggcacc tgtaatccca gctgctcggg aggctgaggc aggagaatca  24660
cttgaacctg ggagatggag gttgcagtga gccaagacag ccccactgca ctccagcctg  24720
ggtgacagag tgagactccg tctcaaaaaa aaaaaaaaaa actaaacaaa aaactggtta  24780
gtggctagac aacaggatgg tatcttccaa gcccatggct gactcagcag ctcctgggtc  24840
aagacactgt gacctgtgtc ccctggcagg aagcatcgcc cctgccacct gcccggtgta  24900
ctctgtacct gtcaggtgac atctgctacc taagcacgtg agaggtggca tttcacagtt  24960
tcagtgtggt gctgacaacc cgggacgcac actgtccttg cagctacaat caggaggtga  25020
atgttgggtt tccagcagag aacactggag aaggcacact tggtgtctgg aagggaaaag  25080
cagggaagag agcatcatca gatgcctgcg ggtgaaggtg ggcccgctat ggccagcgtc  25140
ccttttattt tttatttatt tatttatttg agatggaatc tcgctctgtc gcccagactg  25200
tagtgcagtg gtgcgatcac ggctcactgc aagctccgcc tcacaggttc acgccattct  25260
cctgcctcag cctcccgagt agctgggact acaggcaccc gccaccacgc ccggttaatt  25320
ttttgcattt ttattagaga cggggtttca ccgcgttagc caggatggtc taaatctcct  25380
gaccctgtga tccacccgcc tcggcctccc taagtgcttg gattacaagc gtgagccacc  25440
acgcccggcc cccttttat tttttatttt ttgagacgga gtctcgctct gtcgcccagg  25500
ctagattgca gtggcgtgat ctcggctcac tgcagcctcc gcctcccagg ttcaagtgat  25560
tctcctgcct caacctccca actaattagg attacaagca tgtaccacca tgcctgacta  25620
attttttgta tttttagtag agactgggtt tcaccatgtt ggctaggctg gtctcgaacc  25680
cttagcctca agtaatctgc ctgcctcagc ctcccaaaca gcggggatta caggcatgag  25740
ccactgtgcc caacccaacc ctggatctct tttaaacaag acaatgctcg ctgttgccac  25800
agaacaatgg gtggggtaca tgtggcccag tgtgtttggc cacataactg ccaggccaga  25860
gggaaagaga ctctcagact gtctccactc agatacaaat gtgtgtgttg tgtgcgtgtg  25920
ttctggtctc atatttgttt gttttgagac agggtgtcgc tctgtcactg agtctggagt  25980
gcagtggcgc aatcagagtt cactgcagcc tcaaactctt gggctcagtt gattctccca  26040
cttcagcctc ccaagtagct ggaactacag gtgaacacca ctgtgcccag ctaatttatt  26100
ttatttttag tagagatgag gtctcactat gttgcccagg ctggtcttga cctcctagcc  26160
tcaagcaatc ctcctgcctt ggtctcccaa agtgctggga ttacacgtgc gagccattgc  26220
gcatggcttg tgttcttgtg tttcttcctt tttctttcga gatggcgtct cagtctgcca  26280
cccaggctgg agtgcagtgg tgtgatcata gctcactgta gcctcaactt cctgggctca  26340
agcaatcctc ttgatttcag cctcccgggc ctggccagca tggtgaaacc ccgtctctac  26400
taaaaataca aaaatgtagc caggcgtggt ggtgggcgcc tgtaatccca gctacaccag  26460
aggctgaggc aggagaatcg cttgagcctg gaaggtggag gttgcagcaa gccaagatcg  26520
tgccactgca ctccagcctg ggcaacagag acagactctg tctcaaaaaa aaaaaaaaaa  26580
aacccaaaca agccacattt ggagtttggg gttcccagca ggactatttc ccaagcctga  26640
gcctggctgt ttcttccaga attcgttgca cgcattggct gggatcctcc cccgccctcc  26700
agcctcacag ctattctctg tcctcccacc agcttcatgt actggactga ctggggaact  26760
cccgccaaga tcaagaaagg gggcctgaat ggtgtggaca tctactcgct ggtgactgaa  26820
aacattcagt ggcccaatgg catcacccta ggtatgttcg caggacagcc gtcccagcca  26880
gggccgggca caggctggag gacagacggg ggttgccagg tggctctggg acaagcccaa  26940
gctgctccct gaaggtttcc ctctttcttt tctttgtttt ttcttttttt gagatgaggt  27000
```

cttggtctgt cacccaggct ggagtgcact ggcgcaatcg tagctcactg cagcctccac 27060
ctcccaggct caagtgatcc tcctgcctca ccctcctgag tagctgagat tacagacacg 27120
tgccaccacg gcagactaat tttattttat ttttgggaag agacaaagtc ttgttatgtt 27180
ggcctggctg gtctcaaact cagggtgcaa gcgatcctcc cgcctcagcc ttccaaactg 27240
ctgggattac aggcgtgggc caccgtaccc agcctccttg aagtttttct gacctgcaac 27300
tcccctacct gcccattgga gagggcgtca caggggaggg gttcaggctc acatgtggtt 27360
ggagctgcct ctccaggtgc ttttctgcta ggtccctggc agggggtctt cctgcccgga 27420
gcagcgtggc caggccctca ggaccctctg ggactggcat cagcacgtga cctctcctta 27480
tccacttgtg tgtctagatc tcctcagtgg ccgcctctac tgggttgact ccaaacttca 27540
ctccatctca agcatcgatg tcaacggggg caaccggaag accatcttgg aggatgaaaa 27600
gaggctggcc cacccccttct ccttggccgt ctttgaggtg tggcttacgt acgagatgca 27660
agcacttagg tggcggatag acacagacta tagatcactc aagccaagat gaacgcagaa 27720
aactggttgt gactaggagg aggtcttaga cctgagttat ttctattttc ttctttcttt 27780
tttttttttt ttttgagaca gagttttgct ctcgtttccc aggctggagg gcaatggcat 27840
gatctcggct caccgcaacc tccacctccc aggttcaagt gattctcctg tctcaggctc 27900
cccagtagct gggattacag gcatgcacca ccaccatgcc cggctaattt tgtattttta 27960
gtagagacgg agtttctcca tgttggtcag gctggtctcg aactcccgac ctcaggtgat 28020
ctgcctgcct cggcctccca aagtgctggg attacagact tgagccaccg cgcccagcta 28080
tttctgtttt ctttctttct tcttcttctt tttttttttc taagagacag gatctcactc 28140
tgtccccagg caggagtgca gtgctgtgat catagctcac tgcagcctta acctcctggg 28200
ctcaagtgat cttcccacct cagcctccca agtagctgga actacaggtg cacaccacca 28260
tgcccagctc atttttgtat tttttttttt tttgagacag tctcgttctg tcaccccggc 28320
tggagtgcag tggtacaatc ttggctcact gcaacctctg cctcccaggt tcaagcgatt 28380
ctcctgcctc agcctcctga gtagttgaga ttacaggcat gtgtgccatc atacctggct 28440
gatttttgta ttttttttta gagatggggt ctcagtatgt tgaccaggct tgtcttaaac 28500
tcccggcctc aagtgatcct cccacttcag tctcccaaag tgctgggatt acaggcatga 28560
gccactgcgg ccggtttgtt ttcttttttt tttcgttttt tggagacgga atttcacctt 28620
tgttgcccag gatggagtgc aatggcacga tatcgcctca ccacaacctc tgcctcctgg 28680
gttcaaacca ttttcctgcc tcagccttct tagtagctgg gattacaagc atgtgccacc 28740
acgcccggct gattttgtat ttttagtaga gatggggttt ctccatgttg gccaggctgg 28800
tctcgaactc ctgacctcag gtcattcgcc cacctctgcc tcccaaagtg ctgggattac 28860
aggcgtgagc caccgtgccc ggtggtttgt attcttttta ctgagagtcg tgaaaggcag 28920
tgatcctctg tcacatgtga tcttggctct caggggacat ttggcaattt ctagagattt 28980
tttggttgtc acaagtcaat ggggaagact gttggcattt agtgggtaga ggctggtgac 29040
gctgctgaac acccagaaca gggaagtagc aggccctaga tagagccatc gtggggaaac 29100
cctgctctaa ggaaatggcg ctattttata accccacgtt cctggcatga ttaccaacag 29160
ccaaaagtgg agtcccccca agtgtgttcg tccatttgca ttgcagtaaa ggaatagctg 29220
aggccgggta atttataaag aaaagagatt taaactgggt atggcagttt atgcctataa 29280
tcccagaact ttgggaggct gaggcaggag gatcgcttga gtccaggagt gtgagaccga 29340

-continued

```
gaccagcctg gccaacatga cgaaactctg tctctacaaa aaatacaaaa agtaggccag  29400
gcacggtggt tcacgcctgt aatcccagca ctttgggagg ccgaggcggg cggatcacga  29460
ggtcaggaga tcgagaccat cctggctaac acggtgaaac cccgtctcta ctaaaaatac  29520
aaaaacaaaa ttagccgggt gtggtggcag gcgcctgtag tcccagctac tcgggaggct  29580
gaggcgggag aatggcgtga acccgggagg cggagcttgc agtgagccaa gatcgcgcca  29640
ctgcactcca gcctgggtga ccgagttgag actccgtctc aaaaaaaaaa aaaaaaaaaa  29700
aaatacaaaa agtagccagg tgtggtggca ggcacctgta atcctgggtt ctcgagaccg  29760
aggcatgaga attgcctgac cccaggaggt ggaggctgca gtgagccaag atcatgccac  29820
tgcactccag cctgggcgac agagtgggac tctgtctcaa aaaacaacaa aaaaaaagtt  29880
ctggaaatgg atggtggtga tggtgatact tccacaacag cgtgaatctg cttaaggcca  29940
ccgaactgtg cactcacaaa tagtcgagat ggtacatttt atgttatgtg tatttcacca  30000
caattaaaaa ctagttgtgg gccaggtgtg gtggttcatg cctgtaatcc cagcactttg  30060
ggaggtcaga gggaggtgga tcatgaggtc agcagttcga gaccagccag gccaacatgg  30120
tgaaacccca tctctactaa aaatacaaaa attagccagg cgtggtggca catgcctgta  30180
gtcccagcta cttgagaggc tgaagcagga gaatcgcttg aacctgggag gctaagattg  30240
cagtgagccg agatcgtgcc actgcactcc agcctggacg acagagtgag acttcgtctc  30300
aaaaaaaaaa ccaaaaaaaa aattagctgt gggtcaggca ctgtggctca cgcctgtaat  30360
cccagcactt tgggagaccg aggtaggtgg atggcctgag gtcaggagtt cgaatccagc  30420
ctggccaaca tggtgaaagc ccgtctctac taaaaataca aaaaattagt caggtatgtt  30480
ggcacacctg taatcccagc tactcgggag gctgaagcaa gagaatcgtt tgaacccagg  30540
aggtggacgt tgcagtgagc cgagattggg ccactgtact ccagcctggg caacaaaagt  30600
gaaactctgt ctgaaacaaa caaacaaaca aacaaacaga caaacaaaaa aactagttgt  30660
ggagagaggg tggcctgtgt ctcatcccag tgtttaacgg gatttgtcat cttccttgct  30720
gcctgtttag gacaaagtat tttggacaga tatcatcaac gaagccattt tcagtgccaa  30780
ccgcctcaca ggttccgatg tcaacttgtt ggctgaaaac ctactgtccc cagaggatat  30840
ggttctcttc cacaacctca cccagccaag aggtaagggt gggtcagccc cacccccca  30900
accttgaaac ctccttgtgg aaactctgga atgttctgga aatttctgga atcttctggt  30960
atagctgatg atctcgttcc tgccctgact ccgcttcttc tgccccagga gtgaactggt  31020
gtgagaggac caccctgagc aatggcggct gccagtatct gtgcctccct gccccgcaga  31080
tcaaccccca ctcgcccaag tttacctgcg cctgcccgga cggcatgctg ctggccaggg  31140
acatgaggag ctgcctcaca ggtgtggcac acgccttgtt tctgcgtcct gtgtcctcca  31200
actgcccccct cctgagcctc tctctgctca tctgtcaaat gggtacctca aggtcgttgt  31260
aaggactcat gagtcgggat aaccatactt ttcttggatg gacacatcag caccgggctt  31320
gacatttacc cagttcccct ttgatgcctg gtttcctctt tcccggcccc ctgaagaggt  31380
gatctgattt ctgacaggag ccctgaggga ggaaatggtc ccctttgttg acttttcttt  31440
ttctttattt ttttcttttg agatttgctg tcacccagcc tggaatgcag tggtgccatc  31500
ttggctcact gctacctctc ccactgggtt caagcaattc tcctgcctca gcctcccaag  31560
tagctgggat tacaagcatg cgccaccatg cctggctaag ttttgtattt ttagtacaga  31620
cagggtttct ccatggtggc caggctggtc ttgaactcct gacctcaggt gatcctccca  31680
cctctgcctc ccgaagtgct acgattacag gcatgagcca ccgcgcccat ccccctttgt  31740
```

-continued

```
tgacttttct catcctctga gaaagtctca gttgaggcca gcacctccct caagtgaatt  31800
gaatctccct tttgaacaac aacaaataac aatatgaccc agacgtggtg gctcacacct  31860
gtggtcccag ctactcggga ggctgaggtg tgaggattgc ttgagcccag gaggtcaagg  31920
ctacagagag ctataatcac accacttcac tccagcctgg gggacaaagt gaaaccctgt  31980
ctgaaaaaaa caaaaaaaga aaaaggaaaa agaaacaata cgatcacaaa gtagatattc  32040
atagtgttta ttttcagtac tctttttttt tttttttttt ttttttgaga cggagtcttg  32100
ctctgttgcc caggctggag tgcagtggca cgatcttggc tcactgcagc ctctgcctcc  32160
caggttcaag cgcttggctc actgcaacct ccgcctcctg ggttcaagcg cttcttctgc  32220
ctcagcctcc ccagtagctg ggactatagg cacgtcccac tacgcccagc taattttttg  32280
tatttttag tagagatggg gtttcactat gttagccagg atggtctcga tctcctgacc  32340
tcgtgatctg cctgccttgg gctcccaaag tgttgggatt atgggcatga gccactgcac  32400
ctggcctttt tttttttttt ttttgagatg gagtttcgct cttgttgccc aggctggagt  32460
gcaatggtgt gatctcggct cactgcaacc tctgcctcct gggttcaagc aattctcctg  32520
cctcagcctc ccgagtagct gggattacag gcacctgcca ccacgcctgg ctaatttttg  32580
tacttttagt agagacgggg tttctccatg ttggtcaggc tggtctcaaa ctcctgacct  32640
caggtgatcc acccacctcg gcctcccaaa gttctgggat tacagacatg agccaccgcg  32700
cctggccgtg tctggccttt tttagttatt tctttttttt tttttttttt ttttgagaca  32760
gagtcttact ccgtcgccca ggctggagtg cagcggtgcg atgtctgcgc actgcaagct  32820
ccgcccccctg ggttcatgcc attctcctgc ctcagccttc tgagtagctg ggactgcagg  32880
cgcctgccac tacgcccggc tacttttttg tatatttagt agagatggag tttcactgtg  32940
ttagccagga tggtctcgat ctcctgactt tgtgatccgc ccgcctcggc ctcccaaagt  33000
gctgggatta caggcgtgag ccaccatgcc aggctttttt tttttttttt ttttttgaga  33060
cggagtcttg ctctgtcgcc caggctggag tgcagtgcca tgatctcagc tcactgcaag  33120
ctccacttcc caggctcacg ccattctcca gcctcagcct cccaagtagc tgagactaca  33180
ggggcccgcc accacactcg gctaattttt ttgtattttt agtagagacg gggtttcacc  33240
atgttagcca ggctggtctt gaactcctaa cctcaggcga ttcacctgcc tcggcctccc  33300
aaagtgctgg gattaaaggt atgagccacc tcgcctggtg tgagccacct cgcccagcct  33360
gagccacctc acccagccta agccactgtg cctggcctga ttttggactt tttaaaaatt  33420
ttattaataa ttatttttgg gtttcttttt tttgagacag ggtcttactc tgtcatccag  33480
gccatcctgt ctgtctgtca tcccagtgat gggatcatac cttgctgcag cctctacctc  33540
ctgggctcaa gcgatcctcc cccctcagcc tcctgagtag ctgggagtac aggtgtgcac  33600
caccacacct ggctaatttt tttttttttt tttgtatata gagatggtat tttgccatgt  33660
tgaccaggct agtcttaaac tcctggactc actcaagaga tcctcctgcc ttggcctccc  33720
aaggtcattt gagactttcg tcattaggcg cacacctatg agaagggcct gcaggcacgt  33780
ggcactcaga agacgtttat ttattctttc agaggctgag gctgcagtgg ccacccagga  33840
gacatccacc gtcaggctaa aggtcagctc cacagccgta aggacacagc acacaaccac  33900
ccgacctgtt cccgacacct cccggctgcc tggggccacc cctgggctca ccacggtgga  33960
gatagtgaca atgtctcacc aaggtaaaga ctgggccctc cctaggcccc tcttcaccca  34020
gagacgggtc ccttcagtgg ccacgaacat tttggtcacg agatggagtc caggtgtcgt  34080
```

```
cctcactccc ttgctgacct tctctcactt gggccgtgtg tctctgggcc ctcagtttcc  34140
ctatctgtaa agtgggtcta ataacagttc ttgccctctt tgcaaggatt aaatgggcca  34200
aatcatatga ggggccaggt ccttcaggct cctggttccc aaagtcagcc acgcaccgtg  34260
tgggtcccaa aattttatca aggcacattc gttgcctcag cttcaggcat ctgcccaaaa  34320
aggccaggac taaggcaagg agagggaggg attcctcagt actcagcttt tcacagaggc  34380
tccaaaaggc taaggaatcc agtaacgttt taacacaatt ttacaatttt tttttttgag  34440
acggagtttt gctcttgttg cccaggctgg agtgcagtgg cacgatctcg gctcactgca  34500
acctctggct cccgggttca agcgattctc ctgcctcagt ctcccgagta gctgggatta  34560
caggcatgcg ccaccacgct cggctaattt tgtattttta gtacagaagg ggcttctctg  34620
ttggtcaggc tggtcgtgaa ctctcaacct caggtgagcc acccgcctga gcctcccaaa  34680
gtgctgggat tacaggtgtg agccaccacg cctggccttt tttttgagac agagtctcgc  34740
tctcgcccat gctgtactgc agtgacgcag tctgggctca ctgtaacctc cgcttcccag  34800
gttcaagtga ttcttctgcc gcagcctccc atgtagagta gctgggatta caggcacccg  34860
ccaccatgcc tggctaattc ttgcattttt agtagagatg ggtttcaca gtgttggcca  34920
ggctggtctc aaacttctga cctcaagtca tctgcctgcc ttggccctgc caaagtgctg  34980
ggattataga tgtgagccac cgcgcctggc ctacagttta ttctttggtg gctcacacct  35040
gtaatctcag cactttggga ggccaaggtg ggagaatggc ttgagcccag gagttcaagt  35100
ccagcctggg caacatagca agaccctatc tctactacaa aataaataat aaataaacta  35160
atttttttc ttttaaaacc caactattca acatggcaat gcaatatatt aaaaaaaattt  35220
ttttttctt tgaaacggag tctctcactg tcacccgggc tggagtgcag tgtcgccatc  35280
ttggctcact gcaacctccg cctcccaggt ccaagtgatt ctcctgcttc agcctcccga  35340
gtagctggga ttacaggcac ccaccaccat acccagctaa tatttttgta tttttagtag  35400
agatggggtt tcactatgtt gggcaggctg gtctggaact cctgacctcg tgatctgccc  35460
gaggatcggc ggcctcccaa agtgctgggg attgcaggca tgagccaccg tgcccagcca  35520
aaactttttt atttttattt ttttgggaca cggtctcact gtgtacccca gactggagtg  35580
atagagtgct gtcatggctc actgcagcct caacctccct gggctcaggt gatcttcctg  35640
cttcagtctc ccaggtagct gggactacag gcatgagcca ccacacccag ctaatttttg  35700
aatttttttg tagagacagg gtttcacctt gtggcccaga cttgtctcta actccagggc  35760
tcaagcgatc tgcccacctt ggcctcccaa agtgctgaga ttaatgcaat ttaaaaaatt  35820
ttttggccag gcctggtggc tcatgcctgt attcacaaca ccttgggagg caaaggtggg  35880
cagatcactt gaggtcagga gttcgagact agcctggcca acatggtgaa accccctgtc  35940
tactaaaaaa atacaaaaat tacctgggca cagtggtggg tgcctgtaat cccagctact  36000
tgggatgctg agggtggaga attgcttgaa cctgggaggc agaagttgca gtaagccaag  36060
atcatgccac tggactccag cctcagtgac agagcaaaac tctgtctcca aaaaaattgt  36120
ttttttttt tttttttcaa atcatcacac tacagccaag gcctggccac ttacttttgt  36180
aaataaagtt ttattggagc cagtggacca gtgaggccga atcttgcagg tgtaagatca  36240
cagtctatcc ttgaaaattt tgatattttg ttcattgggt ggtttttcat taatttaaat  36300
tttaaaaaat aacatattaa aggctggtgt ggaggtgcac gcctgcagtc ctagctactc  36360
ccagaggctg aggcgggaga cttgcttgag cccaagagtt gaagtccagc ctgggcaaca  36420
tagcgagacc cccatctcta aaaataaaaa taatgcatta gaatattatt ggattcctgg  36480
```

-continued gcagggcaca gtggctcaca cctgtaatcc cagcactttg ggaggctgag gtgggtggat 36540
cacctgaggt caggagtttg agaccagcct ggccaacatg gtgaaacccc gtctctacta 36600
aaaatacaaa aattagccag gcgtggtggc aggtgcctgt aatcccagct actcgggagg 36660
ctgaagcacg agaatcgctt gaatccagga ggcggaggtt gcagtgagct gagattgcgc 36720
cattgcactc cagcctggag gacaagagtg aaactccatt cccctctgca aagaaaagga 36780
atattatcag attcctaagc tttttggctc ccccttttagt ttgggggctg gggtggtgag 36840
tgtctgacct ggcctcactg tcctccctgg atgtgatgag acccaggtgt gggtcaggat 36900
gtcattcgtt tgtccaccag agggcgccca aactgctttg agctgctggg aaatggtgct 36960
cctagacttt tagcaaacaa acaaaaaaaa atggcacatc ggcaaatttc agaccattct 37020
ttttttttt ttttttggtt ccagagtagc tgaaatcttt gttcagttac aagcaggata 37080
aaatggaaac tgcctgggag aggctgagaa accttcttgc ttgggggagg tggggcactg 37140
ctagaattaa tcgcttcaca gaccagccca tccaggactc ctcaaatttg gcaaaaaagc 37200
cattcattca ttcattcatt tatgtagaga cgagggggat ctggctatat tgcctagatt 37260
ggtctcaaat tcctggcctc aagtgatcct cctgccttgg tctactaatg tgctgcgatt 37320
acaggcatga gccaccgtgc ctagctctag tggacttgaa atgttgcctt gcccagggcc 37380
cttatgttga atggcccagg tccacttgta tggttctgta ccaaggttaa ccccatccca 37440
taatgcctgg gacagttgat gcaggacaat cagcttctgt gccattcaac ctcaggactg 37500
agcatgctgg gcattgtggg gtccgaaggt ggctcccctg tccccttcaa aataccctct 37560
ttttcttttc ttcttttttt ttttttttt tttttgagac gaagtcttgc tctgttgccc 37620
cagctagagt gcagtggtgc gatctcagct ccccgcaacc tctgcttccc gggttcaggc 37680
gattctcctg cctcagcctc ctgagtagct gggattacag gtgcccaccg ccacagctgg 37740
ctaatttttg tatttttagt agagacaggg tttcaccgtg ttggccaggc tggtcttgaa 37800
ctcctgacct caggcaacct gcccacctca gcctcccaaa gtgctgggat tacaggtttg 37860
agccactggg cctggccttt tttttttttt tttgagaggg agtctcactc tgttgcccag 37920
gctggagtgc aatggcgcga tcttgactca ctgcaactcc atttcccggg ttcaagtgat 37980
tctcctccct cagcctccca agtagctggg attacaggtg catgccacca cggccagcta 38040
attttgtatt tttagtagag acagggtttc actatgttga tcatgctggt ctcaaactcc 38100
tgaccttagg tgatctgccc gccttagcct cccaaagtgt tgggattaca ggtgtgagcc 38160
accgcgccca gaccaaaata tgctcatttt aataaaatgc acaagtaggt tgacaagaat 38220
ttcacctgca accttgtcaa ccacctagaa taaaagcctc tgcagccctc ccctaaagac 38280
tcatcaatgt gaggctcaag aaccttctta ggctgggctc ggtggctcat ttctgtaatc 38340
cctgcacttt ggaaggctga ggcaggagga tctcttgagg ccaggagttc aagacaagcc 38400
tgggcaacat agccagacct ctgtttctat cccccacaaa aagaaccttc ttaaaccgga 38460
attgagtcct acaacctcga taactcacaa ataagcccgt gtggcctctc acagacttgg 38520
gaagttctcc aagtgtccag ggagatgtgc caggcgcttt cctgccgtga ccaccgtcct 38580
ctgcctgctc catttcttgg tggccttcct ttagacctgg gcctcactct tgcttctctc 38640
ctgcagctct gggcgacgtt gctggcagag gaaatgagaa gaagcccagt agcgtgaggg 38700
ctctgtccat tgtcctcccc atcggtaagc gcgggccggt cccccagcgt cccccaggtc 38760
acagcctccc gctatgtgac ctcgtgcctg gctggttggg cctgttcact ttttctcctg 38820

```
gacagggaac agccccactg gtgtccttta tcacccccac ggcctctcct ggcttggggc  38880
tgacagtgac aagatcagac agctaagggg tcagatggag gatgtggagc tgggtcccgt  38940
gctgtggaat agcctcaccg agatttgagt gccttctggg gaactggttc ccttgcaggg  39000
ggctgtgtgg agaggcgcgc tctccctgcc tcacccatgc tcatcctaac tcggttacca  39060
tcacatctct tttttctttt tttcttaaat tttaagaaaa aagaaattta atttttttga  39120
gagacagagt cttgctctgt cacccaggct ggagtgcagt ggcaccatca tgcctcgctg  39180
cagcctcaat gtctgggctc aagcgatcct cccacctcag cctcctgagt agctggtgca  39240
agccactata ccccacttcc tatttcttaa aaagtcacag ccctgtgtgt ggctaatcct  39300
ggacagaaat ctagaagaag tcagctactt ctggggcgtg gctcacccag tgggcttcag  39360
gttagatatt tcttatactt atgaggctgg gtgtggtggc ttatgcctgt aatcccagca  39420
ctttgggagg ctgaagtggg tggattgctt gggctcagga gttcgagacc aacctgggca  39480
acatggcgaa accctgtttc tagaaaaggt acaaaaatta gctgggcagg tggcacgtgc  39540
ctgtggtacc agctacttga gggcctgagg caggaggatc gcttgaacct gggaggtcga  39600
ggttgcagtg aactgagatc atgtcactgc actccagcct ggtgacagag caagaccccg  39660
tctcaaaaaa aaaaaaagaa agaaaaaaat tcttatgcat agatttgcct cttttctgtt  39720
tgtttgtttt gagatggagt ctcgctctgt cgcccaggct ggagtacagt ggctcaacct  39780
cggctcactg caacctctgc ctcccgggtt caagcaattc tcctgcctca gcctcctgag  39840
tagctgggac tacaggcgcc cgccaccatg cccagctaat tttgtatttt ttagtagaga  39900
ctgactgggt ttcatcatgt tggccaggct ggtctcgaac tcttgacctc atgatccgcc  39960
cgcctcagcc tcccaaaatg ctgggattac aggcgtgagc caccaggccc aggccgcaag  40020
gcgatctcta aacaaacata aaagaccagg agtcaaggtt atggtacgat gcccgtgttt  40080
tcactccagc cacggagctg ggtctctggt ctcgggggca gctgtgtgac agagcgtgcc  40140
tctccctaca gtgctcctcg tcttcctttg cctgggggtc ttccttctat ggaagaactg  40200
gcggcttaag aacatcaaca gcatcaactt tgacaacccc gtctatcaga agaccacaga  40260
ggatgaggtc cacatttgcc acaaccagga cggctacagc taccccctcgg tgagtgaccc  40320
tctctagaaa gccagagccc atggcggccc cctcccagct ggaggcatat gatcctcaag  40380
ggaccaggcc gaggcttccc cagccctcca gatcgaggac agcattaggt gaatgcttct  40440
gtgcgctcat tcagaatgtc agcggacaat ggccttggtg gtgtagagga atgttggata  40500
agcaaataga gagctccatc agatggtgac agggcaaaga aagtcaaaag gagttcagag  40560
gccgggcgcg gtggctcatg cctgtaatcc caggactttg ggaggccgag gctggcggat  40620
cacctgaagt caggagtttg agaccagctt ggccatcatg acaaaacccc gtctctatta  40680
aaaatacaaa aaattagcca ggcgtgggag tgggcgcctg taatcccagc tactcgggag  40740
gccgaggtag aaaaatcgct tgaacctagg aggcagaggt tgcagtgagc cgagatcgcg  40800
ccactgcatt ccagcccggg aggcaagagc aaaactccat ctcaaaaaaa aaaaaaaaag  40860
gagttcagag gcccggcatg gtggttcaca catgtgatcc cagaacttgg ggaggttgag  40920
gcaggagaat cacctgagct cagagttcaa gaccagcctg ggcagcacag caagacccca  40980
tctctgcaaa aaataaaaat ttagcccagt gtggtgatga gcgcctagtt ccagctacta  41040
gggaggctaa ggcaggagga ttgcttgagg ctaaggtagg agattgagac tgcagtgact  41100
tgtgattgcg tcactgcgct ccagcctggg tgacagagca agcccttgtc tcttaaaaaa  41160
aaaaaaaaat tcaaagaagg gtttccagag ggccaggagg gaggaaggga gaggaggtgt  41220
```

-continued

```
tttatttttt tgcttttatt ttttattttg agacagagtc tctctctgtc acccaggttg  41280
gagtgcagtg ctgtgatctt ggctcactgc aacttctgcc tcctgggttc aagcaattct  41340
tatgcctcag cctcagcctc ctgagtagct gggattacaa cactatgccc gggtaatttt  41400
tgtattttta gtagagacga ggtttcgcca tgttgcccag actggtctcg aactcctgac  41460
ctcaagtgat ccacccgcct tggcctcccc acgtgctggg attgcaggcg tgagccactg  41520
cgcccgcctt gatctttaca caaggggttt agggtaggta gccttctctg aaccaggaga  41580
acagcctgtg cgaaggccct gaggctggac cgtgcctgtt gggtttgagg ccgttgtagc  41640
tggagcaaac agagagaggg gtaaaaaggc aggaggctac caggcaggtt gtgcagagcc  41700
ttgtgggcca ctggggagga ctttggcttt tgccctgaga gcggtgggaa gtgactgaat  41760
ccggtactca ccgtctccct ctggcggctc ctgggggaac atgcttgggg atcaggctgg  41820
gggaggctgc caggcccagg aggtgagaag taggtggcct ccagccgtgt ttcctgaatg  41880
ctggactgat agtttccgct gtttaccatt tgttggcaga gacagatggt cagtctggag  41940
gatgacgtgg cgtgaacatc tgcctggagt cccgtccctg cccagaaccc ttcctgagac  42000
ctcgccggcc ttgttttatt caaagacaga gaagaccaaa gcattgcctg ccagagcttt  42060
gttttatata tttattcatc tgggaggcag aacaggcttc ggacagtgcc catgcaatgg  42120
cttgggttgg gattttggtt tcttcctttc ctcgtgaagg ataagagaaa caggcccggg  42180
gggaccagga tgacacctcc atttctctcc aggaagtttt gagtttctct ccaccgtgac  42240
acaatcctca aacatggaag atgaaagggg aggggatgtc aggcccagag aagcaagtgg  42300
ctttcaacac acaacagcag atggcaccaa cgggaccccc tggccctgcc tcatccacca  42360
atctctaagc caaaccccta aactcaggag tcaacgtgtt tacctcttct atgcaagcct  42420
tgctagacag ccaggttagc ctttgccctg tcacccccga atcatgaccc acccagtgtc  42480
tttcgaggtg ggtttgtacc ttccttaagc caggaaaggg attcatggcg tcggaaatga  42540
tctggctgaa tccgtggtgg caccgagacc aaactcattc accaaatgat gccacttccc  42600
agaggcagag cctgagtcac tggtcaccct taatatttat taagtgcctg agacacccgg  42660
ttaccttggc cgtgaggaca cgtggcctgc acccaggtgt ggctgtcagg acaccagcct  42720
ggtgcccatc ctcccgaccc ctacccactt ccattcccgt ggtctccttg cactttctca  42780
gttcagagtt gtacactgtg ta                                          42802
```

<210> SEQ ID NO 4
<211> LENGTH: 42802
<212> TYPE: DNA
<213> ORGANISM: homo sapien

<400> SEQUENCE: 4

```
ctcttgcagt gaggtgaaga catttgaaaa tcaccccact gcaaactcct ccccctgcta     60
gaaacctcac attgaaatgc tgtaaatgac gtgggccccg agtgcaatcg cgggaagcca    120
gggtttccag ctaggacaca gcaggtcgtg atccgggtcg ggacactgcc tggcagaggc    180
tgcgagcatg gggccctggg gctggaaatt gcgctggacc gtcgccttgc tcctcgccgc    240
ggcggggact gcaggtaagg cttgctccag gcgccagaat aggttgagag ggagcccccg    300
gggggccctt gggaatttat ttttttgggt acaaataatc actccatccc tgggagactt    360
gtggggtaat ggcacggggt ccttcccaaa cggctggagg gggcgctgga ggggggcgct    420
gaggggagcg cgagggtcgg gaggagtctg agggatttaa gggaaacggg gcaccgctgt    480
```

-continued

```
cccccaagtc tccacagggt gagggaccgc atcttctttg agacggagtc tagctctgtc    540
gcccaggatg gagtgcagtg gcacgatctc agctcactgc aacctccgcc tcccgggttt    600
aagcgagtct cctctctcag cctcccgaat agctgggatt acaggcgccc aaccaccacg    660
cccgcctaat ttttgtattt ttagtagaga cgggttttca ccattttggc caggctggtc    720
tcgaaccccg acctcaggtg atctgcccaa aagtgctggg attacaggcg tcagccaccg    780
cgcccggccg ggaccctctc ttctaactcg gagctgggtg tggggacctc cagtcctaaa    840
acaagggatc actcccaccc ccgccttaag tccttctggg ggcgagggcg actggagacc    900
cggatgtcca gcctggaggt caccgcgggc tcaggggtcc cgatccgctt tgcgcgaccc    960
cagggcgcca ctgccatcct gagttgggtg cagtcccggg attccgccgc gtgctccggg   1020
acgggggcca ccccctcccg cccctgcccc cgcccctttg gcccgccccc cgaattccat   1080
tgggtgtagt ccaacaggcc accctcgagc cactcccctt gtccaatgtg aggcggtgga   1140
ggcggaggcg ggcgtcggga ggacggggct tgtgtacgag cggggcgggg ctggcgcgga   1200
agtctgagcc tcaccttgtc cggggcgagg cggatgcagg ggaggcctgg cgttcctccg   1260
cggttcctgt cacaaaggcg acgacaagtc ccgggtcccc ggagccgcct ccgcgacata   1320
cacgagtcgc cctccgttat cctgggccct cctggcgaag tccccggttt ccgctgtgct   1380
ctgtggcgac acctccgtcc ccaccttgtc ctggggggcg ccctcgcccc accagccccg   1440
atcaagttca cagaggggcc cccggccacc ctcaaggcct cggttcctta cgaggttgaa   1500
acgttgcctc agaatctccc cgcccctcct tggtctgcag ccgagatctt cagccacggt   1560
ggggcagcta tcccccggga ccgaccccct ggggtggcct cgcttcttca gaggctgtga   1620
atggcttcgg ttcagctgtc caagcggcga tttttcctct gggtgaaatg gattagattt   1680
tagatttcca caagaggctg gttagtgcat gatcctgagt tagagctttt taggtggctt   1740
taaattagtt gcagagagac agcctcgccc tagacaacag ctacatggcc ctttccctcc   1800
tgagaaccag cctagcctag aaaaggattg ggattgcctg atgaacacaa ggattgcagg   1860
aaactttttt tttaattggc aagggggttg gctttgactg gatggagagc tttgaactgc   1920
cttgaaattc acgctgtaac taacacacca gtttcctctg ggaggccaga gagggaggga   1980
gggtgtaatg aaatacggat gattgttctt ttatttttat ttacttattt atttttttaac   2040
tttttgtaga gatgaggtct cgcttggttg ctcaggctgg tcttgaactc ctggcctcaa   2100
gcgatcctcc tacctcagcc tcccaaagtg ttgggattac aggagtgagc caccgcgccc   2160
caccggggat gatgatgatt gcaaacattc tgccactcag ttttacaaaa gaaagagagg   2220
cactggatta atgtgtatct cactcaccaa tcaacctctt ccttaagata aaatgttaag   2280
gaagtcttag gcaaggcctt gtttgttcat cactttagtt tctctctccc gggatggctg   2340
agaatgtgat gtttcctctg ttgtcaagga gactacaccc ctgatgtttt cctccagact   2400
tctgagagct ggtgtgtgtt tctagcactt tctagctgca ccacctcacg ctgtagctgg   2460
cttcaaggca tatccagggg ggagtttctt gtccatttcc tttacaaagg gaagttgttg   2520
gaatctgaac cgcaagcctt cacttagacc aaaatcaggc aacagcggtg agcgcagctc   2580
caaacgtgtc aatgactcac ccaaatttga gtaagggagt tggctgcttt aacgagccgc   2640
agggtgattc ccttgtcatt tccggaaata cctatcttcc agggaacact gggaaaaaac   2700
agggagacct ttgttgagac agaaaacctg taggggaatt ctgttcctca ttcctgctct   2760
tatctgtaga cttcctccct gataagatcc aattctagat gggtcggttg ctccttgctt   2820
tgatgggtgc tttgatgggc tttattatta ttattattat tattattatt attttgatgg   2880
```

-continued

```
gctttttgat gtccctttc cttccacact ctgtcccaac tgtcaagcaa atagcctttt   2940
gttgctaaga gactgcagat gtaaccgacc agcagcaaac agtgagtcag gctctctctt   3000
ccggaagcaa aatcaattgc tgagatcact ctggggaaaa tacccacctt atttggaaag   3060
aagcactgat caattgatgt ctattttttt ttttttgag ttggagtctc gccctgtcac   3120
ccaggctgga gtgcaatggc ataatctcgc ctcactgcaa tccccgcctc ccgggttcca   3180
gcaattctcc tgcctcagcc tcctgagtag ctggaattat aggcgcctgc cacaacaccc   3240
ggctaatttt tgtatttgta gtagagatgg ggtttcacca cgttggccag gctggtctcg   3300
aactcctgac ctcgtgatcc acccgcctca gcctcccaaa gtccaaggat tgcaggcgtg   3360
acccactgtg ccagccaatc aattgatttc tcattcattt tcagctggct ctgttccctt   3420
aagccagggg attttcgttt gtttgtttcc ccttcaagga aatgattcta gctacagttt   3480
tgatttcctt gtacaactgt tttcagtagc acagggaaag aaaacatcga aagcattcac   3540
cacctcattt gtgtgctggg ggaaaaagca gaaatgtgta ttctcttttt ttgtttcgat   3600
gaccttgttc ctgacttgtt actcgtgact tgagagatca gagggctaga ggactagaat   3660
ttatagaggt gtttttttg tttgtttatt tttgttcgag ttgcccaggc tggagtgcag   3720
tggcgcaatc tcggctcact gcaacctctg cctcccaggt tcaagcgatt cttcggcctc   3780
agcctcctga gtagctggaa ctacaggcgc ccgccaccac acccagctaa tttttgtatt   3840
tttcagtaga gatgggattt caccatattg gtcaagctgg cctcgaactc ctgacctcgt   3900
gatccacccg cctcagtttc ccaaagtgct gggagtacag gcgtgagccg ccgtgcccgg   3960
ccttttttgtg tttttgtgtt tttgagagga gctcattgct ttttaggctt ccctagcgtg   4020
agaaaatctg gggatccatg ctctagttta cttccttttt tttttttttt ttgagatgga   4080
gtctcgctta gattgcctaa tctcagctca ttgcaacttc tgcctccggg gttcaaggga   4140
ttctcgtgtc tcagcctcct gggtagctag gatacgggca cccgctacca tgcctggcta   4200
attttgtact tttagtagag acagggtttc gccacgttgg ccaggctggt ctcgaactcc   4260
tgacctcagg tgagccgcct gccttggcct cccaaagtgc tgagattaca ggcgtgagcc   4320
accgcgcttg gcctaatttg cttttcctga aattcaaatg gtctaatatg aaaaacgcca   4380
accttgcttg aaagaataag aaagaggtgc ggtttcgttg ggccgttgat gtttggaaca   4440
ggactggttt tgtccccttg ctcggaaagg gcagcaactg tgaggacagc tccctgacgt   4500
gctctcactc agcactgttc cgttcctgag cactgtcccc actagctagg ccaagggagc   4560
tcatttggca ggcaactgct gtctggctgc gcctgtggca gtaaaatctg cctttatttt   4620
ttggaggcag ggtcttgccc tgtcgctcag gctgaagtgt gcagttatag ctcactgcag   4680
cctccagctt ctgtactcaa ctgatcctcc tctctcagcc tcctgagtag ctgggactat   4740
acgcacgtgt taccactccc acctcagttt gtttgtttat ttatttattt atttatttat   4800
tgagatggag ttttgctctt gctgcccagg ctggagtgca atggcgcgat ctcggctcac   4860
cgcaacctcc acctcctggt tcaagcgatt ctcctgcctc agcctcctga gtagctggga   4920
ttacaggcat gcaccaccac gcccggctaa ttttgtattt ttcgtagaga tggggtttct   4980
ccacattggt tcaggctgtt ctcgaactcc caacctcagg tgatccaccc gcctcagcct   5040
cccaaagtgc tgggattata ggcgtgagcc cccgaacccg gccactccca gctaagttta   5100
aattttttgt ttgtttgttc gtttgttttt attttttgag acagagtctc ccgcccaggc   5160
tggagcgcag atcactgcat ccttgacctc ccaggcttaa gccatcctcc ccactcagcc   5220
```

-continued

```
tcccaagtag ctgggattac aggtgtgtgc cactatgctt ggctaagttg tgtatttttt   5280
gtagagatgg ggttcaaggg attctcgctt tgttgcctcg gttggtctca aactcctggg   5340
ctcaagcagt cctccctcct cagcctccca aggtgctggg gaaatccact tttgaaacat   5400
tgtctggaga gttgcccagg tggtagatca cagaaatagg tcatcgtggg gtccttccca   5460
tgggtgcagt cttgagccac ctgtggccag caaatatttg gagaataata gtcaggggag   5520
agcttgaggt ccagggaaag gttttgtttt tcttcaggga aaggttttta ttgttcttta   5580
tccctcctta aaggaccttc aggtgttact gacattcccg gtctacccag tggcacattt   5640
agtttgtaag ctgggccctc gtacagaggt agggaggtga gagcattgga ttagtggtca   5700
ccaaagctgc ggtcacctag tggggtgatc agaggctcct cccttaagat cttgattgcc   5760
aacgcctctg gcccaacttt cctttttatt tatcgcaagc ctcctggaat ctcaattgct   5820
ttttgcccac ccggtgtgtc agcacaagaa atgagtcatt tcctccttta agcacagttg   5880
aaattgagct gtgagtcagt gaggtgtgta cgatattgtc aaagcggggt gtgtacagta   5940
ttgacagatc tgtagttggg caagagaatt atcagagttt gtgaccacag cagattccaa   6000
agctcgactc atttcttct ctcttccttc cctttttct tttcttttt tttttttt        6060
tgacagagtc tcgctctgtt gcccaggctg gagtgcagtg gcacaatctg ggctcactgc   6120
agcccctgcc tcctgggttc aaatgattct catgtttcag cctcccgagt agctgcaatt   6180
acaggcattc gggttcaagt gattctcctg cctcagccac ctgagcagct gggattacag   6240
gcgcccgcca ccacgcccgg ctaatttttg tatttttagt agagacgggg tttcaccatg   6300
ttggccaggc tggtctcgaa ctcctgaact caggtgatcc gcccacttcg gcctcccaaa   6360
gtgctgagat tacagacgtg agtcaccgcg cccagcctgt tctgttcttt aattctcaaa   6420
acaccctcta ggaagtagag actgccattc tcccccattt tacagatcag gaaactgagt   6480
cccagaagga tttagtcagt tacccaagtt gttctagtta aatggcctgg aaagccagtg   6540
aagcccagga ttgtctatct aaccccctta ctactctaac tttcagggaa tccacatgaa   6600
tgtgctgggt caaccatcaa agttgaaatg gataaagggg gctggatgcg gtggctgatg   6660
cctgtaatcc tagcactttg ggaggccgag atgggtgggt ggattgcttg agcccaagag   6720
tttgagacca gcctgggcaa catagtgaga cacctgtctc tgcaaaaaat aaataaaaag   6780
ttagctgagt gtgatggtgc acccctctag tcacagctgt tgagttaggc ttaggcagga   6840
ggatcgcatg aacctgggag gtggaggcgg ccgtgagcct cagtcatgcc actgcactcc   6900
aacctgggca acagagtgaa agccggtgtc cgaaagagaa agaaaaaaag acatagatac   6960
atcttttaaa gttaggttgt atgttaatta cctacaactc agtttcaact gtgcttaaag   7020
gaggaaatga ctcatttctt gctacatatc aaattagccc aaaatgtagt ggcttaaaac   7080
aacacattta tgatttctca gtttttgcgt gtcaggaatt tggaagcagc acagctagac   7140
ggttccagct cagggtctct catgaagttg caatcaaaat attggcagga gagaaaaaca   7200
tattttcaga agctgcaggc ataggaagac ttggctgggg ttgaaggatc cacttccaag   7260
atggcgcact cagtggctct tggctggagg cctcagttcc ctgctgcgtg gagctctccc   7320
tccagctgct tgagtggact catgacatgc agctggcctc ccctggagca gtcgatccaa   7380
caatgagcat ggccatgaac taggctcaga agccactccc tgtcgtctct acattttcct   7440
atcagaagca agtcattaaa agtccagtgc cactccaggg gagacgaatt aggctctgcc   7500
ttctgaaagg attatcacag aagatgcggt cctatattct ttttttaaaa ttattctttt   7560
ttttattttg tagagatggg gtcttggtat gttgcctagg ccagtctgga attcctgggc   7620
```

-continued

```
tcaaacaatc ctgtctctgc ctcccaaagt gttgggatta caggcatgag ccactgcacc   7680
tggtcatgtg gtcatatttt ctttttcttt tttttttttt tttgagacag agtctctgtc   7740
gcccaggctg gagtatggtg gcgtgatctc agttcactgc agcctccgcc tcccgggttc   7800
aagcgattct cctgcctcag cctcctgagt agctgggatt acaggcgccc gccaacatgc   7860
ccagctaatt tttttagtag agatggggtt tcaccatgtt agccaggatg gtctcgatct   7920
cctgatttgg tgatccgccc accttggcct cccaaagttt caaccatcga tcagaactta   7980
ttgatgtact tatgtagcta ggcacggtgg cgcgtgcctg taatcccagc tacttggaag   8040
ggttaaggca ggagaatcgc ttgaacctgg gaggcagagg ttacagtgag tcaagatcat   8100
accattgcac tccagtctgg gcaacagaat gagactctgt ctcaaaaaca aaaaacaaac   8160
ccttgtatgt gattttcctg gatagcatct gttacatctt cacaaagata aaaagtcaga   8220
cttggctggg catggtggct cacacctgta atcccagcac tgagaggctg aggcaggcag   8280
atcacttgag gtcaggaatt tgagaccagg ctgggcagca tggtgaaacc ccgtctctac   8340
aaaaaataca aaaattagcc gggtgtggtg tcacgcacct gtattcccaa gctactcagg   8400
aagctaaggc aggagaatca cttgaaccca gaggtggagg tttgcagtga gttgagattg   8460
tgccattgca ctccagcctg ggcgacagag tgagactctg tgtcaaaaat aaaataaaat   8520
aaaattttaa aaaaggcaga tttttttttc ttcttggtat tgttacctta ttatagtaat   8580
aataagtgca tagtgcatgc tgagataagc aatcataatt tgttattgcg gccgggcatg   8640
gtggctccag cctataatcc cagcactttg gtcaggagtt caaggccagc ctggccaata   8700
tagtgaaact ccatctctac taaaatacaa gaaattacct gggcatggtg gcagttgctg   8760
gtgatcccca gctacttggg aggctgaggc aggagaatcg cttgaacctg ggaagcagag   8820
gttgcagtga gccaagattg caccactgca ctccagcctg ggtgacagag tgagactctg   8880
tctgaaaata ataataataa taatttgtta ttgcttttat tgccttagtt tacataggga   8940
atcaaagttt atactttgat ttataaaagt tgctttgatt ctagttcaca gaaccagaat   9000
ctttcatata aaggtattag agggcccagt gtggtggctc atgcctgtaa tcccagcata   9060
ttgggaggct gaggagggag gatcacttta ggagtttgag gccagcctag gcaacatagt   9120
gagaccttgt ctctacaaaa aattccaaca ttagctgggc atggtggcat gtgcctgtag   9180
tcccatttat ttggggggct gaggcaggag gatcacttga gcccacgagg ttcaatccag   9240
gttgcagtaa gccatgatcc tgccactgca ctccagtttg ggtaacagag cgaagctatg   9300
tctcaaaaaa agaaaaaaaa agtattctaa atccaaattt aatatataaa actaaatgca   9360
ggccaagtgt ggtggcatat acctataatc acaacacttt gggaggctga ggtgggagga   9420
ttgcttgagc ccaagagttc aagaccagcc taggtaacac agtaagaccc catctctaca   9480
aaaagtagaa aaattagcct ggcatggtgg tgagtgcttt taatcccaac tacttagggg   9540
gctgagatgg gaagattgct tgagcctcag agtttgaggc tgcagtgggc cgtgatcgct   9600
ccactgatcg ctctaaagtg agaccctgtc tcaaaaaaaa agaaaataga agaaaactaa   9660
atacattcaa taagactttg atctcttttc caaggtgtaa atatattttg ggaaattttc   9720
cagttacttt gttctcattt taatgtaata atctaagtct tggttttcta aggaaaagtt   9780
ttctcttatt atatcttttg ttaatgtttc tctcccattt cttttgatct gatcttcaga   9840
tacatgatta tcttcactgc taaatttgtg ttctctggcc tctacattta taatttctca   9900
taattcttta tctaagtatt tcttccctac ctactgaaga aaactcaagt tttcttccac   9960
```

-continued

```
cttaatgatt atgctgtgtc tgtgagtttt cttcatgact ctttacagta caagtttttt  10020
gtttttgttt ttttaatggt cagatggata gaacaacaca ggttttgttt gttttgtttt  10080
aacttttaaa aaaattataa tagataaagg gtctcactac gttgtccagg ctgatctcat  10140
actcctgggc tcaagcaatc cacccacctc tgcctcccaa agtgctggga ttacagtcat  10200
gagccaacat gcctgggcag tacaggtttt ttttgagacg gagttttgtt cttgttgccg  10260
aggctggagt gcaatggcac aatcttggct caccacaaag tctgcctccc aggttcaagt  10320
gattctcctg cctcagcctc ctgagtagct gggattacag gcatgtgcca ccacgcccag  10380
ctaattttgt atttttagta gagacggggt ttcaccatgt tggccaggct ggtttcgaac  10440
tgctgacctc aggtgatctg cccacctcgg cctcccaaag tgctgggatt acaggcatga  10500
gccaccatgc ccagctgtag tacaggtttt aatatgctaa atactcttcc tttctttatt  10560
aatgtgcatg gaagttctaa tatttttttc ccatacccca gagagtccat attttggaat  10620
caacaacact agcctttgtt gacaagtgtc tctcttgggt tccttctttg tgtcctccac  10680
tgaattttgg ggttcataaa atttcatttg ttgtgcttgc ttaattccct gggaatcaga  10740
ctgttcctga tcggatgaca tttctggtta attctttagt tggcaggaaa tagacacagg  10800
aaacgtggtc agtttctgat tctggcgttg agagaccctt tctccttttc ctctctctca  10860
gtgggcgaca gatgcgaaag aaacgagttc cagtgccaag acgggaaatg catctcctac  10920
aagtgggtct gcgatggcag cgctgagtgc caggatggct ctgatgagtc ccaggagacg  10980
tgctgtgagt cccctttggg catgatatgc atttattttt gtaatagaga cagggtctcg  11040
ccatgttggc caggctggtc ttgaatttct ggtctcaagt gatccgctgg cctcggcctc  11100
ccaaagtgct gggattacag gcaccacgcc tggcctgtga cacgattctt aaccccttttt 11160
tgatgatggc ggctggaaaa gtggccagtg gattttgatg tattcaatca tgaattagga  11220
ggtggggaga gaatgaatta ttggagcttt ccttaaagcc attaaatggc tctattgttt  11280
tttcaattga tgtgaatttc acataacatg aaattaacca gctcagtggc attaatacat  11340
ctgcaatgct gtgtggccac cacctctatc ttgttccaaa actttgcata acctaatgtc  11400
tttttttttt tttttttttg agacggagtc tcgttccatc acccaggctg gagtgcagtg  11460
gtgtgatctc agctcactgc aacctccgcc tcccaggttc acgccatcct cctgcctcag  11520
cctcccgagt agctgggact acaggcaccc tccaccacat ccggctaatt ttttgtatct  11580
ttagtagaga tggggtttca ccatgttagc cgggatggtc tcgatctcct gacctcgtga  11640
tccacctgcc tccgcctccc aaagtgctgg cattacaggc gtgagccacc atgcccggcc  11700
tatttttttt tttaagagat ggagtctaat tctgttgccc aggctggagt ccagtggtac  11760
catcatactt cactgcagcc ttgacctctt gggctcaagt gattctcttg cctcgaactc  11820
ccaaagtatt gggattacag gtgtgagcca ccgcactcag cctaatgtcc agtttttaac  11880
aagctccatt taaatgccct ccgttttgac ccataaaggg gtaggcttgg ccgggcacaa  11940
tggcttgtgt ctgtagtccc agctacttgg gaggctgagg cagaaaggca gaaagattgc  12000
tttataaagc ccaggagttt gagggccacc tgggtggcat agctagacct catctctaaa  12060
aaataagtaa taaataaata tttgtttttg tttttttctt tttcttttct tttttttttt  12120
tttttgagac ggagtcttgc tctgttgccc aggctggagt gcagtggcgc gatctcagct  12180
cactgcaagc tgtgcctcct gggttcatgc cattctcctg cctcagcctc ccgagtagct  12240
gggactacag gcgcccacta ccacgcccag ctaatttttt gtatttttag tagagatggg  12300
gtttcaccac gttagccagg atggtctcaa tctcctgacc tcgtgatccg ccagctttgg  12360
```

-continued

```
cctcccaaag tgttgggatt acaggcgtga gccactgagc ccgccccata tgtatgtata  12420
tatatatttt tttaaaatgg gagaccaggc atggtggctc atgcctagaa tcccagcact  12480
ttgggaagct gaggtaggcg gatcacttga ggccatgagt ttgagaccag cctgctcaac  12540
atgatgaaac ttctatctct actaaaaaaa aaagtgggat taggtcaggc acggtggctc  12600
acacctgtaa tcccagcact ttcagaggcc gaggcaggag gatcatgagg tcaggagatc  12660
gagaccatcc tggctaacac ggtgaaaccc cgtctctact aaaaaaatac aaaaaattag  12720
ccaggcgtgg tggcgggtgc ctgtagtccc agctactcag gaggctgagg caggagaatg  12780
gcgtgaaccc gggaggcgga gcttgcagtg agccaagatc gtgccactgt actccagcct  12840
gggcgacaga gcaagactct gtctcaaaaa aaaaaaaaaa agtgggattg acattctctt  12900
caaagttctg ggttttcct ttgcaaagac aggattggca aggccagtgg gtcttttttg  12960
tgtgtgtgtg tgtgacggag tctcactctg ccacccaggc tggagtgcaa tggcaggatc  13020
tcggctcacc gcaacctcct cctcccaggt taaagtgatt ctcctgcctc agcctcccga  13080
gtagctggga ctacaggtgc ccgccaccac acccaactaa tttttgtatt tttagtagag  13140
acagggtttc actatattgg ccaggctggt cttgaacccc tgacctcacg tgatccaccc  13200
gccttggcct cccaaagtgc tgggattaca ggcgtgagcc actgtgctcg gcctcagtgg  13260
gtctttcctt tgagtgacag ttcaatcctg tctcttctgt agtgtctgtc acctgcaaat  13320
ccggggactt cagctgtggg ggccgtgtca accgctgcat tcctcagttc tggaggtgcg  13380
atggccaagt ggactgcgac aacggctcag acgagcaagg ctgtcgtaag tgtggccctg  13440
cctttgctat tgagcctatc tgagtcctgg ggagtggtct gactttgtct ctacggggtc  13500
ctgctcgagc tgcaaggcag ctgccccgaa ctgggctcca tctcttgggg gctcatacca  13560
agcctcttcc gcccttcaaa tccccccttg accaggaggc attacaaagt ggggatggtg  13620
ctacctcttc gggtttgtca cgcacagtca gggaggctgt ccctgccgag ggctagccac  13680
ctggcacaca cactggcaag ccgctgtgat tcccgctggt cgtgatcccc gtgatcctgt  13740
gatccccgcc ccgtgaggct gaacacatag tgacgcttgc tagccaagcc tcaatgaccc  13800
acgtaacatg aagggggaaa agccagaaag ttctgccaag gagcaaggcc aagaatcccg  13860
aagggaaatg gactttgaag ctgggcgtct tcttggctgt cttaatacaa gtggcacatc  13920
caaatccaaa accccgaaat tcaaagtctt gagcacccga aattctgaaa cgtcttgagc  13980
actgaccttt agaaggaaat gcttattgga gcattttgga tttcggattt ttaccactga  14040
gtgtggagtc ctaattagga aaaaaaccag gctgaccgaa ccaaaggaaa gcaataaaag  14100
aaggcagata gggtcaggca cggtggctca cccctgtaat cccagccttt tgagaggctg  14160
aggcgggtgg atcacttgag gtcaggagtt cgagagcagc ctggccaaca cggtgaaacc  14220
ccatctctac tgaaaataca aaaactagcc aggtatggtg gcgtctgcct gtaatcccag  14280
ctactcggga ggctgagaca ggagaatcac ttgaacctgg gaggcagagg ttgcagtgag  14340
ccaatatcac gccattgcac tccagcctgg gggacaagag cgaaattctg tctcaaaaaa  14400
aaagaagaag aaggccgaca aactatgtaa ctctgccttt ctccatggtc cagaacacac  14460
agccctcctg cgtaaataac tccttatctt cctgctccca gctatcatca gacacctcgg  14520
ctgatagaaa attgcaagtt agctcactgc aacctcggca ttataagtac tgcacaaagc  14580
cctcttcagc gcacagcaca agcaccattc tataaaatct ccagcaagcg gccaggtgca  14640
gtggctcata cctgtaatcc cagcattttg ggagactgag gcgggcggat cacctgaggt  14700
```

```
caggagtttg agaccagcct ggccaacatg gtgaaacccc gtctctatta aaaatacaaa  14760
aaaattagcc aggcgtggtg gcaggtgcct gtaatcccag ctacttggaa ggctgaggca  14820
ggagaatcgc ttgaacccgg gaggtggaag ttgcagtgag ccgagatctt gccatcgcac  14880
tccagcctgg gggacaagag tgagacttcg tctcaaaaaa aaaaaaaaaa attcccagca  14940
agcctttgtc ttctggcagt cagctcctct cttgctgacc tgctcattgc tttcttgcaa  15000
ggtattttcc tacctacttt ctggaataaa tctgtctttc tgtacttaca actacctttt  15060
ttaaaatttc tttcttttt gagatggagt ctcactctgt ttgcccaggc tggagttcag  15120
tggtgcaatc tcagctcact gcaacctcta cctactgggt tcaagcgatt ctcctgcctc  15180
agcttcccga gtagctggga ttacaggcgt gcaccagcac gcaggctaat ttttgtattt  15240
ttagtagaga cggggtttca ccatgttggc caaggtggtc ttgaactcct gacctcaagt  15300
gatcctccca cctcagcctc ccaaagcgct aggattacgg ccatgagcca ctgaggccgg  15360
ctgcacctac aactgtcttg ataaattctt acccccacac cactggtcca gatagtcagt  15420
gctcacccac aacattaagg atattccaaa tttgaaacat tccaaaatca gaaaaatatt  15480
ccaactctga aaatattcca aaatccaaaa aaattcaaaa tccaaaacac ttctggtccc  15540
aagcatttta gagaagggat actcaaccca aaataaggac agcaattcta taaattgtgc  15600
taccatcttg caggtctcag tttaacagct ttacacctat tagcgcacca gtgctcatag  15660
cagtgctggg aaatgtgtac agatgaggaa actgaggcac cgagagggca gtggttcaga  15720
gtccatggcc cctgactgct ccccagcccg cctttccagg ggcctggcct cactgcggca  15780
gcgtccccgg ctatagaatg ggctggtgtt gggagacttc acacggtgat ggtggtctcg  15840
gcccatccat ccctgcagcc cccaagacgt gctcccagga cgagtttcgc tgccacgatg  15900
ggaagtgcat ctctcggcag ttcgtctgtg actcagaccg ggactgcttg gacggctcag  15960
acgaggcctc ctgcccggtg ctcacctgtg gtcccgccag cttccagtgc aacagctcca  16020
cctgcatccc ccagctgtgg gcctgcgaca acgaccccga ctgcgaagat ggctcggatg  16080
agtggccgca gcgctgtagg ggtctttacg tgttccaagg ggacagtagc ccctgctcgg  16140
ccttcgagtt ccactgccta agtggcgagt gcatccactc cagctggcgc tgtgatggtg  16200
gccccgactg caaggacaaa tctgacgagg aaaactgcgg tatgggcggg gccagggtgg  16260
gggcggggcg tcctatcacc tgtccctggg ctcccccagg tgtgggacat gcagtgattt  16320
aggtgccgaa gtggatttcc aacaacatgc caagaaagta ttcccatttc atgtttgttt  16380
cttttttttc ttttctttct ttattttgtt tttgagatgg agtctcactc tgtgattttt  16440
ttcatctcta aatttcctac atccatatgg ccaccatgag gccccaggct ggccgatggt  16500
tgctgttagc ttattgggaa atcactgttt ggaaggtgct ggttgttttt tgttgtttgt  16560
tgtttttgtt tttgtttttg ttttgagacg gagtctcgct ctgtcgccag ggtggagtgc  16620
agtggcgcga tcagctcact gcaacctccg cttcctgggt tcaagccatt ctcctgcctc  16680
agcctcccaa gtagcgcgga ttacaggcat gtgccaccac ctccggctat ttttttttct  16740
atttagtaga gatggggttt caccatgtta gtcaggctgg tcatgaactc ttgacctcag  16800
gtgatccacc cgcctcggcc tcccaaagtg ctgggattac aggcgtgcac tgctgcaccc  16860
agcctttttt tgttttttg agacagggtc ttgctgtcac ccaggttgaa gtaaggtggc  16920
acgattatgg ctcactgcgg ccttgatctc cttggctcaa gcgatcctct cacttcagcc  16980
tctcaagcag ttggaaccac aggctgtacc accaagcctg gccaattttt ttgtacagac  17040
acaggctggt cttgaactcc tggctcaag caatcctcct gccttggcct cccaaagtgc  17100
```

tgggattcca ggcatgagcc gctgcacccg gcaaaaggcc ctgcttcttt ttctctggtt 17160
gtctcttctt gagaaaatca acacactctg tcctgttttc cagctgtggc cacctgtcgc 17220
cctgacgaat tccagtgctc tgatggaaac tgcatccatg gcagccggca gtgtgaccgg 17280
gaatatgact gcaaggacat gagcgatgaa gttggctgcg ttaatggtga gcgctggcca 17340
tctggttttc catcccccat tctctgtgcc ttgctgcttg caaatgattt gtgaagccag 17400
agggcgcttc cctggtcagc tctgcaccag ctgtgcgtct gtgggcaagt gacttgactt 17460
ctcagagcct cacttccttt tgttttgaga cggagtctcg ctctgacacc caggctggag 17520
tgctgtggca caatcacagc tcacggcagc ctctgcctct gatgtccagt gattctcctg 17580
cctcagcctc ccgagtagct gagattaaag gcgtatacca ccacgcccgg ctaatttttt 17640
gtatttttat tagagacagg gtttctccat gttggccagg ctggtcttga actcctggtc 17700
tcaggtgatc cacccgcctc ggcctcccaa agtgctagga ttacaggtgt gagccactgc 17760
gccaggccta atttttttgt atttttagta gagatgcggt tttgccatat tgcccaggct 17820
ggtctcgaac tcctgggctc aagcgatctg cctgccttgg cctcccaaag tgctgggatt 17880
acaggcacaa accaccgtgc ccgacgcgtt ttcttaatga atccatttgc atgcgttctt 17940
atgtgaataa actattatat gaatgagtgc caagcaaact gaggctcaga cacacctgac 18000
cttcctcctt cctctctctg gctctcacag tgacactctg cgagggaccc aacaagttca 18060
agtgtcacag cggcgaatgc atcaccctgg acaaagtctg caacatggct agagactgcc 18120
gggactggtc agatgaaccc atcaaagagt gcggtgagtc tcggtgcagg cggcttgcag 18180
agtttgtggg gagccaggaa agggactgag acatgagtgc tgtagggttt tgggaactcc 18240
actctgccca ccctgtgcaa agggctcctt ttttcatttt gagacagtct cgcacggtcg 18300
cccaggctgg agcgcaatgg cgcgatctcg gctcactgca acctctgcct cccaggttca 18360
agtgattctc ctgcctcagc ctcctgagta gctgggatta caggcgccca ccaccaagcc 18420
cgggtaattt tttgtatgtt tagtagagat ggggtttcac tatgttggcc aggctggtgt 18480
tgaactcctg acctcatgat ccgcccacct cggcctccca aagtgctggg attacaggcg 18540
tgacccaccc catgaaaaaa aattaaaaaa tgaagcgatg ctgggcgcgg tggatcacgc 18600
ctgtaatccc agcactttgg gaagctgagg caggcagatc acgagggcag gagattgaga 18660
ccatcctggc taatacggtg aaaccccatc tctactaaaa ctacaaaaaa ttagccgggt 18720
gtggtggcag gcacctgtga tcccagctac tcaggaggct gaggcaggag aatcgcttga 18780
acccaggagg tggaggttgc agtgagccgg gatcacacca ttgcactcca gcctgggtga 18840
cagagtgaga ctctgtctca aaaaaaaaaa aaaaaaaaaa agcgaattct gaaatacatg 18900
aattcttttc cttagatgcc tgcttctgtc ttgaggtttg ttgttgttat ttcgaaacag 18960
agtcttgctc tgtcgctcag gctggagtgc agtggcatga tcttggctca ccacaacctc 19020
cggctcccag gttcaagcga ttcttctgcc tcagcctcct gagtagctgg gattacagct 19080
gaatgccacc ttgctgggct aatttttgta tttttagtag agatggggtt tcaccatgtt 19140
ggccaggctg gcctcgaact cctgacctcg agtgatctgc ccgcctcctg aagtgctggg 19200
attacaggcg tgagccacct cgtcctggtg agggtttttt tttttcccca accctctgtg 19260
gtggatactg aaagaccata ttaggataac tgtacagtat agagaaggca gtggcaagtt 19320
ttctctgtca tataccagag tgggcttggg catggtggca tactcctgta gtctcagcta 19380
atcaggaggc tgaggaagga ggatcgcttg ggcccaggag ttggagactg tagtgagctg 19440

-continued

```
tgatcacacc accacacttc aatctgggca acagagcaag agaccctatc tctaaaaaaa  19500
agtaagtatt tcggacactg tgggccatac ggtctctggt gcagtttctc aacatggctg  19560
ttgggtgaac acaaccacgc acagaacgca aaccaataca cgtggctgtg ggcccagaaa  19620
atgttattta tggacacaaa aattggaatt tcatataact gttttgtgtc atgaaaatga  19680
tttccctttt tatttttatt tttcttctca agtatttaaa tatgtaaaag ccatttttag  19740
gcctggcagg atggttcaca gctgtaatcc cagcactttg ggaggtcgag gcgggaggat  19800
cacgaggtca ggagatcgag accatcctgg ccaacacagt gaaaccccgt ctctactaaa  19860
aatacaaaaa attaaccagg cttggtggcg cgcgtctgta gtcccagctg ctcaggaggc  19920
tgaggcagga gaatcgcttg aatgcaggag gcggaggttg tagtgagccg aggttgcacc  19980
actgcactcc agcctgagcg acagagtgag agtccgcctc aaacaaaaaa atgtttgccc  20040
atgctggtct tgaactcctg ggctcaagct atctgcctgc cttggtctcc caaagttctg  20100
ggattacagg catgagctac agcgcccgga cttttgttgt tttatatcta tatatctata  20160
tataacttgt tttatgtata tatataactt gttttatata tatacataaa ctgcagtaaa  20220
aaacatgtaa cataaaattt accttctcaa accttattaa gtgcacagtt ctgtgccatt  20280
agcaaattca cactgttgta caacatcaca accaccatct ccagaacttt tttttttttt  20340
tttattcttt ttgagacaga gtctcactcg tcgcacgggc tggagtgcag tggtgcgatc  20400
tcggttcact gcaacctcca cctaccaggt tcaagcaatt ctcctgcctc agccccctca  20460
gtagctggga ttacaggtgc ccgtcctacc acgcccagct aatttttgta ttttcagtag  20520
agactgactg ggtttcacca tgttggccag gctggtctcg aactcctgac ctcaagtgat  20580
cctcccacct cagcctccca aagtgctggg aatacaggca tgagccactg cgcccggccc  20640
cagaactctt ttatcttccc aaactgaagc tctgtcccca tgaaacactc actctccatc  20700
ccctccccaa ctcctggcac ccaccattct actttctgtc cctatgaatg tgatggctct  20760
agggacctcc tctgagtgga atcagacagc attttccttt tttgactggc ttatttcact  20820
gagccaagtg cggtggcaca cgcctgtaat cccaaaactt tgggagaccg aggcgggcgc  20880
atcacctgag gtcaggagtt cgagaccagc ccggccaaca tggtgaaacc ccatctctag  20940
taaaaataca aaaaattagc ctgtcatggt cgtgggtgcc tgtaatccca gctaagtggg  21000
aggctgaggc aggagaatcg cttgtaccca ggaggcggag gtcgcagtga gccgagatcg  21060
tgccattaca ctccagcctg ggcaacaaga gtgaaactcc gtctctccta aaaatacaaa  21120
aaaattagct gggcatggtg gcacatgcct gtagtcccag ctacttggga ggctgaggca  21180
ggagaatcac ttgaacccgg gaggtggagg ttgtaatgag ccaaggttgg cggcgaaggg  21240
atgggtaggg gcccgagagt gaccagtctg catcccctgg ccctgcgcag ggaccaacga  21300
atgcttggac aacaacggcg gctgttccca cgtctgcaat gaccttaaga tcggctacga  21360
gtgcctgtgc cccgacggct tccagctggt ggcccagcga agatgcgaag gtgattcccg  21420
ggtgggactg agccctgggc cccctctgcg cttcctgaca tggcaaccaa acccctcatg  21480
cctcagtttc cccatctgtt aagtgtgctt gaaagcagtt aggagggttt catgagattc  21540
cacctgcatg gaaaactatc attggctggc cagagtttct tgcctctggg gattagtaat  21600
taagaaattt caggccgggt gcgtaatccc tgtaatccca acaccttggg acgccgaggc  21660
gggcagatca cctgaggtcg ggagttccag accagcctga ccaacatgga gaaaccccgt  21720
ctctactaaa aatacaaaat tagccgggct tggtggtgca tgcctataat cccagctact  21780
caggaggctg aggcaggaga atcacttgaa cctgggaggt ggaggttgtg gtgagccaag  21840
```

atcgtgccat tgcactccag cctgggcaac aagagtgaaa ctccatccaa aaaaaaaaga 21900
aaagaaaaga aaaaaaagaa aagaaatttc agctgacaca gcttcacact cttggttggg 21960
ttcccgtggt gaatgatgag gtcaggtgat gactggggat gacacctggc tgtttccttg 22020
attacatctc ccgagaggct gggctgtctc ctggctgcct tcgaaggtgt gggttttggc 22080
ctgggcccca tcgctccgtc tctagccatt ggggaagagc ctccccacca agcctctttc 22140
tctctcttcc agatatcgat gagtgtcagg atcccgacac ctgcagccag ctctgcgtga 22200
acctggaggg tggctacaag tgccagtgtg aggaaggctt ccagctggac ccccacacga 22260
aggcctgcaa ggctgtgggt gagcacggga aggcggcggg tgggggcggc ctcacccctt 22320
gcaggcagca gtggtggggg agtttcatcc tctgaacttt gcacagactc atatcccctg 22380
accgggaggc tgtttgctcc tgagggctct ggcaggggag tctgccgccc tgttaggact 22440
tgggcttgcc agggggatgc ctgcatatgt cctagttttt gggaatatcc agttaacgga 22500
accctcagcc ctactggtgg aacaggaacc ggctttcctt tcagggacaa cctggggagt 22560
gacttcaagg ggttaaagaa aaaaaattag ctgggcatgg tgccacacac ctgtggtccc 22620
agctactcag aaggctgagg cgggaggatt gcttgagggc aggaggattg gttgatcctc 22680
ccacctcagc ctccggagta gctgggacct caggtgcatg ccactatgcc tggctaattt 22740
tctttttct tttttttttt ttttcgagac ggagtctcgc tctgttgccc aggctggagt 22800
gcagtggcag gatctcggct cactgcaagc tccgcctccc gggttcacgc cattctcctg 22860
cctcagcctc cccagtagct gggactacag gagcccgcca ctgcaccagg ccaatttttt 22920
tgtattttta gtagagacgg ggtttcactg tgttagccag gatggtctcg atctcctgac 22980
ttcgtgatcc gcccacctcg gccttccaaa gtgctcggat tacaggcgtg agccactgcg 23040
cccagccgct aattttcata tttttagtaa aaacagggtt tcaccatgtt ggccaggcta 23100
gtcttgaact cctgaaccca agtgatcctc ctgccttggc ctcccaaagt gctgggatta 23160
cagacaccac acctggctat tattattttt tagagacagg gtgctgctct atcttccagc 23220
ctgtagtgca gtgcagcctc catcatagct cgctgcagcc ttgacctcct gggttcacgt 23280
gatcgtcccg cctaagcctc tggaggagct gggagtactg gcatgtgcca ccatgcctgg 23340
ttaatttttt tttttttttt tttgagacag agtctcattc tgtcacccag gctggagtgc 23400
ggtggtgcga tcttggctta ctgaaacctc cacctcccag gttccagcaa ttctcctgcc 23460
tcacccttct gagtagctgg gattacaggt tccggctacc aaacctggct agtttttgta 23520
tgtttagtag agacagggtt tcaccatgtt ggtgaggctg gtctcgattc tcccgcctca 23580
gcctcccaaa gtgctgggat tacaggcttg agccaccgtg cctggctttt tttttttttt 23640
ttttttttgt ggcaataagg tctcattgtc ttgcccaggc tagccttatg ctcctagcct 23700
caagtgatcc tcctccctca gcctcccaaa gtgctgggat tacaggtggg cgccactgtg 23760
cctgttcccg ttgggaggtc ttttccaccc tctttttctg ggtgcctcct ctggctcagc 23820
cgcaccctgc aggatgacac aaggggatgg ggaggcactc ttggttccat cgacgggtcc 23880
cctctgaccc cctgacctcg ctccccggac ccccaggctc catcgcctac ctcttcttca 23940
ccaaccggca cgaggtcagg aagatgacgc tggaccggag cgagtacacc agcctcatcc 24000
ccaacctgag gaacgtggtc gctctggaca cggaggtggc cagcaataga atctactggt 24060
ctgacctgtc ccagagaatg atctgcaggt gagcgtcgcc cctgcctgca gccttggccc 24120
gcaggtgaga tgagggctcc tggcgctgat gcccttctct cctcctgcct cagcacccag 24180

-continued

```
cttgacagag cccacggcgt ctcttcctat gacaccgtca tcagcagaga catccaggcc  24240
cccgacgggc tggctgtgga ctggatccac agcaacatct actggaccga ctctgtcctg  24300
ggcactgtct ctgttgcgga taccaagggc gtgaagagga aaacgttatt cagggagaac  24360
ggctccaagc caagggccat cgtggtggat cctgttcatg ggtgcgtatc cacgacgctg  24420
agggctgcag agggaatgga gggagcagga aggagcttca ggaactggtt agtgggctgg  24480
gcatggtggc tcaaagcacc tgtaatccca gcactttggg aggccaaggt gggtggatca  24540
tcaagaccag cctgaccaac atggtgaaac ctcgtctcta ctaaaaatac aaaaattagc  24600
cgggtgtggt ggtgggcacc tgtaatccca gctgctcggg aggctgaggc aggagaatca  24660
cttgaacctg ggagatggag gttgcagtga gccaagacag ccccactgca ctccagcctg  24720
ggtgacagag tgagactccg tctcaaaaaa aaaaaaaaaa actaaacaaa aaactggtta  24780
gtggctagac aacaggatgg tatcttccaa gcccatggct gactcagcag ctcctgggtc  24840
aagacactgt gacctgtgtc ccctggcagg aagcatcgcc cctgccacct gcccggtgta  24900
ctctgtacct gtcaggtgac atctgctacc taagcacgtg agaggtggca tttcacagtt  24960
tcagtgtggt gctgacaacc cgggacgcac actgtccttg cagctacaat caggaggtga  25020
atgttgggtt tccagcagag aacactggag aaggcacact tggtgtctgg aagggaaaag  25080
cagggaagag agcatcatca gatgcctgcg ggtgaaggtg ggcccgctat ggccagcgtc  25140
ccttttttatt tttatttatt tatttatttg agatggaatc tcgctctgtc gcccagactg  25200
tagtgcagtg gtgcgatcac ggctcactgc aagctccgcc tcacaggttc acgccattct  25260
cctgcctcag cctcccgagt agctgggact acaggcaccc gccaccacgc ccggttaatt  25320
ttttgcattt ttattagaga cggggtttca ccgcgttagc caggatggtc taaatctcct  25380
gaccctgtga tccacccgcc tcggcctccc taagtgcttg gattacaagc gtgagccacc  25440
acgcccggcc cccttttttat tttttatttt ttgagacgga gtctcgctct gtcgcccagg  25500
ctagattgca gtggcgtgat ctcggctcac tgcagcctcc gcctcccagg ttcaagtgat  25560
tctcctgcct caacctccca actaattagg attacaagca tgtaccacca tgcctgacta  25620
attttttgta tttttagtag agactgggtt tcaccatgtt ggctaggctg gtctcgaacc  25680
cttagcctca agtaatctgc ctgcctcagc ctcccaaaca gcggggatta caggcatgag  25740
ccactgtgcc caacccaacc ctggatctct tttaaacaag acaatgctcg ctgttgccac  25800
agaacaatgg gtggggtaca tgtggcccag tgtgtttggc cacataactg ccaggccaga  25860
gggaaagaga ctctcagact gtctccactc agatacaaat gtgtgtgttg tgtgcgtgtg  25920
ttctggtctc atatttgttt gttttgagac agggtgtcgc tctgtcactg agtctggagt  25980
gcagtggcgc aatcagagtt cactgcagcc tcaaactctt gggctcagtt gattctccca  26040
cttcagcctc ccaagtagct ggaactacag gtgaacacca ctgtgcccag ctaatttatt  26100
ttatttttag tagagatgag gtctcactat gttgcccagg ctggtcttga cctcctagcc  26160
tcaagcaatc ctcctgcctt ggtctcccaa agtgctggga ttacacgtgc gagccattgc  26220
gcatggcttg tgttcttgtg tttcttcctt tttctttcga gatggcgtct cagtctgcca  26280
cccaggctgg agtgcagtgg tgtgatcata gctcactgta gcctcaactt cctgggctca  26340
agcaatcctc ttgatttcag cctcccgggc ctggccagca tggtgaaacc ccgtctctac  26400
taaaaataca aaaatgtagc caggcgtggt ggtgggcgcc tgtaatccca gctacaccag  26460
aggctgaggc aggagaatcg cttgagcctg gaaggtggag gttgcagcaa gccaagatcg  26520
tgccactgca ctccagcctg ggcaacagag acagactctg tctcaaaaaa aaaaaaaaaa  26580
```

-continued

```
aacccaaaca agccacattt ggagtttggg gttcccagca ggactatttc ccaagcctga  26640
gcctggctgt ttcttccaga attcgttgca cgcattggct gggatcctcc cccgccctcc  26700
agcctcacag ctattctctg tcctcccacc agcttcatgt actggactga ctggggaact  26760
cccgccaaga tcaagaaagg gggcctgaat ggtgtggaca tctactcgct ggtgactgaa  26820
aacattcagt ggcccaatgg catcacccta ggtatgttcg caggacagcc gtcccagcca  26880
gggccgggca caggctggag gacagacggg ggttgccagg tggctctggg acaagcccaa  26940
gctgctccct gaaggtttcc ctctttcttt tctttgtttt ttcttttttt gagatgaggt  27000
cttggtctgt cacccaggct ggagtgcact ggcgcaatcg tagctcactg cagcctccac  27060
ctcccaggct caagtgatcc tcctgcctca ccctcctgag tagctgagat tacagacacg  27120
tgccaccacg gcagactaat tttattttat ttttgggaag agacaaagtc ttgttatgtt  27180
ggcctggctg gtctcaaact cagggtgcaa gcgatcctcc cgcctcagcc ttccaaactg  27240
ctgggattac aggcgtgggc caccgtaccc agcctccttg aagtttttct gacctgcaac  27300
tcccctacct gcccattgga gagggcgtca caggggaggg gttcaggctc acatgtggtt  27360
ggagctgcct ctccaggtgc ttttctgcta ggtccctggc agggggtctt cctgcccgga  27420
gcagcgtggc caggccctca ggaccctctg ggactggcat cagcacgtga cctctcctta  27480
tccacttgtg tgtctagatc tcctcagtgg ccgcctctac tgggttgact ccaaacttca  27540
ctccatctca agcatcgatg tcaacggggg caaccggaag accatcttgg aggatgaaaa  27600
gaggctggcc cacccccttct ccttggccgt ctttgaggtg tggcttacgt acgagatgca  27660
agcacttagg tggcggatag acacagacta tagatcactc aagccaagat gaacgcagaa  27720
aactggttgt gactaggagg aggtcttaga cctgagttat ttctattttc ttctttcttt  27780
tttttttttt ttttgagaca gagttttgct ctcgtttccc aggctggagg gcaatggcat  27840
gatctcggct caccgcaacc tccacctccc aggttcaagt gattctcctg tctcaggctc  27900
cccagtagct gggattacag gcatgcacca ccaccatgcc cggctaattt tgtattttta  27960
gtagagacgg agtttctcca tgttggtcag gctggtctcg aactcccgac ctcaggtgat  28020
ctgcctgcct cggcctccca aagtgctggg attacagact tgagccaccg cgcccagcta  28080
tttctgtttt ctttctttct tcttcttctt tttttttttc taagagacag gatctcactc  28140
tgtccccagg caggagtgca gtgctgtgat catagctcac tgcagcctta acctcctggg  28200
ctcaagtgat cttcccacct cagcctccca agtagctgga actacaggtg cacaccacca  28260
tgcccagctc atttttgtat tttttttttt tttgagacag tctcgttctg tcaccccggc  28320
tggagtgcag tggtacaatc ttggctcact gcaacctctg cctcccaggt tcaagcgatt  28380
ctcctgcctc agcctcctga gtagttgaga ttacaggcat gtgtgccatc atacctggct  28440
gatttttgta ttttttttta gagatggggt ctcagtatgt tgaccaggct tgtcttaaac  28500
tcccggcctc aagtgatcct cccacttcag tctcccaaag tgctgggatt acaggcatga  28560
gccactgcgg ccggtttgtt ttcttttttt tttcgttttt tggagacgga atttcacctt  28620
tgttgcccag gatggagtgc aatggcacga tatcgcctca ccacaacctc tgcctcctgg  28680
gttcaaacca ttttcctgcc tcagccttct tagtagctgg gattacaagc atgtgccacc  28740
acgcccggct gattttgtat ttttagtaga gatggggttt ctccatgttg gccaggctgg  28800
tctcgaactc ctgacctcag gtcattcgcc cacctctgcc tcccaaagtg ctgggattac  28860
aggcgtgagc caccgtgccc ggtggtttgt attcttttta ctgagagtcg tgaaaggcag  28920
```

```
tgatcctctg tcacatgtga tcttggctct caggggacat ttggcaattt ctagagattt  28980
tttggttgtc acaagtcaat ggggaagact gttggcattt agtgggtaga ggctggtgac  29040
gctgctgaac acccagaaca gggaagtagc aggccctaga tagagccatc gtggggaaac  29100
cctgctctaa ggaaatggcg ctattttata accccacgtt cctggcatga ttaccaacag  29160
ccaaaagtgg agtcccccca agtgtgttcg tccatttgca ttgcagtaaa ggaatagctg  29220
aggccgggta atttataaag aaaagagatt taaactgggt atggcagttt atgcctataa  29280
tcccagaact ttgggaggct gaggcaggag gatcgcttga gtccaggagt gtgagaccga  29340
gaccagcctg gccaacatga cgaaactctg tctctacaaa aatacaaaaa agtaggccag  29400
gcacggtggt tcacgcctgt aatcccagca ctttgggagg ccgaggcggg cggatcacga  29460
ggtcaggaga tcgagaccat cctggctaac acggtgaaac cccgtctcta ctaaaaatac  29520
aaaaacaaaa ttagccgggt gtggtggcag gcgcctgtag tcccagctac tcgggaggct  29580
gaggcgggag aatggcgtga acccgggagg cggagcttgc agtgagccaa gatcgcgcca  29640
ctgcactcca gcctgggtga ccgagttgag actccgtctc aaaaaaaaaa aaaaaaaaaa  29700
aaatacaaaa agtagccagg tgtggtggca ggcacctgta atcctgggtt ctcgagaccg  29760
aggcatgaga attgcctgac cccaggaggt ggaggctgca gtgagccaag atcatgccac  29820
tgcactccag cctgggcgac agagtgggac tctgtctcaa aaaacaacaa aaaaaaagtt  29880
ctggaaatgg atggtggtga tggtgatact tccacaacag cgtgaatctg cttaaggcca  29940
ccgaactgtg cactcacaaa tagtcgagat ggtacatttt atgttatgtg tatttcacca  30000
caattaaaaa ctagttgtgg gccaggtgtg gtggttcatg cctgtaatcc cagcactttg  30060
ggaggtcaga gggaggtgga tcatgaggtc agcagttcga gaccagccag gccaacatgg  30120
tgaaacccca tctctactaa aaatacaaaa attagccagg cgtggtggca catgcctgta  30180
gtcccagcta cttgagaggc tgaagcagga gaatcgcttg aacctgggag gctaagattg  30240
cagtgagccg agatcgtgcc actgcactcc agcctggacg acagagtgag acttcgtctc  30300
aaaaaaaaaa ccaaaaaaaa aattagctgt gggtcaggca ctgtggctca cgcctgtaat  30360
cccagcactt tgggagaccg aggtaggtgg atggcctgag gtcaggagtt cgaatccagc  30420
ctggccaaca tggtgaaagc ccgtctctac taaaaataca aaaaattagt caggtatgtt  30480
ggcacacctg taatcccagc tactcgggag gctgaagcaa gagaatcgtt tgaacccagg  30540
aggtggacgt tgcagtgagc cgagattggg ccactgtact ccagcctggg caacaaaagt  30600
gaaactctgt ctgaaacaaa caaacaaaca aacaaacaga caaacaaaaa aactagttgt  30660
ggagagaggg tggcctgtgt ctcatcccag tgtttaacgg gatttgtcat cttccttgct  30720
gcctgtttag gacaaagtat tttggacaga tatcatcaac gaagccattt tcagtgccaa  30780
ccgcctcaca ggttccgatg tcaacttgtt ggctgaaaac ctactgtccc cagaggatat  30840
ggttctcttc cacaacctca cccagccaag aggtaagggt gggtcagccc cacccccca  30900
accttgaaac ctccttgtgg aaactctgga atgttctgga aatttctgga atcttctggt  30960
atagctgatg atctcgttcc tgccctgact ccgcttcttc tgccccagga gtgaactggt  31020
gtgagaggac caccctgagc aatggcggct gccagtatct gtgcctccct gccccgcaga  31080
tcaaccccca ctcgcccaag tttacctgcg cctgcccgga cggcatgctg ctggccaggg  31140
acatgaggag ctgcctcaca ggtgtggcac acgccttgtt tctgcgtcct gtgtcctcca  31200
actgccccct cctgagcctc tctctgctca tctgtcaaat gggtacctca aggtcgttgt  31260
aaggactcat gagtcgggat aaccatactt ttcttggatg gacacatcag caccgggctt  31320
```

-continued

```
gacatttacc cagttcccct ttgatgcctg gtttcctctt tcccggcccc ctgaagaggt  31380
gatctgattt ctgacaggag ccctgaggga ggaaatggtc ccctttgttg acttttcttt  31440
ttctttattt ttttcttttg agatttgctg tcacccagcc tggaatgcag tggtgccatc  31500
ttggctcact gctacctctc ccactgggtt caagcaattc tcctgcctca gcctcccaag  31560
tagctgggat tacaagcatg cgccaccatg cctggctaag ttttgtattt ttagtacaga  31620
cagggtttct ccatggtggc caggctggtc ttgaactcct gacctcaggt gatcctccca  31680
cctctgcctc ccgaagtgct acgattacag gcatgagcca ccgcgcccat cccccttgt  31740
tgacttttct catcctctga gaaagtctca gttgaggcca gcacctccct caagtgaatt  31800
gaatctccct tttgaacaac aacaaataac aatatgaccc agacgtggtg gctcacacct  31860
gtggtcccag ctactcggga ggctgaggtg tgaggattgc ttgagcccag gaggtcaagg  31920
ctacagagag ctataatcac accacttcac tccagcctgg gggacaaagt gaaaccctgt  31980
ctgaaaaaaa caaaaaaaga aaaaggaaaa agaaacaata cgatcacaaa gtagatattc  32040
atagtgttta ttttcagtac tcttttttt ttttttttt ttttttgaga cggagtcttg  32100
ctctgttgcc caggctggag tgcagtggca cgatcttggc tcactgcagc ctctgcctcc  32160
caggttcaag cgcttggctc actgcaacct ccgcctcctg ggttcaagcg cttcttctgc  32220
ctcagcctcc ccagtagctg ggactatagg cacgtcccac tacgcccagc taattttttg  32280
tattttttag tagagatggg gtttcactat gttagccagg atggtctcga tctcctgacc  32340
tcgtgatctg cctgccttgg gctcccaaag tgttgggatt atgggcatga gccactgcac  32400
ctggcctttt tttttttttt ttttgagatg gagtttcgct cttgttgccc aggctggagt  32460
gcaatggtgt gatctcggct cactgcaacc tctgcctcct gggttcaagc aattctcctg  32520
cctcagcctc ccgagtagct gggattacag gcacctgcca ccacgcctgg ctaattttg  32580
tacttttagt agagacgggg tttctccatg ttggtcaggc tggtctcaaa ctcctgacct  32640
caggtgatcc acccacctcg gcctcccaaa gttctgggat tacagacatg agccaccgcg  32700
cctggccgtg tctggccttt tttagttatt tctttttttt tttttttttt ttttgagaca  32760
gagtcttact ccgtcgccca ggctggagtg cagcggtgcg atgtctgcgc actgcaagct  32820
ccgccccctg ggttcatgcc attctcctgc ctcagccttc tgagtagctg ggactgcagg  32880
cgcctgccac tacgcccggc tactttttg tatatttagt agagatggag tttcactgtg  32940
ttagccagga tggtctcgat ctcctgactt tgtgatccgc ccgcctcggc ctcccaaagt  33000
gctgggatta caggcgtgag ccaccatgcc aggctttttt tttttttttt ttttttgaga  33060
cggagtcttg ctctgtcgcc caggctggag tgcagtgcca tgatctcagc tcactgcaag  33120
ctccacttcc caggctcacg ccattctcca gcctcagcct cccaagtagc tgagactaca  33180
ggggcccgcc accacactcg gctaattttt ttgtattttt agtagagacg gggtttcacc  33240
atgttagcca ggctggtctt gaactcctaa cctcaggcga ttcacctgcc tcggcctccc  33300
aaagtgctgg gattaaaggt atgagccacc tcgcctggtg tgagccacct cgcccagcct  33360
gagccacctc acccagccta agccactgtg cctggcctga ttttggactt tttaaaaatt  33420
ttattaataa ttatttttgg gtttcttttt tttgagacag ggtcttactc tgtcatccag  33480
gccatcctgt ctgtctgtca tcccagtgat gggatcatac cttgctgcag cctctacctc  33540
ctgggctcaa gcgatcctcc cccctcagcc tcctgagtag ctgggagtac aggtgtgcac  33600
caccacacct ggctaatttt tttttttttt tttgtatata gagatggtat tttgccatgt  33660
```

```
tgaccaggct agtcttaaac tcctggactc actcaagaga tcctcctgcc ttggcctccc  33720
aaggtcattt gagactttcg tcattaggcg cacacctatg agaagggcct gcaggcacgt  33780
ggcactcaga agacgtttat ttattctttc agaggctgag gctgcagtgg ccacccagga  33840
gacatccacc gtcaggctaa aggtcagctc cacagccgta aggacacagc acacaaccac  33900
ccgacctgtt cccgacacct cccggctgcc tggggccacc cctgggctca ccacggtgga  33960
gatagtgaca atgtctcacc aaggtaaaga ctgggccctc cctaggcccc tcttcaccca  34020
gagacgggtc ccttcagtgg ccacgaacat tttggtcacg agatggagtc caggtgtcgt  34080
cctcactccc ttgctgacct tctctcactt gggccgtgtg tctctggccc ctcagtttcc  34140
ctatctgtaa agtgggtcta ataacagttc ttgccctctt tgcaaggatt aaatgggcca  34200
aatcatatga ggggccaggt ccttcaggct cctggttccc aaagtcagcc acgcaccgtg  34260
tgggtcccaa aattttatca aggcacattc gttgcctcag cttcaggcat ctgcccaaaa  34320
aggccaggac taaggcaagg agagggaggg attcctcagt actcagcttt tcacagaggc  34380
tccaaaaggc taaggaatcc agtaacgttt taacacaatt ttacaatttt tttttttgag  34440
acggagtttt gctcttgttg cccaggctgg agtgcagtgg cacgatctcg gctcactgca  34500
acctctggct cccgggttca agcgattctc ctgcctcagt ctcccgagta gctgggatta  34560
caggcatgcg ccaccacgct cggctaattt tgtattttta gtacagaagg ggcttctctg  34620
ttggtcaggc tggtcgtgaa ctctcaacct caggtgagcc acccgcctga gcctcccaaa  34680
gtgctgggat tacaggtgtg agccaccacg cctggccttt tttttgagac agagtctcgc  34740
tctcgcccat gctgtactgc agtgacgcag tctgggctca ctgtaacctc cgcttcccag  34800
gttcaagtga ttcttctgcc gcagcctccc atgtagagta gctgggatta caggcacccg  34860
ccaccatgcc tggctaattc ttgcattttt agtagagatg gggtttcaca gtgttggcca  34920
ggctggtctc aaacttctga cctcaagtca tctgcctgcc ttggccctgc caaagtgctg  34980
ggattataga tgtgagccac cgcgcctggc ctacagttta ttctttggtg gctcacacct  35040
gtaatctcag cactttggga ggccaaggtg ggagaatggc ttgagcccag gagttcaagt  35100
ccagcctggg caacatagca agaccctatc tctactacaa aataaataat aaataaacta  35160
atttttttc ttttaaaacc caactattca acatggcaat gcaatatatt aaaaaaattt  35220
tttttttctt tgaaacggag tctctcactg tcacccgggc tggagtgcag tgtcgccatc  35280
ttggctcact gcaacctccg cctcccaggt ccaagtgatt ctcctgcttc agcctcccga  35340
gtagctggga ttacaggcac ccaccaccat acccagctaa tatttttgta tttttagtag  35400
agatggggtt tcactatgtt gggcaggctg gtctggaact cctgacctcg tgatctgccc  35460
gaggatcggc ggcctcccaa agtgctgggg attgcaggca tgagccaccg tgcccagcca  35520
aaactttttt atttttattt ttttgggaca cggtctcact gtgtacccca gactggagtg  35580
atagagtgct gtcatggctc actgcagcct caacctccct gggctcaggt gatcttcctg  35640
cttcagtctc ccaggtagct gggactacag gcatgagcca ccacacccag ctaatttttg  35700
aatttttttg tagagacagg gtttcacctt gtggcccaga cttgtctcta actccagggc  35760
tcaagcgatc tgcccacctt ggcctcccaa agtgctgaga ttaatgcaat ttaaaaaatt  35820
ttttggccag gcctggtggc tcatgcctgt attcacaaca ccttgggagg caaaggtggg  35880
cagatcactt gaggtcagga gttcgagact agcctggcca acatggtgaa accccctgtc  35940
tactaaaaaa atacaaaaat tacctgggca cagtggtggg tgcctgtaat cccagctact  36000
tgggatgctg agggtggaga attgcttgaa cctgggaggc agaagttgca gtaagccaag  36060
```

-continued

```
atcatgccac tggactccag cctcagtgac agagcaaaac tctgtctcca aaaaaattgt  36120
ttttttttt tttttttcaa atcatcacac tacagccaag gcctggccac ttacttttgt  36180
aaataaagtt ttattggagc cagtggacca gtgaggccga atcttgcagg tgtaagatca  36240
cagtctatcc ttgaaaattt tgatattttg ttcattgggt ggtttttcat taatttaaat  36300
tttaaaaaat aacatattaa aggctggtgt ggaggtgcac gcctgcagtc ctagctactc  36360
ccagaggctg aggcgggaga cttgcttgag cccaagagtt gaagtccagc ctgggcaaca  36420
tagcgagacc cccatctcta aaaataaaaa taatgcatta gaatattatt ggattcctgg  36480
gcagggcaca gtggctcaca cctgtaatcc cagcactttg ggaggctgag gtgggtggat  36540
cacctgaggt caggagtttg agaccagcct ggccaacatg gtgaaacccc gtctctacta  36600
aaaatacaaa aattagccag gcgtggtggc aggtgcctgt aatcccagct actcgggagg  36660
ctgaagcacg agaatcgctt gaatccagga ggcggaggtt gcagtgagct gagattgcgc  36720
cattgcactc cagcctggag gacaagagtg aaactccatt cccctctgca aagaaaagga  36780
atattatcag attcctaagc tttttggctc cccctttagt ttgggggctg gggtggtgag  36840
tgtctgacct ggcctcactg tcctccctgg atgtgatgag acccaggtgt gggtcaggat  36900
gtcattcgtt tgtccaccag agggcgccca aactgctttg agctgctggg aaatggtgct  36960
cctagacttt tagcaaacaa acaaaaaaaa atggcacatc ggcaaatttc agaccattct  37020
ttttttttt tttttggtt ccagagtagc tgaaatcttt gttcagttac aagcaggata  37080
aaatggaaac tgcctgggag aggctgagaa accttcttgc ttgggggagg tggggcactg  37140
ctagaattaa tcgcttcaca gaccagccca tccaggactc ctcaaatttg gcaaaaaagc  37200
cattcattca ttcattcatt tatgtagaga cgagggggat ctggctatat tgcctagatt  37260
ggtctcaaat tcctggcctc aagtgatcct cctgccttgg tctactaatg tgctgcgatt  37320
acaggcatga gccaccgtgc ctagctctag tggacttgaa atgttgcctt gcccagggcc  37380
cttatgttga atggcccagg tccacttgta tggttctgta ccaaggttaa ccccatccca  37440
taatgcctgg gacagttgat gcaggacaat cagcttctgt gccattcaac ctcaggactg  37500
agcatgctgg gcattgtggg gtccgaaggt ggctcccctg tccccttcaa aataccctct  37560
ttttctttc ttcttttttt ttttttttt tttttgagac gaagtcttgc tctgttgccc  37620
cagctagagt gcagtggtgc gatctcagct ccccgcaacc tctgcttccc gggttcaggc  37680
gattctcctg cctcagcctc ctgagtagct gggattacag gtgcccaccg ccacagctgg  37740
ctaatttttg tatttttagt agagacaggg tttcaccgtg ttggccaggc tggtcttgaa  37800
ctcctgacct caggcaacct gcccacctca gcctcccaaa gtgctgggat tacaggtttg  37860
agccactggg cctggccttt ttttttttt tttgagaggg agtctcactc tgttgcccag  37920
gctggagtgc aatggcgcga tcttgactca ctgcaactcc atttcccggg ttcaagtgat  37980
tctcctccct cagcctccca agtagctggg attacaggtg catgccacca cggccagcta  38040
attttgtatt tttagtagag acagggtttc actatgttga tcatgctggt ctcaaactcc  38100
tgaccttagg tgatctgccc gccttagcct cccaaagtgt tgggattaca ggtgtgagcc  38160
accgcgccca gaccaaaata tgctcatttt aataaaatgc acaagtaggt tgacaagaat  38220
ttcacctgca accttgtcaa ccacctagaa taaaagcctc tgcagccctc ccctaaagac  38280
tcatcaatgt gaggctcaag aaccttctta ggctgggctc ggtggctcat ttctgtaatc  38340
cctgcacttt ggaaggctga ggcaggagga tctcttgagg ccaggagttc aagacaagcc  38400
```

-continued

```
tgggcaacat agccagacct ctgtttctat cccccacaaa aagaaccttc ttaaaccgga  38460
attgagtcct acaacctcga taactcacaa ataagcccgt gtggcctctc acagacttgg  38520
gaagttctcc aagtgtccag ggagatgtgc caggcgcttt cctgccgtga ccaccgtcct  38580
ctgcctgctc catttcttgg tggccttcct ttagacctgg gcctcactct tgcttctctc  38640
ctgcagctct gggcgacgtt gctggcagag gaaatgagaa gaagcccagt agcgtgaggg  38700
ctctgtccat tgtcctcccc atcggtaagc gcgggccggt cccccagcgt cccccaggtc  38760
acagcctccc gctatgtgac ctcgtgcctg gctggttggg cctgttcact ttttctcctg  38820
gacagggaac agccccactg gtgtccttta tcacccccac ggcctctcct ggcttggggc  38880
tgacagtgac aagatcagac agctaagggg tcagatggag gatgtggagc tgggtcccgt  38940
gctgtggaat agcctcaccg agatttgagt gccttctggg gaactggttc ccttgcaggg  39000
ggctgtgtgg agaggcgcgc tctccctgcc tcacccatgc tcatcctaac tcggttacca  39060
tcacatctct tttttctttt tttcttaaat tttaagaaaa aagaaattta atttttttga  39120
gagacagagt cttgctctgt cacccaggct ggagtgcagt ggcaccatca tgcctcgctg  39180
cagcctcaat gtctgggctc aagcgatcct cccacctcag cctcctgagt agctggtgca  39240
agccactata ccccacttcc tatttcttaa aaagtcacag ccctgtgtgt ggctaatcct  39300
ggacagaaat ctagaagaag tcagctactt ctggggcgtg gctcacccag tgggcttcag  39360
gttagatatt tcttatactt atgaggctgg gtgtggtggc ttatgcctgt aatcccagca  39420
ctttgggagg ctgaagtggg tggattgctt gggctcagga gttcgagacc aacctgggca  39480
acatggcgaa accctgtttc tagaaaaggt acaaaaatta gctgggcagg tggcacgtgc  39540
ctgtggtacc agctacttga gggcctgagg caggaggatc gcttgaacct gggaggtcga  39600
ggttgcagtg aactgagatc atgtcactgc actccagcct ggtgacagag caagaccccg  39660
tctcaaaaaa aaaaaaagaa agaaaaaaat tcttatgcat agatttgcct cttttctgtt  39720
tgtttgtttt gagatggagt ctcgctctgt cgcccaggct ggagtacagt ggctcaacct  39780
cggctcactg caacctctgc ctcccgggtt caagcaattc tcctgcctca gcctcctgag  39840
tagctgggac tacaggcgcc cgccaccatg cccagctaat ttttgtattt ttagtagaga  39900
ctgactgggt ttcatcatgt tggccaggct ggtctcgaac tcttgacctc atgatccgcc  39960
cgcctcagcc tcccaaaatg ctgggattac aggcgtgagc caccaggccc aggccgcaag  40020
gcgatctcta aacaaacata aaagaccagg agtcaaggtt atggtacgat gcccgtgttt  40080
tcactccagc cacggagctg ggtctctggt ctcgggggca gctgtgtgac agagcgtgcc  40140
tctccctaca gtgctcctcg tcttcctttg cctgggggtc ttccttctat ggaagaactg  40200
gcggcttaag aacatcaaca gcatcaactt tgacaacccc gtctatcaga agaccacaga  40260
ggatgaggtc cacatttgcc acaaccagga cggctacagc taccccctcgg tgagtgaccc  40320
tctctagaaa gccagagccc atggcggccc cctcccagct ggaggcatat gatcctcaag  40380
ggaccaggcc gaggcttccc cagccctcca gatcgaggac agcattaggt gaatgcttct  40440
gtgcgctcat tcagaatgtc agcggacaat ggccttggtg gtgtagagga atgttggata  40500
agcaaataga gagctccatc agatggtgac agggcaaaga aagtcaaaag gagttcagag  40560
gccgggcgcg gtggctcatg cctgtaatcc caggactttg ggaggccgag gctggcggat  40620
cacctgaagt caggagtttg agaccagctt ggccatcatg acaaaacccc gtctctatta  40680
aaaatacaaa aaattagcca ggcgtgggag tgggcgcctg taatcccagc tactcgggag  40740
gccgaggtag aaaaatcgct tgaacctagg aggcagaggt tgcagtgagc cgagatcgcg  40800
```

ccactgcatt ccagcccggg aggcaagagc aaaactccat ctcaaaaaaa aaaaaaaaag 40860
gagttcagag gcccggcatg gtggttcaca catgtgatcc cagaacttgg ggaggttgag 40920
gcaggagaat cacctgagct cagagttcaa gaccagcctg ggcagcacag caagacccca 40980
tctctgcaaa aaataaaaat ttagcccagt gtggtgatga gcgcctagtt ccagctacta 41040
gggaggctaa ggcaggagga ttgcttgagg ctaaggtagg agattgagac tgcagtgact 41100
tgtgattgcg tcactgcgct ccagcctggg tgacagagca agcccttgtc tcttaaaaaa 41160
aaaaaaaaat tcaaagaagg gtttccagag ggccaggagg gaggaaggga gaggaggtgt 41220
tttatttttt tgcttttatt ttttattttg agacagagtc tctctctgtc acccaggttg 41280
gagtgcagtg ctgtgatctt ggctcactgc aacttctgcc tcctgggttc aagcaattct 41340
tatgcctcag cctcagcctc ctgagtagct gggattacaa cactatgccc gggtaatttt 41400
tgtattttta gtagagacga ggtttcgcca tgttgcccag actggtctcg aactcctgac 41460
ctcaagtgat ccacccgcct tggcctcccc acgtgctggg attgcaggcg tgagccactg 41520
cgcccgcctt gatctttaca caaggggttt agggtaggta gccttctctg aaccaggaga 41580
acagcctgtg cgaaggccct gaggctggac cgtgcctgtt gggtttgagg ccgttgtagc 41640
tggagcaaac agagagaggg gtaaaaaggc aggaggctac caggcaggtt gtgcagagcc 41700
ttgtgggcca ctggggagga ctttggcttt tgccctgaga gcggtgggaa gtgactgaat 41760
ccggtactca ccgtctccct ctggcggctc ctgggggaac atgcttgggg atcaggctgg 41820
gggaggctgc caggcccagg aggtgagaag taggtggcct ccagccgtgt ttcctgaatg 41880
ctggactgat agtttccgct gtttaccatt tgttggcaga gacagatggt cagtctggag 41940
gatgacgtgg cgtgaacatc tgcctggagt cccgtccctg cccagaaccc ttcctgagac 42000
ctcgccggcc ttgttttatt caaagacaga gaagaccaaa gcattgcctg ccagagcttt 42060
gttttatata tttattcatc tgggaggcag aacaggcttc ggacagtgcc catgcaatgg 42120
cttgggttgg gattttggtt tcttcctttc ctcgtgaagg ataagagaaa caggcccggg 42180
gggaccagga tgacacctcc atttctctcc aggaagtttt gagtttctct ccaccgtgac 42240
acaatcctca aacatggaag atgaaagggg aggggatgtc aggcccagag aagcaagtgg 42300
ctttcaacac acaacagcag atggcaccaa cgggaccccc tggccctgcc tcatccacca 42360
atctctaagc caaaccccta aactcaggag tcaacgtgtt tacctcttct atgcaagcct 42420
tgctagacag ccaggttagc ctttgccctg tcacccccga atcatgaccc acccagtgtc 42480
tttcgaggtg ggtttgtacc ttccttaagc caggaaaggg attcatggcg tcggaaatga 42540
tctggctgaa tccgtggtgg caccgagacc aaactcattc accaaatgat gccacttccc 42600
agaggcagag cctgagtcac tggtcaccct taatatttat taagtgcctg agacacccgg 42660
ttaccttggc cgtgaggaca cgtggcctgc acccaggtgt ggctgtcagg acaccagcct 42720
ggtgcccatc ctcccgaccc ctacccactt ccattcccgt ggtctccttg cactttctca 42780
gttcagagtt gtacactgtg ta 42802

<210> SEQ ID NO 5
<211> LENGTH: 3635
<212> TYPE: DNA
<213> ORGANISM: homo sapien

<400> SEQUENCE: 5
uugcgacguc gaggcgcuca ugguugcagg cgggcgccgc cguucaguuc agggucugag 60

-continued

```
ccuggaggag ugagccaggc agugagacug gcucgggcgg gccgggacgc gucguugcag    120
cagcggcucc cagcucccag ccaggauucc gcgcgccccu ucacgcgccc ugcuccugaa    180
cuucagcucc ugcacagucc uccccaccgc aaggcucaag gcgccgccgg cguggaccgc    240
gcacggccuc uaggucuccu cgccaggaca gcaaccucuc cccuggcccu caugggcacc    300
gucagcucca ggcgguccug guggccgcug ccacugcugc ugcugcugcu gcugcuccug    360
ggucccgcgg gcgcccgugc gcaggaggac gaggacggcg acuacgagga gcuggugcua    420
gccuugcguu ccgaggagga cggccuggcc gaagcacccg agcacggaac cacagccacc    480
uuccaccgcu gcgccaagga uccguggagg uugccuggca ccuacguggu ggugcugaag    540
gaggagaccc accucucgca gucagagcgc acugcccgcc gccugcaggc ccaggcugcc    600
cgccggggau accucaccaa gauccugcau gucuuccaug gccuucuucc uggcuuccug    660
gugaagauga guggcgaccu gcuggagcug gccuugaagu ugccccaugu cgacuacauc    720
gaggaggacu ccucugucuu ugcccagagc aucccgugga accuggagcg gauuaccccu    780
ccacgguacc gggcggauga auaccagccc cccgacggag gcagccuggu ggaggugua u    840
cuccuagaca ccagcauaca gagugaccac cgggaaaucg agggcagggu cauggucacc    900
gacuucgaga augugcccga ggaggacggg acccgcuucc acagacaggc cagcaagugu    960
gacagucaug gcacccaccu ggcagggggug gucagcggcc gggaugccgg cguggccaag   1020
ggugccagca ugcgcagccu gcgcgugcuc aacugccaag ggaagggcac gguuagcggc   1080
acccucauag gccuggaguu uauucggaaa agccagcugg uccagccugu ggggccacug   1140
guggugcugc ugccccuggc gggugggguac agccgcgucc ucaacgccgc cugccagcgc   1200
cuggcgaggg cuggggucgu gcuggucacc gcugccggca acuuccggga cgaugccugc   1260
cucuacuccc cagccucagc ucccgagguc aucacaguug gggccaccaa ugcccaggac   1320
cagccgguga cccuggggac uuuggggacc aacuuuggcc gcugugugga ccucuuugcc   1380
ccaggggagg acaucauugg ugccuccagc gacugcagca ccugcuuugu gucacagagu   1440
gggacaucac aggcugcugc ccacguggcu ggcauugcag ccaugaugcu gucugccgag   1500
ccggagcuca cccuggccga guugaggcag agacugaucc acuucucugc caaagaugcc   1560
aucaaugagg ccugguuccc ugaggaccag cggguacuga cccccaaccu gguggccgcc   1620
cugcccccca gcacccaugg ggcagguugg cagcuguuuu gcaggacugu guggucagca   1680
cacucggggc cuacacggau ggccacagcc aucgcccgcu gcgccccaga ugaggagcug   1740
cugagcugcu ccaguuucuc caggagugga agcggcgggg cgagcgcaug gaggcccaag   1800
ggggcaagcu ggucugccgg gcccacaacg cuuuuggggg ugagggugug uacgccauug   1860
ccaggugcug ccugcuaccc caggccaacu gcagcgucca cacagcucca ccagcugagg   1920
ccagcauggg gacccguguc cacugccacc aacagggcca cguccucaca ggcugcagcu   1980
cccacuggga gguggaggac cuuggcaccc acaagccgcc ugugcugagg ccacgagguc   2040
agcccaacca gugcgugggc cacagggagg ccagcaucca cgcuuccugc ugccaugccc   2100
caggucugga augcaaaguc aaggagcaug gaaucccggc cccucaggag caggugaccg   2160
uggccugcga ggagggcugg acccugacug gcugcagugc ccucccuggg accucccacg   2220
uccugggggc cuacgccgua gacaacacgu guguagucag gagccgggac gucagcacua   2280
caggcagcac cagcgaagag gccgugacag ccguugccau cugcugccgg agccggcacc   2340
uggcgcaggc cucccaggag cuccagugac agccccaucc caggaugggu gucuggggag   2400
ggucaagggc uggggcugag cuuuaaaaug guuccgacuu gucccucucu cagcccucca   2460
```

uggccuggca cgaggggaug gggaugcuuc cgccuucccg gggcugcugg ccuggcccuu 2520
gaguggggca gccuccuugc cuggaacuca cucacucugg gugccuccuc cccaggugga 2580
ggugccagga agcucccucc cucacugugg ggcauuucac cauucaaaca ggucgagcug 2640
ugcucgggug cugccagcug cucccaaugu gccgaugucc gugggcagaa ugacuuuuau 2700
ugagcucuug uuccgugcca ggcauucaau ccucaggucu ccaccaagga ggcaggauuc 2760
uucccaugga uaggggaggg ggcgguaggg gcugcaggga caaacaucgu ugggggguga 2820
gugugaaagg ugcugauggc ccucaucucc agcuaacugu ggagaagccc cugggggcuc 2880
ccugauuaau ggaggcuuag cuuucuggau ggcaucuagc cagaggcugg agacaggugu 2940
gccccuggug gucacaggcu gugccuuggu uuccugagcc accuuuacuc ugcucuaugc 3000
caggcugugc uagcaacacc caaagguggc cugcggggag ccaucaccua ggacugacuc 3060
ggcagugugc aguggugcau gcacugucuc agccaacccg cuccacuacc cggcagggua 3120
cacauucgca ccccuacuuc acagaggaag aaaccuggaa ccagaggggg cgugccugcc 3180
aagcucacac agcaggaacu gggccagaaa cgcagauugg gcuggcucug aagccaagcc 3240
ucuucuuacu ucacccggcu gggcuccuca uuuuuacggg uaacagugag gcugggaagg 3300
ggaacacaga ccaggaagcu cggugaguga uggcagaacg augccugcag gcauggaacu 3360
uuuuccguua ucacccaggc cugauucacu ggccuggcgg agaugcuucu aaggcauggu 3420
cgggggagag ggccaacaac ugucccuccu ugagcaccag ccccacccaa gcaagcagac 3480
auuuaucuuu ugggucuguc cucucuguug ccuuuuuaca gccaacuuuu cuagaccugu 3540
uuugcuuuug uaacuugaag auauuuauuc uggguuuugu agcauuuuua uuaauauggu 3600
gacuuuuuaa aauaaaaaca aacaaacguu guccu 3635

<210> SEQ ID NO 6
<211> LENGTH: 1101
<212> TYPE: DNA
<213> ORGANISM: homo sapien
<400> SEQUENCE: 6
aggcucaagg cgccgccggc guggaccgcg cacggccucu aggucuccuc gccaggacag 60
caaccucucc ccuggcccuc augggcaccg ucagcuccag gcgguccugg uggccgcugc 120
cacugcugcu gcugcugcug cugcuccugg gucccgcggg cgcccgugcg caggaggacg 180
aggacggcga cuacgaggag cuggugcuag ccuugcguuc cgaggaggac ggccuggccg 240
aagcacccga gcacggaacc acagccaccu uccaccgcug cgccaaggau ccguggaggu 300
ugccuggcac cuacguggug gugcugaagg aggagaccca ccucucgcag ucagagcgca 360
cugcccgccg ccugcaggcc caggcugccc gccggggaua ccucaccaag auccugcaug 420
ucuuccaugg ccuucuuccu ggcuuccugg ugaagaugag uggcgaccug cuggagcugg 480
ccuugaaguu gccccauguc gacuacaucg aggaggacuc cucugucuuu gcccagagca 540
ucccguggaa ccuggagcgg auuaccccuc cacgguaccg ggcggaugaa uaccagcccc 600
ccgcauauuu ggaggaucac ugcgggggcc acagaggugc uguucagaug gcacuucaga 660
agacucagga gacccugggg caggagcagu uugacugaca gcccagaggg cugcccucug 720
auuccaccug aggcccugcu uuuccuggcu gcagggguuc cagggccagg ccauuuccgc 780
uggcgcagga cucugcuagc agcaaccugc cugaagucuu ccuuuggccu ggcugagagu 840
uucugagacc ugcgcuggag cggagacgga ggcagccugg uggaggugua ucuccuagac 900
accagcauac agagugacca ccgggaaauc gagggcaggg ucauggucac cgacuucgag 960
aaugugcccg aggaggacgg gacccgcuuc cacagacagg ccagcaagug ugacagucau 1020
ggcacccacc uggcaggggu ggucagcggc cgggaugccg gcguggccaa gggugccagc 1080
augcgcagcc ugcgcgugcu c 1101

<210> SEQ ID NO 7
<211> LENGTH: 2079
<212> TYPE: DNA
<213> ORGANISM: homo sapien

<400> SEQUENCE: 7
augggcaccg ucagcuccag gcgguccugg uggccgcugc cacugcugcu gcugcugcug 60
cugcuccugg gucccgcggg cgcccgugcg caggaggacg aggacggcga cuacgaggag 120
cuggugcuag ccuugcguuc cgaggaggac ggccuggccg aagcacccga gcacggaacc 180
acagccaccu uccaccgcug cgccaaggau ccguggaggu ugccuggcac cuacguggug 240
gugcugaagg aggagaccca ccucucgcag ucagagcgca cugcccgccg ccugcaggcc 300
caggcugccc gccggggaua ccucaccaag auccugcaug ucuuccaugg ccuucuuccu 360
ggcuuccugg ugaagaugag uggcgaccug cuggagcugg ccuugaaguu gccccauguc 420
gacuacaucg aggaggacuc cucugucuuu gcccagagca ucccguggaa ccuggagcgg 480
auuaccccuc cacgguaccg ggcggaugaa uaccagcccc ccgacggagg cagccuggug 540
gagguguauc uccuagacac cagcauacag agugaccacc gggaaaucga gggcaggguc 600
auggucaccg acuucgagaa ugugcccgag gaggacggga cccgcuucca cagacaggcc 660
agcaagugug acagucaugg cacccaccug gcaggggugg ucagcggccg ggaugccggc 720
guggccaagg gugccagcau gcgcagccug cgcgugcuca acugccaagg gaagggcacg 780
guuagcggca cccucauagg ccuggaguuu auucggaaaa gccagcuggu ccagccugug 840
gggccacugg uggugcugcu gccccuggcg ggugggguaca gccgcguccu caacgccgcc 900
ugccagcgcc uggcgagggc uggggucgug cuggucaccg cugccggcaa cuuccgggac 960
gaugccugcc ucuacucccc agccucagcu cccgagguca ucacaguugg ggccaccaau 1020
gcccaggacc agccggugac ccuggggacu uuggggacca acuuuggccg cugugguggac 1080 cucuuugccc caggggagga caucauuggu gccuccagcg acugcagcac cugcuuugug 1140
ucacagagug ggacaucaca ggcugcugcc cacguggcug gcauugcagc caugaugcug 1200
ucugccgagc cggagcucac ccuggccgag uugaggcaga gacugaucca cuucucugcc 1260
aaagauguca ucaaugaggc cugguucccu gaggaccagc ggguacugac ccccaaccug 1320
guggccgccc ugccccccag cacccauggg gcagguuggc agcuguuuug caggacugug 1380
uggucagcac acucggggcc uacacggaug gccacagcca ucgcccgcug cgccccagau 1440
gaggagcugc ugagcugcuc caguuucucc aggaguggga agcggcgggg cgagcgcaug 1500
gaggcccaag gggcaagcu ggucugccgg gcccacaacg cuuuuggggg ugagggugus 1560
uacgccauug ccaggugcug ccugcuaccc caggccaacu gcagcgucca cacagcucca 1620
ccagcugagg ccagcauggg gacccguguc cacugccacc aacagggcca cguccucaca 1680
ggcugcagcu cccacuggga gguggaggac cuuggcaccc acaagccgcc ugugcugagg 1740
ccacgagguc agcccaacca gugcgugggc cacagggagg ccagcaucca cgcuuccugc 1800
ugccaugccc caggucugga augcaaaguc aaggagcaug gaaucccggc cccucaggag 1860
caggugaccg uggccugcga ggagggcugg acccugacug gcugcagugc ccucccuggg 1920
accucccacg uccugggggc cuacgccgua gacaacacgu guguagucag gagccgggac 1980
gucagcacua caggcagcac cagcgaagag gccgugacag ccguugccau cugcugccgg 2040
agccggcacc uggcgcaggc cucccaggag cuccaguga 2079

<210> SEQ ID NO 8
<211> LENGTH: 2333
<212> TYPE: DNA
<213> ORGANISM: homo sapien

<400> SEQUENCE: 8
gugcaaucgc gggaagccag gguuuccagc uaggacacag caggucguga uccgggucgg 60
gacacugccu ggcagaggcu gcgagcaugg ggcccugggg cuggaaauug cgcuggaccg 120
ucgccuugcu ccucgccgcg gcggggacug caguggggcga cagaugcgaa agaaacgagu 180
uccagugcca agacgggaaa ugcaucuccu acaagugggu cugcgauggc agcgcugagu 240
gccaggaugg cucugaugag ucccaggaga cgugcuuguc ugucaccugc aaauccgggg 300
acuucagcug ugggggccgu gucaaccgcu gcauuccuca guucuggagg ugcgauggcc 360
aaguggacug cgacaacggc ucagacgagc aaggcugucu gacacucugc gagggaccca 420
acaaguucaa gugucacagc ggcgaaugca ucacccugga caaagucugc aacauggcua 480
gagacugccg ggacugguca gaugaaccca ucaaagagug cgggaccaac gaaugcuugg 540
acaacaacgg cggcuguucc cacgucugca augaccuuaa gaucggcuac gagugccugu 600
gccccgacgg cuuccagcug guggcccagc gaagaugcga agauaucgau gagugucagg 660
aucccgacac cugcagccag cucugcguga accuggaggg uggcuacaag ugccagugug 720
aggaaggcuu ccagcuggac ccccacacga aggccugcaa ggcugugggc uccaucgccu 780
accucuucuu caccaaccgg cacgagguca ggaagaugac gcuggaccgg agcgaguaca 840
ccagccucau ccccaaccug aggaacgugg ucgcucugga cacggaggug gccagcaaua 900
gaaucuacug gucugaccug ucccagagaa ugaucugcag cacccagcuu gacagagccc 960
acggcgucuc uuccuaugac accgucauca gcagagacau ccaggccccc gacgggcugg 1020
cuguggacug gauccacagc aacaucuacu ggaccgacuc uguccugggc acugucucug 1080
uugcggauac caagggcgug aagaggaaaa cguuauucag ggagaacggc uccaagccaa 1140
gggccaucgu gguggauccu guucauggcu ucauguacug gacugacugg ggaacucccg 1200
ccaagaucaa gaaagggggc cugaauggug uggacaucua cucgcuggug acugaaaaca 1260
uucaguggcc caauggcauc acccuagauc uccucagugg ccgccucuac uggguugacu 1320
ccaaacuuca cuccaucuca agcaucgaug ucaacggggg caaccggaag accaucuugg 1380
aggaugaaaa gaggcuggcc caccccuucu ccuuggccgu cuuugaggac aaaguauuuu 1440
ggacagauau caucaacgaa gccauuuuca gugccaaccg ccucacaggu uccgauguca 1500
auuuguuggc ugaaaaccua cuguccccag aggauauggu ucucuuccac aaccucaccc 1560
agccaagagg agugaacugg ugugagagga ccacccugag caauggcggc ugccaguauc 1620
ugugccuccc ugccccgcag aucaaccccc acucgcccaa guuuaccugc gccugcccgg 1680
acggcaugcu gcuggccagg gacaugagga gcugccucac agaggcugag gcugcagugg 1740
ccacccagga gacauccacc gucaggcuaa aggucagcuc cacagccgua aggacacagc 1800
acacaaccac ccgaccuguu cccgacaccu cccggcugcc uggggccacc ccugggcuca 1860
ccacggugga gauagugaca augucucacc aagcucuggg cgacguugcu ggcagaggaa 1920

-continued augagaagaa gcccaguagc gugagggcuc uguccauugu ccucccccauc gugcuccucg 1980 ucuuccuuug ccugggggguc uuccuucuau ggaagaacug gcggcuuaag aacaucaaca 2040
gcaucaacuu ugacaacccc gucuaucaga agaccacaga ggaugagguc cacauuugcc 2100
acaaccagga cggcuacagc uaccccucga gacagauggu cagucuggag gaugacgugg 2160
cgugaacauc ugccuggagu cccgucccug cccagaaccc uuccugagac cucgccggcc 2220
uuguuuuauu caaagacaga gaagaccaaa gcauugccug ccagagcuuu guuuuauaua 2280
uuuauucauc ugggaggcag aacaggcuuc ggacagugcc caugcaaugg cuu 2333

<210> SEQ ID NO 9
<211> LENGTH: 2768
<212> TYPE: DNA
<213> ORGANISM: homo sapien

<400> SEQUENCE: 9
gugcaaucgc gggaagccag gguuuccagc uaggacacag caggucguga uccgggucgg 60
gacacugccu ggcagaggcu gcgagcaugg ggcccugggg cuggaaauug cgcuggaccg 120
ucgccuugcu ccucgccgcg gcggggacug cagugggcga cagaugcgaa agaaacgagu 180
uccagugcca agacgggaaa ugcaucuccu acaagugggu cugcgauggc agcgcugagu 240
gccaggaugg cucugaugag ucccaggaga cgugcucccc caagacgugc ucccaggacg 300
aguuucgcug ccacgauggg aagugcaucu cucggcaguu cgucugugac ucagaccggg 360
acugcuugga cggcucagac gaggccuccu gcccggugcu caccugugggu cccgccagcu 420 uccagugcaa cagcuccacc ugcauccccc agcugugggc cugcgacaac gaccccgacu 480
gcgaagaugg cucggaugag uggccgcagc gcuguagggg ucuuuacgug uuccaagggg 540
acaguagccc cugcucggcc uucgaguucc acugccuaag uggcgagugc auccacucca 600
gcuggcgcug ugaugguggc cccgacugca aggacaaauc ugacgaggaa aacugcgcug 660
uggccaccug ucgcccugac gaauuccagu gcucugaugg aaacugcauc cauggcagcc 720
ggcaguguga ccgggaauau gacugcaagg acaugagcga ugaaguuggc ugcguuaaug 780
ugacacucug cgagggaccc aacaaguuca agugucacag cggcgaaugc aucacccugg 840
acaaagucug caacauggcu agagacugcc gggacugguc agaugaaccc aucaaagagu 900
gcgggaccaa cgaaugcuug gacaacaacg gcggcuguuc ccacgucugc aaugaccuua 960
agaucggcua cgagugccug ugccccgacg gcuuccagcu gguggcccag cgaagaugcg 1020
aagauaucga ugagugucag gaucccgaca ccugcagcca gcucugcgug aaccuggagg 1080
guggcuacaa gugccagugu gaggaaggcu uccagcugga cccccacacg aaggccugca 1140
aggcuguggg cuccaucgcc uaccucuucu ucaccaaccg gcacgagguc aggaagauga 1200
cgcuggaccg gagcgaguac accagccuca uccccaaccu gaggaacgug gucgcucugg 1260
acacggaggu ggccagcaau agaaucuacu ggucugaccu gucccagaga augaucugca 1320
gcacccagcu ugacagagcc cacggcgucu cuuccuauga caccgucauc agcagggaca 1380
uccaggcccc cgacgggcug gcuguggacu ggauccacag caacaucuac uggaccgacu 1440
cuguccuggg cacugucucu guugcggaua ccaagggcgu gaagaggaaa acguuauuca 1500
gggagaacgg cuccaagcca agggccaucg ugguggaucc uguucauggc uucauguacu 1560
ggacugacug gggaacuccc gccaagauca agaaaggggg ccugaauggu guggacaucu 1620
acucgcuggu gacugaaaac auucaguggc ccaauggcau cacccuagau cuccucagug 1680
gccgccucua cugguugac uccaaacuuc acuccaucuc aagcaucgau gucaaugggg 1740

-continued gcaaccggaa gaccaucuug gaggaugaaa agaggcuggc ccaccccuuc uccuuggccg 1800
ucuuugagga caaaguauuu uggacagaua ucaucaacga agccauuuuc agugccaacc 1860
gccucacagg uuccgauguc aacuuguugg cugaaaaccu acugucccca gaggauaugg 1920
uccucuucca caaccucacc cagccaagag gagugaacug gugugagagg accacccuga 1980
gcaauggcgg cugccaguau cugugccucc cugccccgca gaucaacccc cacucgccca 2040
aguuuaccug cgccugcccg gacggcaugc ugcuggccag ggacaugagg agcugccuca 2100
cagaggcuga ggcugcagug gccacccagg agacauccac cgucaggcua aaggucagcu 2160
ccacagccgu aaggacacag cacacaacca cccggccugu ucccgacacc ucccggcugc 2220
cuggggccac cccugggcuc accacggugg agauagugac aaugucucac caagcucugg 2280
gcgacguugc uggcagagga aaugagaaga agcccaguag ugugagggcu cuguccauug 2340
uccuccccau cgugcuccuc gucuuccuuu gccugggggu cuuccuucua uggaagaacu 2400
ggcggcuuaa gaacaucaac agcaucaacu uugacaaccc cgucuaucag aagaccacag 2460
aggaugaggu ccacauuugc cacaaccagg acggcuacag cuaccccucg agacagaugg 2520
ucagucugga ggaugacgug gcgugaacau cugccuggag ucccgucccu gcccagaacc 2580
cuuccugaga ccucgccggc cuuguuuuau ucaaagacag agaagaccga agcauugccu 2640
gccagagcuu uguuuuauau auuuauucau cugggaggca gaacaggcuu cggacagugc 2700
ccaugcaaug gcuuggguug ggauuuuggu uucuuccuuu ccucgugaag gauaagagaa 2760
acaggccc 2768

<210> SEQ ID NO 10
<211> LENGTH: 2429
<212> TYPE: DNA
<213> ORGANISM: homo sapien

<400> SEQUENCE: 10
gugcaaucgc gggaagccag gguuuccagc uaggacacag caggucguga uccgggucgg 60
gacacugccu ggcagaggcu gcgagcaugg ggcccugggg cuggaaauug cgcuggaccg 120
ucgccuugcu ccucgccgcg gcggggacug caguggcga cagaugcgaa agaaacgagu 180
uccagugcca agacgggaaa ugcaucuccu acaagugggu cugcgauggc agcgcugagu 240
gccaggaugg cucugaugag ucccaggaga cgugcuuguc ugucaccugc aaauccgggg 300
acuucagcug ugggggccgu gucaaccgcu gcauuccuca guucuggagg ugcgauggcc 360
aaguggacug cgacaacggc ucagacgagc aaggcugucc uguggccacc ugucgcccug 420
acgaauucca gugcucugau ggaaacugca uccauggcag ccggcagugu gaccgggaau 480
augacugcaa ggacaugagc gaugaaguug gcugcguuaa ugugacacuc ugcgagggac 540
ccaacaaguu caagugucac agcggcgaau gcaucacccu ggacaaaguc ugcaacaugg 600
cuagagacug ccgggacugg ucagaugaac ccaucaaaga gugcgggacc aacgaaugcu 660
uggacaacaa cggcggcugu ucccacgucu gcaaugaccu uaagaucggc uacgagugcc 720
ugugccccga cggcuuccag cugguggccc agcgaagaug cgaagauauc gaugaguguc 780
aggaucccga caccugcagc cagcucugcg ugaaccugga ggguggcuac aagugccagu 840
gugaggaagg cuuccagcug gacccccaca cgaaggccug caaggcugug ggcuccaucg 900
ccuaccucuu cuucaccaac cggcacgagg ucaggaagau gacgcuggac cggagcgagu 960
acaccagucu cauccccaac cugaggaacg uggucgcucu ggacacggag guggccagca 1020
auagaaucua cuggucugac cugucccaga gaaugaucug cagcacccag cuugacagag 1080
cccacggcgu cucuuccuau gacaccguca ucagcagaga cauccaggcc cccgacgggc 1140
uggcugugga cuggauccac agcaacaucu acuggaccga cucuguccug ggcacugucu 1200
cuguugcgga uaccaagggc gugaagagga aaacguuauu cagggagaac ggcuccaagc 1260
caagggccau cgugguggau ccuguucaug gcuucaugua cuggacugac uggggaacuc 1320
ccgccaagau caagaaaggg ggccugaaug guguggacau cuacucgcug gugacugaaa 1380
acauucagug gcccaauggc aucacccuag aucuccucag uggccgccuc uacuggguug 1440
acuccaaacu ucacuccauc ucaagcaucg augucaacgg gggcaaccgg aagaccaucu 1500
uggaggauga aaagaggcug gcccaccccu ucuccuuggc cgucuuugag gacaaaguau 1560
uuuggacaga uaucaucaac gaagccauuu ucagugccaa ccgccucaca gguuccgaug 1620
ucaacuuguu ggcugaaaac cuacuguccc cagaggauau gguucucuuc cacaaccuca 1680
cccagccaag agaggcugag gcugcagugg ccacccagga gacauccacc gucaggcuaa 1740
aggucagcuc cacagccgua aggacacagc acacaaccac ccggccuguu cccgacaccu 1800
cccggcugcc uggggccacc ccugggcuca ccacggugga gauagugaca augucucacc 1860
aagcucuggg cgacguugcu ggcagaggaa augagaagaa gcccaguagc gugagggcuc 1920
uguccauugu ccuccccauc gugcuccucg ucuuccuuug ccugggggue uuccuucuau 1980 ggaagaacug gcggcuuaag aacaucaaca gcaucaacuu ugacaacccc gucuaucaga 2040
agaccacaga ggaugagguc cacauuugcc acaaccagga cggcuacagc uaccccucga 2100
gacagauggu cagucuggag gaugacgugg cgugaacauc ugccuggagu cccgucccug 2160
cccagaaccc uuccugagac cucgccagcc uuguuuuauu caaagacaga gaagaccaaa 2220
gcauugccug ccagagcuuu guuuuauaua uuuauucauc ugggaggcag aacaggcuuc 2280
ggacagugcc caugcaaugg cuuggguugg gauuuugguu ucuuccuuuc cucgugaagg 2340
auaagagaaa caggcccggg gggaccagga ugacaccucc auuucucucc aggaaguuuu 2400
gaguuucucu ccaccgugac acaauccuc 2429

<210> SEQ ID NO 11
<211> LENGTH: 2656
<212> TYPE: DNA
<213> ORGANISM: homo sapien

<400> SEQUENCE: 11
gugcaaucgc gggaagccag gguuuccagc uaggacacag caggucguga uccgggucgg 60
gacacugccu ggcagaggcu gcgagcaugg ggcccugggg cuggaaauug cgcuggaccg 120
ucgccuugcu ccucgccgcg gcggggacug caguggcgga cagaugcgaa agaaacgagu 180
uccagugcaa cagcuccacc ugcauccccc agcugugggc cugcgacaac gaccccgacu 240
gcgaagaugg cucggaugag uggccgcagc gcuguagggg ucuuuacgug uuccaagggg 300
acaguagccc cugcucggcc uucgaguucc acugccuaag uggcgagugc auccacucca 360
gcuggcgcug ugaugguggc cccgacugca aggacaaauc ugacgaggaa aacugcgcug 420
uggccaccug ucgcccugac gaauuccagu gcucugaugg aaacugcauc cauggcagcc 480
ggcaguguga ccgggaauau gacugcaagg acaugagcga ugaaguuggc ugcguuaaug 540
ugacacucug cgagggaccc aacaaguuca agugucacag cggcgaaugc aucacccugg 600
acaaagucug caacauggcu agagacugcc gggacugguc agaugaaccc aucaaagagu 660
gcgggaccaa cgaaugcuug gacaacaacg gcggcuguuc ccacgucugc aaugaccuua 720
agaucggcua cgagugccug ugccccgacg gcuuccagcu gguggcccag cgaagaugcg 780
aagauaucga ugagugucag gaucccgaca ccugcagcca gcucugcgug aaccuggagg 840
guggcuacaa gugccagugu gaggaaggcu uccagcugga cccccacacg aaggccugca 900
aggcuguggg cuccaucgcc uaccucuucu ucaccaaccg gcacgagguc aggaagauga 960
cgcuggaccg gagcgaguac accagccuca uccccaaccu gaggaacgug gucgcucugg 1020
acacggaggu ggccagcaau agaaucuacu ggucugaccu gucccagaga augaucugca 1080
gcacccagcu ugacagagcc cacggcgucu cuuccuauga caccgucauc agcagggaca 1140
uccaggcccc cgacgggcug gcuguggacu ggauccacag caacaucuac uggaccgacu 1200
cuguccuggg cacugucucu guugcggaua ccaagggcgu gaagaggaaa acguuauuca 1260
gggagaacgg cuccaagcca agggccaucg ugguggaucc uguucauggc uucauguacu 1320
ggacugacug gggaacuccc gccaagauca agaaaggggg ccugaauggu guggacaucu 1380
acucgcuggu gacugaaaac auucaguggc ccaauggcau cacccuagau cuccucagug 1440
gccgccucua cugguugac uccaaacuuc acuccaucuc aagcaucgau gucaaugggg 1500
gcaaccggaa gaccaucuug gaggaugaaa agaggcuggc ccaccccuuc uccuuggccg 1560
ucuuugagga caaaguauuu uggacagaua ucaucaacga agccauuuuc agugccaacc 1620
gccucacagg uuccgauguc aacuuguugg cugaaaaccu acuguccccca gaggauaugg 1680 uccucuucca caaccucacc cagccaagag gagugaacug gugugagagg accacccuga 1740
gcaauggcgg cugccaguau cugugccucc cugccccgca gaucaacccc cacucgccca 1800
aguuuaccug cgccugcccg gacggcaugc ugcuggccag ggacaugagg agcugccuca 1860
cagaggcuga ggcugcagug gccacccagg agacauccac cgucaggcua aaggucagcu 1920
ccacagccgu aaggacacag cacacaacca cccggccugu ucccgacacc ucccggcugc 1980
cuggggccac cccugggcuc accacggugg agauagugac aaugucucac caagcucugg 2040
gcgacguugc uggcagagga aaugagaaga agcccaguag cgugagggcu cuguccauug 2100
uccuccccau cgugcuccuc gucuuccuuu gccugggggu cuuccuucua uggaagaacu 2160
ggcggcuuaa gaacaucaac agcaucaacu uugacaaccc cgucuaucag aagaccacag 2220
aggaugaggu ccacauuugc cacaaccagg acggcuacag cuaccccucg agacagaugg 2280
ucagucugga ggaugacgug gcgugaacau cugccuggag ucccgucccu gcccagaacc 2340
cuuccugaga ccucgccggc cuuguuuuau ucaaagacag agaagaccaa agcauugccu 2400
gccagagcuu uguuuuauau auuuauucau cugggaggca gaacaggcuu cggacagugc 2460
ccaugcaaug gcuuggguug ggauuuuggu uucuuccuuu ccucgugaag gauaagagaa 2520
acaggcccgg ggggaccagg augacaccuc cauuucucuc caggaaguuu ugaguuucuc 2580
uccaccguga cacaauccuc aaacauggaa gaugaaaggg caggggaugu caggcccaga 2640
gaagcaagug gcuuuc 2656

<210> SEQ ID NO 12
<211> LENGTH: 3144
<212> TYPE: DNA
<213> ORGANISM: homo sapien

<400> SEQUENCE: 12
gccaggguuu ccagcuagga cacagcaggu cgugauccgg gucgggacac ugccuggcag 60
aggcugcgag cauggggccc uggggcugga aauugcgcug gaccgucgcc uugcuccucg 120

-continued

```
ccgcggcggg gacugcagug ggcgacagau gcgaaagaaa cgaguuccag ugccaagacg    180
ggaaaugcau cuccuacaag ugggucugcg auggcagcgc ugagugccag gauggcucug    240
augaguccca ggagacgugc uugucuguca ccugcaaauc cggggacuuc agcuguggggg   300
gccgugucaa ccgcugcauu ccucaguucu ggaggugcga uggccaagug gacugcgaca    360
acggcucaga cgagcaaggc uguccccca agacgugcuc ccaggacgag uuucgcugcc    420
acgaugggaa gugcaucucu cggcaguucg ucugugacuc agaccgggac ugcuuggacg    480
gcucagacga ggccuccugc ccggugcuca ccuguggucc cgccagcuuc cagugcaaca    540
gcuccaccug cauccccag cuguggccu gcgacaacga ccccgacugc gaagauggcu      600
cggaugagug gccgcagcgc uguaggggguc uuuacguguu ccaaggggac aguagccccu   660
gcucggccuu cgaguuccac ugccuaagug gcgagugcau ccacuccagc uggcgcugug    720
augguggccc cgacugcaag gacaaaucug acgaggaaaa cugcgcugug gccaccuguc    780
gcccugacga auuccagugc ucugauggaa acugcaucca uggcagccgg cagugugacc    840
gggaauauga cugcaaggac augagcgaug aaguuggcug cguuaaugug acacucugcg    900
agggacccaa caaguucaag ugucacagcg gcgaaugcau cacccuggac aaagucugca    960
acauggcuag agacugccgg gacuggucag augaacccau caaagagugc gggaccaacg   1020
aaugcuugga caacaacggc ggcuguuccc acgucugcaa ugaccuuaag aucggcuacg   1080
agugccugug ccccgacggc uuccagcugg uggcccagcg aagaugcgaa gauaucgaug   1140
agugucagga ucccgacacc ugcagccagc ucugcgugaa ccuggagggu ggcuacaagu   1200
gccaguguga ggaaggcuuc cagcuggacc cccacacgaa ggccugcaag gcugugggcu   1260
ccaucgccua ccucuucuuc accaaccggc acgaggucag gaagaugacg cuggaccgga   1320
gcgaguacac cagccucauc cccaaccuga ggaacguggu cgcucuggac acggaggugg   1380
ccagcaauag aaucuacugg ucugaccugu cccagagaau gaucugcagc acccagcuug   1440
acagagccca cggcgucucu uccuaugaca ccgucaucag cagagacauc caggcccccg   1500
acgggcuggc uguggacugg auccacagca acaucuacug gaccgacucu guccugggca   1560
cugucucugu ugcggauacc aagggcguga agaggaaaac guuauucagg gagaacggcu   1620
ccaagccaag ggccaucgug guggauccug uucauggcuu cauguacugg acugacuggg   1680
gaacucccgc caagaucaag aaagggggcc ugaauggugu ggacaucuac ucgcugguga   1740
cugaaaacau ucaguggccc aauggcauca cccuagaucu ccucaguggc cgccuuuacu   1800
ggguugacuc caaacuucac uccaucucaa gcaucgaugu caacgggggc aaccggaaga   1860
ccaucuugga ggaugaaaag aggcuggccc accccuucuc cuuggccguc uuugaggaca   1920
aaguauuuug gacagauauc aucaacgaag ccauuuucag ugccaaccgc cucacagguu   1980
ccgaugucaa cuuguuggcu gaaaaccuac uguccccaga ggauaugguu cucuuccaca   2040
accucaccca gccaagagga gugaacuggu gugagaggac cacccugagc aauggcggcu   2100
gccaguaucu gugccucccu gccccgcaga ucaacccccca cucgcccaag uuuaccugcg  2160
ccugcccgga cggcaugcug cuggccaggg acaugaggag cugccucaca gaggcugagg   2220
cugcaguggc cacccaggag acauccaccg ucaggcuaaa ggucagcucc acagccguaa   2280
ggacacagca cacaaccacc cgaccuguuc ccgacaccuc ccggcugccu ggggccaccc   2340
cugggcucac cacgguggag auagugacaa ugucucacca agcucugggc gacguugcug   2400
gcagaggaaa ugagaagaag cccaguagcg ugagggcucu guccauuguc cuccccaucg   2460
ugcuccucgu cuuccuuugc cuggggggucu uccuucuaug gaagaacugg cggcuuaaga  2520
```

acaucaacag caucaacuuu gacaaccccg ucuaucagaa gaccacagag gaugaggucc 2580
acauuugcca caaccaggac ggcuacagcu accccucgau ggucagucug gaggaugacg 2640
uggcgugaac aucugccugg agucccgucc cugcccagaa cccuuccuga gaccucgccg 2700
gccuuguuuu auucaaagac agagaagacc aaagcauugc cugccagagc uuuguuuuau 2760
auauuuauuc aucugggagg cagaacaggc uucggacagu gcccaugcaa uggcuugggu 2820
ugggauuuug guuucuuccu uuccucguga aggauaagag aaacaggccc gggggaccca 2880
ggaugacacc uccauuucuc uccaggaagu uuugaguuuc ucuccaccgu gacacaaucc 2940
ucaaacaugg aagaugaaag ggcaggggau gucaggccca gagaagcaag uggcuuucaa 3000
cacacaacag cagauggcac caacgggacc cccuggcccu gccucaucca ccaaucucua 3060
agccaaaccc cuaaacucag gagucaacgu guuuaccucu ucuaugcaag ccuugcuaga 3120
cagccagguu agccuuugcc cugu 3144

<210> SEQ ID NO 13
<211> LENGTH: 3522
<212> TYPE: DNA
<213> ORGANISM: homo sapien

<400> SEQUENCE: 13
ccaggguuuc cagcuaggac acagcagguc gugauccggg ucgggacacu gccuggcaga 60
ggcugcgagc auggggcccu ggggcuggaa auugcgcugg accgucgccu ugcuccucgc 120
cgcggcgggg acugcagugg gcgacagaug ugaaagaaac gaguuccagu gccaagacgg 180
gaaaugcauc uccuacaagu gggucugcga uggcagcgcu gagugccagg auggcucuga 240
ugagucccag gagacgugcu ugucugucac cugcaaaucc ggggacuuca gcuguggggg 300
ccgugucaac cgcugcauuc cucaguucug gaggugcgau ggccaagugg acugcgacaa 360
cggcucagac gagcaaggcu guccccccaa gacgugcucc caggacgagu uucgcugcca 420
cgaugggaag ugcaucucuc ggcaguucgu cugugacuca gaccgggacu gcuuggacgg 480
cucagacgag gccuccugcc cggugcucac cugugguccc gccagcuucc agugcaacag 540
cuccaccugc aucccccagc ugugggccug cgacaacgac cccgacugcg aagauggcuc 600
ggaugagugg ccgcagcgcu guaggggucu uuacguguuc caaggggaca guagccccug 660
cucggccuuc gaguuccacu gccuaagugg cgagugcauc cacuccagcu ggcgcuguga 720
ugguggcccc gacugcaagg acaaaucuga cgaggaaaac ugcgcugugg ccaccugucg 780
cccugacgaa uuccagugcu cugauggaaa cugcauccau ggcagccggc agugugaccg 840
ggaauaugac ugcaaggaca ugagcgauga aguuggcugc guuaauguga cacucugcga 900
gggacccaac aaguucaagu gucacagcgg cgaaugcauc acccuggaca aagucugcaa 960
cauggcuaga gacugccggg acuggucaga ugaacccauc aaagagugcg ggaccaacga 1020
augcuuggac aacaacggcg gcuguuccca cgucugcaau gaccuuaaga ucggcuacga 1080
gugccugugc cccgacggcu uccagcuggu ggcccagcga agaugcgaag auaucgauga 1140
gugucaggau cccgacaccu gcagccagcu cugcgugaac cuggagggug gcuacaagug 1200
ccagugugag gaaggcuucc agcuggaccc ccacacgaag gccugcaagg cugugggcuc 1260
caucgccuac cucuucuuca ccaaccggca cgaggucagg aagaugacgc uggaccggag 1320
cgaguacacc agccucaucc ccaaccugag gaacgugguc gcucuggaca cggagguggc 1380
cagcaauaga aucuacuggu cugaccuguc ccagagaaug aucugcagca cccagcuuga 1440

```
cagagcccac ggcgucucuu ccuaugacac cgucaucagc agggacaucc aggcccccga   1500
cgggcuggcu guggacugga uccacagcaa caucuacugg accgacucug uccugggcac   1560
ugucucuguu gcggauacca agggcgugaa gaggaaaacg uuauucaggg agaacggcuc   1620
caagccaagg gccaucgugg uggauccugu ucauggcuuc auguacugga cugacugggg   1680
aacucccgcc aagaucaaga aagggggccu gaauggugug gacaucuacu cgcuggugac   1740
ugaaaacauu caguggccca auggcaucac ccuagaucuc cucaguggcc gccucuacug   1800
gguugacucc aaacuucacu ccaucucaag caucgauguc aauggggca accggaagac   1860
caucuuggag gaugaaaaga ggcuggccca ccccuucucc uuggccgucu uugaggacaa   1920
aguauuuugg acagauauca ucaacgaagc cauuuucagu gccaaccgcc ucacagguuc   1980
cgaugucaac uuguuggcug aaaaccuacu guccccagag gauauggucc ucuuccacaa   2040
ccucacccag ccaagaggag ugaacuggug ugagaggacc acccugagca auggcggcug   2100
ccaguaucug ugccucccug ccccgcagau caaccccac ucgcccaagu uuaccugcgc   2160
cugcccggac ggcaugcugc uggccaggga caugaggagc ugccucacag aggcugaggc   2220
ugcaguggcc acccaggaga cauccaccgu caggcuaaag gucagcucca cagccguaag   2280
gacacagcac acaaccaccc ggccuguucc cgacaccucc cggcugccug ggccaccccc   2340
ugggcucacc acgguggaga uagugacaau gucucaccaa gcucugggcg acguugcugg   2400
cagaggaaau gagaagaagc ccaguagcgu gagggcucug uccauugucc uccccaucgu   2460
gcuccucguc uuccuuugcc ugggggucuu ccuucuaugg aagaacuggc ggcuuaagaa   2520
caucaacagc aucaacuuug acaaccccgu cuaucagaag accacagagg augaggucca   2580
cauuugccac aaccaggacg gcuacagcua ccccucgaga cagaugguca gucuggagga   2640
ugacguggcg ugaacaucug ccuggagucc cgucccugcc cagaacccuu ccugagaccu   2700
cgccggccuu guuuuauuca aagacagaga agaccaaagc auugccugcc agagcuuugu   2760
uuuauauauu uauucaucug ggaggcagaa caggcuucgg acagugccca ugcaauggcu   2820
uggguuggga uuuugguuuc uuccuuuccu cgugaaggau aagagaaaca ggcccggggg   2880
gaccaggaug acaccuccau uucucuccag gaaguuuuga guuucucucc accgugacac   2940
aauccucaaa cauggaagau gaaagggcag ggaugucag gcccagagaa gcaaguggcu   3000
uucaacacac aacagcagau ggcaccaacg ggacccccug gcccugccuc auccaccaau   3060
cucuaagcca aaccccuaaa cucaggaguc aacguguuua ccucuucuau gcaagccuug   3120
cuagacagcc agguuagccu uugcccuguc acccccgaau caugacccac ccagugucuu   3180
ucgaggugg uuuguaccuu ccuuaagcca ggaaagggau ucauggcguc ggaaaugauc   3240
uggcugaauc cgugguggca ccgagaccaa acucauucac caaaugaugc cacuucccag   3300
aggcagagcc ugagucaccg gucacccuua auauuuauua agugccugag acacccgguu   3360
accuuggccg ugaggacacg uggccugcac ccaggugugg cugucaggac accagccugg   3420
ugcccauccu cccgaccccu acccacuucc auucccgugg ucuccuugca cuuucucagu   3480
ucagaguugu acacugugua aaaaaaaaaa aaaaaaaaaa aa                      3522
```

```
<210> SEQ ID NO 14
<211> LENGTH: 2600
<212> TYPE: DNA
<213> ORGANISM: homo sapien

<400> SEQUENCE: 14

cagaggcugc gagcaugggg cccuggggcu ggaaauugcg cuggaccguc gccuugcucc     60
```

-continued

```
ucgccgcggc ggggacugca gugggcgaca gaugcgaaag aaacgaguuc cagugccaag    120
acgggaaaug caucuccuac aagugggucu gcgauggcag cgcugagugc caggauggcu    180
cugaugaguc ccaggagacg ugcuugucug ucaccugcaa auccggggac uucagcugug    240
ggggccgugu caaccgcugc auuccucagu ucuggaggug cgauggccaa guggacugcg    300
acaacggcuc agacgagcaa ggcugucccc ccaagacgug cucccaggac gaguuucgcu    360
gccacgaugg gaagugcauc ucucggcagu ucgucuguga cucagaccgg gacugcuugg    420
acggcucaga cgaggccucc ugcccggugc ucaccugugg ucccgccagc uuccagugca    480
acagcuccac cugcaucccc cagcuguggg ccugcgacaa cgaccccgac ugcgaagaug    540
gcucggauga guggccgcag cgcuguaggg gucuuuacgu guuccaaggg gacaguagcc    600
ccugcucggc cuucgaguuc cacugccuaa guggcgagug cauccacucc agcuggcgcu    660
gugauggugg ccccgacugc aaggacaaau cugacgagga aaacugcgcu guggccaccu    720
gucgcccuga cgaauuccag ugcucugaug gaaacugcau ccauggcagc cggcagugug    780
accgggaaua ugacugcaag gacaugagcg augaaguugg cugcguuaau gugacacucu    840
gcgagggacc caacaaguuc aagugucaca gcggcgaaug caucacccug gacaaagucu    900
gcaacauggc uagagacugc cgggacuggu cagaugaacc caucaaagag ugcgggacca    960
acgaaugcuu ggacaacaac ggcggcuguu cccacgucug caaugaccuu aagaucggcu   1020
acgagugccu gugccccgac ggcuuccagc ugguggccca gcgaagaugc gaagauaucg   1080
augaguguca ggaucccgac accugcagcc agcucugcgu gaaccuggag gguggcuaca   1140
agugccagug ugaggaaggc uuccagcugg acccccacac gaaggccugc aaggcugugg   1200
gcuccaucgc cuaccucuuc uucaccaacc ggcacgaggu caggaagaug acgcuggacc   1260
ggagcgagua caccagccuc auccccaacc ugaggaacgu ggucgcucug gacacggagg   1320
uggccagcaa uagaaucuac uggucugacc ugucccagag aaugaucugc agcacccagc   1380
uugacagagc ccacggcguc ucuuccuaug acaccgucau cagcagggac auccaggccc   1440
ccgacgggcu ggcuguggac uggauccaca gcaacaucua cuggaccgac ucuguccugg   1500
gcacugucuc uguugcggau accaagggcg ugaagaggaa aacguuauuc agggagaacg   1560
gcuccaagcc aagggccauc gugguggauc cuguucaugg cuucauguac uggacugacu   1620
ggggaacucc cgccaagauc aagaaagggg gccugaaugg uguggacauc uacucgcugg   1680
ugacugaaaa cauucagugg cccaauggca ucacccuaga ucuccucagu ggccgccucu   1740
acugggguuga cuccaaacuu cacuccaucu caagcaucga ugucaacggg ggcaaccgga   1800
agaccaucuu ggaggaugaa aagaggcugg cccaccccuu cuccuuggcc gucuuugagg   1860
acaaaguauu uuggacagau aucaucaacg aagccauuuu cagugccaac cgccucacag   1920
guuccgaugu caacuuguug gcugaaaacc uacugucccc agaggauaug guucucuucc   1980
acaaccucac ccagccaaga ggagugaacu ggugugagag gaccacccug agcaauggcg   2040
gcugccagua ucugugccuc ccugccccgc agaucaaccc ccacucgccc aaguuuaccu   2100
gcgccugccc ggacggcaug cugcuggcca gggacaugag gagcugccuc acagaggcug   2160
aggcugcagu ggccacccag gagacaucca ccgucaggcu aaaggucagc uccacagccg   2220
uaaggacaca gcacacaacc acccggccug uucccgacac cucccggcug ccuggggcca   2280
ccccugggcu caccacggug gagauaguga caaugucuca ccaagcucug ggcgacguug   2340
cuggcagagg aaaugagaag aagcccagua gcgugagggc ucuguccauu guccucccca   2400
```

```
ucgugcuccu cgucuuccuu ugccuggggg ucuuccuucu auggaagaac uggcggcuua   2460

agaacaucaa cagcaucaac uuugacaacc ccgucuauca gaagaccaca gaggaugagg   2520

uccacauuug ccacaaccag gacggcuaca gcuaccccuc gagacagaug gucagucugg   2580

aggaugacgu ggcgugaaca                                               2600
```

<210> SEQ ID NO 15
<211> LENGTH: 2583
<212> TYPE: DNA
<213> ORGANISM: homo sapien

<400> SEQUENCE: 15

```
auggggcccu ggggcuggaa auugcgcugg accgucgccu ugcuccucgc cgcggcgggg     60

acugcagugg gcgacagaug ugaaagaaac gaguuccagu gccaagacgg gaaaugcauc    120

uccuacaagu gggucugcga uggcagcgcu gagugccagg auggcucuga ugagucccag    180

gagacgugcu ugucugucac cugcaaaucc ggggacuuca gcugugggggg ccgugucaac   240

cgcugcauuc cucaguucug gagggugcgau ggccaagugg acugcgacaa cggcucagac   300

gagcaaggcu guccccccaa gacgugcucc caggacgagu uucgcugcca cgaugggaag    360

ugcaucucuc ggcaguucgu cugugacuca gaccgggacu gcuuggacgg cucagacgag    420

gccuccugcc cggugcucac cuguggucc gccagcuucc agugcaacag cuccaccugc    480

aucccccagc ugugggccug cgacaacgac cccgacugcg aagauggcuc ggaugagugg    540

ccgcagcgcu guaggggucu uuacguguuc caaggggaca guagccccug cucggccuuc    600

gaguuccacu gccuaagugg cgagugcauc cacuccagcu ggcgcuguga ugguggcccc    660

gacugcaagg acaaaucuga cgaggaaaac ugcgcugugg ccaccugucg cccugacgaa    720

uuccagugcu cugauggaaa cugcauccau ggcagccggc agugugaccg ggaauaugac    780

ugcaaggaca ugagcgauga aguuggcugc guuaauguga cacucugcga gggacccaac    840

aaguucaagu gucacagcgg cgaaugcauc acccuggaca aagucugcaa cauggcuaga    900

gacugccggg acuggucaga ugaacccauc aaagagugcg ggaccaacga augcuuggac    960

aacaacggcg gcuguuccca cgucugcaau gaccuuaaga ucggcuacga gugccugugc   1020

cccgacggcu uccagcuggu ggcccagcga agaugcgaag auaucgauga gugucaggau   1080

cccgacaccu gcagccagcu cugcgugaac cuggagggug gcuacaagug ccagugugag   1140

gaaggcuucc agcuggaccc ccacacgaag gccugcaagg cugugggcuc caucgccuac   1200

cucuucuuca ccaaccggca cgaggucagg aagaugacgc uggaccggag cgaguacacc   1260

agccucaucc ccaaccugag gaacgugguc gcucuggaca cggagguggc cagcaauaga   1320

aucuacuggu cugaccuguc ccagagaaug aucugcagca cccagcuuga cagagcccac   1380

ggcgucucuu ccuaugacac cgucaucagc agggacaucc aggcccccga cgggcuggcu   1440

guggacugga uccacagcaa caucuacugg accgacucug uccugggcac ugucucuguu   1500

gcggauacca agggcgugaa gaggaaaacg uuauucaggg agaacggcuc caagccaagg   1560

gccaucgugg uggauccugu ucauggcuuc auguacugga cugacugggg aacucccgcc   1620

aagaucaaga aagggggccu gaauggugug gacaucuacu cgcuggugac ugaaaacauu   1680

caguggccca auggcaucac ccuagaucuc cucaguggcc gccucuacug gguugacucc   1740

aaacuucacu ccaucucaag caucgauguc aaugggggca accggaagac caucuuggag   1800

gaugaaaaga ggcuggccca ccccuucucc uuggccgucu uugaggacaa aguauuuugg   1860

acagauauca ucaacgaagc cauuuucagu gccaaccgcc ucacagguuc cgaugucaac   1920
```

uuguuggcug aaaaccuacu guccccagag gauauggucc ucuuccacaa ccucacccag 1980
ccaagaggag ugaacuggug ugagaggacc acccugagca auggcggcug ccaguaucug 2040
ugccucccug ccccgcagau caaccccac ucgcccaagu uuaccugcgc cugcccggac 2100
ggcaugcugc uggccaggga caugaggagc ugccucacag aggcugaggc ugcaguggcc 2160
acccaggaga cauccaccgu caggcuaaag gucagcucca cagccguaag gacacagcac 2220
acaaccaccc ggccuguucc cgacaccucc cggcugccug ggccaccccc ugggcucacc 2280
acgguggaga uagugacaau gucucaccaa gcucugggcg acguugcugg cagaggaaau 2340
gagaagaagc ccaguagcgu gagggcucug uccauugucc uccccaucgu gcuccucguc 2400
uuccuuugcc ugggggucuu ccuucuaugg aagaacuggc ggcuuaagaa caucaacagc 2460
aucaacuuug acaaccccgu cuaucagaag accacagagg augaggucca cauuugccac 2520
aaccaggacg gcuacagcua ccccucgaga cagaugguca gucuggagga ugacguggcg 2580
uag 2583

<210> SEQ ID NO 16
<211> LENGTH: 5356
<212> TYPE: DNA
<213> ORGANISM: homo sapien

<400> SEQUENCE: 16
gaggggaggc cuggcguucc uccgcgguuc cugucacaaa ggcgacgaca agucccgggu 60
ccccggagcc gccuccgcga cauacacgag ucgcccuccg uuauccuggg cccuccuggc 120
gaaguccccg guuuccgcug ugcucugugg cgacaccucc guccccaccu uguccugggg 180
ggcgcccucg ccccaccagc cccgaucaag uucacagagg ggcccccggc cacccucaag 240
gccucgguuc cuuacgaggu ugaaacguug ccucagaauc uccccgcccc uccuuggucu 300
gcagccgaga ucuucagcca cgugggcgac agaugcgaaa gaaacgaguu ccagugccaa 360
gacgggaaau gcaucuccua caaguggguc ugcgauggca gcgcugagug ccaggauggc 420
ucugaugagu cccaggagac gugcuugucu gucaccugca aauccgggga cuucagcugu 480
gggggccgug ucaaccgcug cauuccucag uucuggaggu gcgauggcca aguggacugc 540
gacaacggcu cagacgagca aggcuguccc cccaagacgu gcucccagga cgaguuucgc 600
ugccacgaug ggaagugcau cucucggcag uucgucugug acucagaccg ggacugcuug 660
gacggcucag acgaggccuc cugcccggug cucaccugug gucccgccag cuuccagugc 720
aacagcucca ccugcauccc ccagcugugg gccugcgaca acgaccccga cugcgaagau 780
ggcucggaug aguggccgca gcgcuguagg ggucuuuacg uguuccaagg ggacaguagc 840
cccugcucgg ccuucgaguu ccacugccua aguggcgagu gcauccacuc cagcuggcgc 900
ugugauggug gccccgacug caaggacaaa ucugacgagg aaaacugcgc uguggccacc 960
ugucgcccug acgaauucca gugcucugau ggaaacugca uccauggcag ccggcagugu 1020
gaccgggaau augacugcaa ggacaugagc gaugaaguug gcugcguuaa ugugacacuc 1080
ugcgagggac ccaacaaguu caagugucac agcggcgaau gcaucacccu ggacaaaguc 1140
ugcaacaugg cuagagacug ccgggacugg ucagaugaac ccaucaaaga gugcgggacc 1200
aacgaaugcu uggacaacaa cggcggcugu ucccacgucu gcaaugaccu uaagaucggc 1260
uacgagugcc ugugccccga cggcuuccag cugguggccc agcgaagaug cgaagauauc 1320
gaugaguguc aggaucccga caccugcagc cagcucugcg ugaaccugga gggguggcuac 1380

-continued

```
aagugccagu gugaggaagg cuuccagcug gacccccaca cgaaggccug caaggcugug   1440
ggcuccaucg ccuaccucuu cuucaccaac cggcacgagg ucaggaagau gacgcuggac   1500
cggagcgagu acaccagccu cauccccaac cugaggaacg uggucgcucu ggacacggag   1560
guggccagca auagaaucua cuggucugac cugucccaga gaaugaucug cagcacccag   1620
cuugacagag cccacggcgu cucuuccuau gacaccguca ucagcaggga cauccaggcc   1680
cccgacgggc uggcugugga cuggauccac agcaacaucu acuggaccga cucuguccug   1740
ggcacugucu cuguugcgga uaccaagggc gugaagagga aaacguuauu cagggagaac   1800
ggcuccaagc caagggccau cgugguggau ccuguucaug gcuucaugua cuggacugac   1860
uggggaacuc ccgccaagau caagaaaggg ggccugaaug guguggacau cuacucgcug   1920
gugacugaaa acauucagug gcccaauggc aucacccuag aucuccucag uggccgccuc   1980
uacugggguug acuccaaacu ucacuccauc ucaagcaucg augucaaugg gggcaaccgg   2040
aagaccaucu uggaggauga aaagaggcug gcccaccccu ucuccuuggc cgucuuugag   2100
gacaaaguau uuggacaga uaucaucaac gaagccauuu ucagugccaa ccgccucaca   2160
gguuccgaug ucaacuuguu ggcugaaaac cuacuguccc cagaggauau gguccucuuc   2220
cacaaccuca cccagccaag aggagugaac uggugugaga ggaccacccu gagcaauggc   2280
ggcugccagu aucugugccu cccugccccg cagaucaacc cccacucgcc caaguuuacc   2340
ugcgccugcc cggacggcau gcugcuggcc agggacauga ggagcugccu cacagaggcu   2400
gaggcugcag uggccaccca ggagacaucc accgucaggc uaaaggucag cuccacagcc   2460
guaaggacac agcacacaac cacccggccu guucccgaca ccucccggcu gccuggggcc   2520
accccugggc ucaccacggu ggggauagug acaaugucuc accaagcucu gggcgacguu   2580
gcuggcagag gaaaugagaa gaagcccagu agcgugaggg cucuguccau uguccucccc   2640
aucgugcucc ucgucuuccu uugccugggg gucuuccuuc uauggaagaa cuggcggcuu   2700
aagaacauca acagcaucaa cuuugacaac cccgucuauc agaagaccac agaggaugag   2760
guccacauuu gccacaacca ggacggcuac agcuaccccu cgagacagau ggucagucug   2820
gaggaugacg uggcgugaac aucugccugg agucccgucc cugcccagaa cccuuccuga   2880
gaccucgccg gccuuguuuu auucaaagac agagaagacc aaagcauugc cugccagagc   2940
uuuguuuuau auauuuauuc aucugggagg cagaacaggc uucggacagu gcccaugcaa   3000
uggcuugggu ugggauuuug guuucuuccu uuccucguga aggauaagag aaacaggccc   3060
ggggggacca ggaugacacc uccauuucuc uccaggaagu uuugaguuuc ucuccaccgu   3120
gacacaaucc ucaaacaugg aagaugaaag ggcaggggau gucaggccca gagaagcaag   3180
uggcuuucaa cacacaacag cagauggcac caacgggacc cccuggcccu gccucaucca   3240
ccaaucucua agccaaaccc cuaaacucag gagucaacgu guuuaccucu ucuaugcaag   3300
ccuugcuaga cagccagguu agccuuugcc cugucacccc cgaaucauga cccacccagu   3360
gucuuucgag guggguuugu accuuccuua agccaggaaa gggauucaug gcgucggaaa   3420
ugaucuggcu gaauccgugg uggcaccgag accaaacuca uucaccaaau gaugccacuu   3480
cccagaggca gagccugagu caccggucac ccuuaauauu uauuaagugc cugagacacc   3540
cgguuaccuu ggccgugagg acacguggcc ugcacccagg uguggcuguc aggacaccag   3600
ccuggugccc auccucccga ccccuaccca cuuccauucc cguggucucc uugcacuuuc   3660
ucaguucaga guuguacacu guguacauuu ggcauuugug uuauuauuuu gcacuguuuu   3720
cugucgugug uguugggaug ggaucccagg ccagggaaag cccgugucaa ugaaugccgg   3780
```

ggacagagag gggcagguug accgggacuu caaagccgug aucgugaaua ucgagaacug 3840
ccauugucgu cuuuauguccc gcccaccuag ugcuuccacu ucuaugcaaa ugccuccaag 3900
ccauucacuu ccccaaucuu gucguugaug gguauguguu uaaaacaugc acggugaggc 3960
cgggcgcagu ggcucacgcc uguaauccca gcacuuuggg aggccgaggc ggguggauca 4020
ugaggucagg agaucgagac cauccuggcu aacaagguga aaccccgucu cuacuaaaaa 4080
uacaaaaaau uagccgggcg cgguggugggg caccuguagu cccagcuacu cgggaggcug 4140
aggcaggaga augguguga cccgggaagc ggagcuugca gugagccgag auugcgccac 4200
ugcaguccgc agucuggccu gggcgacaga gcgagacucc gucucaaaaa aaaaaaacaa 4260
aaaaaaacca ugcauggugc aucagcagcc cauggccucu ggccaggcau ggcgaggcug 4320
aggugggagg augguuugag cucaggcauu ugaggcuguc gugagcuaug auuaugccac 4380
ugcuuuccag ccugggcaac auaguaagac cccaucucuu aaaaaaugaa uuuggccaga 4440
cacaggugcc ucacgccugu aaucccagca cuuugggagg cugagcugga ucacuugagu 4500
ucaggaguug gagaccaggc cugagcaaca aagcgagauc ccaucucuac aaaaaccaaa 4560
aaguuaaaaa ucagcugggu augguggcac gugccuguga ucccagcuac uugggaggcu 4620
gaggcaggag gaucgccuga gcccaggagg uggagguugc agugagccau gaucgagcca 4680
cugcacucca gccugggcaa cagaugaaga cccuauuuca gaaauacaac uauaaaaaaa 4740
uaaauaaauc cuccagucug gaucguuuga cgggacuuca gguucuuucu gaaaucgccg 4800
uguuacuguu gcacugaugu ccggagagac agugacagcc uccgucagac ucccgcguga 4860
agaugucaca agggauuggc aauuguccc agggacaaaa cacugugucc cccccagugc 4920
agggaaccgu gauaagccuu ucugguuucg gagcacguaa augcgucccu guacagauag 4980
uggggauuuu uuguuauguu ugcacuuugu auauugguug aaacuguuau cacuuauaua 5040
uauauauaca cacauauaua uaaaaucuau uuauuuuugc aaacccuggu ugcuguauuu 5100
guucagugac uauucucggg gcccugugua gggggguuauu gccucugaaa ugccucuucu 5160
uuauguacaa agauuauuug cacgaacugg acugugugca acgcuuuuug ggagaaugau 5220
guccccguug uauguaugag uggcuucugg gagaugggug ucacuuuuua aaccacugua 5280
uagaagguuu uuguagccug aaugucuuac ugugaucaau uaaauuucuu aaaagaaaaa 5340
aaaaaaaaaa aaaaca 5356

<210> SEQ ID NO 17
<211> LENGTH: 3635
<212> TYPE: DNA
<213> ORGANISM: homo sapien

<400> SEQUENCE: 17
uugcgacguc gaggcgcuca ugguugcagg cgggcgccgc cguucaguuc agggucugag 60
ccuggaggag ugagccaggc agugagacug gcucgggcgg gccgggacgc gucguugcag 120
cagcggcucc cagcucccag ccaggauucc gcgcgccccu ucacgcgccc ugcuccugaa 180
cuucagcucc ugcacagucc uccccaccgc aaggcucaag gcgccgccgg cguggaccgc 240
gcacggccuc uaggucuccu cgccaggaca gcaaccucuc cccuggcccu caugggcacc 300
gucagcucca ggcgguccug guggccgcug ccacugcugc ugcugcugcu gcugcuccug 360 gguccgcgg gcgcccgugc gcaggaggac gaggacggcg acuacgagga gcuggugcua 420
gccuugcuuu ccgaggagga cggccuggcc gaagcacccg agcacggaac cacagccacc 480

```
uuccaccgcu gcgccaagga uccguggagg uugccuggca ccuacguggu ggugcugaag    540
gaggagaccc accucucgca gucagagcgc acugcccgcc gccugcaggc ccaggcugcc    600
cgccggggau accucaccaa gauccugcau gucuuccaug gccuucuucc uggcuuccug    660
gugaagauga guggcgaccu gcuggagcug gccuugaagu ugccccaugu cgacuacauc    720
gaggaggacu ccucugucuu ugcccagagc aucccgugga accuggagcg gauuaccccu    780
ccacgguacc gggcggauga auaccagccc cccgacggag gcagccuggu ggagguguau    840
cuccuagaca ccagcauaca gagugaccac cgggaaaucg agggcagggu cauggucacc    900
gacuucgaga augugcccga ggaggacggg acccgcuucc acagacaggc cagcaagugu    960
gacagucaug gcacccaccu ggcaggggug gucagcggcc gggaugccgg cguggccaag   1020
ggugccagca ugcgcagccu gcgcgugcuc aacugccaag ggaagggcac gguuagcggc   1080
acccucauag gccuggaguu uauucggaaa agccagcugg uccagccugu ggggccacug   1140
guggugcugc ugccccuggc ggguggguac agccgcgucc ucaacgccgc cugccagcgc   1200
cuggcgaggg cuggggucgu gcuggucacc gcugccggca acuuccggga cgaugccugc   1260
cucuacuccc cagccucagc ucccgagguc aucacaguug ggccaccaa ugcccaggac    1320
cagccgguga cccuggggac uuuggggacc aacuuuggcc gcugugugga ccucuuugcc   1380
ccaggggagg acaucauugg ugccuccagc gacugcagca ccugcuuugu gucacagagu   1440
gggacaucac aggcugcugc ccacguggcu ggcauugcag ccaugaugcu gucugccgag   1500
ccggagcuca cccuggccga guugaggcag agacugaucc acuucucugc caaagaugcc   1560
aucaaugagg ccugguuccc ugaggaccag cggguacuga cccccaaccu gguggccgcc   1620
cugccccca gcacccaugg ggcagguugg cagcuguuuu gcaggacugu gugguc agca    1680
cacucggggc cuacacggau ggccacagcc aucgcccgcu gcgccccaga ugaggagcug   1740
cugagcugcu ccaguuucuc caggagugga agcggcgggg cgagcgcaug gaggcccaag   1800
ggggcaagcu ggucugccgg gcccacaacg cuuuuggggg ugagggugc uacgccauug    1860
ccaggugcug ccugcuaccc caggccaacu gcagcgucca cacagcucca ccagcugagg   1920
ccagcauggg gacccguguc cacugccacc aacagggcca cguccucaca ggcugcagcu   1980
cccacuggga gguggaggac cuuggcaccc acaagccgcc ugugcugagg ccacgagguc   2040
agcccaacca gugcgugggc cacagggagg ccagcaucca cgcuuccugc ugccaugccc   2100
caggucugga augcaaaguc aaggagcaug gaaucccggc cccucaggag cagguga ccg  2160
uggccugcga ggagggcugg acccugacug gcugcagugc ccucccuggg accucccacg   2220
uccugggggc cuacgccgua gacaacacgu guguagucag gagccgggac gucagcacua   2280
caggcagcac cagcgaagag gccgugacag ccguugccau cugcugccgg agccggcacc   2340
uggcgcaggc cucccaggag cuccagugac agccccaucc caggaugggu gucuggggag   2400
ggucaagggc uggggcugag cuuuaaaaug guuccgacuu gucccucucu cagcccucca   2460
uggccuggca cgaggggaug ggaugcuuc cgccuucccg ggcugcugg ccuggcccuu      2520
gaguggggca gccuccuugc cuggaacuca cucacucugg gugccuccuc cccaggugga   2580
ggugccagga agcucccucc cucacugugg ggcauuucac cauucaaaca ggucgagcug   2640
ugcucgggug cugccagcug cucccaaugu gccgaugucc gugggcagaa ugacuuuuau   2700
ugagcucuug uuccgugcca ggcauucaau ccucaggucu ccaccaagga ggcaggauuc   2760
uucccaugga uaggggaggg ggcgguaggg gcugcaggga caaacaucgu ugggggguga   2820
gugugaaagg ugcugauggc ccucaucucc agcuaacugu ggagaagccc cugggggcuc   2880
```

ccugauuaau ggaggcuuag cuuucuggau ggcaucuagc cagaggcugg agacaggugu 2940
gccccuggug gucacaggcu gugccuuggu uuccugagcc accuuuacuc ugcucuaugc 3000
caggcugugc uagcaacacc caaaggug gc cugcggggag ccaucaccua ggacugacuc 3060
ggcagugugc aguggugcau gcacugucuc agccaacccg cuccacuacc cggcagggua 3120
cacauucgca ccccuacuuc acagaggaag aaaccuggaa ccagaggggg cgugccugcc 3180
aagcucacac agcaggaacu gggccagaaa cgcagauugg gcuggcucug aagccaagcc 3240
ucuucuuacu ucacccggcu gggcuccuca uuuuuacggg uaacagugag gcugggaagg 3300
ggaacacaga ccaggaagcu cggugaguga uggcagaacg augccugcag gcauggaacu 3360
uuuuccguua ucacccaggc cugauucacu ggccuggcgg agaugcuucu aaggcauggu 3420
cgggggagag ggccaacaac ugucccuccu ugagcaccag ccccacccaa gcaagcagac 3480
auuuaucuuu ugggucuguc cucucuguug ccuuuuuaca gccaacuuuu cuagaccugu 3540
uuugcuuuug uaacuugaag auauuuauuc ugggguuuugu agcauuuuua uuaauauggu 3600
gacuuuuuaa aauaaaaaca aacaaacguu guccu 3635

<210> SEQ ID NO 18
<211> LENGTH: 1101
<212> TYPE: DNA
<213> ORGANISM: homo sapien

<400> SEQUENCE: 18
aggcucaagg cgccgccggc guggaccgcg cacggccucu aggucucccuc gccaggacag 60 caaccucucc ccuggccccuc augggcaccg ucagcuccag gcgguccugg uggccgcugc 120
cacugcugcu gcugcugcug cugcuccugg gucccgcggg cgcccgugcg caggaggacg 180
aggacggcga cuacgaggag cuggugcuag ccuugcuuuc cgaggaggac ggccuggccg 240
aagcacccga gcacggaacc acagccaccu uccaccgcug cgccaaggau ccguggaggu 300
ugccuggcac cuacguggug gugcugaagg aggagaccca ccucucgcag ucagagcgca 360
cugcccgccg ccugcaggcc caggcugccc gccggggaua ccucaccaag auccugcaug 420
ucuuccaugg ccuucuuccu ggcuuccugg ugaagaugag uggcgaccug cuggagcugg 480
ccuugaaguu gccccauguc gacuacaucg aggaggacuc cucugucuuu gcccagagca 540
ucccguggaa ccuggagcgg auuaccccuc cacgguaccg ggcggaugaa uaccagcccc 600
ccgcauauuu ggaggaucac ugcgggggcc acagaggugc uguucagaug gcacuucaga 660
agacucagga gacccugggg caggagcagu uugacugaca gcccagaggg cugcccucug 720
auuccaccug aggcccugcu uuuccuggcu gcagggguuc cagggccagg ccauuuccgc 780
uggcgcagga cucugcuagc agcaaccugc cugaagucuu ccuuuggccu ggcugagagu 840
uucugagacc ugcgcuggag cggagacgga ggcagccugg uggaggugua ucuccuagac 900
accagcauac agagugacca ccgggaaauc gagggcaggg ucauggucac cgacuucgag 960
aaugugcccg aggaggacgg gacccgcuuc cacagacagg ccagcaagug ugacagucau 1020
ggcacccacc uggcaggggu ggucagcggc cgggaugccg gcguggccaa gggugccagc 1080
augcgcagcc ugcgcgugcu c 1101

<210> SEQ ID NO 19
<211> LENGTH: 2079
<212> TYPE: DNA
<213> ORGANISM: homo sapien

<400> SEQUENCE: 19
augggcaccg ucagcuccag gcgguccugg uggccgcugc cacugcugcu gcugcugcug 60
cugcuccugg gucccgcggg cgcccgugcg caggaggacg aggacggcga cuacgaggag 120
cugguggcuag ccuugcuuuc cgaggaggac ggccuggccg aagcacccga gcacggaacc 180
acagccaccu uccaccgcug cgccaaggau ccguggaggu ugccuggcac cuacguggug 240
gugcugaagg aggagaccca ccucucgcag ucagagcgca cugcccgccg ccugcaggcc 300
caggcugccc gccggggaua ccucaccaag auccugcaug ucuuccaugg ccuucuuccu 360
ggcuuccugg ugaagaugag uggcgaccug cuggagcugg ccuugaaguu gccccauguc 420
gacuacaucg aggaggacuc cucugucuuu gcccagagca ucccguggaa ccuggagcgg 480
auuacccccuc cacgguaccg ggcggaugaa uaccagcccc ccgacggagg cagccuggug 540
gagguguauc ucuagacac cagcauacag agugaccacc gggaaaucga gggcaggguc 600
augggucaccg acuucgagaa ugugcccgag gaggacggga cccgcuucca cagacaggcc 660
agcaagugug acagucaugg cacccaccug gcaggggugg ucagcggccg ggaugccggc 720
guggccaagg gugccagcau gcgcagccug cgcgugcuca acugccaagg gaagggcacg 780
guuagcggca cccucauagg ccuggaguuu auucggaaaa gccagcuggu ccagccugug 840
gggccacugg uggugcugcu gccccuggcg ggugguaca gccgcguccu caacgccgcc 900
ugccagcgcc uggcgagggc uggggucgug cuggucaccg cugccggcaa cuuccgggac 960
gaugccugcc ucuacucccc agccucagcu cccgagguca ucacaguugg ggccaccaau 1020
gcccaggacc agccggugac ccuggggacu uggggacca acuuuggccg cugugguggac 1080
cucuuugccc caggggagga caucauuggu gccuccagcg acugcagcac cugcuuugug 1140
ucacagagug ggacaucaca ggcugcugcc cacguggcug gcauugcagc caugaugcug 1200
ucugccgagc cggagcucac ccuggccgag uugaggcaga gacugaucca cuucucugcc 1260
aaagauguca ucaaugaggc cugguucccu gaggaccagc ggguacugac ccccaaccug 1320
guggccgccc ugccccccag cacccauggg gcagguuggc agcuguuuug caggacugug 1380
uggucagcac acucggggcc uacacggaug gccacagcca ucgcccgcug cgccccagau 1440
gaggagcugc ugagcugcuc caguuucucc aggaguggga agcggcgggg cgagcgcaug 1500
gaggcccaag gggggcaagcu ggucugccgg gcccacaacg cuuuuggggg ugagggguguc 1560
uacgccauug ccaggugcug ccugcuaccc caggccaacu gcagcgucca cacagcucca 1620
ccagcugagg ccagcauggg gacccguguc cacugccacc aacagggcca cguccucaca 1680
ggcugcagcu cccacuggga ggugggaggac cuuggcaccc acaagccgcc ugugcugagg 1740
ccacgagguc agcccaacca gugcguggc cacagggagg ccagcaucca cgcuuccugc 1800
ugccaugccc caggucugga augcaaaguc aaggagcaug gaaucccggc cccucaggag 1860
caggugaccg uggccugcga ggagggcugg acccugacug gcugcagugc ccucccuggg 1920
accucccacg uccugggggc cuacgccgua gacaacacgu guguagucag gagccgggac 1980
gucagcacua caggcagcac cagcgaagag gccgugacag ccguugccau cugcugccgg 2040
agccggcacc uggcgcaggc cucccaggag cuccaguga 2079

<210> SEQ ID NO 20
<211> LENGTH: 3635
<212> TYPE: DNA
<213> ORGANISM: homo sapien

<400> SEQUENCE: 20

-continued

```
ttgcgacgtc gaggcgctca tggttgcagg cgggcgccgc cgttcagttc agggtctgag     60
cctggaggag tgagccaggc agtgagactg gctcgggcgg gccgggacgc gtcgttgcag    120
cagcggctcc cagctcccag ccaggattcc gcgcgcccct tcacgcgccc tgctcctgaa    180
cttcagctcc tgcacagtcc tccccaccgc aaggctcaag gcgccgccgg cgtggaccgc    240
gcacggcctc taggtctcct cgccaggaca gcaacctctc ccctggccct catgggcacc    300
gtcagctcca ggcggtcctg gtggccgctg ccactgctgc tgctgctgct gctgctcctg    360
ggtcccgcgg gcgcccgtgc gcaggaggac gaggacggcg actacgagga gctggtgcta    420
gccttgcgtt ccgaggagga cggcctggcc gaagcacccg agcacggaac cacagccacc    480
ttccaccgct gcgccaagga tccgtggagg ttgcctggca cctacgtggt ggtgctgaag    540
gaggagaccc acctctcgca gtcagagcgc actgcccgcc gcctgcaggc ccaggctgcc    600
cgccggggat acctcaccaa gatcctgcat gtcttccatg gccttcttcc tggcttcctg    660
gtgaagatga gtggcgacct gctggagctg gccttgaagt tgccccatgt cgactacatc    720
gaggaggact cctctgtctt tgcccagagc atcccgtgga acctggagcg gattacccct    780
ccacggtacc gggcggatga ataccagccc cccgacggag gcagcctggt ggaggtgtat    840
ctcctagaca ccagcataca gagtgaccac cgggaaatcg agggcagggt catggtcacc    900
gacttcgaga atgtgcccga ggaggacggg acccgcttcc acagacaggc cagcaagtgt    960
gacagtcatg gcacccacct ggcaggggtg gtcagcggcc gggatgccgg cgtggccaag   1020
ggtgccagca tgcgcagcct gcgcgtgctc aactgccaag ggaagggcac ggttagcggc   1080
accctcatag gcctggagtt tattcggaaa agccagctgg tccagcctgt ggggccactg   1140
gtggtgctgc tgcccctggc gggtgggtac agccgcgtcc tcaacgccgc ctgccagcgc   1200
ctggcgaggg ctggggtcgt gctggtcacc gctgccggca acttccggga cgatgcctgc   1260
ctctactccc cagcctcagc tcccgaggtc atcacagttg gggccaccaa tgcccaggac   1320
cagccggtga ccctggggac tttggggacc aactttggcc gctgtgtgga cctctttgcc   1380
ccaggggagg acatcattgg tgcctccagc gactgcagca cctgctttgt gtcacagagt   1440
gggacatcac aggctgctgc ccacgtggct ggcattgcag ccatgatgct gtctgccgag   1500
ccggagctca ccctggccga gttgaggcag agactgatcc acttctctgc caaagatgcc   1560
atcaatgagg cctggttccc tgaggaccag cgggtactga cccccaacct ggtggccgcc   1620
ctgcccccca gcacccatgg ggcaggttgg cagctgtttt gcaggactgt gtggtcagca   1680
cactcggggc ctacacggat ggccacagcc atcgcccgct gcgccccaga tgaggagctg   1740
ctgagctgct ccagtttctc caggagtgga agcggcgggg cgagcgcatg gaggcccaag   1800
ggggcaagct ggtctgccgg gcccacaacg cttttggggg tgagggtgtc tacgccattg   1860
ccaggtgctg cctgctaccc caggccaact gcagcgtcca cacagctcca ccagctgagg   1920
ccagcatggg gacccgtgtc cactgccacc aacagggcca cgtcctcaca ggctgcagct   1980
cccactggga ggtggaggac cttggcaccc acaagccgcc tgtgctgagg ccacgaggtc   2040
agcccaacca gtgcgtgggc cacagggagg ccagcatcca cgcttcctgc tgccatgccc   2100
caggtctgga atgcaaagtc aaggagcatg gaatcccggc ccctcaggag caggtgaccg   2160
tggcctgcga ggagggctgg accctgactg gctgcagtgc cctccctggg acctcccacg   2220
tcctgggggc ctacgccgta gacaacacgt gtgtagtcag gagccgggac gtcagcacta   2280
caggcagcac cagcgaagag gccgtgacag ccgttgccat ctgctgccgg agccggcacc   2340
```

```
tggcgcaggc ctcccaggag ctccagtgac agccccatcc caggatgggt gtctggggag   2400
ggtcaagggc tggggctgag ctttaaaatg gttccgactt gtccctctct cagccctcca   2460
tggcctggca cgaggggatg ggatgcttc cgccttcccg gggctgctgg cctggccctt   2520
gagtggggca gcctccttgc ctggaactca ctcactctgg gtgcctcctc cccaggtgga   2580
ggtgccagga agctccctcc ctcactgtgg ggcatttcac cattcaaaca ggtcgagctg   2640
tgctcgggtg ctgccagctg ctcccaatgt gccgatgtcc gtgggcagaa tgacttttat   2700
tgagctcttg ttccgtgcca ggcattcaat cctcaggtct ccaccaagga ggcaggattc   2760
ttcccatgga taggggaggg ggcggtaggg gctgcaggga caaacatcgt tggggggtga   2820
gtgtgaaagg tgctgatggc cctcatctcc agctaactgt ggagaagccc ctgggggctc   2880
cctgattaat ggaggcttag ctttctggat ggcatctagc cagaggctgg agacaggtgt   2940
gcccctggtg gtcacaggct gtgccttggt ttcctgagcc acctttactc tgctctatgc   3000
caggctgtgc tagcaacacc caaaggtggc ctgcggggag ccatcaccta ggactgactc   3060
ggcagtgtgc agtggtgcat gcactgtctc agccaacccg ctccactacc cggcagggta   3120
cacattcgca cccctacttc acagaggaag aaacctggaa ccagaggggg cgtgcctgcc   3180
aagctcacac agcaggaact gggccagaaa cgcagattgg gctggctctg aagccaagcc   3240
tcttcttact tcacccggct gggctcctca tttttacggg taacagtgag gctgggaagg   3300
ggaacacaga ccaggaagct cggtgagtga tggcagaacg atgcctgcag gcatggaact   3360
ttttccgtta tcacccaggc ctgattcact ggcctggcgg agatgcttct aaggcatggt   3420
cgggggagag ggccaacaac tgtccctcct tgagcaccag ccccacccaa gcaagcagac   3480
atttatcttt tgggtctgtc ctctctgttg ccttttttaca gccaactttt ctagacctgt   3540
tttgcttttg taacttgaag atatttattc tgggttttgt agcattttta ttaatatggt   3600
gactttttaa aataaaaaca aacaaacgtt gtcct                              3635
```

<210> SEQ ID NO 21
<211> LENGTH: 1101
<212> TYPE: DNA
<213> ORGANISM: homo sapien

<400> SEQUENCE: 21

```
aggctcaagg cgccgccggc gtggaccgcg cacggcctct aggtctcctc gccaggacag     60
caacctctcc cctggccctc atgggcaccg tcagctccag gcggtcctgg tggccgctgc    120
cactgctgct gctgctgctg ctgctcctgg gtcccgcggg cgcccgtgcg caggaggacg    180
aggacggcga ctacgaggag ctggtgctag ccttgcgttc cgaggaggac ggcctggccg    240
aagcacccga gcacggaacc acagccacct tccaccgctg cgccaaggat ccgtggaggt    300
tgcctggcac ctacgtggtg gtgctgaagg aggagaccca cctctcgcag tcagagcgca    360
ctgcccgccg cctgcaggcc caggctgccc gccggggata cctcaccaag atcctgcatg    420
tcttccatgg ccttcttcct ggcttcctgg tgaagatgag tggcgacctg ctggagctgg    480
ccttgaagtt gccccatgtc gactacatcg aggaggactc ctctgtcttt gcccagagca    540
tcccgtggaa cctggagcgg attacccctc cacggtaccg ggcggatgaa taccagcccc    600
ccgcatattt ggaggatcac tgcgggggcc acagaggtgc tgttcagatg gcacttcaga    660
agactcagga gaccctgggg caggagcagt ttgactgaca gcccagaggg ctgccctctg    720
attccacctg aggccctgct tttcctggct gcaggggttc cagggccagg ccatttccgc    780
tggcgcagga ctctgctagc agcaacctgc ctgaagtctt cctttggcct ggctgagagt    840
```

ttctgagacc tgcgctggag cggagacgga ggcagcctgg tggaggtgta tctcctagac 900
accagcatac agagtgacca ccgggaaatc gagggcaggg tcatggtcac cgacttcgag 960
aatgtgcccg aggaggacgg gacccgcttc cacagacagg ccagcaagtg tgacagtcat 1020
ggcacccacc tggcaggggt ggtcagcggc cgggatgccg gcgtggccaa gggtgccagc 1080
atgcgcagcc tgcgcgtgct c 1101

<210> SEQ ID NO 22
<211> LENGTH: 2079
<212> TYPE: DNA
<213> ORGANISM: homo sapien

<400> SEQUENCE: 22
atgggcaccg tcagctccag gcggtcctgg tggccgctgc cactgctgct gctgctgctg 60
ctgctcctgg gtcccgcggg cgcccgtgcg caggaggacg aggacggcga ctacgaggag 120
ctggtgctag ccttgcgttc cgaggaggac ggcctggccg aagcacccga gcacggaacc 180
acagccacct tccaccgctg cgccaaggat ccgtggaggt tgcctggcac ctacgtggtg 240
gtgctgaagg aggagaccca cctctcgcag tcagagcgca ctgcccgccg cctgcaggcc 300
caggctgccc gccggggata cctcaccaag atcctgcatg tcttccatgg ccttcttcct 360
ggcttcctgg tgaagatgag tggcgacctg ctggagctgg ccttgaagtt gccccatgtc 420
gactacatcg aggaggactc ctctgtcttt gcccagagca tcccgtggaa cctggagcgg 480
attacccctc cacggtaccg ggcggatgaa taccagcccc ccgacggagg cagcctggtg 540
gaggtgtatc tcctagacac cagcatacag agtgaccacc gggaaatcga gggcagggtc 600
atggtcaccg acttcgagaa tgtgcccgag gaggacggga cccgcttcca cagacaggcc 660
agcaagtgtg acagtcatgg cacccacctg gcaggggtgg tcagcggccg ggatgccggc 720
gtggccaagg gtgccagcat gcgcagcctg cgcgtgctca actgccaagg gaagggcacg 780
gttagcggca ccctcatagg cctggagttt attcggaaaa gccagctggt ccagcctgtg 840
gggccactgg tggtgctgct gcccctggcg ggtgggtaca gccgcgtcct caacgccgcc 900
tgccagcgcc tggcgagggc tggggtcgtg ctggtcaccg ctgccggcaa cttccgggac 960
gatgcctgcc tctactcccc agcctcagct cccgaggtca tcacagttgg ggccaccaat 1020
gcccaggacc agccggtgac cctggggact ttggggacca actttggccg ctgtgtggac 1080
ctctttgccc caggggagga catcattggt gcctccagcg actgcagcac ctgctttgtg 1140
tcacagagtg ggacatcaca ggctgctgcc cacgtggctg gcattgcagc catgatgctg 1200
tctgccgagc cggagctcac cctggccgag ttgaggcaga gactgatcca cttctctgcc 1260
aaagatgtca tcaatgaggc ctggttccct gaggaccagc gggtactgac ccccaacctg 1320
gtggccgccc tgccccccag cacccatggg gcaggttggc agctgttttg caggactgtg 1380
tggtcagcac actcggggcc tacacggatg gccacagcca tcgcccgctg cgccccagat 1440
gaggagctgc tgagctgctc cagtttctcc aggagtggga agcggcgggg cgagcgcatg 1500
gaggcccaag gggcaagct ggtctgccgg gcccacaacg cttttggggg tgagggtgtc 1560
tacgccattg ccaggtgctg cctgctaccc caggccaact gcagcgtcca cacagctcca 1620
ccagctgagg ccagcatggg gacccgtgtc cactgccacc aacagggcca cgtcctcaca 1680
ggctgcagct cccactggga ggtggaggac cttggcaccc acaagccgcc tgtgctgagg 1740
ccacgaggtc agcccaacca gtgcgtgggc cacagggagg ccagcatcca cgcttcctgc 1800

```
tgccatgccc caggtctgga atgcaaagtc aaggagcatg gaatcccggc ccctcaggag   1860

caggtgaccg tggcctgcga ggagggctgg accctgactg gctgcagtgc cctccctggg   1920

acctcccacg tcctgggggc ctacgccgta gacaacacgt gtgtagtcag gagccgggac   1980

gtcagcacta caggcagcac cagcgaagag gccgtgacag ccgttgccat ctgctgccgg   2040

agccggcacc tggcgcaggc ctcccaggag ctccagtga                          2079
```

<210> SEQ ID NO 23
<211> LENGTH: 2333
<212> TYPE: DNA
<213> ORGANISM: homo sapien

<400> SEQUENCE: 23

```
gtgcaatcgc gggaagccag ggtttccagc taggacacag caggtcgtga tccgggtcgg     60

gacactgcct ggcagaggct gcgagcatgg ggccctgggg ctggaaattg cgctggaccg    120

tcgccttgct cctcgccgcg gcggggactg cagtgggcga cagatgcgaa agaaacgagt    180

tccagtgcca agacgggaaa tgcatctcct acaagtgggt ctgcgatggc agcgctgagt    240

gccaggatgg ctctgatgag tcccaggaga cgtgcttgtc tgtcacctgc aaatccgggg    300

acttcagctg tgggggccgt gtcaaccgct gcattcctca gttctggagg tgcgatggcc    360

aagtggactg cgacaacggc tcagacgagc aaggctgtct gacactctgc gagggaccca    420

acaagttcaa gtgtcacagc ggcgaatgca tcaccctgga caaagtctgc aacatggcta    480

gagactgccg ggactggtca gatgaaccca tcaaagagtg cgggaccaac gaatgcttgg    540

acaacaacgg cggctgttcc cacgtctgca atgaccttaa gatcggctac gagtgcctgt    600

gccccgacgg cttccagctg gtggcccagc gaagatgcga agatatcgat gagtgtcagg    660

atcccgacac ctgcagccag ctctgcgtga acctggaggg tggctacaag tgccagtgtg    720

aggaaggctt ccagctggac ccccacacga aggcctgcaa ggctgtgggc tccatcgcct    780

acctcttctt caccaaccgg cacgaggtca ggaagatgac gctggaccgg agcgagtaca    840

ccagcctcat ccccaacctg aggaacgtgg tcgctctgga cacggaggtg gccagcaata    900

gaatctactg gtctgacctg tcccagagaa tgatctgcag cacccagctt gacagagccc    960

acggcgtctc ttcctatgac accgtcatca gcagagacat ccaggccccc gacgggctgg   1020

ctgtggactg gatccacagc aacatctact ggaccgactc tgtcctgggc actgtctctg   1080

ttgcggatac caagggcgtg aagaggaaaa cgttattcag ggagaacggc tccaagccaa   1140

gggccatcgt ggtggatcct gttcatggct tcatgtactg gactgactgg ggaactcccg   1200

ccaagatcaa gaaagggggc ctgaatggtg tggacatcta ctcgctggtg actgaaaaca   1260

ttcagtggcc caatggcatc accctagatc tcctcagtgg ccgcctctac tgggttgact   1320

ccaaacttca ctccatctca agcatcgatg tcaacggggg caaccggaag accatcttgg   1380

aggatgaaaa gaggctggcc cacccccttct ccttggccgt ctttgaggac aaagtatttt   1440

ggacagatat catcaacgaa gccattttca gtgccaaccg cctcacaggt tccgatgtca   1500

atttgttggc tgaaaaccta ctgtccccag aggatatggt tctcttccac aacctcaccc   1560

agccaagagg agtgaactgg tgtgagagga ccaccctgag caatggcggc tgccagtatc   1620

tgtgcctccc tgccccgcag atcaaccccc actcgcccaa gtttacctgc gcctgcccgg   1680

acggcatgct gctggccagg gacatgagga gctgcctcac agaggctgag gctgcagtgg   1740

ccacccagga gacatccacc gtcaggctaa aggtcagctc cacagccgta aggacacagc   1800

acacaaccac ccgacctgtt cccgacacct cccggctgcc tggggccacc cctgggctca   1860
```

```
ccacggtgga gatagtgaca atgtctcacc aagctctggg cgacgttgct ggcagaggaa   1920

atgagaagaa gcccagtagc gtgagggctc tgtccattgt cctccccatc gtgctcctcg   1980

tcttcctttg cctgggggtc ttccttctat ggaagaactg gcggcttaag aacatcaaca   2040

gcatcaactt tgacaacccc gtctatcaga agaccacaga ggatgaggtc cacatttgcc   2100

acaaccagga cggctacagc taccccctcga gacagatggt cagtctggag gatgacgtgg   2160

cgtgaacatc tgcctggagt cccgtccctg cccagaaccc ttcctgagac ctcgccggcc   2220

ttgttttatt caaagacaga gaagaccaaa gcattgcctg ccagagcttt gttttatata   2280

tttattcatc tgggaggcag aacaggcttc ggacagtgcc catgcaatgg ctt          2333
```

<210> SEQ ID NO 24
<211> LENGTH: 2768
<212> TYPE: DNA
<213> ORGANISM: homo sapien

<400> SEQUENCE: 24

```
gtgcaatcgc gggaagccag ggtttccagc taggacacag caggtcgtga tccgggtcgg     60

gacactgcct ggcagaggct gcgagcatgg ggccctgggg ctggaaattg cgctggaccg    120

tcgccttgct cctcgccgcg gcggggactg cagtgggcga cagatgcgaa agaaacgagt    180

tccagtgcca agacgggaaa tgcatctcct acaagtgggt ctgcgatggc agcgctgagt    240

gccaggatgg ctctgatgag tcccaggaga cgtgctcccc caagacgtgc tcccaggacg    300

agtttcgctg ccacgatggg aagtgcatct ctcggcagtt cgtctgtgac tcagaccggg    360

actgcttgga cggctcagac gaggcctcct gcccggtgct cacctgtggt cccgccagct    420

tccagtgcaa cagctccacc tgcatccccc agctgtgggc ctgcgacaac gaccccgact    480

gcgaagatgg ctcggatgag tggccgcagc gctgtagggg tctttacgtg ttccaagggg    540

acagtagccc ctgctcggcc ttcgagttcc actgcctaag tggcgagtgc atccactcca    600

gctggcgctg tgatggtggc cccgactgca aggacaaatc tgacgaggaa aactgcgctg    660

tggccacctg tcgccctgac gaattccagt gctctgatgg aaactgcatc catggcagcc    720

ggcagtgtga ccgggaatat gactgcaagg acatgagcga tgaagttggc tgcgttaatg    780

tgacactctg cgagggaccc aacaagttca agtgtcacag cggcgaatgc atcaccctgg    840

acaaagtctg caacatggct agagactgcc gggactggtc agatgaaccc atcaaagagt    900

gcgggaccaa cgaatgcttg gacaacaacg gcggctgttc ccacgtctgc aatgacctta    960

agatcggcta cgagtgcctg tgccccgacg gcttccagct ggtggcccag cgaagatgcg   1020

aagatatcga tgagtgtcag gatcccgaca cctgcagcca gctctgcgtg aacctggagg   1080

gtggctacaa gtgccagtgt gaggaaggct tccagctgga cccccacacg aaggcctgca   1140

aggctgtggg ctccatcgcc tacctcttct tcaccaaccg gcacgaggtc aggaagatga   1200

cgctggaccg gagcgagtac accagcctca tccccaacct gaggaacgtg gtcgctctgg   1260

acacggaggt ggccagcaat agaatctact ggtctgacct gtcccagaga atgatctgca   1320

gcacccagct tgacagagcc cacggcgtct cttcctatga caccgtcatc agcagggaca   1380

tccaggcccc cgacgggctg gctgtggact ggatccacag caacatctac tggaccgact   1440

ctgtcctggg cactgtctct gttgcggata ccaagggcgt gaagaggaaa acgttattca   1500

gggagaacgg ctccaagcca agggccatcg tggtggatcc tgttcatggc ttcatgtact   1560

ggactgactg ggaactcccc gccaagatca agaaaggggg cctgaatggt gtggacatct   1620
```

```
actcgctggt gactgaaaac attcagtggc ccaatggcat caccctagat ctcctcagtg   1680
gccgcctcta ctgggttgac tccaaacttc actccatctc aagcatcgat gtcaatgggg   1740
gcaaccggaa gaccatcttg gaggatgaaa agaggctggc ccaccccttc tccttggccg   1800
tctttgagga caaagtattt tggacagata tcatcaacga agccattttc agtgccaacc   1860
gcctcacagg ttccgatgtc aacttgttgg ctgaaaacct actgtcccca gaggatatgg   1920
tcctcttcca caacctcacc cagccaagag gagtgaactg gtgtgagagg accaccctga   1980
gcaatggcgg ctgccagtat ctgtgcctcc ctgccccgca gatcaacccc cactcgccca   2040
agtttacctg cgcctgcccg gacggcatgc tgctggccag ggacatgagg agctgcctca   2100
cagaggctga ggctgcagtg gccacccagg agacatccac cgtcaggcta aaggtcagct   2160
ccacagccgt aaggacacag cacacaacca cccggcctgt tcccgacacc tcccggctgc   2220
ctggggccac ccctgggctc accacggtgg agatagtgac aatgtctcac caagctctgg   2280
gcgacgttgc tggcagagga aatgagaaga agcccagtag tgtgagggct ctgtccattg   2340
tcctccccat cgtgctcctc gtcttccttt gcctgggggt cttccttcta tggaagaact   2400
ggcggcttaa gaacatcaac agcatcaact ttgacaaccc cgtctatcag aagaccacag   2460
aggatgaggt ccacatttgc cacaaccagg acggctacag ctacccctcg agacagatgg   2520
tcagtctgga ggatgacgtg gcgtgaacat ctgcctggag tcccgtccct gcccagaacc   2580
cttcctgaga cctcgccggc cttgttttat tcaaagacag agaagaccga agcattgcct   2640
gccagagctt tgttttatat atttattcat ctgggaggca gaacaggctt cggacagtgc   2700
ccatgcaatg gcttgggttg ggattttggt ttcttccttt cctcgtgaag gataagagaa   2760
acaggccc                                                            2768
```

<210> SEQ ID NO 25
<211> LENGTH: 2429
<212> TYPE: DNA
<213> ORGANISM: homo sapien

<400> SEQUENCE: 25

```
gtgcaatcgc gggaagccag ggtttccagc taggacacag caggtcgtga tccgggtcgg     60
gacactgcct ggcagaggct gcgagcatgg ggccctgggg ctggaaattg cgctggaccg    120
tcgccttgct cctcgccgcg gcggggactg cagtgggcga cagatgcgaa agaaacgagt    180
tccagtgcca agacgggaaa tgcatctcct acaagtgggt ctgcgatggc agcgctgagt    240
gccaggatgg ctctgatgag tcccaggaga cgtgcttgtc tgtcacctgc aaatccgggg    300
acttcagctg tgggggccgt gtcaaccgct gcattcctca gttctggagg tgcgatggcc    360
aagtggactg cgacaacggc tcagacgagc aaggctgtcc tgtggccacc tgtcgccctg    420
acgaattcca gtgctctgat ggaaactgca tccatggcag ccggcagtgt gaccgggaat    480
atgactgcaa ggacatgagc gatgaagttg gctgcgttaa tgtgacactc tgcgagggac    540
ccaacaagtt caagtgtcac agcggcgaat gcatcaccct ggacaaagtc tgcaacatgg    600
ctagagactg ccgggactgg tcagatgaac ccatcaaaga gtgcgggacc aacgaatgct    660
tggacaacaa cggcggctgt tcccacgtct gcaatgacct taagatcggc tacgagtgcc    720
tgtgccccga cggcttccag ctggtggccc agcgaagatg cgaagatatc gatgagtgtc    780
aggatcccga cacctgcagc cagctctgcg tgaacctgga gggtggctac aagtgccagt    840
gtgaggaagg cttccagctg gacccccaca cgaaggcctg caaggctgtg ggctccatcg    900
cctacctctt cttcaccaac cggcacgagg tcaggaagat gacgctggac cggagcgagt    960
```

acaccagtct catccccaac ctgaggaacg tggtcgctct ggacacggag gtggccagca 1020
atagaatcta ctggtctgac ctgtcccaga gaatgatctg cagcacccag cttgacagag 1080
cccacggcgt ctcttcctat gacaccgtca tcagcagaga catccaggcc cccgacgggc 1140
tggctgtgga ctggatccac agcaacatct actggaccga ctctgtcctg ggcactgtct 1200
ctgttgcgga taccaagggc gtgaagagga aaacgttatt cagggagaac ggctccaagc 1260
caagggccat cgtggtggat cctgttcatg gcttcatgta ctggactgac tggggaactc 1320
ccgccaagat caagaaaggg ggcctgaatg gtgtggacat ctactcgctg gtgactgaaa 1380
acattcagtg gcccaatggc atcaccctag atctcctcag tggccgcctc tactgggttg 1440
actccaaact tcactccatc tcaagcatcg atgtcaacgg gggcaaccgg aagaccatct 1500
tggaggatga aaagaggctg gcccacccct tctccttggc cgtctttgag gacaaagtat 1560
tttggacaga tatcatcaac gaagccattt tcagtgccaa ccgcctcaca ggttccgatg 1620
tcaacttgtt ggctgaaaac ctactgtccc cagaggatat ggttctcttc cacaacctca 1680
cccagccaag agaggctgag gctgcagtgg ccacccagga gacatccacc gtcaggctaa 1740
aggtcagctc cacagccgta aggacacagc acacaaccac ccggcctgtt cccgacacct 1800
cccggctgcc tggggccacc cctgggctca ccacggtgga gatagtgaca atgtctcacc 1860
aagctctggg cgacgttgct ggcagaggaa atgagaagaa gcccagtagc gtgagggctc 1920
tgtccattgt cctccccatc gtgctcctcg tcttcctttg cctgggggtc ttccttctat 1980
ggaagaactg gcggcttaag aacatcaaca gcatcaactt tgacaacccc gtctatcaga 2040
agaccacaga ggatgaggtc cacatttgcc acaaccagga cggctacagc taccccctcga 2100 gacagatggt cagtctggag gatgacgtgg cgtgaacatc tgcctggagt cccgtccctg 2160
cccagaaccc ttcctgagac ctcgccagcc ttgttttatt caaagacaga gaagaccaaa 2220
gcattgcctg ccagagcttt gttttatata tttattcatc tgggaggcag aacaggcttc 2280
ggacagtgcc catgcaatgg cttgggttgg gattttggtt tcttcctttc ctcgtgaagg 2340
ataagagaaa caggcccggg gggaccagga tgacacctcc atttctctcc aggaagtttt 2400
gagtttctct ccaccgtgac acaatcctc 2429

<210> SEQ ID NO 26
<211> LENGTH: 2656
<212> TYPE: DNA
<213> ORGANISM: homo sapien

<400> SEQUENCE: 26
gtgcaatcgc gggaagccag ggtttccagc taggacacag caggtcgtga tccgggtcgg 60
gacactgcct ggcagaggct gcgagcatgg ggccctgggg ctggaaattg cgctggaccg 120
tcgccttgct cctcgccgcg gcggggactg cagtgggcga cagatgcgaa agaaacgagt 180
tccagtgcaa cagctccacc tgcatccccc agctgtgggc ctgcgacaac gaccccgact 240
gcgaagatgg ctcggatgag tggccgcagc gctgtagggg tctttacgtg ttccaagggg 300
acagtagccc ctgctcggcc ttcgagttcc actgcctaag tggcgagtgc atccactcca 360
gctggcgctg tgatggtggc cccgactgca aggacaaatc tgacgaggaa aactgcgctg 420
tggccacctg tcgccctgac gaattccagt gctctgatgg aaactgcatc catggcagcc 480
ggcagtgtga ccgggaatat gactgcaagg acatgagcga tgaagttggc tgcgttaatg 540
tgacactctg cgagggaccc aacaagttca agtgtcacag cggcgaatgc atcaccctgg 600
acaaagtctg caacatggct agagactgcc gggactggtc agatgaaccc atcaaagagt 660
gcgggaccaa cgaatgcttg gacaacaacg gcggctgttc ccacgtctgc aatgacctta 720
agatcggcta cgagtgcctg tgccccgacg gcttccagct ggtggcccag cgaagatgcg 780
aagatatcga tgagtgtcag gatcccgaca cctgcagcca gctctgcgtg aacctggagg 840
gtggctacaa gtgccagtgt gaggaaggct tccagctgga cccccacacg aaggcctgca 900
aggctgtggg ctccatcgcc tacctcttct tcaccaaccg gcacgaggtc aggaagatga 960
cgctggaccg gagcgagtac accagcctca tccccaacct gaggaacgtg gtcgctctgg 1020
acacggaggt ggccagcaat agaatctact ggtctgacct gtcccagaga atgatctgca 1080
gcacccagct tgacagagcc cacggcgtct cttcctatga caccgtcatc agcagggaca 1140
tccaggcccc cgacgggctg gctgtggact ggatccacag caacatctac tggaccgact 1200
ctgtcctggg cactgtctct gttgcggata ccaagggcgt gaagaggaaa acgttattca 1260
gggagaacgg ctccaagcca agggccatcg tggtggatcc tgttcatggc ttcatgtact 1320
ggactgactg ggaactcccc gccaagatca agaaaggggg cctgaatggt gtggacatct 1380
actcgctggt gactgaaaac attcagtggc ccaatggcat caccctagat ctcctcagtg 1440
gccgcctcta ctgggttgac tccaaacttc actccatctc aagcatcgat gtcaatgggg 1500
gcaaccggaa gaccatcttg gaggatgaaa agaggctggc ccaccccttc tccttggccg 1560
tctttgagga caaagtattt tggacagata tcatcaacga agccattttc agtgccaacc 1620
gcctcacagg ttccgatgtc aacttgttgg ctgaaaacct actgtcccca gaggatatgg 1680
tcctcttcca caacctcacc cagccaagag gagtgaactg gtgtgagagg accaccctga 1740
gcaatggcgg ctgccagtat ctgtgcctcc ctgccccgca gatcaacccc cactcgccca 1800
agtttacctg cgcctgcccg gacggcatgc tgctggccag ggacatgagg agctgcctca 1860
cagaggctga ggctgcagtg gccacccagg agacatccac cgtcaggcta aaggtcagct 1920
ccacagccgt aaggacacag cacacaacca cccggcctgt tcccgacacc tcccggctgc 1980
ctggggccac ccctgggctc accacggtgg agatagtgac aatgtctcac caagctctgg 2040
gcgacgttgc tggcagagga aatgagaaga agcccagtag cgtgagggct ctgtccattg 2100
tcctccccat cgtgctcctc gtcttccttt gcctgggggt cttccttcta tggaagaact 2160
ggcggcttaa gaacatcaac agcatcaact ttgacaaccc cgtctatcag aagaccacag 2220
aggatgaggt ccacatttgc cacaaccagg acggctacag ctacccctcg agacagatgg 2280
tcagtctgga ggatgacgtg gcgtgaacat ctgcctggag tcccgtccct gcccagaacc 2340
cttcctgaga cctcgccggc cttgttttat tcaaagacag agaagaccaa agcattgcct 2400
gccagagctt tgttttatat atttattcat ctgggaggca gaacaggctt cggacagtgc 2460
ccatgcaatg gcttgggttg ggattttggt ttcttccttt cctcgtgaag gataagagaa 2520
acaggcccgg ggggaccagg atgacacctc catttctctc caggaagttt tgagtttctc 2580
tccaccgtga cacaatcctc aaacatggaa gatgaaaggg caggggatgt caggcccaga 2640
gaagcaagtg gctttc 2656

<210> SEQ ID NO 27
<211> LENGTH: 3144
<212> TYPE: DNA
<213> ORGANISM: homo sapien

<400> SEQUENCE: 27
gccagggttt ccagctagga cacagcaggt cgtgatccgg gtcgggacac tgcctggcag 60

-continued

```
aggctgcgag catggggccc tggggctgga aattgcgctg gaccgtcgcc ttgctcctcg    120
ccgcggcggg gactgcagtg ggcgacagat gcgaaagaaa cgagttccag tgccaagacg    180
ggaaatgcat ctcctacaag tgggtctgcg atggcagcgc tgagtgccag gatggctctg    240
atgagtccca ggagacgtgc ttgtctgtca cctgcaaatc cggggacttc agctgtgggg    300
gccgtgtcaa ccgctgcatt cctcagttct ggaggtgcga tggccaagtg gactgcgaca    360
acggctcaga cgagcaaggc tgtccccca agacgtgctc ccaggacgag tttcgctgcc    420
acgatgggaa gtgcatctct cggcagttcg tctgtgactc agaccgggac tgcttggacg    480
gctcagacga ggcctcctgc ccggtgctca cctgtggtcc cgccagcttc cagtgcaaca    540
gctccacctg catcccccag ctgtgggcct gcgacaacga ccccgactgc gaagatggct    600
cggatgagtg gccgcagcgc tgtaggggtc tttacgtgtt ccaaggggac agtagcccct    660
gctcggcctt cgagttccac tgcctaagtg gcgagtgcat ccactccagc tggcgctgtg    720
atggtggccc cgactgcaag gacaaatctg acgaggaaaa ctgcgctgtg gccacctgtc    780
gccctgacga attccagtgc tctgatggaa actgcatcca tggcagccgg cagtgtgacc    840
gggaatatga ctgcaaggac atgagcgatg aagttggctg cgttaatgtg acactctgcg    900
agggacccaa caagttcaag tgtcacagcg gcgaatgcat caccctggac aaagtctgca    960
acatggctag agactgccgg gactggtcag atgaacccat caaagagtgc gggaccaacg   1020
aatgcttgga caacaacggc ggctgttccc acgtctgcaa tgaccttaag atcggctacg   1080
agtgcctgtg ccccgacggc ttccagctgg tggcccagcg aagatgcgaa gatatcgatg   1140
agtgtcagga tcccgacacc tgcagccagc tctgcgtgaa cctggagggt ggctacaagt   1200
gccagtgtga ggaaggcttc cagctggacc cccacacgaa ggcctgcaag gctgtgggct   1260
ccatcgccta cctcttcttc accaaccggc acgaggtcag gaagatgacg ctggaccgga   1320
gcgagtacac cagcctcatc cccaacctga ggaacgtggt cgctctggac acggaggtgg   1380
ccagcaatag aatctactgg tctgacctgt cccagagaat gatctgcagc acccagcttg   1440
acagagccca cggcgtctct tcctatgaca ccgtcatcag cagagacatc caggcccccg   1500
acgggctggc tgtggactgg atccacagca acatctactg gaccgactct gtcctgggca   1560
ctgtctctgt tgcggatacc aagggcgtga agaggaaaac gttattcagg gagaacggct   1620
ccaagccaag ggccatcgtg gtggatcctg ttcatggctt catgtactgg actgactggg   1680
gaactcccgc caagatcaag aaagggggcc tgaatggtgt ggacatctac tcgctggtga   1740
ctgaaaacat tcagtggccc aatggcatca ccctagatct cctcagtggc cgcctttact   1800
gggttgactc caaacttcac tccatctcaa gcatcgatgt caacgggggc aaccggaaga   1860
ccatcttgga ggatgaaaag aggctggccc accccttctc cttggccgtc tttgaggaca   1920
aagtattttg gacagatatc atcaacgaag ccattttcag tgccaaccgc ctcacaggtt   1980
ccgatgtcaa cttgttggct gaaaacctac tgtccccaga ggatatggtt ctcttccaca   2040
acctcaccca gccaagagga gtgaactggt gtgagaggac caccctgagc aatggcggct   2100
gccagtatct gtgcctccct gccccgcaga tcaaccccca ctcgcccaag tttacctgcg   2160
cctgcccgga cggcatgctg ctggccaggg acatgaggag ctgcctcaca gaggctgagg   2220
ctgcagtggc cacccaggag acatccaccg tcaggctaaa ggtcagctcc acagccgtaa   2280
ggacacagca cacaaccacc cgacctgttc ccgacacctc ccggctgcct ggggccaccc   2340
ctgggctcac cacggtggag atagtgacaa tgtctcacca agctctgggc gacgttgctg   2400
```

-continued

```
gcagaggaaa tgagaagaag cccagtagcg tgagggctct gtccattgtc ctccccatcg   2460

tgctcctcgt cttcctttgc ctgggggtct tccttctatg gaagaactgg cggcttaaga   2520

acatcaacag catcaacttt gacaaccccg tctatcagaa gaccacagag gatgaggtcc   2580

acatttgcca caaccaggac ggctacagct accccctcgat ggtcagtctg gaggatgacg   2640

tggcgtgaac atctgcctgg agtcccgtcc ctgcccagaa cccttcctga gacctcgccg   2700

gccttgtttt attcaaagac agagaagacc aaagcattgc ctgccagagc tttgttttat   2760

atatttattc atctgggagg cagaacaggc ttcggacagt gcccatgcaa tggcttgggt   2820

tgggattttg gtttcttcct ttcctcgtga aggataagag aaacaggccc ggggggacca   2880

ggatgacacc tccatttctc tccaggaagt tttgagtttc tctccaccgt gacacaatcc   2940

tcaaacatgg aagatgaaag ggcaggggat gtcaggccca gagaagcaag tggctttcaa   3000

cacacaacag cagatggcac caacgggacc ccctggccct gcctcatcca ccaatctcta   3060

agccaaaccc ctaaactcag gagtcaacgt gtttacctct tctatgcaag ccttgctaga   3120

cagccaggtt agcctttgcc ctgt                                           3144
```

<210> SEQ ID NO 28
<211> LENGTH: 3522
<212> TYPE: DNA
<213> ORGANISM: homo sapien

<400> SEQUENCE: 28

```
ccagggtttc cagctaggac acagcaggtc gtgatccggg tcgggacact gcctggcaga     60

ggctgcgagc atggggccct ggggctggaa attgcgctgg accgtcgcct tgctcctcgc    120

cgcggcgggg actgcagtgg gcgacagatg tgaaagaaac gagttccagt gccaagacgg    180

gaaatgcatc tcctacaagt gggtctgcga tggcagcgct gagtgccagg atggctctga    240

tgagtcccag gagacgtgct tgtctgtcac ctgcaaatcc ggggacttca gctgtggggg    300

ccgtgtcaac cgctgcattc ctcagttctg gaggtgcgat ggccaagtgg actgcgacaa    360

cggctcagac gagcaaggct gtccccccaa gacgtgctcc caggacgagt ttcgctgcca    420

cgatgggaag tgcatctctc ggcagttcgt ctgtgactca gaccgggact gcttggacgg    480

ctcagacgag gcctcctgcc cggtgctcac ctgtggtccc gccagcttcc agtgcaacag    540

ctccacctgc atcccccagc tgtgggcctg cgacaacgac cccgactgcg aagatggctc    600

ggatgagtgg ccgcagcgct gtaggggtct ttacgtgttc caaggggaca gtagcccctg    660

ctcggccttc gagttccact gcctaagtgg cgagtgcatc cactccagct ggcgctgtga    720

tggtggcccc gactgcaagg acaaatctga cgaggaaaac tgcgctgtgg ccacctgtcg    780

ccctgacgaa ttccagtgct ctgatggaaa ctgcatccat ggcagccggc agtgtgaccg    840

ggaatatgac tgcaaggaca tgagcgatga agttggctgc gttaatgtga cactctgcga    900

gggacccaac aagttcaagt gtcacagcgg cgaatgcatc accctggaca aagtctgcaa    960

catggctaga gactgccggg actggtcaga tgaacccatc aaagagtgcg ggaccaacga   1020

atgcttggac aacaacggcg gctgttccca cgtctgcaat gaccttaaga tcggctacga   1080

gtgcctgtgc cccgacggct tccagctggt ggcccagcga agatgcgaag atatcgatga   1140

gtgtcaggat cccgacacct gcagccagct ctgcgtgaac ctggagggtg gctacaagtg   1200

ccagtgtgag gaaggcttcc agctggaccc ccacacgaag gcctgcaagg ctgtgggctc   1260

catcgcctac ctcttcttca ccaaccggca cgaggtcagg aagatgacgc tggaccggag   1320

cgagtacacc agcctcatcc ccaacctgag gaacgtggtc gctctggaca cggaggtggc   1380
```

```
cagcaataga atctactggt ctgacctgtc ccagagaatg atctgcagca cccagcttga   1440
cagagcccac ggcgtctctt cctatgacac cgtcatcagc agggacatcc aggcccccga   1500
cgggctggct gtggactgga tccacagcaa catctactgg accgactctg tcctgggcac   1560
tgtctctgtt gcggatacca agggcgtgaa gaggaaaacg ttattcaggg agaacggctc   1620
caagccaagg gccatcgtgg tggatcctgt tcatggcttc atgtactgga ctgactgggg   1680
aactcccgcc aagatcaaga aagggggcct gaatggtgtg gacatctact cgctggtgac   1740
tgaaaacatt cagtggccca atggcatcac cctagatctc ctcagtggcc gcctctactg   1800
ggttgactcc aaacttcact ccatctcaag catcgatgtc aatgggggca accggaagac   1860
catcttggag gatgaaaaga ggctggccca ccccttctcc ttggccgtct ttgaggacaa   1920
agtattttgg acagatatca tcaacgaagc cattttcagt gccaaccgcc tcacaggttc   1980
cgatgtcaac ttgttggctg aaaacctact gtccccagag gatatggtcc tcttccacaa   2040
cctcacccag ccaagaggag tgaactggtg tgagaggacc accctgagca atggcggctg   2100
ccagtatctg tgcctccctg ccccgcagat caaccccccac tcgcccaagt ttacctgcgc   2160
ctgcccggac ggcatgctgc tggccaggga catgaggagc tgcctcacag aggctgaggc   2220
tgcagtggcc acccaggaga catccaccgt caggctaaag gtcagctcca cagccgtaag   2280
gacacagcac acaaccaccc ggcctgttcc cgacacctcc cggctgcctg gggccacccc   2340
tgggctcacc acggtggaga tagtgacaat gtctcaccaa gctctgggcg acgttgctgg   2400
cagaggaaat gagaagaagc ccagtagcgt gagggctctg tccattgtcc tccccatcgt   2460
gctcctcgtc ttcctttgcc tgggggtctt ccttctatgg aagaactggc ggcttaagaa   2520
catcaacagc atcaactttg acaaccccgt ctatcagaag accacagagg atgaggtcca   2580
catttgccac aaccaggacg gctacagcta cccctcgaga cagatggtca gtctggagga   2640
tgacgtggcg tgaacatctg cctggagtcc cgtccctgcc cagaaccctt cctgagacct   2700
cgccggcctt gttttattca aagacagaga agaccaaagc attgcctgcc agagctttgt   2760
tttatatatt tattcatctg ggaggcagaa caggcttcgg acagtgccca tgcaatggct   2820
tgggttggga ttttggtttc ttcctttcct cgtgaaggat aagagaaaca ggcccggggg   2880
gaccaggatg acacctccat ttctctccag gaagttttga gtttctctcc accgtgacac   2940
aatcctcaaa catggaagat gaaagggcag gggatgtcag gcccagagaa gcaagtggct   3000
ttcaacacac aacagcagat ggcaccaacg ggacccccctg gccctgcctc atccaccaat   3060
ctctaagcca aacccctaaa ctcaggagtc aacgtgttta cctcttctat gcaagccttg   3120
ctagacagcc aggttagcct ttgccctgtc acccccgaat catgacccac ccagtgtctt   3180
tcgaggtggg tttgtacctt ccttaagcca ggaaagggat tcatggcgtc ggaaatgatc   3240
tggctgaatc cgtggtggca ccgagaccaa actcattcac caaatgatgc cacttcccag   3300
aggcagagcc tgagtcaccg gtcaccctta atatttatta agtgcctgag acacccggtt   3360
accttggccg tgaggacacg tggcctgcac ccaggtgtgg ctgtcaggac accagcctgg   3420
tgcccatcct cccgacccct acccacttcc attcccgtgg tctccttgca ctttctcagt   3480
tcagagttgt acactgtgta aaaaaaaaaa aaaaaaaaaa aa                      3522
```

<210> SEQ ID NO 29
<211> LENGTH: 2600
<212> TYPE: DNA
<213> ORGANISM: homo sapien -continued

<400> SEQUENCE: 29
cagaggctgc gagcatgggg ccctggggct ggaaattgcg ctggaccgtc gccttgctcc 60
tcgccgcggc ggggactgca gtgggcgaca gatgcgaaag aaacgagttc cagtgccaag 120
acgggaaatg catctcctac aagtgggtct gcgatggcag cgctgagtgc caggatggct 180
ctgatgagtc ccaggagacg tgcttgtctg tcacctgcaa atccggggac ttcagctgtg 240
ggggccgtgt caaccgctgc attcctcagt tctggaggtg cgatggccaa gtggactgcg 300
acaacggctc agacgagcaa ggctgtcccc ccaagacgtg ctcccaggac gagtttcgct 360
gccacgatgg gaagtgcatc tctcggcagt tcgtctgtga ctcagaccgg gactgcttgg 420
acggctcaga cgaggcctcc tgcccggtgc tcacctgtgg tcccgccagc ttccagtgca 480
acagctccac ctgcatcccc cagctgtggg cctgcgacaa cgaccccgac tgcgaagatg 540
gctcggatga gtggccgcag cgctgtaggg gtctttacgt gttccaaggg gacagtagcc 600
cctgctcggc cttcgagttc cactgcctaa gtggcgagtg catccactcc agctggcgct 660
gtgatggtgg ccccgactgc aaggacaaat ctgacgagga aaactgcgct gtggccacct 720
gtcgccctga cgaattccag tgctctgatg gaaactgcat ccatggcagc cggcagtgtg 780
accgggaata tgactgcaag gacatgagcg atgaagttgg ctgcgttaat gtgacactct 840
gcgagggacc caacaagttc aagtgtcaca gcggcgaatg catcaccctg gacaaagtct 900
gcaacatggc tagagactgc cgggactggt cagatgaacc catcaaagag tgcgggacca 960
acgaatgctt ggacaacaac ggcggctgtt cccacgtctg caatgacctt aagatcggct 1020
acgagtgcct gtgccccgac ggcttccagc tggtggccca gcgaagatgc gaagatatcg 1080
atgagtgtca ggatcccgac acctgcagcc agctctgcgt gaacctggag ggtggctaca 1140
agtgccagtg tgaggaaggc ttccagctgg acccccacac gaaggcctgc aaggctgtgg 1200
gctccatcgc ctacctcttc ttcaccaacc ggcacgaggt caggaagatg acgctggacc 1260
ggagcgagta caccagcctc atccccaacc tgaggaacgt ggtcgctctg gacacggagg 1320
tggccagcaa tagaatctac tggtctgacc tgtcccagag aatgatctgc agcacccagc 1380
ttgacagagc ccacggcgtc tcttcctatg acaccgtcat cagcagggac atccaggccc 1440
ccgacgggct ggctgtggac tggatccaca gcaacatcta ctggaccgac tctgtcctgg 1500
gcactgtctc tgttgcggat accaagggcg tgaagaggaa aacgttattc agggagaacg 1560
gctccaagcc aagggccatc gtggtggatc ctgttcatgg cttcatgtac tggactgact 1620
ggggaactcc cgccaagatc aagaaagggg gcctgaatgg tgtggacatc tactcgctgg 1680
tgactgaaaa cattcagtgg cccaatggca tcaccctaga tctcctcagt ggccgcctct 1740
actgggttga ctccaaactt cactccatct caagcatcga tgtcaacggg ggcaaccgga 1800
agaccatctt ggaggatgaa aagaggctgg cccacccctt ctccttggcc gtctttgagg 1860
acaaagtatt ttggacagat atcatcaacg aagccatttt cagtgccaac cgcctcacag 1920
gttccgatgt caacttgttg gctgaaaacc tactgtcccc agaggatatg gttctcttcc 1980
acaacctcac ccagccaaga ggagtgaact ggtgtgagag gaccaccctg agcaatggcg 2040
gctgccagta tctgtgcctc cctgccccgc agatcaaccc ccactcgccc aagtttacct 2100
gcgcctgccc ggacggcatg ctgctggcca gggacatgag gagctgcctc acagaggctg 2160
aggctgcagt ggccacccag gagacatcca ccgtcaggct aaaggtcagc tccacagccg 2220
taaggacaca gcacacaacc acccggcctg ttcccgacac ctcccggctg cctggggcca 2280
cccctgggct caccacggtg gagatagtga caatgtctca ccaagctctg ggcgacgttg 2340
ctggcagagg aaatgagaag aagcccagta gcgtgagggc tctgtccatt gtcctcccca 2400
tcgtgctcct cgtcttcctt tgcctggggg tcttccttct atggaagaac tggcggctta 2460
agaacatcaa cagcatcaac tttgacaacc ccgtctatca gaagaccaca gaggatgagg 2520
tccacatttg ccacaaccag gacggctaca gctacccctc gagacagatg gtcagtctgg 2580
aggatgacgt ggcgtgaaca 2600

<210> SEQ ID NO 30
<211> LENGTH: 2583
<212> TYPE: DNA
<213> ORGANISM: homo sapien

<400> SEQUENCE: 30
atggggccct ggggctggaa attgcgctgg accgtcgcct tgctcctcgc cgcggcgggg 60
actgcagtgg gcgacagatg tgaaagaaac gagttccagt gccaagacgg gaaatgcatc 120
tcctacaagt gggtctgcga tggcagcgct gagtgccagg atggctctga tgagtcccag 180
gagacgtgct tgtctgtcac ctgcaaatcc ggggacttca gctgtggggg ccgtgtcaac 240
cgctgcattc ctcagttctg gaggtgcgat ggccaagtgg actgcgacaa cggctcagac 300
gagcaaggct gtcccccaa gacgtgctcc caggacgagt ttcgctgcca cgatgggaag 360
tgcatctctc ggcagttcgt ctgtgactca gaccgggact gcttggacgg ctcagacgag 420
gcctcctgcc cggtgctcac ctgtggtccc gccagcttcc agtgcaacag ctccacctgc 480
atcccccagc tgtgggcctg cgacaacgac cccgactgcg aagatggctc ggatgagtgg 540
ccgcagcgct gtaggggtct ttacgtgttc caaggggaca gtagcccctg ctcggccttc 600
gagttccact gcctaagtgg cgagtgcatc cactccagct ggcgctgtga tggtggcccc 660
gactgcaagg acaaatctga cgaggaaaac tgcgctgtgg ccacctgtcg ccctgacgaa 720
ttccagtgct ctgatggaaa ctgcatccat ggcagccggc agtgtgaccg ggaatatgac 780
tgcaaggaca tgagcgatga agttggctgc gttaatgtga cactctgcga gggacccaac 840
aagttcaagt gtcacagcgg cgaatgcatc accctggaca aagtctgcaa catggctaga 900
gactgccggg actggtcaga tgaacccatc aaagagtgcg ggaccaacga atgcttggac 960
aacaacggcg gctgttccca cgtctgcaat gaccttaaga tcggctacga gtgcctgtgc 1020
cccgacggct tccagctggt ggcccagcga agatgcgaag atatcgatga gtgtcaggat 1080
cccgacacct gcagccagct ctgcgtgaac ctggagggtg gctacaagtg ccagtgtgag 1140
gaaggcttcc agctggaccc ccacacgaag gcctgcaagg ctgtgggctc catcgcctac 1200
ctcttcttca ccaaccggca cgaggtcagg aagatgacgc tggaccggag cgagtacacc 1260
agcctcatcc ccaacctgag gaacgtggtc gctctggaca cggaggtggc cagcaataga 1320
atctactggt ctgacctgtc ccagagaatg atctgcagca cccagcttga cagagcccac 1380
ggcgtctctt cctatgacac cgtcatcagc agggacatcc aggcccccga cgggctggct 1440
gtggactgga tccacagcaa catctactgg accgactctg tcctgggcac tgtctctgtt 1500
gcggatacca agggcgtgaa gaggaaaacg ttattcaggg agaacggctc caagccaagg 1560
gccatcgtgg tggatcctgt tcatggcttc atgtactgga ctgactgggg aactcccgcc 1620
aagatcaaga aagggggcct gaatggtgtg gacatctact cgctggtgac tgaaaacatt 1680
cagtggccca atggcatcac cctagatctc ctcagtggcc gcctctactg ggttgactcc 1740
aaacttcact ccatctcaag catcgatgtc aatgggggca accggaagac catcttggag 1800

-continued gatgaaaaga ggctggccca ccccttctcc ttggccgtct ttgaggacaa agtattttgg 1860
acagatatca tcaacgaagc cattttcagt gccaaccgcc tcacaggttc cgatgtcaac 1920
ttgttggctg aaaacctact gtccccagag gatatggtcc tcttccacaa cctcacccag 1980
ccaagaggag tgaactggtg tgagaggacc accctgagca atggcggctg ccagtatctg 2040
tgcctccctg ccccgcagat caacccccac tcgcccaagt ttacctgcgc ctgcccggac 2100
ggcatgctgc tggccaggga catgaggagc tgcctcacag aggctgaggc tgcagtggcc 2160
acccaggaga catccaccgt caggctaaag gtcagctcca cagccgtaag gacacagcac 2220
acaaccaccc ggcctgttcc cgacacctcc cggctgcctg ggccaccccc tgggctcacc 2280
acggtggaga tagtgacaat gtctcaccaa gctctgggcg acgttgctgg cagaggaaat 2340
gagaagaagc ccagtagcgt gagggctctg tccattgtcc tccccatcgt gctcctcgtc 2400
ttcctttgcc tgggggtctt ccttctatgg aagaactggc ggcttaagaa catcaacagc 2460
atcaactttg acaaccccgt ctatcagaag accacagagg atgaggtcca catttgccac 2520
aaccaggacg gctacagcta cccctcgaga cagatggtca gtctggagga tgacgtggcg 2580
tag 2583

<210> SEQ ID NO 31
<211> LENGTH: 5356
<212> TYPE: DNA
<213> ORGANISM: homo sapien

<400> SEQUENCE: 31
gaggggaggc ctggcgttcc tccgcggttc ctgtcacaaa ggcgacgaca agtcccgggt 60
ccccggagcc gcctccgcga catacacgag tcgccctccg ttatcctggg ccctcctggc 120
gaagtccccg gtttccgctg tgctctgtgg cgacacctcc gtccccacct tgtcctgggg 180
ggcgccctcg ccccaccagc cccgatcaag ttcacagagg ggcccccggc caccctcaag 240
gcctcggttc cttacgaggt tgaaacgttg cctcagaatc tccccgcccc tccttggtct 300
gcagccgaga tcttcagcca cgtgggcgac agatgcgaaa gaaacgagtt ccagtgccaa 360
gacgggaaat gcatctccta caagtgggtc tgcgatggca gcgctgagtg ccaggatggc 420
tctgatgagt cccaggagac gtgcttgtct gtcacctgca aatccgggga cttcagctgt 480
gggggccgtg tcaaccgctg cattcctcag ttctggaggt gcgatggcca agtggactgc 540
gacaacggct cagacgagca aggctgtccc cccaagacgt gctcccagga cgagtttcgc 600
tgccacgatg ggaagtgcat ctctcggcag ttcgtctgtg actcagaccg ggactgcttg 660
gacggctcag acgaggcctc ctgcccggtg ctcacctgtg gtcccgccag cttccagtgc 720
aacagctcca cctgcatccc ccagctgtgg gcctgcgaca acgaccccga ctgcgaagat 780
ggctcggatg agtggccgca gcgctgtagg ggtctttacg tgttccaagg ggacagtagc 840
ccctgctcgg ccttcgagtt ccactgccta agtggcgagt gcatccactc cagctggcgc 900
tgtgatggtg gccccgactg caaggacaaa tctgacgagg aaaactgcgc tgtggccacc 960
tgtcgccctg acgaattcca gtgctctgat ggaaactgca tccatggcag ccggcagtgt 1020
gaccgggaat atgactgcaa ggacatgagc gatgaagttg gctgcgttaa tgtgacactc 1080
tgcgagggac ccaacaagtt caagtgtcac agcggcgaat gcatcaccct ggacaaagtc 1140
tgcaacatgg ctagagactg ccgggactgg tcagatgaac ccatcaaaga gtgcgggacc 1200
aacgaatgct tggacaacaa cggcggctgt tcccacgtct gcaatgacct taagatcggc 1260
tacgagtgcc tgtgccccga cggcttccag ctggtggccc agcgaagatg cgaagatatc 1320

-continued

```
gatgagtgtc aggatcccga cacctgcagc cagctctgcg tgaacctgga gggtggctac   1380
aagtgccagt gtgaggaagg cttccagctg gacccccaca cgaaggcctg caaggctgtg   1440
ggctccatcg cctacctctt cttcaccaac cggcacgagg tcaggaagat gacgctggac   1500
cggagcgagt acaccagcct catccccaac ctgaggaacg tggtcgctct ggacacggag   1560
gtggccagca atagaatcta ctggtctgac ctgtcccaga gaatgatctg cagcacccag   1620
cttgacagag cccacggcgt ctcttcctat gacaccgtca tcagcaggga catccaggcc   1680
cccgacgggc tggctgtgga ctggatccac agcaacatct actggaccga ctctgtcctg   1740
ggcactgtct ctgttgcgga taccaagggc gtgaagagga aaacgttatt cagggagaac   1800
ggctccaagc caagggccat cgtggtggat cctgttcatg gcttcatgta ctggactgac   1860
tggggaactc ccgccaagat caagaaaggg ggcctgaatg gtgtggacat ctactcgctg   1920
gtgactgaaa acattcagtg gcccaatggc atcaccctag atctcctcag tggccgcctc   1980
tactgggttg actccaaact tcactccatc tcaagcatcg atgtcaatgg gggcaaccgg   2040
aagaccatct tggaggatga aaagaggctg gcccacccct tctccttggc cgtctttgag   2100
gacaaagtat tttggacaga tatcatcaac gaagccattt tcagtgccaa ccgcctcaca   2160
ggttccgatg tcaacttgtt ggctgaaaac ctactgtccc cagaggatat ggtcctcttc   2220
cacaacctca cccagccaag aggagtgaac tggtgtgaga ggaccaccct gagcaatggc   2280
ggctgccagt atctgtgcct ccctgccccg cagatcaacc cccactcgcc caagtttacc   2340
tgcgcctgcc cggacggcat gctgctggcc agggacatga ggagctgcct cacagaggct   2400
gaggctgcag tggccaccca ggagacatcc accgtcaggc taaaggtcag ctccacagcc   2460
gtaaggacac agcacacaac cacccggcct gttcccgaca cctcccggct gcctggggcc   2520
acccctgggc tcaccacggt ggggatagtg acaatgtctc accaagctct gggcgacgtt   2580
gctggcagag gaaatgagaa gaagcccagt agcgtgaggg ctctgtccat tgtcctcccc   2640
atcgtgctcc tcgtcttcct ttgcctgggg gtcttccttc tatggaagaa ctggcggctt   2700
aagaacatca acagcatcaa ctttgacaac cccgtctatc agaagaccac agaggatgag   2760
gtccacattt gccacaacca ggacggctac agctacccct cgagacagat ggtcagtctg   2820
gaggatgacg tggcgtgaac atctgcctgg agtcccgtcc ctgcccagaa cccttcctga   2880
gacctcgccg gccttgtttt attcaaagac agagaagacc aaagcattgc ctgccagagc   2940
tttgttttat atatttattc atctgggagg cagaacaggc ttcggacagt gcccatgcaa   3000
tggcttgggt tgggattttg gtttcttcct ttcctcgtga aggataagag aaacaggccc   3060
ggggggacca ggatgacacc tccatttctc tccaggaagt tttgagtttc tctccaccgt   3120
gacacaatcc tcaaacatgg aagatgaaag ggcaggggat gtcaggccca gagaagcaag   3180
tggctttcaa cacacaacag cagatggcac caacgggacc ccctggccct gcctcatcca   3240
ccaatctcta agccaaaccc ctaaactcag gagtcaacgt gtttacctct tctatgcaag   3300
ccttgctaga cagccaggtt agcctttgcc ctgtcacccc cgaatcatga cccacccagt   3360
gtctttcgag gtgggtttgt accttcctta agccaggaaa gggattcatg gcgtcggaaa   3420
tgatctggct gaatccgtgg tggcaccgag accaaactca ttcaccaaat gatgccactt   3480
cccagaggca gagcctgagt caccggtcac ccttaatatt tattaagtgc ctgagacacc   3540
cggttacctt ggccgtgagg acacgtggcc tgcacccagg tgtggctgtc aggacaccag   3600
cctggtgccc atcctcccga cccctaccca cttccattcc cgtggtctcc ttgcactttc   3660
```

-continued

```
tcagttcaga gttgtacact gtgtacattt ggcatttgtg ttattatttt gcactgtttt   3720

ctgtcgtgtg tgttgggatg ggatcccagg ccagggaaag cccgtgtcaa tgaatgccgg   3780

ggacagagag gggcaggttg accgggactt caaagccgtg atcgtgaata tcgagaactg   3840

ccattgtcgt ctttatgtcc gcccacctag tgcttccact tctatgcaaa tgcctccaag   3900

ccattcactt ccccaatctt gtcgttgatg ggtatgtgtt taaaacatgc acggtgaggc   3960

cgggcgcagt ggctcacgcc tgtaatccca gcactttggg aggccgaggc gggtggatca   4020

tgaggtcagg agatcgagac catcctggct aacaaggtga aaccccgtct ctactaaaaa   4080

tacaaaaaat tagccgggcg cggtggtggg cacctgtagt cccagctact cgggaggctg   4140

aggcaggaga atggtgtgaa cccgggaagc ggagcttgca gtgagccgag attgcgccac   4200

tgcagtccgc agtctggcct gggcgacaga gcgagactcc gtctcaaaaa aaaaaaaacaa   4260

aaaaaaacca tgcatggtgc atcagcagcc catggcctct ggccaggcat ggcgaggctg   4320

aggtgggagg atggtttgag ctcaggcatt tgaggctgtc gtgagctatg attatgccac   4380

tgctttccag cctgggcaac atagtaagac cccatctctt aaaaaatgaa tttggccaga   4440

cacaggtgcc tcacgcctgt aatcccagca ctttgggagg ctgagctgga tcacttgagt   4500

tcaggagttg gagaccaggc ctgagcaaca aagcgagatc ccatctctac aaaaaccaaa   4560

aagttaaaaa tcagctgggt atggtggcac gtgcctgtga tcccagctac ttgggaggct   4620

gaggcaggag gatcgcctga gcccaggagg tggaggttgc agtgagccat gatcgagcca   4680

ctgcactcca gcctgggcaa cagatgaaga ccctatttca gaaatacaac tataaaaaaa   4740

taaataaatc ctccagtctg gatcgtttga cgggacttca ggttctttct gaaatcgccg   4800

tgttactgtt gcactgatgt ccggagagac agtgacagcc tccgtcagac tcccgcgtga   4860

agatgtcaca agggattggc aattgtcccc agggacaaaa cactgtgtcc cccccagtgc   4920

agggaaccgt gataagcctt tctggtttcg gagcacgtaa atgcgtccct gtacagatag   4980

tggggatttt ttgttatgtt tgcactttgt atattggttg aaactgttat cacttatata   5040

tatatataca cacatatata taaaatctat ttatttttgc aaaccctggt tgctgtattt   5100

gttcagtgac tattctcggg gccctgtgta gggggttatt gcctctgaaa tgcctcttct   5160

ttatgtacaa agattatttg cacgaactgg actgtgtgca acgcttttttg ggagaatgat   5220

gtccccgttg tatgtatgag tggcttctgg gagatgggtg tcacttttta aaccactgta   5280

tagaaggttt ttgtagcctg aatgtcttac tgtgatcaat taaatttctt aaaagaaaaa   5340

aaaaaaaaaa aaaaca                                                 5356
```

<210> SEQ ID NO 32
<211> LENGTH: 3635
<212> TYPE: DNA
<213> ORGANISM: homo sapien

<400> SEQUENCE: 32

```
ttgcgacgtc gaggcgctca tggttgcagg cgggcgccgc cgttcagttc agggtctgag     60

cctggaggag tgagccaggc agtgagactg gctcgggcgg gccgggacgc gtcgttgcag    120

cagcggctcc cagctcccag ccaggattcc gcgcgcccct tcacgcgccc tgctcctgaa    180

cttcagctcc tgcacagtcc tccccaccgc aaggctcaag gcgccgccgg cgtggaccgc    240

gcacggcctc taggtctcct cgccaggaca gcaacctctc ccctggccct catgggcacc    300

gtcagctcca ggcggtcctg gtggccgctg ccactgctgc tgctgctgct gctgctcctg    360

ggtcccgcgg gcgcccgtgc gcaggaggac gaggacggcg actacgagga gctggtgcta    420
```

-continued

```
gccttgcttt ccgaggagga cggcctggcc gaagcacccg agcacggaac cacagccacc    480
ttccaccgct gcgccaagga tccgtggagg ttgcctggca cctacgtggt ggtgctgaag    540
gaggagaccc acctctcgca gtcagagcgc actgcccgcc gcctgcaggc ccaggctgcc    600
cgccggggat acctcaccaa gatcctgcat gtcttccatg gccttcttcc tggcttcctg    660
gtgaagatga gtggcgacct gctggagctg gccttgaagt tgccccatgt cgactacatc    720
gaggaggact cctctgtctt tgcccagagc atcccgtgga acctggagcg gattacccct    780
ccacggtacc gggcggatga ataccagccc cccgacggag gcagcctggt ggaggtgtat    840
ctcctagaca ccagcataca gagtgaccac cgggaaatcg agggcagggt catggtcacc    900
gacttcgaga atgtgcccga ggaggacggg acccgcttcc acagacaggc cagcaagtgt    960
gacagtcatg gcacccacct ggcaggggtg gtcagcggcc gggatgccgg cgtggccaag   1020
ggtgccagca tgcgcagcct gcgcgtgctc aactgccaag ggaagggcac ggttagcggc   1080
accctcatag gcctggagtt tattcggaaa agccagctgg tccagcctgt ggggccactg   1140
gtggtgctgc tgcccctggc gggtgggtac agccgcgtcc tcaacgccgc ctgccagcgc   1200
ctggcgaggg ctggggtcgt gctggtcacc gctgccggca acttccggga cgatgcctgc   1260
ctctactccc cagcctcagc tcccgaggtc atcacagttg gggccaccaa tgcccaggac   1320
cagccggtga ccctggggac tttggggacc aactttggcc gctgtgtgga cctctttgcc   1380
ccaggggagg acatcattgg tgcctccagc gactgcagca cctgctttgt gtcacagagt   1440
gggacatcac aggctgctgc ccacgtggct ggcattgcag ccatgatgct gtctgccgag   1500
ccggagctca ccctggccga gttgaggcag agactgatcc acttctctgc caaagatgcc   1560
atcaatgagg cctggttccc tgaggaccag cgggtactga cccccaacct ggtggccgcc   1620
ctgcccccca gcacccatgg ggcaggttgg cagctgtttt gcaggactgt gtggtcagca   1680
cactcggggc ctacacggat ggccacagcc atcgcccgct gcgccccaga tgaggagctg   1740
ctgagctgct ccagtttctc caggagtgga agcggcgggg cgagcgcatg gaggcccaag   1800
ggggcaagct ggtctgccgg gcccacaacg cttttggggg tgagggtgtc tacgccattg   1860
ccaggtgctg cctgctaccc caggccaact gcagcgtcca cacagctcca ccagctgagg   1920
ccagcatggg gacccgtgtc cactgccacc aacagggcca cgtcctcaca ggctgcagct   1980
cccactggga ggtggaggac cttggcaccc acaagccgcc tgtgctgagg ccacgaggtc   2040
agcccaacca gtgcgtgggc cacagggagg ccagcatcca cgcttcctgc tgccatgccc   2100
caggtctgga atgcaaagtc aaggagcatg gaatcccggc ccctcaggag caggtgaccg   2160
tggcctgcga ggagggctgg accctgactg gctgcagtgc cctccctggg acctcccacg   2220
tcctgggggc ctacgccgta gacaacacgt gtgtagtcag gagccgggac gtcagcacta   2280
caggcagcac cagcgaagag gccgtgacag ccgttgccat ctgctgccgg agccggcacc   2340
tggcgcaggc ctcccaggag ctccagtgac agccccatcc caggatgggt gtctggggag   2400
ggtcaagggc tggggctgag ctttaaaatg gttccgactt gtccctctct cagccctcca   2460
tggcctggca cgaggggatg gggatgcttc cgccttcccg gggctgctgg cctggccctt   2520
gagtggggca gcctccttgc ctggaactca ctcactctgg gtgcctcctc cccaggtgga   2580
ggtgccagga agctccctcc ctcactgtgg ggcatttcac cattcaaaca ggtcgagctg   2640
tgctcgggtg ctgccagctg ctcccaatgt gccgatgtcc gtgggcagaa tgacttttat   2700
tgagctcttg ttccgtgcca ggcattcaat cctcaggtct ccaccaagga ggcaggattc   2760
```

ttcccatgga taggggaggg ggcggtaggg gctgcaggga caaacatcgt tggggggtga 2820
gtgtgaaagg tgctgatggc cctcatctcc agctaactgt ggagaagccc ctgggggctc 2880
cctgattaat ggaggcttag ctttctggat ggcatctagc cagaggctgg agacaggtgt 2940
gcccctggtg gtcacaggct gtgccttggt ttcctgagcc acctttactc tgctctatgc 3000
caggctgtgc tagcaacacc caaaggtggc ctgcggggag ccatcaccta ggactgactc 3060
ggcagtgtgc agtggtgcat gcactgtctc agccaacccg ctccactacc cggcagggta 3120
cacattcgca cccctacttc acagaggaag aaacctggaa ccagaggggg cgtgcctgcc 3180
aagctcacac agcaggaact gggccagaaa cgcagattgg gctggctctg aagccaagcc 3240
tcttcttact tcacccggct gggctcctca tttttacggg taacagtgag gctgggaagg 3300
ggaacacaga ccaggaagct cggtgagtga tggcagaacg atgcctgcag gcatggaact 3360
ttttccgtta tcacccaggc ctgattcact ggcctggcgg agatgcttct aaggcatggt 3420
cgggggagag ggccaacaac tgtccctcct tgagcaccag ccccacccaa gcaagcagac 3480
atttatcttt tgggtctgtc ctctctgttg cctttttaca gccaactttt ctagacctgt 3540
tttgcttttg taacttgaag atatttattc tgggttttgt agcattttta ttaatatggt 3600
gactttttaa aataaaaaca aacaaacgtt gtcct 3635

<210> SEQ ID NO 33
<211> LENGTH: 1101
<212> TYPE: DNA
<213> ORGANISM: homo sapien

<400> SEQUENCE: 33
aggctcaagg cgccgccggc gtggaccgcg cacggcctct aggtctcctc gccaggacag 60
caacctctcc cctggccctc atgggcaccg tcagctccag gcggtcctgg tggccgctgc 120
cactgctgct gctgctgctg ctgctcctgg gtcccgcggg cgcccgtgcg caggaggacg 180
aggacggcga ctacgaggag ctggtgctag ccttgctttc cgaggaggac ggcctggccg 240
aagcacccga gcacggaacc acagccacct tccaccgctg cgccaaggat ccgtggaggt 300
tgcctggcac ctacgtggtg gtgctgaagg aggagaccca cctctcgcag tcagagcgca 360
ctgcccgccg cctgcaggcc caggctgccc gccggggata cctcaccaag atcctgcatg 420
tcttccatgg ccttcttcct ggcttcctgg tgaagatgag tggcgacctg ctggagctgg 480
ccttgaagtt gccccatgtc gactacatcg aggaggactc ctctgtcttt gcccagagca 540
tcccgtggaa cctggagcgg attacccctc cacggtaccg ggcggatgaa taccagcccc 600
ccgcatattt ggaggatcac tgcgggggcc acagaggtgc tgttcagatg gcacttcaga 660
agactcagga gaccctgggg caggagcagt ttgactgaca gcccagaggg ctgccctctg 720
attccacctg aggccctgct tttcctggct gcaggggttc cagggccagg ccatttccgc 780
tggcgcagga ctctgctagc agcaacctgc ctgaagtctt cctttggcct ggctgagagt 840
ttctgagacc tgcgctggag cggagacgga ggcagcctgg tggaggtgta tctcctagac 900
accagcatac agagtgacca ccgggaaatc gagggcaggg tcatggtcac cgacttcgag 960
aatgtgcccg aggaggacgg gacccgcttc cacagacagg ccagcaagtg tgacagtcat 1020
ggcacccacc tggcaggggt ggtcagcggc cgggatgccg gcgtggccaa gggtgccagc 1080
atgcgcagcc tgcgcgtgct c 1101

<210> SEQ ID NO 34
<211> LENGTH: 2079

<212> TYPE: DNA
<213> ORGANISM: homo sapien

<400> SEQUENCE: 34
atgggcaccg tcagctccag gcggtcctgg tggccgctgc cactgctgct gctgctgctg 60
ctgctcctgg gtcccgcggg cgcccgtgcg caggaggacg aggacggcga ctacgaggag 120
ctggtgctag ccttgctttc cgaggaggac ggcctggccg aagcacccga gcacggaacc 180
acagccacct tccaccgctg cgccaaggat ccgtggaggt tgcctggcac ctacgtggtg 240
gtgctgaagg aggagaccca cctctcgcag tcagagcgca ctgcccgccg cctgcaggcc 300
caggctgccc gccggggata cctcaccaag atcctgcatg tcttccatgg ccttcttcct 360
ggcttcctgg tgaagatgag tggcgacctg ctggagctgg ccttgaagtt gccccatgtc 420
gactacatcg aggaggactc ctctgtcttt gcccagagca tcccgtggaa cctggagcgg 480
attacccctc cacggtaccg ggcggatgaa taccagcccc ccgacggagg cagcctggtg 540
gaggtgtatc tcctagacac cagcatacag agtgaccacc gggaaatcga gggcagggtc 600
atggtcaccg acttcgagaa tgtgcccgag gaggacggga cccgcttcca cagacaggcc 660
agcaagtgtg acagtcatgg cacccacctg gcaggggtgg tcagcggccg ggatgccggc 720
gtggccaagg gtgccagcat gcgcagcctg cgcgtgctca actgccaagg gaagggcacg 780
gttagcggca ccctcatagg cctggagttt attcggaaaa gccagctggt ccagcctgtg 840
gggccactgg tggtgctgct gcccctggcg ggtgggtaca gccgcgtcct caacgccgcc 900
tgccagcgcc tggcgagggc tggggtcgtg ctggtcaccg ctgccggcaa cttccgggac 960
gatgcctgcc tctactcccc agcctcagct cccgaggtca tcacagttgg ggccaccaat 1020
gcccaggacc agccggtgac cctggggact ttggggacca actttggccg ctgtgtggac 1080
ctctttgccc caggggagga catcattggt gcctccagcg actgcagcac ctgctttgtg 1140
tcacagagtg ggacatcaca ggctgctgcc cacgtggctg gcattgcagc catgatgctg 1200
tctgccgagc cggagctcac cctggccgag ttgaggcaga gactgatcca cttctctgcc 1260
aaagatgtca tcaatgaggc ctggttccct gaggaccagc gggtactgac ccccaacctg 1320
gtggccgccc tgccccccag cacccatggg gcaggttggc agctgttttg caggactgtg 1380
tggtcagcac actcggggcc tacacggatg gccacagcca tcgcccgctg cgccccagat 1440
gaggagctgc tgagctgctc cagtttctcc aggagtggga agcggcgggg cgagcgcatg 1500
gaggcccaag gggcaagct ggtctgccgg gcccacaacg cttttggggg tgagggtgtc 1560
tacgccattg ccaggtgctg cctgctaccc caggccaact gcagcgtcca cacagctcca 1620
ccagctgagg ccagcatggg gacccgtgtc cactgccacc aacagggcca cgtcctcaca 1680
ggctgcagct cccactggga ggtggaggac cttggcaccc acaagccgcc tgtgctgagg 1740
ccacgaggtc agcccaacca gtgcgtgggc cacagggagg ccagcatcca cgcttcctgc 1800
tgccatgccc caggtctgga atgcaaagtc aaggagcatg gaatcccggc ccctcaggag 1860
caggtgaccg tggcctgcga ggagggctgg accctgactg gctgcagtgc cctccctggg 1920
acctcccacg tcctgggggc ctacgccgta gacaacacgt gtgtagtcag gagccgggac 1980
gtcagcacta caggcagcac cagcgaagag gccgtgacag ccgttgccat ctgctgccgg 2040
agccggcacc tggcgcaggc ctcccaggag ctccagtga 2079

<210> SEQ ID NO 35
<211> LENGTH: 692
<212> TYPE: PRT

<213> ORGANISM: homo sapien

<400> SEQUENCE: 35

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400
```

```
Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690


<210> SEQ ID NO 36
<211> LENGTH: 800
<212> TYPE: PRT
<213> ORGANISM: homo sapien

<400> SEQUENCE: 36

Glu Thr Cys Leu Ser Val Thr Cys Lys Ser Gly Asp Phe Ser Cys Gly
1               5                   10                  15

Gly Arg Val Asn Arg Cys Ile Pro Gln Phe Trp Arg Cys Asp Gly Gln
            20                  25                  30

Val Asp Cys Asp Asn Gly Ser Asp Glu Gln Gly Cys Pro Pro Lys Thr
        35                  40                  45

Cys Ser Gln Asp Glu Phe Arg Cys His Asp Gly Lys Cys Ile Ser Arg
    50                  55                  60

Gln Phe Val Cys Asp Ser Asp Arg Asp Cys Leu Asp Gly Ser Asp Glu
65                  70                  75                  80
```

-continued

```
Ala Ser Cys Pro Val Leu Thr Cys Gly Pro Ala Ser Phe Gln Cys Asn
                85                  90                  95

Ser Ser Thr Cys Ile Pro Gln Leu Trp Ala Cys Asp Asn Asp Pro Asp
            100                 105                 110

Cys Glu Asp Gly Ser Asp Glu Trp Pro Gln Arg Cys Arg Gly Leu Tyr
        115                 120                 125

Val Phe Gln Gly Asp Ser Ser Pro Cys Ser Ala Phe Glu Phe His Cys
    130                 135                 140

Leu Ser Gly Glu Cys Ile His Ser Ser Trp Arg Cys Asp Gly Gly Pro
145                 150                 155                 160

Asp Cys Lys Asp Lys Ser Asp Glu Glu Asn Cys Ala Val Ala Thr Cys
                165                 170                 175

Arg Pro Asp Glu Phe Gln Cys Ser Asp Gly Asn Cys Ile His Gly Ser
            180                 185                 190

Arg Gln Cys Asp Arg Glu Tyr Asp Cys Lys Asp Met Ser Asp Glu Val
        195                 200                 205

Gly Cys Val Asn Val Thr Leu Cys Glu Gly Pro Asn Lys Phe Lys Cys
    210                 215                 220

His Ser Gly Glu Cys Ile Thr Leu Asp Lys Val Cys Asn Met Ala Arg
225                 230                 235                 240

Asp Cys Arg Asp Trp Ser Asp Glu Pro Ile Lys Glu Cys Gly Thr Asn
                245                 250                 255

Glu Cys Leu Asp Asn Asn Gly Gly Cys Ser His Val Cys Asn Asp Leu
            260                 265                 270

Lys Ile Gly Tyr Glu Cys Leu Cys Pro Asp Gly Phe Gln Leu Val Ala
        275                 280                 285

Gln Arg Arg Cys Glu Asp Ile Asp Glu Cys Gln Asp Pro Asp Thr Cys
    290                 295                 300

Ser Gln Leu Cys Val Asn Leu Glu Gly Gly Tyr Lys Cys Gln Cys Glu
305                 310                 315                 320

Glu Gly Phe Gln Leu Asp Pro His Thr Lys Ala Cys Lys Ala Val Gly
                325                 330                 335

Ser Ile Ala Tyr Leu Phe Phe Thr Asn Arg His Glu Val Arg Lys Met
            340                 345                 350

Thr Leu Asp Arg Ser Glu Tyr Thr Ser Leu Ile Pro Asn Leu Arg Asn
        355                 360                 365

Val Val Ala Leu Asp Thr Glu Val Ala Ser Asn Arg Ile Tyr Trp Ser
    370                 375                 380

Asp Leu Ser Gln Arg Met Ile Cys Ser Thr Gln Leu Asp Arg Ala His
385                 390                 395                 400

Gly Val Ser Ser Tyr Asp Thr Val Ile Ser Arg Asp Ile Gln Ala Pro
                405                 410                 415

Asp Gly Leu Ala Val Asp Trp Ile His Ser Asn Ile Tyr Trp Thr Asp
            420                 425                 430

Ser Val Leu Gly Thr Val Ser Val Ala Asp Thr Lys Gly Val Lys Arg
        435                 440                 445

Lys Thr Leu Phe Arg Glu Asn Gly Ser Lys Pro Arg Ala Ile Val Val
    450                 455                 460

Asp Pro Val His Gly Phe Met Tyr Trp Thr Asp Trp Gly Thr Pro Ala
465                 470                 475                 480

Lys Ile Lys Lys Gly Gly Leu Asn Gly Val Asp Ile Tyr Ser Leu Val
                485                 490                 495
```

```
Thr Glu Asn Ile Gln Trp Pro Asn Gly Ile Thr Leu Asp Leu Leu Ser
            500                 505                 510

Gly Arg Leu Tyr Trp Val Asp Ser Lys Leu His Ser Ile Ser Ser Ile
        515                 520                 525

Asp Val Asn Gly Gly Asn Arg Lys Thr Ile Leu Glu Asp Glu Lys Arg
    530                 535                 540

Leu Ala His Pro Phe Ser Leu Ala Val Phe Glu Asp Lys Val Phe Trp
545                 550                 555                 560

Thr Asp Ile Ile Asn Glu Ala Ile Phe Ser Ala Asn Arg Leu Thr Gly
                565                 570                 575

Ser Asp Val Asn Leu Leu Ala Glu Asn Leu Leu Ser Pro Glu Asp Met
            580                 585                 590

Val Leu Phe His Asn Leu Thr Gln Pro Arg Gly Val Asn Trp Cys Glu
        595                 600                 605

Arg Thr Thr Leu Ser Asn Gly Gly Cys Gln Tyr Leu Cys Leu Pro Ala
    610                 615                 620

Pro Gln Ile Asn Pro His Ser Pro Lys Phe Thr Cys Ala Cys Pro Asp
625                 630                 635                 640

Gly Met Leu Leu Ala Arg Asp Met Arg Ser Cys Leu Thr Glu Ala Glu
                645                 650                 655

Ala Ala Val Ala Thr Gln Glu Thr Ser Thr Val Arg Leu Lys Val Ser
            660                 665                 670

Ser Thr Ala Val Arg Thr Gln His Thr Thr Thr Arg Pro Val Pro Asp
        675                 680                 685

Thr Ser Arg Leu Pro Gly Ala Thr Pro Gly Leu Thr Thr Val Glu Ile
    690                 695                 700

Val Thr Met Ser His Gln Ala Leu Gly Asp Val Ala Gly Arg Gly Asn
705                 710                 715                 720

Glu Lys Lys Pro Ser Ser Val Arg Ala Leu Ser Ile Val Leu Pro Ile
                725                 730                 735

Val Leu Leu Val Phe Leu Cys Leu Gly Val Phe Leu Leu Trp Lys Asn
            740                 745                 750

Trp Arg Leu Lys Asn Ile Asn Ser Ile Asn Phe Asp Asn Pro Val Tyr
        755                 760                 765

Gln Lys Thr Thr Glu Asp Glu Val His Ile Cys His Asn Gln Asp Gly
    770                 775                 780

Tyr Ser Tyr Pro Ser Arg Gln Met Val Ser Leu Glu Asp Asp Val Ala
785                 790                 795                 800


<210> SEQ ID NO 37
<211> LENGTH: 682
<212> TYPE: PRT
<213> ORGANISM: homo sapien

<400> SEQUENCE: 37

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80
```

-continued

```
Arg Cys Ile Pro Gln Phe Trp Arg Cys Asp Gly Gln Val Asp Cys Asp
                85                  90                  95

Asn Gly Ser Asp Glu Gln Gly Cys Pro Val Ala Thr Cys Arg Pro Asp
            100                 105                 110

Glu Phe Gln Cys Ser Asp Gly Asn Cys Ile His Gly Ser Arg Gln Cys
        115                 120                 125

Asp Arg Glu Tyr Asp Cys Lys Asp Met Ser Asp Glu Val Gly Cys Val
    130                 135                 140

Asn Val Thr Leu Cys Glu Gly Pro Asn Lys Phe Lys Cys His Ser Gly
145                 150                 155                 160

Glu Cys Ile Thr Leu Asp Lys Val Cys Asn Met Ala Arg Asp Cys Arg
                165                 170                 175

Asp Trp Ser Asp Glu Pro Ile Lys Glu Cys Gly Thr Asn Glu Cys Leu
            180                 185                 190

Asp Asn Asn Gly Gly Cys Ser His Val Cys Asn Asp Leu Lys Ile Gly
        195                 200                 205

Tyr Glu Cys Leu Cys Pro Asp Gly Phe Gln Leu Val Ala Gln Arg Arg
    210                 215                 220

Cys Glu Asp Ile Asp Glu Cys Gln Asp Pro Asp Thr Cys Ser Gln Leu
225                 230                 235                 240

Cys Val Asn Leu Glu Gly Gly Tyr Lys Cys Gln Cys Glu Glu Gly Phe
                245                 250                 255

Gln Leu Asp Pro His Thr Lys Ala Cys Lys Ala Val Gly Ser Ile Ala
            260                 265                 270

Tyr Leu Phe Phe Thr Asn Arg His Glu Val Arg Lys Met Thr Leu Asp
        275                 280                 285

Arg Ser Glu Tyr Thr Ser Leu Ile Pro Asn Leu Arg Asn Val Val Ala
    290                 295                 300

Leu Asp Thr Glu Val Ala Ser Asn Arg Ile Tyr Trp Ser Asp Leu Ser
305                 310                 315                 320

Gln Arg Met Ile Cys Ser Thr Gln Leu Asp Arg Ala His Gly Val Ser
                325                 330                 335

Ser Tyr Asp Thr Val Ile Ser Arg Asp Ile Gln Ala Pro Asp Gly Leu
            340                 345                 350

Ala Val Asp Trp Ile His Ser Asn Ile Tyr Trp Thr Asp Ser Val Leu
        355                 360                 365

Gly Thr Val Ser Val Ala Asp Thr Lys Gly Val Lys Arg Lys Thr Leu
    370                 375                 380

Phe Arg Glu Asn Gly Ser Lys Pro Arg Ala Ile Val Val Asp Pro Val
385                 390                 395                 400

His Gly Phe Met Tyr Trp Thr Asp Trp Gly Thr Pro Ala Lys Ile Lys
                405                 410                 415

Lys Gly Gly Leu Asn Gly Val Asp Ile Tyr Ser Leu Val Thr Glu Asn
            420                 425                 430

Ile Gln Trp Pro Asn Gly Ile Thr Leu Asp Leu Leu Ser Gly Arg Leu
        435                 440                 445

Tyr Trp Val Asp Ser Lys Leu His Ser Ile Ser Ser Ile Asp Val Asn
    450                 455                 460

Gly Gly Asn Arg Lys Thr Ile Leu Glu Asp Glu Lys Arg Leu Ala His
465                 470                 475                 480

Pro Phe Ser Leu Ala Val Phe Glu Asp Lys Val Phe Trp Thr Asp Ile
                485                 490                 495
```

```
Ile Asn Glu Ala Ile Phe Ser Ala Asn Arg Leu Thr Gly Ser Asp Val
            500                 505                 510

Asn Leu Leu Ala Glu Asn Leu Leu Ser Pro Glu Asp Met Val Leu Phe
        515                 520                 525

His Asn Leu Thr Gln Pro Arg Glu Ala Glu Ala Ala Val Ala Thr Gln
    530                 535                 540

Glu Thr Ser Thr Val Arg Leu Lys Val Ser Ser Thr Ala Val Arg Thr
545                 550                 555                 560

Gln His Thr Thr Thr Arg Pro Val Pro Asp Thr Ser Arg Leu Pro Gly
                565                 570                 575

Ala Thr Pro Gly Leu Thr Thr Val Glu Ile Val Thr Met Ser His Gln
            580                 585                 590

Ala Leu Gly Asp Val Ala Gly Arg Gly Asn Glu Lys Lys Pro Ser Ser
        595                 600                 605

Val Arg Ala Leu Ser Ile Val Leu Pro Ile Val Leu Leu Val Phe Leu
    610                 615                 620

Cys Leu Gly Val Phe Leu Leu Trp Lys Asn Trp Arg Leu Lys Asn Ile
625                 630                 635                 640

Asn Ser Ile Asn Phe Asp Asn Pro Val Tyr Gln Lys Thr Thr Glu Asp
                645                 650                 655

Glu Val His Ile Cys His Asn Gln Asp Gly Tyr Ser Tyr Pro Ser Arg
            660                 665                 670

Gln Met Val Ser Leu Glu Asp Asp Val Ala
        675                 680


<210> SEQ ID NO 38
<211> LENGTH: 692
<212> TYPE: PRT
<213> ORGANISM: homo sapien

<400> SEQUENCE: 38

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Leu Thr Leu Cys Glu Gly Pro Asn
            100                 105                 110

Lys Phe Lys Cys His Ser Gly Glu Cys Ile Thr Leu Asp Lys Val Cys
        115                 120                 125

Asn Met Ala Arg Asp Cys Arg Asp Trp Ser Asp Glu Pro Ile Lys Glu
    130                 135                 140

Cys Gly Thr Asn Glu Cys Leu Asp Asn Asn Gly Gly Cys Ser His Val
145                 150                 155                 160

Cys Asn Asp Leu Lys Ile Gly Tyr Glu Cys Leu Cys Pro Asp Gly Phe
                165                 170                 175

Gln Leu Val Ala Gln Arg Arg Cys Glu Asp Ile Asp Glu Cys Gln Asp
            180                 185                 190
```

-continued

```
Pro Asp Thr Cys Ser Gln Leu Cys Val Asn Leu Glu Gly Gly Tyr Lys
        195                 200                 205

Cys Gln Cys Glu Glu Gly Phe Gln Leu Asp Pro His Thr Lys Ala Cys
    210                 215                 220

Lys Ala Val Gly Ser Ile Ala Tyr Leu Phe Phe Thr Asn Arg His Glu
225                 230                 235                 240

Val Arg Lys Met Thr Leu Asp Arg Ser Glu Tyr Thr Ser Leu Ile Pro
                245                 250                 255

Asn Leu Arg Asn Val Val Ala Leu Asp Thr Glu Val Ala Ser Asn Arg
            260                 265                 270

Ile Tyr Trp Ser Asp Leu Ser Gln Arg Met Ile Cys Ser Thr Gln Leu
        275                 280                 285

Asp Arg Ala His Gly Val Ser Ser Tyr Asp Thr Val Ile Ser Arg Asp
    290                 295                 300

Ile Gln Ala Pro Asp Gly Leu Ala Val Asp Trp Ile His Ser Asn Ile
305                 310                 315                 320

Tyr Trp Thr Asp Ser Val Leu Gly Thr Val Ser Val Ala Asp Thr Lys
                325                 330                 335

Gly Val Lys Arg Lys Thr Leu Phe Arg Glu Asn Gly Ser Lys Pro Arg
            340                 345                 350

Ala Ile Val Val Asp Pro Val His Gly Phe Met Tyr Trp Thr Asp Trp
        355                 360                 365

Gly Thr Pro Ala Lys Ile Lys Lys Gly Gly Leu Asn Gly Val Asp Ile
    370                 375                 380

Tyr Ser Leu Val Thr Glu Asn Ile Gln Trp Pro Asn Gly Ile Thr Leu
385                 390                 395                 400

Asp Leu Leu Ser Gly Arg Leu Tyr Trp Val Asp Ser Lys Leu His Ser
                405                 410                 415

Ile Ser Ser Ile Asp Val Asn Gly Gly Asn Arg Lys Thr Ile Leu Glu
            420                 425                 430

Asp Glu Lys Arg Leu Ala His Pro Phe Ser Leu Ala Val Phe Glu Asp
        435                 440                 445

Lys Val Phe Trp Thr Asp Ile Ile Asn Glu Ala Ile Phe Ser Ala Asn
    450                 455                 460

Arg Leu Thr Gly Ser Asp Val Asn Leu Leu Ala Glu Asn Leu Leu Ser
465                 470                 475                 480

Pro Glu Asp Met Val Leu Phe His Asn Leu Thr Gln Pro Arg Gly Val
                485                 490                 495

Asn Trp Cys Glu Arg Thr Thr Leu Ser Asn Gly Gly Cys Gln Tyr Leu
            500                 505                 510

Cys Leu Pro Ala Pro Gln Ile Asn Pro His Ser Pro Lys Phe Thr Cys
        515                 520                 525

Ala Cys Pro Asp Gly Met Leu Leu Ala Arg Asp Met Arg Ser Cys Leu
    530                 535                 540

Thr Glu Ala Glu Ala Ala Val Ala Thr Gln Glu Thr Ser Thr Val Arg
545                 550                 555                 560

Leu Lys Val Ser Ser Thr Ala Val Arg Thr Gln His Thr Thr Thr Arg
                565                 570                 575

Pro Val Pro Asp Thr Ser Arg Leu Pro Gly Ala Thr Pro Gly Leu Thr
            580                 585                 590

Thr Val Glu Ile Val Thr Met Ser His Gln Ala Leu Gly Asp Val Ala
        595                 600                 605
```

```
Gly Arg Gly Asn Glu Lys Lys Pro Ser Ser Val Arg Ala Leu Ser Ile
    610                 615                 620

Val Leu Pro Ile Val Leu Leu Val Phe Leu Cys Leu Gly Val Phe Leu
625                 630                 635                 640

Leu Trp Lys Asn Trp Arg Leu Lys Asn Ile Asn Ser Ile Asn Phe Asp
                645                 650                 655

Asn Pro Val Tyr Gln Lys Thr Thr Glu Asp Glu Val His Ile Cys His
            660                 665                 670

Asn Gln Asp Gly Tyr Ser Tyr Pro Ser Arg Gln Met Val Ser Leu Glu
        675                 680                 685

Asp Asp Val Ala
    690


<210> SEQ ID NO 39
<211> LENGTH: 819
<212> TYPE: PRT
<213> ORGANISM: homo sapien

<400> SEQUENCE: 39

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Ser
    50                  55                  60

Pro Lys Thr Cys Ser Gln Asp Glu Phe Arg Cys His Asp Gly Lys Cys
65                  70                  75                  80

Ile Ser Arg Gln Phe Val Cys Asp Ser Asp Arg Asp Cys Leu Asp Gly
                85                  90                  95

Ser Asp Glu Ala Ser Cys Pro Val Leu Thr Cys Gly Pro Ala Ser Phe
            100                 105                 110

Gln Cys Asn Ser Ser Thr Cys Ile Pro Gln Leu Trp Ala Cys Asp Asn
        115                 120                 125

Asp Pro Asp Cys Glu Asp Gly Ser Asp Glu Trp Pro Gln Arg Cys Arg
    130                 135                 140

Gly Leu Tyr Val Phe Gln Gly Asp Ser Ser Pro Cys Ser Ala Phe Glu
145                 150                 155                 160

Phe His Cys Leu Ser Gly Glu Cys Ile His Ser Ser Trp Arg Cys Asp
                165                 170                 175

Gly Gly Pro Asp Cys Lys Asp Lys Ser Asp Glu Glu Asn Cys Ala Val
            180                 185                 190

Ala Thr Cys Arg Pro Asp Glu Phe Gln Cys Ser Asp Gly Asn Cys Ile
        195                 200                 205

His Gly Ser Arg Gln Cys Asp Arg Glu Tyr Asp Cys Lys Asp Met Ser
    210                 215                 220

Asp Glu Val Gly Cys Val Asn Val Thr Leu Cys Glu Gly Pro Asn Lys
225                 230                 235                 240

Phe Lys Cys His Ser Gly Glu Cys Ile Thr Leu Asp Lys Val Cys Asn
                245                 250                 255

Met Ala Arg Asp Cys Arg Asp Trp Ser Asp Glu Pro Ile Lys Glu Cys
            260                 265                 270

Gly Thr Asn Glu Cys Leu Asp Asn Asn Gly Gly Cys Ser His Val Cys
        275                 280                 285
```

Asn Asp Leu Lys Ile Gly Tyr Glu Cys Leu Cys Pro Asp Gly Phe Gln
    290                 295                 300

Leu Val Ala Gln Arg Arg Cys Glu Asp Ile Asp Glu Cys Gln Asp Pro
305                 310                 315                 320

Asp Thr Cys Ser Gln Leu Cys Val Asn Leu Glu Gly Gly Tyr Lys Cys
                325                 330                 335

Gln Cys Glu Glu Gly Phe Gln Leu Asp Pro His Thr Lys Ala Cys Lys
            340                 345                 350

Ala Val Gly Ser Ile Ala Tyr Leu Phe Phe Thr Asn Arg His Glu Val
        355                 360                 365

Arg Lys Met Thr Leu Asp Arg Ser Glu Tyr Thr Ser Leu Ile Pro Asn
    370                 375                 380

Leu Arg Asn Val Val Ala Leu Asp Thr Glu Val Ala Ser Asn Arg Ile
385                 390                 395                 400

Tyr Trp Ser Asp Leu Ser Gln Arg Met Ile Cys Ser Thr Gln Leu Asp
                405                 410                 415

Arg Ala His Gly Val Ser Ser Tyr Asp Thr Val Ile Ser Arg Asp Ile
            420                 425                 430

Gln Ala Pro Asp Gly Leu Ala Val Asp Trp Ile His Ser Asn Ile Tyr
        435                 440                 445

Trp Thr Asp Ser Val Leu Gly Thr Val Ser Val Ala Asp Thr Lys Gly
    450                 455                 460

Val Lys Arg Lys Thr Leu Phe Arg Glu Asn Gly Ser Lys Pro Arg Ala
465                 470                 475                 480

Ile Val Val Asp Pro Val His Gly Phe Met Tyr Trp Thr Asp Trp Gly
                485                 490                 495

Thr Pro Ala Lys Ile Lys Lys Gly Gly Leu Asn Gly Val Asp Ile Tyr
            500                 505                 510

Ser Leu Val Thr Glu Asn Ile Gln Trp Pro Asn Gly Ile Thr Leu Asp
        515                 520                 525

Leu Leu Ser Gly Arg Leu Tyr Trp Val Asp Ser Lys Leu His Ser Ile
    530                 535                 540

Ser Ser Ile Asp Val Asn Gly Gly Asn Arg Lys Thr Ile Leu Glu Asp
545                 550                 555                 560

Glu Lys Arg Leu Ala His Pro Phe Ser Leu Ala Val Phe Glu Asp Lys
                565                 570                 575

Val Phe Trp Thr Asp Ile Ile Asn Glu Ala Ile Phe Ser Ala Asn Arg
            580                 585                 590

Leu Thr Gly Ser Asp Val Asn Leu Leu Ala Glu Asn Leu Leu Ser Pro
        595                 600                 605

Glu Asp Met Val Leu Phe His Asn Leu Thr Gln Pro Arg Gly Val Asn
    610                 615                 620

Trp Cys Glu Arg Thr Thr Leu Ser Asn Gly Gly Cys Gln Tyr Leu Cys
625                 630                 635                 640

Leu Pro Ala Pro Gln Ile Asn Pro His Ser Pro Lys Phe Thr Cys Ala
                645                 650                 655

Cys Pro Asp Gly Met Leu Leu Ala Arg Asp Met Arg Ser Cys Leu Thr
            660                 665                 670

Glu Ala Glu Ala Ala Val Ala Thr Gln Glu Thr Ser Thr Val Arg Leu
        675                 680                 685

Lys Val Ser Ser Thr Ala Val Arg Thr Gln His Thr Thr Thr Arg Pro
    690                 695                 700

```
Val Pro Asp Thr Ser Arg Leu Pro Gly Ala Thr Pro Gly Leu Thr Thr
705                 710                 715                 720

Val Glu Ile Val Thr Met Ser His Gln Ala Leu Gly Asp Val Ala Gly
                725                 730                 735

Arg Gly Asn Glu Lys Lys Pro Ser Ser Val Arg Ala Leu Ser Ile Val
            740                 745                 750

Leu Pro Ile Val Leu Leu Val Phe Leu Cys Leu Gly Val Phe Leu Leu
        755                 760                 765

Trp Lys Asn Trp Arg Leu Lys Asn Ile Asn Ser Ile Asn Phe Asp Asn
    770                 775                 780

Pro Val Tyr Gln Lys Thr Thr Glu Asp Glu Val His Ile Cys His Asn
785                 790                 795                 800

Gln Asp Gly Tyr Ser Tyr Pro Ser Arg Gln Met Val Ser Leu Glu Asp
                805                 810                 815

Asp Val Ala


<210> SEQ ID NO 40
<211> LENGTH: 858
<212> TYPE: PRT
<213> ORGANISM: homo sapien

<400> SEQUENCE: 40

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255
```

-continued

```
Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
        355                 360                 365

Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
```

-continued

```
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Met Val Ser Leu Glu Asp Asp Val Ala
    850                 855


<210> SEQ ID NO 41
<211> LENGTH: 739
<212> TYPE: PRT
<213> ORGANISM: homo sapien

<400> SEQUENCE: 41

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Asn Ser Ser Thr Cys Ile Pro Gln Leu Trp Ala Cys Asp Asn
        35                  40                  45

Asp Pro Asp Cys Glu Asp Gly Ser Asp Glu Trp Pro Gln Arg Cys Arg
    50                  55                  60

Gly Leu Tyr Val Phe Gln Gly Asp Ser Ser Pro Cys Ser Ala Phe Glu
65                  70                  75                  80

Phe His Cys Leu Ser Gly Glu Cys Ile His Ser Ser Trp Arg Cys Asp
                85                  90                  95

Gly Gly Pro Asp Cys Lys Asp Lys Ser Asp Glu Glu Asn Cys Ala Val
            100                 105                 110

Ala Thr Cys Arg Pro Asp Glu Phe Gln Cys Ser Asp Gly Asn Cys Ile
        115                 120                 125

His Gly Ser Arg Gln Cys Asp Arg Glu Tyr Asp Cys Lys Asp Met Ser
    130                 135                 140

Asp Glu Val Gly Cys Val Asn Val Thr Leu Cys Glu Gly Pro Asn Lys
145                 150                 155                 160

Phe Lys Cys His Ser Gly Glu Cys Ile Thr Leu Asp Lys Val Cys Asn
                165                 170                 175

Met Ala Arg Asp Cys Arg Asp Trp Ser Asp Glu Pro Ile Lys Glu Cys
            180                 185                 190
```

-continued

```
Gly Thr Asn Glu Cys Leu Asp Asn Asn Gly Gly Cys Ser His Val Cys
        195                 200                 205

Asn Asp Leu Lys Ile Gly Tyr Glu Cys Leu Cys Pro Asp Gly Phe Gln
    210                 215                 220

Leu Val Ala Gln Arg Arg Cys Glu Asp Ile Asp Glu Cys Gln Asp Pro
225                 230                 235                 240

Asp Thr Cys Ser Gln Leu Cys Val Asn Leu Glu Gly Gly Tyr Lys Cys
                245                 250                 255

Gln Cys Glu Glu Gly Phe Gln Leu Asp Pro His Thr Lys Ala Cys Lys
            260                 265                 270

Ala Val Gly Ser Ile Ala Tyr Leu Phe Phe Thr Asn Arg His Glu Val
        275                 280                 285

Arg Lys Met Thr Leu Asp Arg Ser Glu Tyr Thr Ser Leu Ile Pro Asn
    290                 295                 300

Leu Arg Asn Val Val Ala Leu Asp Thr Glu Val Ala Ser Asn Arg Ile
305                 310                 315                 320

Tyr Trp Ser Asp Leu Ser Gln Arg Met Ile Cys Ser Thr Gln Leu Asp
                325                 330                 335

Arg Ala His Gly Val Ser Ser Tyr Asp Thr Val Ile Ser Arg Asp Ile
            340                 345                 350

Gln Ala Pro Asp Gly Leu Ala Val Asp Trp Ile His Ser Asn Ile Tyr
        355                 360                 365

Trp Thr Asp Ser Val Leu Gly Thr Val Ser Val Ala Asp Thr Lys Gly
    370                 375                 380

Val Lys Arg Lys Thr Leu Phe Arg Glu Asn Gly Ser Lys Pro Arg Ala
385                 390                 395                 400

Ile Val Val Asp Pro Val His Gly Phe Met Tyr Trp Thr Asp Trp Gly
                405                 410                 415

Thr Pro Ala Lys Ile Lys Lys Gly Gly Leu Asn Gly Val Asp Ile Tyr
            420                 425                 430

Ser Leu Val Thr Glu Asn Ile Gln Trp Pro Asn Gly Ile Thr Leu Asp
        435                 440                 445

Leu Leu Ser Gly Arg Leu Tyr Trp Val Asp Ser Lys Leu His Ser Ile
    450                 455                 460

Ser Ser Ile Asp Val Asn Gly Gly Asn Arg Lys Thr Ile Leu Glu Asp
465                 470                 475                 480

Glu Lys Arg Leu Ala His Pro Phe Ser Leu Ala Val Phe Glu Asp Lys
                485                 490                 495

Val Phe Trp Thr Asp Ile Ile Asn Glu Ala Ile Phe Ser Ala Asn Arg
            500                 505                 510

Leu Thr Gly Ser Asp Val Asn Leu Leu Ala Glu Asn Leu Leu Ser Pro
        515                 520                 525

Glu Asp Met Val Leu Phe His Asn Leu Thr Gln Pro Arg Gly Val Asn
    530                 535                 540

Trp Cys Glu Arg Thr Thr Leu Ser Asn Gly Gly Cys Gln Tyr Leu Cys
545                 550                 555                 560

Leu Pro Ala Pro Gln Ile Asn Pro His Ser Pro Lys Phe Thr Cys Ala
                565                 570                 575

Cys Pro Asp Gly Met Leu Leu Ala Arg Asp Met Arg Ser Cys Leu Thr
            580                 585                 590

Glu Ala Glu Ala Ala Val Ala Thr Gln Glu Thr Ser Thr Val Arg Leu
        595                 600                 605

Lys Val Ser Ser Thr Ala Val Arg Thr Gln His Thr Thr Thr Arg Pro
```

```
    610                 615                 620

Val Pro Asp Thr Ser Arg Leu Pro Gly Ala Thr Pro Gly Leu Thr Thr
625                 630                 635                 640

Val Glu Ile Val Thr Met Ser His Gln Ala Leu Gly Asp Val Ala Gly
                645                 650                 655

Arg Gly Asn Glu Lys Lys Pro Ser Ser Val Arg Ala Leu Ser Ile Val
            660                 665                 670

Leu Pro Ile Val Leu Leu Val Phe Leu Cys Leu Gly Val Phe Leu Leu
        675                 680                 685

Trp Lys Asn Trp Arg Leu Lys Asn Ile Asn Ser Ile Asn Phe Asp Asn
    690                 695                 700

Pro Val Tyr Gln Lys Thr Thr Glu Asp Glu Val His Ile Cys His Asn
705                 710                 715                 720

Gln Asp Gly Tyr Ser Tyr Pro Ser Arg Gln Met Val Ser Leu Glu Asp
                725                 730                 735

Asp Val Ala


<210> SEQ ID NO 42
<211> LENGTH: 692
<212> TYPE: PRT
<213> ORGANISM: homo sapien

<400> SEQUENCE: 42

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Leu Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
```

-continued

```
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670
```

```
Thr Ala Val Ala Ile Cys Cys Arg Ser Arg His Leu Ala Gln Ala Ser
        675                 680                 685

Gln Glu Leu Gln
    690


<210> SEQ ID NO 43
<211> LENGTH: 20
<212> TYPE: DNA
<213> ORGANISM: artificial sequence
<220> FEATURE:
<223> OTHER INFORMATION: PCSK9 gRNA

<400> SEQUENCE: 43

cccggtcctt ggcgcgcggt                                              20


<210> SEQ ID NO 44
<211> LENGTH: 20
<212> TYPE: DNA
<213> ORGANISM: artificial sequence
<220> FEATURE:
<223> OTHER INFORMATION: PCSK9 gRNA

<400> SEQUENCE: 44

aggacgagga cggcgacacg                                              20


<210> SEQ ID NO 45
<211> LENGTH: 20
<212> TYPE: DNA
<213> ORGANISM: artificial sequence
<220> FEATURE:
<223> OTHER INFORMATION: PCSK9 gRNA

<400> SEQUENCE: 45

ccgtgctcgg gtgcttcggc                                              20


<210> SEQ ID NO 46
<211> LENGTH: 20
<212> TYPE: DNA
<213> ORGANISM: artificial sequence
<220> FEATURE:
<223> OTHER INFORMATION: PCSK9 gRNA

<400> SEQUENCE: 46

ccggtccttg gcgcgcggtg                                              20


<210> SEQ ID NO 47
<211> LENGTH: 20
<212> TYPE: DNA
<213> ORGANISM: artificial sequence
<220> FEATURE:
<223> OTHER INFORMATION: PCSK9 gRNA

<400> SEQUENCE: 47

cttcggccgg ccgtcctcct                                              20


<210> SEQ ID NO 48
<211> LENGTH: 20
<212> TYPE: DNA
<213> ORGANISM: artificial sequence
<220> FEATURE:
<223> OTHER INFORMATION: PCSK9 gRNA

<400> SEQUENCE: 48

agccacccca ccgcgcgcca                                              20
```

<210> SEQ ID NO 49
<211> LENGTH: 20
<212> TYPE: DNA
<213> ORGANISM: artificial sequence
<220> FEATURE:
<223> OTHER INFORMATION: PCSK9 gRNA

<400> SEQUENCE: 49
ggttccgtgc tcgggtgctt 20

<210> SEQ ID NO 50
<211> LENGTH: 20
<212> TYPE: DNA
<213> ORGANISM: artificial sequence
<220> FEATURE:
<223> OTHER INFORMATION: PCSK9 gRNA

<400> SEQUENCE: 50
tcccggtcct tggcgcgcgg 20

<210> SEQ ID NO 51
<211> LENGTH: 20
<212> TYPE: DNA
<213> ORGANISM: artificial sequence
<220> FEATURE:
<223> OTHER INFORMATION: PCSK9 gRNA

<400> SEQUENCE: 51
gaggacggcg acacgaggag 20

<210> SEQ ID NO 52
<211> LENGTH: 20
<212> TYPE: DNA
<213> ORGANISM: artificial sequence
<220> FEATURE:
<223> OTHER INFORMATION: PCSK9 gRNA

<400> SEQUENCE: 52
accgcgcgcc aaggaccggg 20

<210> SEQ ID NO 53
<211> LENGTH: 20
<212> TYPE: DNA
<213> ORGANISM: artificial sequence
<220> FEATURE:
<223> OTHER INFORMATION: PCSK9 gRNA

<400> SEQUENCE: 53
ccgcgcgcca aggaccggga 20

<210> SEQ ID NO 54
<211> LENGTH: 20
<212> TYPE: DNA
<213> ORGANISM: artificial sequence
<220> FEATURE:
<223> OTHER INFORMATION: PCSK9 gRNA

<400> SEQUENCE: 54
cccaccgcgc gccaaggacc 20

<210> SEQ ID NO 55
<211> LENGTH: 20
<212> TYPE: DNA
<213> ORGANISM: artificial sequence
<220> FEATURE:
<223> OTHER INFORMATION: PCSK9 gRNA

<400> SEQUENCE: 55
gccggccgtc ctcctcggcg 20

<210> SEQ ID NO 56
<211> LENGTH: 20
<212> TYPE: DNA
<213> ORGANISM: artificial sequence
<220> FEATURE:
<223> OTHER INFORMATION: PCSK9 gRNA

<400> SEQUENCE: 56
ggtggctgtg gttccgtgct 20

<210> SEQ ID NO 57
<211> LENGTH: 20
<212> TYPE: DNA
<213> ORGANISM: artificial sequence
<220> FEATURE:
<223> OTHER INFORMATION: PCSK9 gRNA

<400> SEQUENCE: 57
ccctcccggt ccttggcgcg 20

<210> SEQ ID NO 58
<211> LENGTH: 20
<212> TYPE: DNA
<213> ORGANISM: artificial sequence
<220> FEATURE:
<223> OTHER INFORMATION: PCSK9 gRNA

<400> SEQUENCE: 58
aggacggcga cacgaggagc 20

<210> SEQ ID NO 59
<211> LENGTH: 20
<212> TYPE: DNA
<213> ORGANISM: artificial sequence
<220> FEATURE:
<223> OTHER INFORMATION: PCSK9 gRNA

<400> SEQUENCE: 59
accgggaggg ccggcaccac 20

<210> SEQ ID NO 60
<211> LENGTH: 20
<212> TYPE: DNA
<213> ORGANISM: artificial sequence
<220> FEATURE:
<223> OTHER INFORMATION: PCSK9 gRNA

<400> SEQUENCE: 60
gtggctgtgg ttccgtgctc 20

<210> SEQ ID NO 61
<211> LENGTH: 20
<212> TYPE: DNA
<213> ORGANISM: artificial sequence
<220> FEATURE:
<223> OTHER INFORMATION: PCSK9 gRNA

<400> SEQUENCE: 61
ccccaccgcg cgccaaggac 20

<210> SEQ ID NO 62

<211> LENGTH: 20
<212> TYPE: DNA
<213> ORGANISM: artificial sequence
<220> FEATURE:
<223> OTHER INFORMATION: PCSK9 gRNA

<400> SEQUENCE: 62
gtgccggccc tcccggtcct 20

<210> SEQ ID NO 63
<211> LENGTH: 20
<212> TYPE: DNA
<213> ORGANISM: artificial sequence
<220> FEATURE:
<223> OTHER INFORMATION: PCSK9 gRNA

<400> SEQUENCE: 63
aggagcgggc agccgcgccg 20

<210> SEQ ID NO 64
<211> LENGTH: 20
<212> TYPE: DNA
<213> ORGANISM: artificial sequence
<220> FEATURE:
<223> OTHER INFORMATION: PCSK9 gRNA

<400> SEQUENCE: 64
cgggagggcc ggcaccacgg 20

<210> SEQ ID NO 65
<211> LENGTH: 20
<212> TYPE: DNA
<213> ORGANISM: artificial sequence
<220> FEATURE:
<223> OTHER INFORMATION: PCSK9 gRNA

<400> SEQUENCE: 65
agcgggcagc cgcgccgagg 20

<210> SEQ ID NO 66
<211> LENGTH: 20
<212> TYPE: DNA
<213> ORGANISM: artificial sequence
<220> FEATURE:
<223> OTHER INFORMATION: PCSK9 gRNA

<400> SEQUENCE: 66
ccgggagggc cggcaccacg 20

<210> SEQ ID NO 67
<211> LENGTH: 20
<212> TYPE: DNA
<213> ORGANISM: artificial sequence
<220> FEATURE:
<223> OTHER INFORMATION: PCSK9 gRNA

<400> SEQUENCE: 67
gaccgggagg gccggcacca 20

<210> SEQ ID NO 68
<211> LENGTH: 20
<212> TYPE: DNA
<213> ORGANISM: artificial sequence
<220> FEATURE:
<223> OTHER INFORMATION: PCSK9 gRNA

<400> SEQUENCE: 68
gtccttggcg cgcggtgggg 20

<210> SEQ ID NO 69
<211> LENGTH: 20
<212> TYPE: DNA
<213> ORGANISM: artificial sequence
<220> FEATURE:
<223> OTHER INFORMATION: LDLR gRNA

<400> SEQUENCE: 69
gtcataggaa gagacgccgt 20

<210> SEQ ID NO 70
<211> LENGTH: 20
<212> TYPE: DNA
<213> ORGANISM: artificial sequence
<220> FEATURE:
<223> OTHER INFORMATION: LDLR gRNA

<400> SEQUENCE: 70
cggataccaa gggcgtgaag 20

<210> SEQ ID NO 71
<211> LENGTH: 20
<212> TYPE: DNA
<213> ORGANISM: artificial sequence
<220> FEATURE:
<223> OTHER INFORMATION: LDLR gRNA

<400> SEQUENCE: 71
tgtcatagga agagacgccg 20

<210> SEQ ID NO 72
<211> LENGTH: 20
<212> TYPE: DNA
<213> ORGANISM: artificial sequence
<220> FEATURE:
<223> OTHER INFORMATION: LDLR gRNA

<400> SEQUENCE: 72
cgtggtcgct ctggacacgg 20

<210> SEQ ID NO 73
<211> LENGTH: 20
<212> TYPE: DNA
<213> ORGANISM: artificial sequence
<220> FEATURE:
<223> OTHER INFORMATION: LDLR gRNA

<400> SEQUENCE: 73
tgtctctgtt gcggatacca 20

<210> SEQ ID NO 74
<211> LENGTH: 20
<212> TYPE: DNA
<213> ORGANISM: artificial sequence
<220> FEATURE:
<223> OTHER INFORMATION: LDLR gRNA

<400> SEQUENCE: 74
gtccacagcc agcccgtcgg 20

<210> SEQ ID NO 75
<211> LENGTH: 20
<212> TYPE: DNA

<213> ORGANISM: artificial sequence
<220> FEATURE:
<223> OTHER INFORMATION: LDLR gRNA

<400> SEQUENCE: 75
agaccagtag attctattgc 20

<210> SEQ ID NO 76
<211> LENGTH: 20
<212> TYPE: DNA
<213> ORGANISM: artificial sequence
<220> FEATURE:
<223> OTHER INFORMATION: LDLR gRNA

<400> SEQUENCE: 76
cggtccagta gatgttgctg 20

<210> SEQ ID NO 77
<211> LENGTH: 20
<212> TYPE: DNA
<213> ORGANISM: artificial sequence
<220> FEATURE:
<223> OTHER INFORMATION: LDLR gRNA

<400> SEQUENCE: 77
cgccgtgggc tctgtcaagc 20

<210> SEQ ID NO 78
<211> LENGTH: 20
<212> TYPE: DNA
<213> ORGANISM: artificial sequence
<220> FEATURE:
<223> OTHER INFORMATION: LDLR gRNA

<400> SEQUENCE: 78
gaacgtggtc gctctggaca 20

<210> SEQ ID NO 79
<211> LENGTH: 20
<212> TYPE: DNA
<213> ORGANISM: artificial sequence
<220> FEATURE:
<223> OTHER INFORMATION: LDLR gRNA

<400> SEQUENCE: 79
ctactggacc gactctgtcc 20

<210> SEQ ID NO 80
<211> LENGTH: 20
<212> TYPE: DNA
<213> ORGANISM: artificial sequence
<220> FEATURE:
<223> OTHER INFORMATION: LDLR gRNA

<400> SEQUENCE: 80
agagacatcc aggcccccga 20

<210> SEQ ID NO 81
<211> LENGTH: 20
<212> TYPE: DNA
<213> ORGANISM: artificial sequence
<220> FEATURE:
<223> OTHER INFORMATION: LDLR gRNA

<400> SEQUENCE: 81
tctgctgatg acggtgtcat 20

<210> SEQ ID NO 82
<211> LENGTH: 20
<212> TYPE: DNA
<213> ORGANISM: artificial sequence
<220> FEATURE:
<223> OTHER INFORMATION: LDLR gRNA

<400> SEQUENCE: 82
gagacatcca ggcccccgac 20

<210> SEQ ID NO 83
<211> LENGTH: 20
<212> TYPE: DNA
<213> ORGANISM: artificial sequence
<220> FEATURE:
<223> OTHER INFORMATION: LDLR gRNA

<400> SEQUENCE: 83
gccgtgggct ctgtcaagct 20

<210> SEQ ID NO 84
<211> LENGTH: 20
<212> TYPE: DNA
<213> ORGANISM: artificial sequence
<220> FEATURE:
<223> OTHER INFORMATION: LDLR gRNA

<400> SEQUENCE: 84
gtctctgttg cggataccaa 20

<210> SEQ ID NO 85
<211> LENGTH: 20
<212> TYPE: DNA
<213> ORGANISM: artificial sequence
<220> FEATURE:
<223> OTHER INFORMATION: LDLR gRNA

<400> SEQUENCE: 85
ggtcgctctg gacacggagg 20

<210> SEQ ID NO 86
<211> LENGTH: 20
<212> TYPE: DNA
<213> ORGANISM: artificial sequence
<220> FEATURE:
<223> OTHER INFORMATION: LDLR gRNA

<400> SEQUENCE: 86
tggccagcaa tagaatctac 20

<210> SEQ ID NO 87
<211> LENGTH: 20
<212> TYPE: DNA
<213> ORGANISM: artificial sequence
<220> FEATURE:
<223> OTHER INFORMATION: LDLR gRNA

<400> SEQUENCE: 87
catccaggcc cccgacgggc 20

<210> SEQ ID NO 88
<211> LENGTH: 20
<212> TYPE: DNA
<213> ORGANISM: artificial sequence
<220> FEATURE:

-continued

```
<223> OTHER INFORMATION: LDLR gRNA

<400> SEQUENCE: 88

gggtgctgca gatcattctc                                                  20


<210> SEQ ID NO 89
<211> LENGTH: 20
<212> TYPE: DNA
<213> ORGANISM: artificial sequence
<220> FEATURE:
<223> OTHER INFORMATION: LDLR gRNA

<400> SEQUENCE: 89

tactggaccg actctgtcct                                                  20
```